US009388217B2

(12) United States Patent
Baker et al.

(10) Patent No.: US 9,388,217 B2
(45) Date of Patent: *Jul. 12, 2016

(54) POLYPEPTIDES FOR TREATING AND/OR LIMITING INFLUENZA INFECTION

(71) Applicant: University of Washington through its Center for Commercialization, Seattle, WA (US)

(72) Inventors: David Baker, Seattle, WA (US); Timothy A. Whitehead, East Grand Rapids, MI (US); Sarel Fleishman, Ness Ziona (IL)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/384,901

(22) PCT Filed: Mar. 12, 2013

(86) PCT No.: PCT/US2013/030311
§ 371 (c)(1),
(2) Date: Sep. 12, 2014

(87) PCT Pub. No.: WO2013/138259
PCT Pub. Date: Sep. 19, 2013

(65) Prior Publication Data
US 2015/0038408 A1    Feb. 5, 2015

Related U.S. Application Data

(60) Provisional application No. 61/610,311, filed on Mar. 13, 2012.

(51) Int. Cl.
| | |
|---|---|
| *A61K 38/00* | (2006.01) |
| *A61K 38/16* | (2006.01) |
| *A61K 38/10* | (2006.01) |
| *C07K 14/00* | (2006.01) |
| *C07K 7/08* | (2006.01) |
| *G01N 33/53* | (2006.01) |
| *G01N 33/569* | (2006.01) |

(52) U.S. Cl.
CPC . *C07K 14/00* (2013.01); *C07K 7/08* (2013.01); *G01N 33/56983* (2013.01); *A61K 38/00* (2013.01); *G01N 2333/11* (2013.01)

(58) Field of Classification Search
CPC ....... A61K 38/00; A61K 38/16; A61K 38/10; C07K 14/00; C07K 7/08; G01N 33/369; G01N 33/569; G01N 33/53

USPC ......... 514/3.7, 21.3, 21.4; 530/324, 325, 326, 530/327, 350, 387.9
See application file for complete search history.

(56) References Cited

U.S. PATENT DOCUMENTS

| 8,470,327 B2 | 6/2013 | Throsby et al. |
| 8,540,995 B2 | 9/2013 | Mookkan et al. |
| 8,569,255 B2 | 10/2013 | Wong |
| 2009/0191233 A1 | 7/2009 | Bonnet et al. |

FOREIGN PATENT DOCUMENTS

| EP | 2003198 A2 | 12/2008 |
| EP | 2327714 A1 | 6/2011 |
| WO | 00/59932 | 3/2000 |
| WO | 2005/037187 | 4/2005 |
| WO | 2012/018907 | 2/2012 |
| WO | 2013/082531 | 6/2013 |
| WO | 2013/121442 | 8/2013 |
| WO | 2014/152946 | 9/2014 |

OTHER PUBLICATIONS

Lane et al, "Nucleomorph genome of Hemiselmis andersenii reveals complete intron loss and compaction as a driver of protein structure and function," PNAS, 2007, 104(50): 19908-19913.*
ABW98089 sequence from Lane et al, PNAS, 2007, 104(50), 19908-19913.*
Araya et al. (Oct. 2012) "A fundamental protein property, thermodynamic stability, revealed solely from large-scale measurements of protein function," Proceedings of the National Academy of Sciences USA, 109(42):16858-16863.
Araya, CL and Fowler, DM (Sep. 2011) "Deep mutational scanning: assessing protein function on a massive scale," Trends Biotechnol, 29(9):435-42.
Balakrishnan, S. et al. (Apr. 2011) "Learning generative models for protein fold families," Proteins, 79(4):1061-1078.
Beck, A. et al. (May 2010) "Strategies and challenges for the next generation of therapeutic antibodies," Nature Reviews Immunology, 10(5):345-52.

(Continued)

*Primary Examiner* — Julie Ha
(74) *Attorney, Agent, or Firm* — McDonnell Boehnen Hulbert & Berghoff LLP

(57) ABSTRACT

Polypeptides that recognize and are strong binders to Influenza A hemagglutinin and can be used, for example, to treat and/or limit development of an influenza infection are disclosed. Isolated nucleic acids encoding the polypeptides of the invention, recombinant expression vectors comprising the nucleic acids encoding the polypeptides of the invention operatively linked to a suitable control sequence, and recombinant host cells comprising the recombinant expression vectors of the invention are disclosed. Antibodies that selectively bind to the polypeptides of the invention, and pharmaceutical compositions comprising one or more polypeptides according to the invention and a pharmaceutically acceptable carrier are disclosed. Additionally, methods for treating and/or limiting an influenza infection, methods for diagnosing an influenza infection, or monitoring progression of an influenza infection, methods for identifying candidate influenza vaccines, and methods for identifying candidate compounds for treating, limiting, and/or diagnosing influenza infection are disclosed.

20 Claims, 12 Drawing Sheets

(56) References Cited

OTHER PUBLICATIONS

Benatuil, L. et al. (Apr. 2010) "An improved yeast transformation method for the generation of very large human antibody libraries," Protein Eng Des Sel, 23(4):155-159.
Ben-Shimon, A. and Eisenstein, M. (Sep. 2010) "Computational mapping of anchoring spots on protein surfaces," J. Mol. Biol., 402(1):259-277.
Bershtein, S. et al. (Dec. 2006) Robustness-epistasis link shapes the fitness landscape of a randomly drifting protein, Nature, 444(7121):929-932.
Binz, HK and Pluckthun, A. (Aug. 2005) "Engineered proteins as specific binding reagents," Curr. Opin. Biotechnol., 16(4):459-469.
Binz, HK et al. (May 2004) "High-affinity binders selected from designed ankyrin repeat protein libraries," Nat. Biotechnol., 22(5):575-582.
Binz, HK et al. (Oct. 2005) "Engineering novel binding proteins from nonimmunoglobulin domains," Nat. Biotechnol., 23(10):1257-1268.
Binz, HK et al. (Sep. 2003) "Designing repeat proteins: well-expressed, soluble and stable proteins from combinatorial libraries of consensus ankyrin repeat proteins," J. Mol. Biol., 332(2):489-503.
Bogan, AA and Thorn, KS (Jul. 1998) "Anatomy of hot spots in protein interfaces," J Mol Biol,280(1):1-9.
Bournazos et al. (Sep. 2014) "Broadly neutralizing anti-HIV-1 antibodies require Fc effector functions for in vivo activity," Cell, 158(6):1243-1253.
Bowie, JU et al. (Jul. 1991) "A method to identify protein sequences that fold into a known three-dimensional structure," Science, 253(5016):164-170.
Bowie, JU et al. (Mar. 1990) "Deciphering the message in protein sequences: tolerance to amino acid substitutions," Science, 247(4948):1306-1310.
Braisted, AC and Wells, JA (Jun. 1996) "Minimizing a binding domain from protein A," Proc Natl Acad Sci USA, 93 (12):5688-92.
Buckle, AM et al. (Aug. 1994) "Protein-protein recognition: crystal structural analysis of a barnase-barstar complex at 2.0-A resolution," Biochemistry, 33(30):8878-89.
Castro, MJ and Anderson, S. (Sep. 1996) "Alanine point-mutations in the reactive region of bovine pancreatic trypsin inhibitor: effects on the kinetics and thermodynamics of binding to beta-trypsin and alpha-chymotrypsin," Biochemistry, 35(35):11435-46.
CDC (Accessed Jun. 2015) "Influenza Antiviral Drug Resistance," available online at: http://www.cdc.gov/flu/about/qa/antiviralresistance.htm.
Chao, G. et al. (Sep. 2004) "Fine epitope mapping of anti-epidermal growth factor receptor antibodies through random mutagenesis and yeast surface display," J Mol Biol, 342(2):539-550.
Chen, R. et al. (Jul. 2003) "ZDOCK: an initial-stage protein-docking algorithm," Proteins, 52(1):80-87.
Choi et al. (Jan. 2013) "A structural bioinformatics approach for identifying proteins predisposed to bind linear epitopes on pre-selected target proteins," Protein Engineering, Design & Selection, 26(4):283-9.
Clackson, T. et al. (Apr. 1998) "Structural and functional analysis of the 1:1 growth hormone: receptor complex reveals the molecular basis for receptor affinity," J Mol Biol, 277(5):1111-28.
Connaris et al. (Apr. 2014) "Prevention of influenza by targeting host receptors using engineered proteins," Proceedings of the National Academy of Sciences, 111(17):6401-6406.
Corti, D. et al. (Aug. 2011) "A neutralizing antibody selected from plasma cells that binds to group 1 and group 2 influenza A hemagglutinins," Science, 333(6044):850-856.
Cunningham, BC and Wells, JA (Jun. 1989) "High-resolution epitope mapping of hGH-receptor interactions by alanine-scanning mutagenesis," Science, 244(4908):1081-1085.
Dauter, Z. (Oct. 1999) "Data-collection strategies," Acta Crystallogr D Biol Crystallogr, 55(Pt. 10):1703-17.
De Clercq (Dec. 2006) "Antiviral agents active against influenza A viruses," Nature Reviews Drug Discovery, 5 (12):1015-1025.
Delano, WL (2002) "The PyMol molecular graphics systems," DeLano Scientific, San Carlos, CA, USA. http://www.pymol.org—retrieved May 2015.
DeLano, WL (2009) "PyMOL molecular viewer: Updates and refinements," Abstr Pap Am Chem S, 238—retrieved May 2015.
DiLillo et al. (Feb. 2014) "Broadly neutralizing hemagglutinin stalk-specific antibodies require FcyR interactions for protection against influenza virus in vivo," Nature Medicine, 20(2):143-151.
Dutta, S. et al. (May 2010) "Determinants of BH3 binding specificity for Mcl-1 versus Bcl-xL," J Mol Biol, 398 (5):747-762.
Efron, B. et al. (2002) "Least angle regression," Ann Stat, 32(2):407-499—retrieved May 2015.
Ekiert and IA Wilson (Apr. 2012) "Broadly neutralizing antibodies against influenza virus and prospects for universal therapies," Current Opinion in Virology, 2(2):134-141.
Falcone et al. (Jun. 2013) "Influenza virus a(H1N1)pdm09 hemagglutinin polymorphism and associated disease in southern Germany during the 2010/11 influenza season," Archives of Virology, 158(6):1297-1303.
Fleishman, SJ et al. (2011) "RosettaScripts: A Scripting Language Interface to the Rosetta Macromolecular Modeling Suite," PLoS One, 6(6):e20161—retrieved May 2015.
Fleishman, SJ et al. (Apr. 2011) "Restricted sidechain plasticity in the structures of native proteins and complexes," Protein Science, 20(4):753-757.
Fleishman, SJ et al. (Nov. 2011) "Hotspot-centric de novo design of protein binders," Journal of Molecular Biology, 413(5):1047-1062.
Fowler, DM et al. (Sep. 2010) "High-resolution mapping of protein sequence-function relationships," Nat Methods, 7 (9):741-746.
Friesen et al. (Jan. 2014) "A common solution to group 2 influenza virus neutralization," Proceedings of the National Academy of Sciences USA, 111(1):445-50.
Gibson et al. (May 2009) "Enzymatic assembly of DNA molecules up to several hundred kilobases," Nature Methods, 6(5):343-345.
Girard et al. (Jul. 2010) "The 2009 A (H1N1) influenza virus pandemic: A review," Vaccine, 28(31):4895-4902.
Grigoryan, G. et al. (Apr. 2009) "Design of protein-interaction specificity gives selective bZIP-binding peptides," Nature, 458(7240):859-864.
Guharoy, M. and Chakrabarti, P. (Oct. 2005) "Conservation and relative importance of residues across protein-protein interfaces," Proc. Natl. Acad. Sci. USA, 102(43)15447-15452.
Hackel, BJ et al. (Sep. 2008) "Picomolar affinity fibronectin domains engineered utilizing loop length diversity, recursive mutagenesis, and loop shuffling," Journal of Molecular Biology, 381(5):1238-52.
Havranek, JJ and Harbury, PB (Jan. 2003) "Automated design of specificity in molecular recognition," Nat. Struct. Biol., 10(1):45-52.
Hietpas, RT et al. (May 2011) "Experimental illumination of a fitness landscape," Proc Natl Acad Sci USA, 108 (19):7896-7901.
Hoover and J. Lubkowski (May 2002) "DNAWorks: an automated method for designing oligonucleotides for PCR-based gene synthesis," Nucleic Acids Research, 30(10):e43.
Hu, Z. et al. (Jun. 2000) "Conservation of polar residues as hot spots at protein interfaces," Proteins, 39(4):331-42.
Huang, H. and Yuan, HS (May 2007) "The conserved asparagine in the HNH motif serves an important structural role in metal finger endonucleases," Journal of Molecular Biology, 368(3):812-21.
Schreiber, G. and Fersht, AR (May 1996) "Rapid, electrostatically assisted association of proteins," Nat Struct Biol, 3(5):427-31.
Schreiber, G. et al. (Jul. 1997) "The role of Glu73 of barnase in catalylsis and the binding of barstar," J Mol Biol, 270 (1):111-122.
Seo et al. (Dec. 2010) "MyD88 signaling is indispensable for primary influenza A virus infection but dispensable for secondary infection," Journal of Virology, 84(24):12713-12722.
Sharabi, O. et al. (May 2011) "Triathlon for energy functions: who is the winner for design of protein-protein interactions?" Proteins, 79(5):1487-1498.
Shrestha et al. (Jun. 2013) "Identifying the Interaction Between Influenza and Pneumococcal Pneumonia Using Incidence Data," Science Translational Medicine, 5(191):191ra184.
Shriver et al. (Aug. 2009) "Context-specific target definition in influenza a virus hemagglutinin-glycan receptor interactions," Chemistry & Biology, 16(8):803-14.

(56) References Cited

OTHER PUBLICATIONS

Shultzaberger, RK et al. (Jul. 2010) "The fitness landscapes of cis-acting binding sites in different promoter and environmental contexts," PLoS genetics, 6(7):e1001042.

Sitkoff, D. et al. (Feb. 1994) "Accurate Calculation of Hydration Free-Energies Using Macroscopic Solvent Models," J Phys Chem, 98(7):1978-1988.

Sitkoff, D. et al. (Feb. 1996) "Calculation of alkane to water solvation free energies using continuum solvent models," J Phys Chem, 100(7):2744-2752.

Smee, DF et al. (Mar. 2001) "Cyclopentane neuraminidase inhibitors with potent in vitro anti-influenza virus activities," Antimicrob Agents Chemother, 45(3):743-748.

Sorzano et al. (Aug. 2010) "A clustering approach to multireference alignment of single-particle projections in electron microscopy," Journal of Structural Biology, 171(2):197-206.

Stanfield, RL et al. (Sep. 2004) "Crystal structure of a shark single-domain antibody V region in complex with lysozyme," Science, 305(5691):1770-3.

Stebbins, CE and Galán, JE (Dec. 2000) "Modulation of host signaling by a bacterial mimic: structure of the *Salmonella* effector SptP bound to Rac1," Molecular Cell, 6(6):1449-1460.

Stevenson, CE et al. (Dec. 2006) "Crystal structure of the MYB domain of the RAD transcription factor from Antirrhinum majus," Proteins: Structure, Function, and Bioinformatics, 65(4):1041-5.

Subway et al. (Jul. 2005) "Automated molecular microscopy: the new Leginon system," Journal of Structural Biology, 151(1):41-60.

Tanaka et al. (Feb. 2014) "The effect of intravenous peramivir, compared with oral oseltamivir, on the outcome of post-influenza influenza pneumococcal pneumonia in mice," Antiviral Therapy, 20:11-19.

Tang et al. (Jan. 2007) "EMAN2: an extensible image processing suite for electron microscopy," Journal of Structural Biology, 157(1):38-46.

Tharakaraman et al. (May 2014) "Broadly neutralizing influenza hemagglutinin stem-specific antibody CR8020 targets residues that are prone to escape due to host selection pressure," Cell Host & Microbe, 15(5):644-651.

Voss et al. (May 2009) "DoG Picker and TiltPicker: software tools to facilitate particle selection in single particle electron microscopy," Journal of Structural Biology, 166(2):205-213.

Wallis, R. et al. (Oct. 1995) "Protein-protein interactions in colicin E9 DNase-immunity protein complexes. 1. Diffusion-controlled association and femtomolar binding for the cognate complex," Biochemistry, 34(42):13743-50.

Webster et al. (Mar. 1992) "Evolution and ecology of influenza A viruses," Microbiological Reviews, 56(1):152-179.

Weiss, MS and Hilgenfeld, R. (Apr. 1997) "On the use of the merging R factor as a quality indicator for X-ray data," J Appl Crystallogr, 30(Pt. 2):203-205.

Whitehead et al. (May 2012) "Optimization of affinity, specificity and function of designed influenza inhibitors using deep sequencing," Nature Biotechnology, 30(6):543-548.

Wu, X. et al. (Sep. 2011) "Focused evolution of HIV-1 neutralizing antibodies revealed by structures and deep sequencing," Science, 333(6049):1593-1602.

Zahnd, C. et al. (Apr. 2004) "Directed in vitro evolution and crystallographic analysis of a peptide-binding single chain antibody fragment (scFv) with low picomolar affinity," Journal of Biological Chemistry, 279(18):18870-7.

Zanghellini, A. et al. (Dec. 2006) "New algorithms and an in silico benchmark for computational enzyme design," Protein Sci, 15(12):2785-94.

Stebbins, et al. "Structural mimicry in bacterial virulence," Nature, 412:701-705, Aug. 2001.

Studier, "Protein production by auto-induction in high-density shaking cultures," Protein Expression and Purification, 41:207-234, Mar. 2005.

Fleishman, et al, "Computatio design of proteins targeting the conserved stem region of influenza hemagglutinin," Science, 332 (6031): 816-821, May 2011.

Humphris, EL and Kortemme, T. (Dec. 2008) "Prediction of protein-protein interface sequence diversity using flexible backbone computational protein design," Structure, 16(12):1777-88.

Hwang, H. et al. (Nov. 2008) "Protein-protein docking benchmark version 3.0," Proteins, 73(3):705-709.

Ichinohe et al. (Jan. 2009) "Inflammasome recognition of influenza virus is essential for adaptive immune responses," Journal of Experimental Medicine, 206(1):79-87.

Ishikawa et al. (Sep. 2005) "Development of functional human blood and immune systems in NOD/SCID/IL2 receptor {gamma} chain-(null)mice," Blood, 106(5):1565-1573.

ISR/WO dated Nov. 6, 2013 for PCT/US2013/030311.

Ivachtchenko et al. (Jan. 2014) "Novel oral anti-influenza prodrug candidate AV5075S," Journal of Antimicrobial Chemotherapy, 69(5):1311-24.

Jin, L. and Wells, JA (Dec. 1994) "Dissecting the energetics of an antibody-antigen interface by alanine shaving and molecular grafting," Protein Sci, 3(12):2351-7.

Joachimiak, A. (Oct. 2009) "High-throughput crystallography for structural genomics," Curr Opin Struct Biol, 19 (5):573-84.

Joughin, BA et al. (May 2005) "Action-at-a-distance interactions enhance protein binding affinity," Protein Sci, 14 (5):1363-1369.

Kashyap, AK et al. (Apr. 2008) "Combinatorial antibody libraries from survivors of the Turkish H5N1 avian influenza outbreak reveal virus neutralization strategies," Proceedings of the National Academy of Sciences USA, 105 (16):5986-91.

Keeble, AH et al. (Mar. 2006) "Calorimetric dissection of colicin DNase—immunity protein complex specificity," Biochemistry, 45(10):3243-3254.

Kellogg, EH et al. (Mar. 2011) "Role of conformational sampling in computing mutation-induced changes in protein structure and stability," Proteins, 79(3):830-838.

Koide, A. and Koide, S. (2007) "Monobodies: antibody mimics based on the scaffold of the fibronectin type III domain," Methods Mol Biol, 352:95-109—retrieved May 2015.

Kortemme, T. et al. (Feb. 2004) "Computational alanine scanning of protein-protein interfaces," Sci STKE, 2004(219): pl2.

Koyama et al. (Oct. 2007) "Differential role of TLR- and RLR-signaling in the immune responses to influenza A virus infection and vaccination," Journal of Immunology, 179(7):4711-4720.

Krammer and P. Palese (Oct. 2013) "Influenza virus hemagglutinin stalk-based antibodies and vaccines," Current Opinion in Virology, 3(5):521-530.

Kruger, DM and Gohlke, H. (Jul. 2010) "DrugScorePPI webserver: fast and accurate in silico alanine scanning for scoring protein-protein interactions," Nucleic Acids Res., 38(Web Server Issue):W480-W486.

Kuhlmann, UC et al. (Sep. 2000) "Specificity in protein-protein interactions: the structural basis for dual recognition in endonuclease colicin-immunity protein complexes," J Mol Biol, 301(5):1163-78.

Kunkel, LM et al. (Jul. 1985) "Specific cloning of DNA fragments absent from the DNA of a male patient with an X chromosome deletion," Proceedings of the National Academy of Sciences USA, 82(14):4778-82.

Lambert and AS Fauci (Nov. 2010) "Influenza vaccines for the future," New England Journal of Medicine, 363 (21):2036-2044.

Lander et al. (Apr. 2009) "Appion: an integrated, database-driven pipeline to facilitate EM image processing," Journal of Structural Biology, 166(1):95-102.

Idusogie, EE et al. (Apr. 2000) "Mapping of the C1q binding site on rituxan, a chimeric antibody with a human IgG1 Fc," J Immunol, 164(8):4178-84.

Leaver-Fay, A. et al. (2011) "ROSETTA3: an object-oriented software suite for the simulation and design of macromolecules," Methods Enzymol, 487:545-574—retrieved May 2015.

Levin, KB et al. (Oct. 2009) "Following evolutionary paths to protein-protein interactions with high affinity and selectivity," Nature Structure and Molecular Biology, 16(10):1049-1055.

Ludtke et al. (Dec. 1999) "EMAN: semiautomated software for high-resolution single-particle reconstructions," 128 (1):82-97.

(56) References Cited

OTHER PUBLICATIONS

Ma, B. et al. (May 2003) "Protein-protein interactions: structurally conserved residues distinguish between binding sites and exposed protein surfaces," Proc. Natl. Acad. Sci. USA, 100(10):5772-5777.

Mandell, DJ et al. (Aug. 2009) "Sub-angstrom accuracy in protein loop reconstruction by robotics-inspired conformational sampling," Nat Methods, 6(8):551-2.

Marshall, SA et al. (May 2005) "One- and two-body decomposable Poisson-Boltzmann methods for protein design calculations," Protein Sci, 14(5)1293-1304.

McCullers (Apr. 2014) "The co-pathogenesis of influenza viruses with bacteria in the lung," Nature Reviews Microbiology, 12(4):252-262.

Moore, GE (Jun. 1995) "Lithography and the future of Moore's law," Proc. SPIE 2438, Advances in Resist Technology and Processing XII.

Moretti et al. (Nov. 2013) "Community-wide evaluation of methods for predicting the effect of mutations on protein-protein interactions," Proteins: Structure, Function, and Bioinformatics, 81(11):1980-7.

Murphy, PM et al. (Jun. 2009) "Alteration of enzyme specificity by computational loop remodeling and design," Proceedings of the National Academy of Sciences USA, 106(23):9215-9220.

Nassar, N. et al. (Dec. 1998) "Structures of Cdc42 bound to the active and catalytically compromised forms of Cdc42GAP," Nature Structural Biology, 5(12):1047-1052.

Nguyen, JT et al. (Feb. 2010) "Triple combination of amantadine, ribavirin, and oseltamivir is highly active and synergistic against drug resistant influenza strains in vitro," PLoS One, 5(2):e9332.

Nguyen, JT et al. (Oct. 2009) "Triple combination of oseltamivir, amantadine, and ribavirin displays synergistic activity against multiple influenza virus strains in vitro," Antimicrob Agents Chemother, 53(10):4115-4126.

O'Keefe et al. (Aug. 2003) "Potent anti-influenza activity of cyanovirin-N and interactions with viral hemagglutinin," Antimicrobial Agents and Chemotherapy, 47(8):2518-25.

Ofran, Y. and Rost, B. (Jul. 2007) "Protein-protein interaction hotspots carved into sequences," PLoS Comput Biol, 3 (7):e119.

Ohbo et al. (Feb. 1996) "Modulation of hematopoiesis in mice with a truncated mutant of the interleukin-2 receptor gamma chain," Blood, 87(3):956-967.

Pal, G. et al. (Aug. 2006) "Comprehensive and quantitative mapping of energy landscapes for protein-protein interactions by rapid combinatorial scanning," J Biol Chem, 281(31):22378-85.

Patrick et al. (Jun. 2003) "User-friendly algorithms for estimating completeness and diversity in randomized protein-encoding libraries," Protein Engineering, 16(6):451-457.

Patwardhan, RP et al. (Dec. 2009) "High-resolution analysis of DNA regulatory elements by synthetic saturation mutagenesis," Nat Biotechnol, 27(12):1173-1175.

Pierce, B. and Weng, Z. (Jun. 2007) "ZRANK: reranking protein docking predictions with an optimized energy function," Proteins, 67(4):1078-1086.

Pitt, JN and Ferre-D'Amare, AR (Oct. 2010) "Rapid construction of empirical RNA fitness landscapes," Science, 330 (6002):376-379.

Richards, FM (1977) "Areas, Volumes, Packing, and Protein Structure," Annu Rev Biophys Bio, 6:151-176—retrieved May 2015.

Richardson, JS et al. (Nov. 1992) "Looking at proteins: representations, folding, packing, and design," Biophys. J., 63 (5):1185-1209.

Rittinger, K. et al. (Aug. 1997) "Crystal structure of a small G protein in complex with the GTPase-activating protein rhoGAP," Nature, 388(6643):693-7.

Rittinger, K. et al. (Oct. 1997) "Structure at 1.65 A of RhoA and its GTPase-activating protein in complex with a transition-state analogue," Nature, 389(6652):758-62.

Rohl, CA et al. (2004) "Protein structure prediction using Rosetta," Methods Enzymol, 383:66-93—retrieved May 2015.

Schreiber, G. and Fersht, AR (Apr. 1995) "Energetics of protein-protein interactions: analysis of the barnase-barstar interface by single mutations and double mutant cycles," J Mol Biol, 248(2):478-486.

Schreiber, G. and Fersht, AR (May 1993) "Interaction of barnase with its polypeptide inhibitor barstar studied by protein engineering," Biochemistry, 32(19):5145-5150.

\* cited by examiner (A)

(B)

(a)

(A.)

HA (H1 Spanish black; H5 Avian red) [nM]

(B.)

HA (H1 Spanish black; H5 Avian blue) [nM]

SEQUENCE LISTING

```
<160> NUMBER OF SEQ ID NOS: 354

<210> SEQ ID NO 1
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is selected from the group consisting of Ser,
      Ala, Phe, His, Lys, Met, Asn, Gln, Thr, Val, Tyr, and Asp
<220> FEATURE:
<221> NAME/KEY: MISC_FEATURE
```

```
<222> LOCATION: (2)..(2)
<223> OTHER INFORMATION: X can be any amino acid
<220> FEATURE:
<221> NAME/KEY: MISC_FEATURE
<222> LOCATION: (4)..(4)
<223> OTHER INFORMATION: X is selected from the group consisting of Asp,
      Ala, Glu, Gly, Asn, Pro, Ser, and Tyr
<220> FEATURE:
<221> NAME/KEY: MISC_FEATURE
<222> LOCATION: (5)..(5)
<223> OTHER INFORMATION: X is selected from the group consisting of Leu
      and Phe
<220> FEATURE:
<221> NAME/KEY: MISC_FEATURE
<222> LOCATION: (6)..(6)
<223> OTHER INFORMATION: X can be any amino acid
<220> FEATURE:
<221> NAME/KEY: MISC_FEATURE
<222> LOCATION: (7)..(7)
<223> OTHER INFORMATION: X is selected from the group consisting of Met,
      Phe, His, Ile, Leu, Gln, and Thr
<220> FEATURE:
<221> NAME/KEY: MISC_FEATURE
<222> LOCATION: (8)..(8)
<223> OTHER INFORMATION: X is selected from the group consisting of Arg,
      Gly, Lys, Gln, and Thr
<220> FEATURE:
<221> NAME/KEY: MISC_FEATURE
<222> LOCATION: (9)..(9)
<223> OTHER INFORMATION: X is selected from the group consisting of Ile,
      Asn, Gln, Val, and Trp
<220> FEATURE:
<221> NAME/KEY: MISC_FEATURE
<222> LOCATION: (10)..(10)
<223> OTHER INFORMATION: X is selected from the group consisting of Met,
      Gly, Ile, Lys, Leu, Asn, Arg, Ser, Thr, Val, His, and Tyr
<220> FEATURE:
<221> NAME/KEY: MISC_FEATURE
<222> LOCATION: (11)..(11)
<223> OTHER INFORMATION: X is selected from the group consisting of Trp
      and Phe
<220> FEATURE:
<221> NAME/KEY: MISC_FEATURE
<222> LOCATION: (12)..(12)
<223> OTHER INFORMATION: X is selected from the group consisting of Ile,
      Phe, Ser, Thr, and Val
<220> FEATURE:
<221> NAME/KEY: MISC_FEATURE
<222> LOCATION: (13)..(13)
<223> OTHER INFORMATION: X is selected from the group consisting of Tyr,
      Cys, Asp, Phe, His, Asn, and Ser
<220> FEATURE:
<221> NAME/KEY: MISC_FEATURE
<222> LOCATION: (14)..(14)
<223> OTHER INFORMATION: X is selected from the group consisting of Val,
      Ala, Phe, Ile, Leu, Asn, Gln, Thr, and Tyr
<220> FEATURE:
<221> NAME/KEY: MISC_FEATURE
<222> LOCATION: (15)..(15)
<223> OTHER INFORMATION: X is selected from the group consisting of Phe,
      Glu, and Leu
<220> FEATURE:
<221> NAME/KEY: MISC_FEATURE
<222> LOCATION: (16)..(16)
<223> OTHER INFORMATION: X is selected from the group consisting of Ala,
      Gly, Lys, Arg, and Ser
<220> FEATURE:
<221> NAME/KEY: MISC_FEATURE
<222> LOCATION: (17)..(17)
<223> OTHER INFORMATION: X is selected from the group consisting of Phe,
      Cys, His, Lys, Leu, Met, Asn, Gln, Arg, Thr, Val, Trp, and Tyr

<400> SEQUENCE: 1

Xaa Xaa Phe Xaa Xaa Xaa Xaa Xaa Xaa Xaa Xaa Xaa Xaa Xaa Xaa
1               5                   10                  15

Xaa
```

```
<210> SEQ ID NO 2
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is selected from the group consisting of Ser,
      Ala, Phe, His, Lys, Met, Asn, Gln, Thr, Val, Tyr, and Asp
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (4)..(4)
<223> OTHER INFORMATION: X is selected from the group consisting of Asp,
      Ala, Glu, Gly, Asn, Pro, Ser, and Tyr
<220> FEATURE:
<221> NAME/KEY: MISC_FEATURE
<222> LOCATION: (5)..(5)
<223> OTHER INFORMATION: X is selected from the group consisting of Leu
      and Phe
<220> FEATURE:
<221> NAME/KEY: MISC_FEATURE
<222> LOCATION: (6)..(6)
<223> OTHER INFORMATION: X can be any amino acid
<220> FEATURE:
<221> NAME/KEY: MISC_FEATURE
<222> LOCATION: (7)..(7)
<223> OTHER INFORMATION: X is selected from the group consisting of Met,
      Phe, His, Ile, Leu, Gln, and Thr
<220> FEATURE:
<221> NAME/KEY: MISC_FEATURE
<222> LOCATION: (8)..(8)
<223> OTHER INFORMATION: X is selected from the group consisting of Arg,
      Gly, Lys, Gln, and Thr
<220> FEATURE:
<221> NAME/KEY: MISC_FEATURE
<222> LOCATION: (9)..(9)
<223> OTHER INFORMATION: X is selected from the group consisting of Ile,
      Asn, Gln, Val, and Trp
<220> FEATURE:
<221> NAME/KEY: MISC_FEATURE
<222> LOCATION: (10)..(10)
<223> OTHER INFORMATION: X is selected from the group consisting of Met,
      Gly, Ile, Lys, Leu, Asn, Arg, Ser, Thr, Val, His, and Tyr
<220> FEATURE:
<221> NAME/KEY: MISC_FEATURE
<222> LOCATION: (11)..(11)
<223> OTHER INFORMATION: X is selected from the group consisting of Trp
      and Phe
<220> FEATURE:
<221> NAME/KEY: MISC_FEATURE
<222> LOCATION: (12)..(12)
<223> OTHER INFORMATION: X is selected from the group consisting of Ile,
      Phe, Ser, Thr, and Val
<220> FEATURE:
<221> NAME/KEY: MISC_FEATURE
<222> LOCATION: (13)..(13)
<223> OTHER INFORMATION: X is selected from the group consisting of Tyr,
      Cys, Asp, Phe, His, Asn, and Ser
<220> FEATURE:
<221> NAME/KEY: MISC_FEATURE
<222> LOCATION: (14)..(14)
<223> OTHER INFORMATION: X is selected from the group consisting of Val,
      Ala, Phe, Ile, Leu, Asn, Gln, Thr, and Tyr
<220> FEATURE:
<221> NAME/KEY: MISC_FEATURE
<222> LOCATION: (15)..(15)
<223> OTHER INFORMATION: X is selected from the group consisting of Phe,
      Glu, and Leu
<220> FEATURE:
<221> NAME/KEY: MISC_FEATURE
<222> LOCATION: (16)..(16)
<223> OTHER INFORMATION: X is selected from the group consisting of Ala,
```

```
                    Gly, Lys, Arg, and Ser
<220> FEATURE:
<221> NAME/KEY: MISC_FEATURE
<222> LOCATION: (17)..(17)
<223> OTHER INFORMATION: X is selected from the group consisting of Phe,
      Cys, His, Lys, Leu, Met, Asn, Gln, Arg, Thr, Val, Trp, and Tyr
<220> FEATURE:
<221> NAME/KEY: MISC_FEATURE
<222> LOCATION: (18)..(21)
<223> OTHER INFORMATION: X can be any amino acid
<220> FEATURE:
<221> NAME/KEY: MISC_FEATURE
<222> LOCATION: (22)..(25)
<223> OTHER INFORMATION: X can be any amino acid or absent
<220> FEATURE:
<221> NAME/KEY: MISC_FEATURE
<222> LOCATION: (26)..(26)
<223> OTHER INFORMATION: X is Phe or Tyr

<400> SEQUENCE: 2

Xaa Xaa Phe Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Lys or Asn
<220> FEATURE:
<221> NAME/KEY: MISC_FEATURE
<222> LOCATION: (3)..(3)
<223> OTHER INFORMATION: X is Lys, Pro or Thr

<400> SEQUENCE: 3

Xaa Arg Xaa Ile Pro
1               5

<210> SEQ ID NO 4
<211> LENGTH: 96
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(48)
<223> OTHER INFORMATION: Amino acids are optionally absent
<220> FEATURE:
<221> NAME/KEY: MISC_FEATURE
<222> LOCATION: (33)..(33)
<223> OTHER INFORMATION: X is D or Y
<220> FEATURE:
<221> NAME/KEY: MISC_FEATURE
<222> LOCATION: (34)..(34)
<223> OTHER INFORMATION: X is V or absent
<220> FEATURE:
<221> NAME/KEY: MISC_FEATURE
<222> LOCATION: (37)..(37)
<223> OTHER INFORMATION: X is A or D
<220> FEATURE:
<221> NAME/KEY: MISC_FEATURE
<222> LOCATION: (38)..(38)
<223> OTHER INFORMATION: X is A, K or R
<220> FEATURE:
<221> NAME/KEY: MISC_FEATURE
<222> LOCATION: (41)..(41)
<223> OTHER INFORMATION: X is Q or K
```

```
<220> FEATURE:
<221> NAME/KEY: MISC_FEATURE
<222> LOCATION: (45)..(45)
<223> OTHER INFORMATION: X is E or A
<220> FEATURE:
<221> NAME/KEY: MISC_FEATURE
<222> LOCATION: (47)..(47)
<223> OTHER INFORMATION: X is N or absent
<220> FEATURE:
<221> NAME/KEY: MISC_FEATURE
<222> LOCATION: (48)..(48)
<223> OTHER INFORMATION: X is D or absent
<220> FEATURE:
<221> NAME/KEY: MISC_FEATURE
<222> LOCATION: (49)..(49)
<223> OTHER INFORMATION: X is selected from the group consisting of Ser,
      Ala, Phe, His, Lys, Met, Asn, Gln, Thr, Val, Tyr, and Asp
<220> FEATURE:
<221> NAME/KEY: MISC_FEATURE
<222> LOCATION: (50)..(50)
<223> OTHER INFORMATION: X can be any amino acid
<220> FEATURE:
<221> NAME/KEY: MISC_FEATURE
<222> LOCATION: (52)..(52)
<223> OTHER INFORMATION: X is selected from the group consisting of Asp,
      Ala, Glu, Gly, Asn, Pro, Ser, and Tyr
<220> FEATURE:
<221> NAME/KEY: MISC_FEATURE
<222> LOCATION: (53)..(53)
<223> OTHER INFORMATION: X is selected from the group consisting of Leu
      and Phe
<220> FEATURE:
<221> NAME/KEY: MISC_FEATURE
<222> LOCATION: (54)..(54)
<223> OTHER INFORMATION: X can be any amino acid
<220> FEATURE:
<221> NAME/KEY: MISC_FEATURE
<222> LOCATION: (55)..(55)
<223> OTHER INFORMATION: X is selected from the group consisting of Met,
      Phe, His, Ile, Leu, Gln, and Thr
<220> FEATURE:
<221> NAME/KEY: MISC_FEATURE
<222> LOCATION: (56)..(56)
<223> OTHER INFORMATION: X is selected from the group consisting of Arg,
      Gly, Lys, Gln, and Thr
<220> FEATURE:
<221> NAME/KEY: MISC_FEATURE
<222> LOCATION: (57)..(57)
<223> OTHER INFORMATION: X is selected from the group consisting of Ile,
      Asn, Gln, Val, and Trp
<220> FEATURE:
<221> NAME/KEY: MISC_FEATURE
<222> LOCATION: (58)..(58)
<223> OTHER INFORMATION: X is selected from the group consisting of Met,
      Gly, Ile, Lys, Leu, Asn, Arg, Ser, Thr, Val, His, and Tyr
<220> FEATURE:
<221> NAME/KEY: MISC_FEATURE
<222> LOCATION: (59)..(59)
<223> OTHER INFORMATION: X is selected from the group consisting of Trp
      and Phe
<220> FEATURE:
<221> NAME/KEY: MISC_FEATURE
<222> LOCATION: (60)..(60)
<223> OTHER INFORMATION: X is selected from the group consisting of Ile,
      Phe, Ser, Thr, and Val
<220> FEATURE:
<221> NAME/KEY: MISC_FEATURE
<222> LOCATION: (61)..(61)
<223> OTHER INFORMATION: X is selected from the group consisting of Tyr,
      Cys, Asp, Phe, His, Asn, and Ser
<220> FEATURE:
<221> NAME/KEY: MISC_FEATURE
<222> LOCATION: (62)..(62)
<223> OTHER INFORMATION: X is selected from the group consisting of Val,
      Ala, Phe, Ile, Leu, Asn, Gln, Thr, and Tyr
<220> FEATURE:
<221> NAME/KEY: MISC_FEATURE
<222> LOCATION: (63)..(63)
<223> OTHER INFORMATION: X is selected from the group consisting of Phe,
```

```
      Glu, and Leu
<220> FEATURE:
<221> NAME/KEY: MISC_FEATURE
<222> LOCATION: (64)..(64)
<223> OTHER INFORMATION: X is selected from the group consisting of Ala,
      Gly, Lys, Arg, and Ser
<220> FEATURE:
<221> NAME/KEY: MISC_FEATURE
<222> LOCATION: (65)..(65)
<223> OTHER INFORMATION: X is selected from the group consisting of Phe,
      Cys, His, Lys, Leu, Met, Asn, Gln, Arg, Thr, Val, Trp, and Tyr
<220> FEATURE:
<221> NAME/KEY: MISC_FEATURE
<222> LOCATION: (66)..(69)
<223> OTHER INFORMATION: X can be any amino acid
<220> FEATURE:
<221> NAME/KEY: MISC_FEATURE
<222> LOCATION: (70)..(73)
<223> OTHER INFORMATION: X can be any amino acid or absent
<220> FEATURE:
<221> NAME/KEY: MISC_FEATURE
<222> LOCATION: (74)..(74)
<223> OTHER INFORMATION: X is Phe or Tyr
<220> FEATURE:
<221> NAME/KEY: MISC_FEATURE
<222> LOCATION: (75)..(96)
<223> OTHER INFORMATION: Amino acids are optionally absent
<220> FEATURE:
<221> NAME/KEY: MISC_FEATURE
<222> LOCATION: (75)..(75)
<223> OTHER INFORMATION: X is L, A, or V
<220> FEATURE:
<221> NAME/KEY: MISC_FEATURE
<222> LOCATION: (78)..(78)
<223> OTHER INFORMATION: X is Q or P
<220> FEATURE:
<221> NAME/KEY: MISC_FEATURE
<222> LOCATION: (89)..(89)
<223> OTHER INFORMATION: X is Q or L

<400> SEQUENCE: 4

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Xaa Xaa Glu Ala Xaa Xaa Val Leu Xaa Ala Val Tyr Xaa Thr Xaa Xaa
        35                  40                  45

Xaa Xaa Phe Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa His Ala Xaa Lys Leu
65                  70                  75                  80

Ala Arg Arg Leu Leu Glu Leu Lys Xaa Ala Ala Ser Ser Pro Leu Pro
                85                  90                  95

<210> SEQ ID NO 5
<211> LENGTH: 46
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: X is D, V or Y
<220> FEATURE:
<221> NAME/KEY: MISC_FEATURE
<222> LOCATION: (36)..(36)
<223> OTHER INFORMATION: X is A or D
<220> FEATURE:
<221> NAME/KEY: MISC_FEATURE
<222> LOCATION: (37)..(37)
<223> OTHER INFORMATION: X is A, K or R
```

```
<220> FEATURE:
<221> NAME/KEY: MISC_FEATURE
<222> LOCATION: (40)..(40)
<223> OTHER INFORMATION: X is Q or K
<220> FEATURE:
<221> NAME/KEY: MISC_FEATURE
<222> LOCATION: (44)..(44)
<223> OTHER INFORMATION: X is E or A
<220> FEATURE:
<221> NAME/KEY: MISC_FEATURE
<222> LOCATION: (46)..(46)
<223> OTHER INFORMATION: X is N or D

<400> SEQUENCE: 5

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Xaa Glu Ala Xaa Xaa Val Leu Xaa Ala Val Tyr Xaa Thr Xaa
        35                  40                  45

<210> SEQ ID NO 6
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is L, A, or V
<220> FEATURE:
<221> NAME/KEY: MISC_FEATURE
<222> LOCATION: (4)..(4)
<223> OTHER INFORMATION: X is Q or P
<220> FEATURE:
<221> NAME/KEY: MISC_FEATURE
<222> LOCATION: (15)..(15)
<223> OTHER INFORMATION: X is Q or L

<400> SEQUENCE: 6

Xaa His Ala Xaa Lys Leu Ala Arg Arg Leu Leu Glu Leu Lys Xaa Ala
1               5                   10                  15

Ala Ser Ser Pro Leu Pro
            20

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Ser Ala Phe Asp Leu Ala Met Arg Ile Met Trp Ile Tyr Val Phe Ala
1               5                   10                  15

Phe

<210> SEQ ID NO 8
<211> LENGTH: 23
<212> TYPE: PRT
<213> ORGANISM: Artificial Sequence
<220> FEATURE:
<223> OTHER INFORMATION: Synthetic

<400> SEQUENCE: 8

Ser Ala Phe Asp Leu Ala Met Arg Ile Met Trp Ile Tyr Val Phe Ala
1               5                   10                  15
```

Phe Lys Arg Pro Ile Pro Phe
            20

<210> SEQ ID NO 9
<211> LENGTH: 23
<212> TYPE: PRT
<213> ORGANISM: Artificial Sequence
<220> FEATURE:
<223> OTHER INFORMATION: Synthetic

<400> SEQUENCE: 9

Asp Ala Phe Asp Leu Ala Met Arg Ile Met Trp Ile Tyr Val Phe Ala
1               5                   10                  15

Phe Asn Arg Pro Ile Pro Phe
            20

<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Asp Ala Phe Asp Leu Ala Met Arg Ile Met Trp Ile Tyr Val Phe Ala
1               5                   10                  15

Phe

<210> SEQ ID NO 11
<211> LENGTH: 23
<212> TYPE: PRT
<213> ORGANISM: Artificial Sequence
<220> FEATURE:
<223> OTHER INFORMATION: Synthetic

<400> SEQUENCE: 11

Ser Ala Phe Asp Leu Ala Met Arg Ile Met Trp Ile Tyr Val Phe Ala
1               5                   10                  15

Phe Asn Arg Pro Ile Pro Phe
            20

<210> SEQ ID NO 12
<211> LENGTH: 608
<212> TYPE: PRT
<213> ORGANISM: Artificial Sequence
<220> FEATURE:
<223> OTHER INFORMATION: Synthetic

<400> SEQUENCE: 12

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Thr Ile Cys Ile Gly
                35                  40                  45

Tyr His Ala Asn Asn Ser Thr Asp Thr Val Thr Val Leu Glu Lys
        50                  55                  60

Asn Val Thr Val Thr His Ser Val Asn Leu Leu Glu Asp Ser His Asn
65                  70                  75                  80

Gly Lys Leu Cys Lys Leu Lys Gly Ile Ala Pro Leu Gln Leu Gly Lys
                85                  90                  95

```
Cys Asn Ile Ala Gly Trp Leu Leu Gly Asn Pro Glu Cys Asp Leu Leu
            100                 105                 110

Leu Thr Ala Ser Ser Trp Ser Tyr Ile Val Glu Thr Ser Asn Ser Glu
        115                 120                 125

Asn Gly Thr Cys Tyr Pro Gly Asp Phe Ile Asp Tyr Glu Glu Leu Arg
    130                 135                 140

Glu Gln Leu Ser Ser Val Ser Ser Phe Glu Lys Phe Glu Ile Phe Pro
145                 150                 155                 160

Lys Thr Ser Ser Trp Pro Asn His Glu Thr Thr Lys Gly Val Thr Ala
                165                 170                 175

Ala Cys Ser Tyr Ala Gly Ala Ser Ser Phe Tyr Arg Asn Leu Leu Trp
            180                 185                 190

Leu Thr Lys Lys Gly Ser Ser Tyr Pro Lys Leu Ser Lys Ser Tyr Val
        195                 200                 205

Asn Asn Lys Gly Lys Glu Val Leu Val Leu Trp Gly Val His His Pro
    210                 215                 220

Pro Thr Gly Thr Asp Gln Gln Ser Leu Tyr Gln Asn Ala Asp Ala Tyr
225                 230                 235                 240

Val Ser Val Gly Ser Ser Lys Tyr Asn Arg Arg Phe Thr Pro Glu Ile
                245                 250                 255

Ala Ala Arg Pro Lys Val Arg Asp Gln Ala Gly Arg Met Asn Tyr Tyr
            260                 265                 270

Trp Thr Leu Leu Glu Pro Gly Asp Thr Ile Thr Phe Glu Ala Thr Gly
        275                 280                 285

Asn Leu Ile Ala Pro Trp Tyr Ala Phe Ala Leu Asn Arg Gly Ser Gly
    290                 295                 300

Ser Gly Ile Ile Thr Ser Asp Ala Pro Val His Asp Cys Asn Thr Lys
305                 310                 315                 320

Cys Gln Thr Pro His Gly Ala Ile Asn Ser Ser Leu Pro Phe Gln Asn
                325                 330                 335

Ile His Pro Val Thr Ile Gly Glu Cys Pro Lys Tyr Val Arg Ser Thr
            340                 345                 350

Lys Leu Arg Met Ala Thr Gly Leu Arg Asn Ile Pro Ser Ile Gln Ser
        355                 360                 365

Arg Gly Leu Phe Gly Ala Ile Ala Gly Phe Ile Glu Gly Gly Trp Thr
    370                 375                 380

Gly Met Ile Asp Gly Trp Tyr Gly Tyr His His Gln Asn Glu Gln Gly
385                 390                 395                 400

Ser Gly Tyr Ala Ala Asp Gln Lys Ser Thr Gln Asn Ala Ile Asp Gly
                405                 410                 415

Ile Thr Asn Lys Val Asn Ser Val Ile Glu Lys Met Asn Thr Gln Phe
            420                 425                 430

Thr Ala Val Gly Lys Glu Phe Asn Asn Leu Glu Arg Arg Ile Glu Asn
        435                 440                 445

Leu Asn Lys Lys Val Asp Asp Gly Phe Leu Asp Ile Trp Thr Tyr Asn
    450                 455                 460

Ala Glu Leu Leu Val Leu Leu Glu Asn Glu Arg Thr Leu Asp Phe His
465                 470                 475                 480

Asp Ser Asn Val Arg Asn Leu Tyr Glu Lys Val Lys Ser Gln Leu Lys
                485                 490                 495

Asn Asn Ala Lys Glu Ile Gly Asn Gly Cys Phe Glu Phe Tyr His Lys
            500                 505                 510

Cys Asp Asp Ala Cys Met Glu Ser Val Arg Asn Gly Thr Tyr Asp Tyr
```

```
            515                 520                 525
Pro Lys Tyr Ser Glu Ser Lys Leu Asn Arg Glu Glu Ile Asp Gly
        530                 535                 540

Val Ser Gly Gly Gly Leu Asn Asp Ile Phe Glu Ala Gln Lys Ile
545                 550                 555                 560

Glu Trp His Glu Arg Leu Val Pro Arg Gly Ser Pro Gly Ser Gly Tyr
                565                 570                 575

Ile Pro Glu Ala Pro Arg Asp Gly Gln Ala Tyr Val Arg Lys Asp Gly
            580                 585                 590

Glu Trp Val Leu Leu Ser Thr Phe Leu Gly His His His His His His
        595                 600                 605

<210> SEQ ID NO 13
<211> LENGTH: 607
<212> TYPE: PRT
<213> ORGANISM: Artificial Sequence
<220> FEATURE:
<223> OTHER INFORMATION: Synthetic

<400> SEQUENCE: 13

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Thr Ile Cys Ile Gly
        35                  40                  45

Tyr His Ala Asn Asn Ser Thr Asp Thr Val Asp Thr Ile Phe Glu Lys
    50                  55                  60

Asn Val Ala Val Thr His Ser Val Asn Leu Leu Glu Asp Arg His Asn
65                  70                  75                  80

Gly Lys Leu Cys Lys Leu Lys Gly Ile Ala Pro Leu Gln Leu Gly Lys
                85                  90                  95

Cys Asn Ile Thr Gly Trp Leu Leu Gly Asn Pro Glu Cys Asp Ser Leu
            100                 105                 110

Leu Pro Ala Arg Ser Trp Ser Tyr Ile Val Glu Thr Pro Asn Ser Glu
        115                 120                 125

Asn Gly Ala Cys Tyr Pro Gly Asp Phe Ile Asp Tyr Glu Glu Leu Arg
    130                 135                 140

Glu Gln Leu Ser Ser Val Ser Ser Leu Glu Arg Phe Glu Ile Phe Pro
145                 150                 155                 160

Lys Glu Ser Ser Trp Pro Asn His Thr Phe Asn Gly Val Thr Val Ser
                165                 170                 175

Cys Ser His Arg Gly Lys Ser Ser Phe Tyr Arg Asn Leu Leu Trp Leu
            180                 185                 190

Thr Lys Lys Gly Asp Ser Tyr Pro Lys Leu Thr Asn Ser Tyr Val Asn
        195                 200                 205

Asn Lys Gly Lys Glu Val Leu Val Leu Trp Gly Val His His Pro Ser
    210                 215                 220

Ser Ser Asp Glu Gln Gln Ser Leu Tyr Ser Asn Gly Asn Ala Tyr Val
225                 230                 235                 240

Ser Val Ala Ser Ser Asn Tyr Asn Arg Arg Phe Thr Pro Glu Ile Ala
                245                 250                 255

Ala Arg Pro Lys Val Lys Asp Gln His Gly Arg Met Asn Tyr Tyr Trp
            260                 265                 270

Thr Leu Leu Glu Pro Gly Asp Thr Ile Ile Phe Glu Ala Thr Gly Asn
```

```
                275                 280                 285
Leu Ile Ala Pro Trp Tyr Ala Phe Ala Leu Ser Arg Gly Phe Glu Ser
    290                 295                 300

Gly Ile Ile Thr Ser Asn Ala Ser Met His Glu Cys Asn Thr Lys Cys
305                 310                 315                 320

Gln Thr Pro Gln Gly Ser Ile Asn Ser Asn Leu Pro Phe Gln Asn Ile
                325                 330                 335

His Pro Val Thr Ile Gly Glu Cys Pro Lys Tyr Val Arg Ser Thr Lys
            340                 345                 350

Leu Arg Met Val Thr Gly Leu Arg Asn Ile Pro Ser Ile Gln Tyr Arg
        355                 360                 365

Gly Leu Phe Gly Ala Ile Ala Gly Phe Ile Glu Gly Gly Trp Thr Gly
    370                 375                 380

Met Ile Asp Gly Trp Tyr Gly Tyr His His Gln Asn Glu Gln Gly Ser
385                 390                 395                 400

Gly Tyr Ala Ala Asp Gln Lys Ser Thr Gln Asn Ala Ile Asn Gly Ile
                405                 410                 415

Thr Asn Lys Val Asn Ser Ile Ile Glu Lys Met Asn Thr Gln Phe Thr
            420                 425                 430

Ala Val Gly Lys Glu Phe Asn Asn Leu Glu Lys Arg Met Glu Asn Leu
        435                 440                 445

Asn Lys Lys Val Asp Asp Gly Phe Leu Asp Ile Trp Thr Tyr Asn Ala
    450                 455                 460

Glu Leu Leu Val Leu Leu Glu Asn Glu Arg Thr Leu Asp Phe His Asp
465                 470                 475                 480

Leu Asn Val Lys Asn Leu Tyr Glu Lys Val Lys Ser Gln Leu Lys Asn
                485                 490                 495

Asn Ala Lys Glu Ile Gly Asn Gly Cys Phe Glu Phe Tyr His Lys Cys
            500                 505                 510

Asp Asn Glu Cys Met Glu Ser Val Arg Asn Gly Thr Tyr Asp Tyr Pro
        515                 520                 525

Lys Tyr Ser Glu Glu Ser Lys Leu Asn Arg Glu Lys Ile Asp Gly Val
    530                 535                 540

Ser Gly Gly Gly Gly Leu Asn Asp Ile Phe Glu Ala Gln Lys Ile Glu
545                 550                 555                 560

Trp His Glu Arg Leu Val Pro Arg Gly Ser Pro Gly Ser Gly Tyr Ile
                565                 570                 575

Pro Glu Ala Pro Arg Asp Gly Gln Ala Tyr Val Arg Lys Asp Gly Glu
            580                 585                 590

Trp Val Leu Leu Ser Thr Phe Leu Gly His His His His His His
        595                 600                 605

<210> SEQ ID NO 14

<400> SEQUENCE: 14

000

<210> SEQ ID NO 15
<211> LENGTH: 17
<212> TYPE: PRT
<213> ORGANISM: Artificial Sequence
<220> FEATURE:
<223> OTHER INFORMATION: Synthetic

<400> SEQUENCE: 15
```

His Ala Phe Asp Leu Ala Met Arg Ile His Trp Ile Tyr Val Phe Ala
1               5                   10                  15

Phe

<210> SEQ ID NO 16
<211> LENGTH: 23
<212> TYPE: PRT
<213> ORGANISM: Artificial Sequence
<220> FEATURE:
<223> OTHER INFORMATION: Synthetic

<400> SEQUENCE: 16

His Ala Phe Asp Leu Ala Met Arg Ile His Trp Ile Tyr Val Phe Ala
1               5                   10                  15

Phe Lys Arg Lys Ile Pro Phe
            20

<210> SEQ ID NO 17
<211> LENGTH: 17
<212> TYPE: PRT
<213> ORGANISM: Artificial Sequence
<220> FEATURE:
<223> OTHER INFORMATION: Synthetic

<400> SEQUENCE: 17

Ser Ala Phe Asp Leu Ala Met Arg Ile Ile Trp Ile Tyr Val Phe Ala
1               5                   10                  15

Tyr

<210> SEQ ID NO 18
<211> LENGTH: 23
<212> TYPE: PRT
<213> ORGANISM: Artificial Sequence
<220> FEATURE:
<223> OTHER INFORMATION: Synthetic

<400> SEQUENCE: 18

Ser Ala Phe Asp Leu Ala Met Arg Ile Ile Trp Ile Tyr Val Phe Ala
1               5                   10                  15

Tyr Lys Arg Lys Ile Pro Phe
            20

<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Ser Ala Phe Asp Leu Ala Met Arg Ile Asn Trp Ile Tyr Val Phe Ala
1               5                   10                  15

Phe

<210> SEQ ID NO 20
<211> LENGTH: 23
<212> TYPE: PRT
<213> ORGANISM: Artificial Sequence
<220> FEATURE:
<223> OTHER INFORMATION: Synthetic

<400> SEQUENCE: 20

Ser Ala Phe Asp Leu Ala Met Arg Ile Asn Trp Ile Tyr Val Phe Ala
1               5                   10                  15

```
Phe Lys Arg Pro Ile Pro Phe
            20

<210> SEQ ID NO 21
<211> LENGTH: 17
<212> TYPE: PRT
<213> ORGANISM: Artificial Sequence
<220> FEATURE:
<223> OTHER INFORMATION: Synthetic

<400> SEQUENCE: 21

Ser Ala Phe Asp Leu Ala Met Arg Ile Asn Trp Ile Tyr Val Phe Ala
1               5                   10                  15

Phe

<210> SEQ ID NO 22
<211> LENGTH: 23
<212> TYPE: PRT
<213> ORGANISM: Artificial Sequence
<220> FEATURE:
<223> OTHER INFORMATION: Synthetic

<400> SEQUENCE: 22

Ser Ala Phe Asp Leu Ala Met Arg Ile Asn Trp Ile Tyr Val Phe Ala
1               5                   10                  15

Phe Lys Arg Lys Ile Pro Phe
            20

<210> SEQ ID NO 23
<211> LENGTH: 17
<212> TYPE: PRT
<213> ORGANISM: Artificial Sequence
<220> FEATURE:
<223> OTHER INFORMATION: Synthetic

<400> SEQUENCE: 23

Ser Ala Phe Asp Leu Ala Met Thr Ile His Trp Ile Tyr Asn Phe Ala
1               5                   10                  15

Phe

<210> SEQ ID NO 24
<211> LENGTH: 23
<212> TYPE: PRT
<213> ORGANISM: Artificial Sequence
<220> FEATURE:
<223> OTHER INFORMATION: Synthetic

<400> SEQUENCE: 24

Ser Ala Phe Asp Leu Ala Met Thr Ile His Trp Ile Tyr Asn Phe Ala
1               5                   10                  15

Phe Lys Arg Lys Ile Pro Phe
            20

<210> SEQ ID NO 25
<211> LENGTH: 17
<212> TYPE: PRT
<213> ORGANISM: Artificial Sequence
<220> FEATURE:
<223> OTHER INFORMATION: Synthetic

<400> SEQUENCE: 25

Ser Ala Phe Asp Leu Ala Met Arg Ile Asn Trp Ile Tyr Val Phe Ala
1               5                   10                  15
```

Phe

<210> SEQ ID NO 26
<211> LENGTH: 23
<212> TYPE: PRT
<213> ORGANISM: Artificial Sequence
<220> FEATURE:
<223> OTHER INFORMATION: Synthetic

<400> SEQUENCE: 26

Ser Ala Phe Asp Leu Ala Met Arg Ile Asn Trp Ile Tyr Val Phe Ala
1               5                   10                  15

Phe Lys Arg Thr Ile Pro Phe
            20

<210> SEQ ID NO 27
<211> LENGTH: 17
<212> TYPE: PRT
<213> ORGANISM: Artificial Sequence
<220> FEATURE:
<223> OTHER INFORMATION: Synthetic

<400> SEQUENCE: 27

Ser Ala Phe Asp Leu Ala Met Arg Ile His Trp Ile Tyr Ile Phe Ala
1               5                   10                  15

Phe

<210> SEQ ID NO 28
<211> LENGTH: 23
<212> TYPE: PRT
<213> ORGANISM: Artificial Sequence
<220> FEATURE:
<223> OTHER INFORMATION: Synthetic

<400> SEQUENCE: 28

Ser Ala Phe Asp Leu Ala Met Arg Ile His Trp Ile Tyr Ile Phe Ala
1               5                   10                  15

Phe Lys Arg Pro Ile Pro Phe
            20

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Ser Ala Phe Asp Leu Ala Met Arg Ile His Trp Ile Tyr Asn Phe Ala
1               5                   10                  15

Phe

<210> SEQ ID NO 30
<211> LENGTH: 23
<212> TYPE: PRT
<213> ORGANISM: Artificial Sequence
<220> FEATURE:
<223> OTHER INFORMATION: Synthetic

<400> SEQUENCE: 30

Ser Ala Phe Asp Leu Ala Met Arg Ile His Trp Ile Tyr Asn Phe Ala
1               5                   10                  15

Phe Lys Arg Lys Ile Pro Phe
            20

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Ser Ala Phe Asp Leu Ala Met Arg Ile His Trp Ile Tyr Asn Phe Ala
1               5                   10                  15

Tyr

<210> SEQ ID NO 32
<211> LENGTH: 23
<212> TYPE: PRT
<213> ORGANISM: Artificial Sequence
<220> FEATURE:
<223> OTHER INFORMATION: Synthetic

<400> SEQUENCE: 32

Ser Ala Phe Asp Leu Ala Met Arg Ile His Trp Ile Tyr Asn Phe Ala
1               5                   10                  15

Tyr Lys Arg Thr Ile Pro Phe
            20

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

Ser Ala Phe Asp Leu Ala Met Arg Ile His Trp Ile Tyr Asn Phe Ala
1               5                   10                  15

Phe

<210> SEQ ID NO 34
<211> LENGTH: 23
<212> TYPE: PRT
<213> ORGANISM: Artificial Sequence
<220> FEATURE:
<223> OTHER INFORMATION: Synthetic

<400> SEQUENCE: 34

Ser Ala Phe Asp Leu Ala Met Arg Ile His Trp Ile Tyr Asn Phe Ala
1               5                   10                  15

Phe Lys Arg Lys Ile Pro Phe
            20

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Ser Ala Phe Asp Leu Ala Met Arg Ile His Trp Ile Tyr Ile Phe Ala
1               5                   10                  15

Phe

```
<210> SEQ ID NO 36
<211> LENGTH: 23
<212> TYPE: PRT
<213> ORGANISM: Artificial Sequence
<220> FEATURE:
<223> OTHER INFORMATION: Synthetic

<400> SEQUENCE: 36

Ser Ala Phe Asp Leu Ala Met Arg Ile His Trp Ile Tyr Ile Phe Ala
1               5                   10                  15

Phe Lys Arg Thr Ile Pro Phe
            20

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Ser Ala Phe Asp Leu Ala Met Arg Ile His Trp Ile Tyr Asn Phe Ala
1               5                   10                  15

Phe

<210> SEQ ID NO 38
<211> LENGTH: 23
<212> TYPE: PRT
<213> ORGANISM: Artificial Sequence
<220> FEATURE:
<223> OTHER INFORMATION: Synthetic

<400> SEQUENCE: 38

Ser Ala Phe Asp Leu Ala Met Arg Ile His Trp Ile Tyr Asn Phe Ala
1               5                   10                  15

Phe Lys Arg Lys Ile Pro Phe
            20

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Ser Ala Phe Asp Leu Ala Met Lys Ile His Trp Ile Tyr Asn Phe Ala
1               5                   10                  15

Phe

<210> SEQ ID NO 40
<211> LENGTH: 23
<212> TYPE: PRT
<213> ORGANISM: Artificial Sequence
<220> FEATURE:
<223> OTHER INFORMATION: Synthetic

<400> SEQUENCE: 40

Ser Ala Phe Asp Leu Ala Met Lys Ile His Trp Ile Tyr Asn Phe Ala
1               5                   10                  15

Phe Lys Arg Thr Ile Pro Phe
            20

<210> SEQ ID NO 41
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 41

Ser Ala Phe Asp Leu Ala Met Lys Ile His Trp Ile Tyr Ile Phe Ala
1               5                   10                  15
Phe

<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Ser Ala Phe Asp Leu Ala Met Lys Ile His Trp Ile Tyr Ile Phe Ala
1               5                   10                  15
Phe Lys Arg Thr Ile Pro Phe
            20

<210> SEQ ID NO 43

<400> SEQUENCE: 43

000

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

His Ala Phe Asp Leu Ala Met Arg Ile Met Trp Ile Tyr Val Phe Ala
1               5                   10                  15
Phe

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Ser Ala Phe Asp Leu Ala Met Lys Ile Met Trp Ile Tyr Val Phe Ala
1               5                   10                  15
Phe

<210> SEQ ID NO 46
<211> LENGTH: 17
<212> TYPE: PRT
<213> ORGANISM: Artificial Sequence
<220> FEATURE:
<223> OTHER INFORMATION: Synthetic

<400> SEQUENCE: 46

Ser Ala Phe Asp Leu Ala Met Arg Ile His Trp Ile Tyr Val Phe Ala
1               5                   10                  15
```

Phe

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Ser Ala Phe Asp Leu Ala Met Arg Ile Asn Trp Ile Tyr Val Phe Ala
1               5                   10                  15

Phe

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Ser Ala Phe Asp Leu Ala Met Arg Ile Tyr Trp Ile Tyr Val Phe Ala
1               5                   10                  15

Phe

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Ser Ala Phe Asp Leu Ala Met Arg Ile Met Trp Ile Tyr Phe Phe Ala
1               5                   10                  15

Phe

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Ser Ala Phe Asp Leu Ala Met Arg Ile Met Trp Ile Tyr Leu Phe Ala
1               5                   10                  15

Phe

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Ser Ala Phe Asp Leu Ala Met Arg Ile Met Trp Ile Tyr Thr Phe Ala
1               5                   10                  15

Phe

<210> SEQ ID NO 52

<211> LENGTH: 17
<212> TYPE: PRT
<213> ORGANISM: Artificial Sequence
<220> FEATURE:
<223> OTHER INFORMATION: Synthetic

<400> SEQUENCE: 52

Ser Ala Phe Asp Leu Ala Met Arg Ile Met Trp Ile Tyr Asn Phe Ala
1               5                   10                  15

Phe

<210> SEQ ID NO 53
<211> LENGTH: 17
<212> TYPE: PRT
<213> ORGANISM: Artificial Sequence
<220> FEATURE:
<223> OTHER INFORMATION: Synthetic

<400> SEQUENCE: 53

Ser Ala Phe Asp Leu Ala Met Arg Ile Met Trp Ile Tyr Val Phe Ala
1               5                   10                  15

Trp

<210> SEQ ID NO 54
<211> LENGTH: 605
<212> TYPE: PRT
<213> ORGANISM: Artificial Sequence
<220> FEATURE:
<223> OTHER INFORMATION: Synthetic

<400> SEQUENCE: 54

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro Gly Asp Thr Ile Cys Ile Gly
            35                  40                  45

Tyr His Ala Asn Asn Ser Thr Asp Thr Val Thr Val Leu Glu Lys
        50                  55                  60

Asn Val Thr Val Thr His Ser Val Asn Leu Leu Glu Asp Ser His Asn
65                  70                  75                  80

Gly Lys Leu Cys Arg Leu Lys Gly Ile Ala Pro Leu Gln Leu Gly Asn
                85                  90                  95

Cys Ser Val Ala Gly Trp Ile Leu Gly Asn Pro Glu Cys Glu Ser Leu
            100                 105                 110

Ile Ser Lys Glu Ser Trp Ser Tyr Ile Val Glu Thr Pro Asn Pro Glu
        115                 120                 125

Asn Gly Thr Cys Tyr Pro Gly Tyr Phe Ala Asp Tyr Glu Glu Leu Arg
    130                 135                 140

Glu Gln Leu Ser Ser Val Ser Ser Phe Glu Arg Phe Glu Ile Phe Pro
145                 150                 155                 160

Lys Glu Ser Ser Trp Pro Asn His Thr Val Thr Gly Val Thr Ala Ser
                165                 170                 175

Cys Ser His Asn Gly Lys Ser Ser Phe Tyr Arg Asn Leu Leu Trp Leu
            180                 185                 190

Thr Glu Lys Asn Gly Leu Tyr Pro Asn Leu Ser Asn Ser Tyr Val Asn
        195                 200                 205

Asn Lys Glu Lys Glu Val Leu Val Leu Trp Gly Val His Pro Ser
    210                 215                 220

Asn Ile Gly Val Gln Arg Ala Ile Tyr His Thr Glu Asn Ala Tyr Val
225                 230                 235                 240

Ser Val Val Ser Ser His Tyr Ser Arg Arg Phe Thr Pro Glu Ile Ala
            245                 250                 255

Lys Arg Pro Lys Val Arg Gly Gln Glu Gly Arg Ile Asn Tyr Tyr Trp
        260                 265                 270

Thr Leu Leu Glu Pro Gly Asp Thr Ile Ile Phe Glu Ala Asn Gly Asn
    275                 280                 285

Leu Ile Ala Pro Trp Tyr Ala Phe Ala Leu Ser Arg Gly Phe Gly Ser
290                 295                 300

Gly Ile Ile Thr Ser Asn Ala Pro Met Asn Glu Cys Asp Ala Lys Cys
305                 310                 315                 320

Gln Thr Pro Gln Gly Ala Ile Asn Ser Ser Leu Pro Phe Gln Asn Val
            325                 330                 335

His Pro Val Thr Ile Gly Glu Cys Pro Lys Tyr Val Arg Ser Thr Lys
        340                 345                 350

Leu Arg Met Val Thr Gly Leu Arg Asn Ile Pro Ser Ile Gln Ser Arg
    355                 360                 365

Gly Leu Phe Gly Ala Ile Ala Gly Phe Ile Glu Gly Gly Trp Thr Gly
370                 375                 380

Met Met Asp Gly Trp Tyr Gly Tyr His His Gln Asn Glu Gln Gly Ser
385                 390                 395                 400

Gly Tyr Ala Ala Asp Gln Lys Ser Thr Gln Asn Ala Ile Asn Gly Ile
            405                 410                 415

Thr Asn Lys Val Asn Ser Val Ile Glu Lys Met Asn Thr Gln Phe Thr
        420                 425                 430

Ala Val Gly Lys Glu Phe Asn Lys Leu Glu Arg Arg Met Glu Asn Leu
    435                 440                 445

Asn Lys Lys Val Asp Asp Gly Phe Leu Asp Ile Trp Thr Tyr Asn Ala
450                 455                 460

Glu Leu Leu Val Leu Leu Glu Asn Glu Arg Thr Leu Asp Phe His Asp
465                 470                 475                 480

Ser Asn Val Lys Asn Leu Tyr Glu Lys Val Lys Ser Gln Leu Lys Asn
            485                 490                 495

Asn Ala Lys Glu Ile Gly Asn Gly Cys Phe Glu Phe Tyr His Lys Cys
        500                 505                 510

Asn Asn Glu Cys Met Glu Ser Val Lys Asn Gly Thr Tyr Asp Tyr Pro
    515                 520                 525

Lys Tyr Ser Glu Glu Ser Lys Leu Asn Arg Glu Lys Ile Asp Ser Gly
    530                 535                 540

Gly Gly Gly Leu Asn Asp Ile Phe Glu Ala Gln Lys Ile Glu Trp His
545                 550                 555                 560

Glu Arg Leu Val Pro Arg Gly Ser Pro Gly Ser Gly Tyr Ile Pro Glu
            565                 570                 575

Ala Pro Arg Asp Gly Gln Ala Tyr Val Arg Lys Asp Gly Glu Trp Val
        580                 585                 590

Leu Leu Ser Thr Phe Leu Gly His His His His His
    595                 600                 605

<210> SEQ ID NO 55
<211> LENGTH: 23
<212> TYPE: PRT
<213> ORGANISM: Artificial Sequence
<220> FEATURE:

<223> OTHER INFORMATION: Synthetic

<400> SEQUENCE: 55

His Ala Phe Asp Leu Ala Met Arg Ile Met Trp Ile Tyr Val Phe Ala
1               5                   10                  15

Phe Lys Arg Pro Ile Pro Phe
            20

<210> SEQ ID NO 56
<211> LENGTH: 23
<212> TYPE: PRT
<213> ORGANISM: Artificial Sequence
<220> FEATURE:
<223> OTHER INFORMATION: Synthetic

<400> SEQUENCE: 56

Ser Ala Phe Asp Leu Ala Met Lys Ile Met Trp Ile Tyr Val Phe Ala
1               5                   10                  15

Phe Lys Arg Pro Ile Pro Phe
            20

<210> SEQ ID NO 57
<211> LENGTH: 23
<212> TYPE: PRT
<213> ORGANISM: Artificial Sequence
<220> FEATURE:
<223> OTHER INFORMATION: Synthetic

<400> SEQUENCE: 57

Ser Ala Phe Asp Leu Ala Met Arg Ile His Trp Ile Tyr Val Phe Ala
1               5                   10                  15

Phe Lys Arg Pro Ile Pro Phe
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic

<400> SEQUENCE: 58

Ser Ala Phe Asp Leu Ala Met Arg Ile Asn Trp Ile Tyr Val Phe Ala
1               5                   10                  15

Phe Lys Arg Pro Ile Pro Phe
            20

<210> SEQ ID NO 59
<211> LENGTH: 23
<212> TYPE: PRT
<213> ORGANISM: Artificial Sequence
<220> FEATURE:
<223> OTHER INFORMATION: Synthetic

<400> SEQUENCE: 59

Ser Ala Phe Asp Leu Ala Met Arg Ile Tyr Trp Ile Tyr Val Phe Ala
1               5                   10                  15

Phe Lys Arg Pro Ile Pro Phe
            20

<210> SEQ ID NO 60
<211> LENGTH: 23
<212> TYPE: PRT
<213> ORGANISM: Artificial Sequence

```
<220> FEATURE:
<223> OTHER INFORMATION: Synthetic

<400> SEQUENCE: 60

Ser Ala Phe Asp Leu Ala Met Arg Ile Met Trp Ile Tyr Phe Phe Ala
1               5                   10                  15

Phe Lys Arg Pro Ile Pro Phe
            20

<210> SEQ ID NO 61
<211> LENGTH: 23
<212> TYPE: PRT
<213> ORGANISM: Artificial Sequence
<220> FEATURE:
<223> OTHER INFORMATION: Synthetic

<400> SEQUENCE: 61

Ser Ala Phe Asp Leu Ala Met Arg Ile Met Trp Ile Tyr Leu Phe Ala
1               5                   10                  15

Phe Lys Arg Pro Ile Pro Phe
            20

<210> SEQ ID NO 62
<211> LENGTH: 23
<212> TYPE: PRT
<213> ORGANISM: Artificial Sequence
<220> FEATURE:
<223> OTHER INFORMATION: Synthetic

<400> SEQUENCE: 62

Ser Ala Phe Asp Leu Ala Met Arg Ile Met Trp Ile Tyr Thr Phe Ala
1               5                   10                  15

Phe Lys Arg Pro Ile Pro Phe
            20

<210> SEQ ID NO 63
<211> LENGTH: 23
<212> TYPE: PRT
<213> ORGANISM: Artificial Sequence
<220> FEATURE:
<223> OTHER INFORMATION: Synthetic

<400> SEQUENCE: 63

Ser Ala Phe Asp Leu Ala Met Arg Ile Met Trp Ile Tyr Asn Phe Ala
1               5                   10                  15

Phe Lys Arg Pro Ile Pro Phe
            20

<210> SEQ ID NO 64
<211> LENGTH: 23
<212> TYPE: PRT
<213> ORGANISM: Artificial Sequence
<220> FEATURE:
<223> OTHER INFORMATION: Synthetic

<400> SEQUENCE: 64

Ser Ala Phe Asp Leu Ala Met Arg Ile Met Trp Ile Tyr Val Phe Ala
1               5                   10                  15

Trp Lys Arg Pro Ile Pro Phe
            20

<210> SEQ ID NO 65
<211> LENGTH: 93
<212> TYPE: PRT
```

<213> ORGANISM: Artificial Sequence
<220> FEATURE:
<223> OTHER INFORMATION: Synthetic

<400> SEQUENCE: 65

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Glu Ala Val Leu Gln Ala Val Tyr Glu Thr Glu Ser Ala
        35                  40                  45

Phe Asp Leu Ala Met Arg Ile Met Trp Ile Tyr Val Phe Ala Phe Lys
    50                  55                  60

Arg Pro Ile Pro Phe Pro His Ala Gln Lys Leu Ala Arg Arg Leu Leu
65                  70                  75                  80

Glu Leu Lys Gln Ala Ala Ser Ser Pro Leu Pro Leu Glu
                85                  90

<210> SEQ ID NO 66
<211> LENGTH: 93
<212> TYPE: PRT
<213> ORGANISM: Artificial Sequence
<220> FEATURE:
<223> OTHER INFORMATION: Synthetic

<400> SEQUENCE: 66

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Glu Ala Val Leu Gln Ala Val Tyr Glu Thr Glu Ser Ala
        35                  40                  45

Phe Asp Leu Ala Met Arg Ile Met Trp Ile Tyr Ala Phe Ala Phe Asn
    50                  55                  60

Arg Pro Ile Pro Phe Ser His Ala Gln Lys Leu Ala Arg Arg Leu Leu
65                  70                  75                  80

Glu Leu Lys Gln Ala Ala Ser Ser Pro Leu Pro Leu Glu
                85                  90

<210> SEQ ID NO 67
<211> LENGTH: 93
<212> TYPE: PRT
<213> ORGANISM: Artificial Sequence
<220> FEATURE:
<223> OTHER INFORMATION: Synthetic

<400> SEQUENCE: 67

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Glu Ala Val Leu Gln Ala Val Tyr Glu Thr Glu Asp Ala
        35                  40                  45

Phe Asp Leu Ala Met Arg Ile Met Trp Ile Tyr Val Phe Ala Phe Asn
    50                  55                  60

Arg Pro Ile Pro Phe Ser His Ala Gln Lys Leu Ala Arg Arg Leu Leu
65                  70                  75                  80

Glu Leu Lys Gln Ala Ala Ser Ser Pro Leu Pro Leu Glu
                85                  90

<210> SEQ ID NO 68
<211> LENGTH: 93
<212> TYPE: PRT
<213> ORGANISM: Artificial Sequence
<220> FEATURE:
<223> OTHER INFORMATION: Synthetic

<400> SEQUENCE: 68

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
                20                  25                  30

Val Glu Ala Glu Ala Val Leu Gln Ala Val Tyr Glu Thr Glu Ser Ala
            35                  40                  45

Phe Asp Leu Ala Met Arg Ile Met Trp Ile Tyr Val Phe Ala Phe Asn
    50                  55                  60

Arg Pro Ile Pro Phe Ser His Ala Gln Lys Leu Ala Arg Arg Leu Leu
65                  70                  75                  80

Glu Leu Lys Gln Ala Ala Ser Ser Pro Leu Pro Leu Glu
                85                  90

<210> SEQ ID NO 69
<211> LENGTH: 91
<212> TYPE: PRT
<213> ORGANISM: Artificial Sequence
<220> FEATURE:
<223> OTHER INFORMATION: Synthetic

<400> SEQUENCE: 69

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
                20                  25                  30

Asp Glu Ala Ala Ala Val Leu Gln Ala Val Tyr Glu Thr Asn His Ala
            35                  40                  45

Phe Asp Leu Ala Met Arg Ile His Trp Ile Tyr Val Phe Ala Phe Lys
    50                  55                  60

Arg Lys Ile Pro Phe Leu His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 70
<211> LENGTH: 91
<212> TYPE: PRT
<213> ORGANISM: Artificial Sequence
<220> FEATURE:
<223> OTHER INFORMATION: Synthetic

<400> SEQUENCE: 70

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
                20                  25                  30

Val Glu Ala Ala Ala Val Leu Lys Ala Val Tyr Ala Thr Asn Ser Ala
            35                  40                  45

Phe Asp Leu Ala Met Arg Ile Ile Trp Ile Tyr Val Phe Ala Tyr Lys
    50                  55                  60

Arg Lys Ile Pro Phe Ala His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 71
<211> LENGTH: 91
<212> TYPE: PRT
<213> ORGANISM: Artificial Sequence
<220> FEATURE:
<223> OTHER INFORMATION: Synthetic

<400> SEQUENCE: 71

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
                20                  25                  30

Phe Glu Ala Asp Lys Val Leu Gln Ala Val Tyr Glu Thr Asn Ser Ala
            35                  40                  45

Phe Asp Leu Ala Met Arg Ile Asn Trp Ile Tyr Val Phe Ala Phe Lys
        50                  55                  60

Arg Pro Ile Pro Phe Val His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 72
<211> LENGTH: 91
<212> TYPE: PRT
<213> ORGANISM: Artificial Sequence
<220> FEATURE:
<223> OTHER INFORMATION: Synthetic

<400> SEQUENCE: 72

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
                20                  25                  30

Val Glu Ala Ala Ala Val Leu Lys Ala Val Tyr Glu Thr Asn Ser Ala
            35                  40                  45

Phe Asp Leu Ala Met Arg Ile Asn Trp Ile Tyr Val Phe Ala Phe Lys
        50                  55                  60

Arg Lys Ile Pro Phe Ala His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 73
<211> LENGTH: 91
<212> TYPE: PRT
<213> ORGANISM: Artificial Sequence
<220> FEATURE:
<223> OTHER INFORMATION: Synthetic

<400> SEQUENCE: 73

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
                20                  25                  30

Val Glu Ala Asp Lys Val Leu Gln Ala Val Tyr Asp Thr Asn Ser Ala

```
                 35                  40                  45

Phe Asp Leu Ala Met Thr Ile His Trp Ile Tyr Asn Phe Ala Phe Lys
 50                  55                  60

Arg Lys Ile Pro Phe Leu His Ala Pro Lys Leu Ala Arg Arg Leu Leu
 65                  70                  75                  80

Glu Leu Lys Leu Ala Ala Ser Ser Pro Leu Pro
                 85                  90

<210> SEQ ID NO 74
<211> LENGTH: 91
<212> TYPE: PRT
<213> ORGANISM: Artificial Sequence
<220> FEATURE:
<223> OTHER INFORMATION: Synthetic

<400> SEQUENCE: 74

Met Ser Asn Ala Met Asp Gly Gln Gln Leu Asn Arg Leu Leu Leu Glu
 1               5                  10                  15

Trp Ile Gly Ala Trp Asp Pro Phe Gly Leu Gly Lys Asp Ala Tyr Asp
                 20                  25                  30

Asp Glu Ala Asp Arg Val Leu Gln Ala Val Tyr Glu Thr Asn Ser Ala
                 35                  40                  45

Phe Asp Leu Ala Met Arg Ile Asn Trp Ile Tyr Val Phe Ala Phe Lys
 50                  55                  60

Arg Thr Ile Pro Phe Ala His Ala Gln Lys Leu Ala Arg Arg Leu Leu
 65                  70                  75                  80

Glu Leu Lys Gln Ala Ala Ser Ser Pro Leu Pro
                 85                  90

<210> SEQ ID NO 75
<211> LENGTH: 91
<212> TYPE: PRT
<213> ORGANISM: Artificial Sequence
<220> FEATURE:
<223> OTHER INFORMATION: Synthetic

<400> SEQUENCE: 75

Met Ser Asn Ala Met Asp Gly Gln Gln Leu Asn Arg Leu Leu Leu Glu
 1               5                  10                  15

Trp Ile Gly Ala Trp Asp Pro Phe Gly Leu Gly Lys Asp Ala Tyr Asp
                 20                  25                  30

Tyr Glu Ala Asp Lys Val Leu Gln Ala Val Tyr Glu Thr Asn Ser Ala
                 35                  40                  45

Phe Asp Leu Ala Met Arg Ile His Trp Ile Tyr Ile Phe Ala Phe Lys
 50                  55                  60

Arg Pro Ile Pro Phe Val His Ala Gln Lys Leu Ala Arg Arg Leu Leu
 65                  70                  75                  80

Glu Leu Lys Gln Ala Ala Ser Ser Pro Leu Pro
                 85                  90

<210> SEQ ID NO 76
<211> LENGTH: 91
<212> TYPE: PRT
<213> ORGANISM: Artificial Sequence
<220> FEATURE:
<223> OTHER INFORMATION: Synthetic

<400> SEQUENCE: 76

Met Ser Asn Ala Met Asp Gly Gln Gln Leu Asn Arg Leu Leu Leu Glu
 1               5                  10                  15
```

Trp Ile Gly Ala Trp Asp Pro Phe Gly Leu Gly Lys Asp Ala Tyr Asp
            20                  25                  30

Val Glu Ala Asp Ala Val Leu Lys Ala Val Tyr Glu Thr Asn Ser Ala
        35                  40                  45

Phe Asp Leu Ala Met Arg Ile His Trp Ile Tyr Asn Phe Ala Phe Lys
    50                  55                  60

Arg Lys Ile Pro Phe Val His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 77
<211> LENGTH: 91
<212> TYPE: PRT
<213> ORGANISM: Artificial Sequence
<220> FEATURE:
<223> OTHER INFORMATION: Synthetic

<400> SEQUENCE: 77

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Asp Glu Ala Asp Lys Val Leu Gln Ala Val Tyr Ala Thr Asn Ser Ala
        35                  40                  45

Phe Asp Leu Ala Met Arg Ile His Trp Ile Tyr Asn Phe Ala Tyr Lys
    50                  55                  60

Arg Thr Ile Pro Phe Val His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 78
<211> LENGTH: 91
<212> TYPE: PRT
<213> ORGANISM: Artificial Sequence
<220> FEATURE:
<223> OTHER INFORMATION: Synthetic

<400> SEQUENCE: 78

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Asp Glu Ala Ala Arg Val Leu Lys Ala Val Tyr Ala Thr Asp Ser Ala
        35                  40                  45

Phe Asp Leu Ala Met Arg Ile His Trp Ile Tyr Asn Phe Ala Phe Lys
    50                  55                  60

Arg Lys Ile Pro Phe Leu His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 79
<211> LENGTH: 91
<212> TYPE: PRT
<213> ORGANISM: Artificial Sequence
<220> FEATURE:
<223> OTHER INFORMATION: Synthetic

<400> SEQUENCE: 79

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Asp Lys Val Leu Gln Ala Val Tyr Ala Thr Asn Ser Ala
        35                  40                  45

Phe Asp Leu Ala Met Arg Ile His Trp Ile Tyr Ile Phe Ala Phe Lys
    50                  55                  60

Arg Thr Ile Pro Phe Ile His Ala Gln Lys Leu Ala Arg Arg Leu Leu
65                  70                  75                  80

Glu Leu Lys Gln Ala Ala Ser Ser Pro Leu Pro
            85                  90

<210> SEQ ID NO 80
<211> LENGTH: 91
<212> TYPE: PRT
<213> ORGANISM: Artificial Sequence
<220> FEATURE:
<223> OTHER INFORMATION: Synthetic

<400> SEQUENCE: 80

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Tyr Glu Ala Asp Glu Val Leu Lys Ala Val Tyr Ala Thr Asn Ser Ala
        35                  40                  45

Phe Asp Leu Ala Met Arg Ile His Trp Ile Tyr Asn Phe Ala Phe Lys
    50                  55                  60

Arg Lys Ile Pro Phe Thr His Ala Gln Lys Leu Ala Arg Arg Leu Leu
65                  70                  75                  80

Glu Leu Lys Gln Ala Ala Ser Ser Pro Leu Pro
            85                  90

<210> SEQ ID NO 81
<211> LENGTH: 93
<212> TYPE: PRT
<213> ORGANISM: Artificial Sequence
<220> FEATURE:
<223> OTHER INFORMATION: Synthetic

<400> SEQUENCE: 81

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Ala Lys Val Leu Gln Ala Val Tyr Glu Thr Asn Ser Ala
        35                  40                  45

Phe Asp Leu Ala Met Lys Ile His Trp Ile Tyr Asn Phe Ala Phe Lys
    50                  55                  60

Arg Thr Ile Pro Phe Val His Ala Gln Lys Leu Ala Arg Arg Leu Leu
65                  70                  75                  80

Glu Leu Lys Gln Ala Ala Ser Ser Pro Leu Pro Leu Glu
            85                  90

<210> SEQ ID NO 82

```
<211> LENGTH: 91
<212> TYPE: PRT
<213> ORGANISM: Artificial Sequence
<220> FEATURE:
<223> OTHER INFORMATION: Synthetic

<400> SEQUENCE: 82

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Asp Lys Val Leu Gln Ala Val Tyr Ala Thr Asn Ser Ala
        35                  40                  45

Phe Asp Leu Ala Met Lys Ile His Trp Ile Tyr Ile Phe Ala Phe Lys
    50                  55                  60

Arg Thr Ile Pro Phe Ile His Ala Gln Lys Leu Ala Arg Arg Leu Leu
65                  70                  75                  80

Glu Leu Lys Gln Ala Ala Ser Ser Pro Leu Pro
                85                  90

<210> SEQ ID NO 83
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is selected from the group consisting of Phe
      and Val
<220> FEATURE:
<221> NAME/KEY: MISC_FEATURE
<222> LOCATION: (2)..(2)
<223> OTHER INFORMATION: X is selected from the group consisting of Ser,
      Ala, Phe, Gly, Ile, Lys, Leu, Met, Asn, Pro, Gln, Arg, Thr, and
      Val
<220> FEATURE:
<221> NAME/KEY: MISC_FEATURE
<222> LOCATION: (3)..(3)
<223> OTHER INFORMATION: X is selected from the group consisting of Glu,
      and Asp
<220> FEATURE:
<221> NAME/KEY: MISC_FEATURE
<222> LOCATION: (4)..(4)
<223> OTHER INFORMATION: X is selected from the group consisting of Asn,
      His, Ile, Lys, Leu, Met, Arg, Ser, and Thr
<220> FEATURE:
<221> NAME/KEY: MISC_FEATURE
<222> LOCATION: (5)..(5)
<223> OTHER INFORMATION: X is selected from the group consisting of Leu,
      Phe, Ile, Met, Asn, Gln, and Val
<220> FEATURE:
<221> NAME/KEY: MISC_FEATURE
<222> LOCATION: (6)..(6)
<223> OTHER INFORMATION: X is selected from the group consisting of Ala,
      Asp, Lys, Met, Asn, Gln, Arg, Glu, and Val
<220> FEATURE:
<221> NAME/KEY: MISC_FEATURE
<222> LOCATION: (7)..(7)
<223> OTHER INFORMATION: X is selected from the group consisting of Phe,
      Asp, Asn, and Tyr
<220> FEATURE:
<221> NAME/KEY: MISC_FEATURE
<222> LOCATION: (8)..(8)
<223> OTHER INFORMATION: X is selected from the group consisting of Glu,
      Ala, Asp, Gly, His, Lys, Leu, Met, Asn, Gln, Arg, Ser, Thr, Val,
      and Trp
<220> FEATURE:
<221> NAME/KEY: MISC_FEATURE
<222> LOCATION: (9)..(9)
<223> OTHER INFORMATION: X is selected from the group consisting of Leu,
```

```
         Phe, Ile, Met, and Val
<220> FEATURE:
<221> NAME/KEY: MISC_FEATURE
<222> LOCATION: (11)..(11)
<223> OTHER INFORMATION: X is selected from the group consisting of Leu,
      Ile, Met, and Tyr
<220> FEATURE:
<221> NAME/KEY: MISC_FEATURE
<222> LOCATION: (12)..(12)
<223> OTHER INFORMATION: X is selected from the group consisting of Ser,
      Ala, Gly, and Tyr

<400> SEQUENCE: 83

Xaa Xaa Xaa Xaa Xaa Xaa Xaa Xaa Xaa Ala Xaa Xaa Phe
1               5                   10

<210> SEQ ID NO 84
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is selected from the group consisting of Phe
      and Val
<220> FEATURE:
<221> NAME/KEY: MISC_FEATURE
<222> LOCATION: (2)..(2)
<223> OTHER INFORMATION: X is selected from the group consisting of Ser,
      Ala, Phe, Gly, Ile, Lys, Leu, Met, Asn, Pro, Gln, Arg, Thr, and
      Val
<220> FEATURE:
<221> NAME/KEY: MISC_FEATURE
<222> LOCATION: (3)..(3)
<223> OTHER INFORMATION: X is selected from the group consisting of Glu,
      and Asp
<220> FEATURE:
<221> NAME/KEY: MISC_FEATURE
<222> LOCATION: (4)..(4)
<223> OTHER INFORMATION: X is selected from the group consisting of Asn,
      His, Ile, Lys, Leu, Met, Arg, Ser, and Thr
<220> FEATURE:
<221> NAME/KEY: MISC_FEATURE
<222> LOCATION: (5)..(5)
<223> OTHER INFORMATION: X is selected from the group consisting of Leu,
      Phe, Ile, Met, Asn, Gln, and Val
<220> FEATURE:
<221> NAME/KEY: MISC_FEATURE
<222> LOCATION: (6)..(6)
<223> OTHER INFORMATION: X is selected from the group consisting of Ala,
      Asp, Lys, Met, Asn, Gln, Arg, Glu, and Val
<220> FEATURE:
<221> NAME/KEY: MISC_FEATURE
<222> LOCATION: (7)..(7)
<223> OTHER INFORMATION: X is selected from the group consisting of Phe,
      Asp, Asn, and Tyr
<220> FEATURE:
<221> NAME/KEY: MISC_FEATURE
<222> LOCATION: (8)..(8)
<223> OTHER INFORMATION: X is selected from the group consisting of Glu,
      Ala, Asp, Gly, His, Lys, Leu, Met, Asn, Gln, Arg, Ser, Thr, Val,
      and Trp
<220> FEATURE:
<221> NAME/KEY: MISC_FEATURE
<222> LOCATION: (9)..(9)
<223> OTHER INFORMATION: X is selected from the group consisting of Leu,
      Phe, Ile, Met, and Val
<220> FEATURE:
<221> NAME/KEY: MISC_FEATURE
<222> LOCATION: (11)..(11)
<223> OTHER INFORMATION: X is selected from the group consisting of Leu,
      Ile, Met, and Tyr
<220> FEATURE:
<221> NAME/KEY: MISC_FEATURE
<222> LOCATION: (12)..(12)
```

```
<223> OTHER INFORMATION: X is selected from the group consisting of Ser,
      Ala, Gly, and Tyr
<220> FEATURE:
<221> NAME/KEY: MISC_FEATURE
<222> LOCATION: (14)..(18)
<223> OTHER INFORMATION: X is any amino acid
<220> FEATURE:
<221> NAME/KEY: MISC_FEATURE
<222> LOCATION: (19)..(28)
<223> OTHER INFORMATION: X is any amino acid or absent
<220> FEATURE:
<221> NAME/KEY: MISC_FEATURE
<222> LOCATION: (29)..(29)
<223> OTHER INFORMATION: X is selected from the group consisting of Gln,
      Tyr, Phe, Met, Arg, Lys, and Gly
<220> FEATURE:
<221> NAME/KEY: MISC_FEATURE
<222> LOCATION: (30)..(30)
<223> OTHER INFORMATION: X is selected from the group consisting of Tyr,
      Asp, Met, Asn, and Ser
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: MISC_FEATURE
<222> LOCATION: (32)..(32)
<223> OTHER INFORMATION: X is selected from the group consisting of Ser,
      Arg, and Lys

<400> SEQUENCE: 84

Xaa Xaa Xaa Xaa Xaa Xaa Xaa Xaa Xaa Ala Xaa Xaa Phe Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 85
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: X is Ala, Lys, Arg, Gly, or Thr

<400> SEQUENCE: 85

Thr Asn Lys Asp Thr Pro Asp Arg Trp Xaa Lys Val Ala
1               5                   10

<210> SEQ ID NO 86
<211> LENGTH: 56
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(12)
<223> OTHER INFORMATION: amino acids can be absent
<220> FEATURE:
<221> NAME/KEY: MISC_FEATURE
<222> LOCATION: (1)..(1)
<223> OTHER INFORMATION: X is absent or Met
<220> FEATURE:
<221> NAME/KEY: MISC_FEATURE
<222> LOCATION: (12)..(12)
<223> OTHER INFORMATION: X is selected from group consisting of Gly,
      Arg, Lys, Asp
<220> FEATURE:
<221> NAME/KEY: MISC_FEATURE
<222> LOCATION: (13)..(13)
<223> OTHER INFORMATION: X is selected from the group consisting of Phe
```

```
        and Val
<220> FEATURE:
<221> NAME/KEY: MISC_FEATURE
<222> LOCATION: (14)..(14)
<223> OTHER INFORMATION: X is selected from the group consisting of Ser,
      Ala, Phe, Gly, Ile, Lys, Leu, Met, Asn, Pro, Gln, Arg, Thr, and
      Val
<220> FEATURE:
<221> NAME/KEY: MISC_FEATURE
<222> LOCATION: (15)..(15)
<223> OTHER INFORMATION: X is selected from the group consisting of Glu,
      and Asp
<220> FEATURE:
<221> NAME/KEY: MISC_FEATURE
<222> LOCATION: (16)..(16)
<223> OTHER INFORMATION: X is selected from the group consisting of Asn,
      His, Ile, Lys, Leu, Met, Arg, Ser, and Thr
<220> FEATURE:
<221> NAME/KEY: MISC_FEATURE
<222> LOCATION: (17)..(17)
<223> OTHER INFORMATION: X is selected from the group consisting of Leu,
      Phe, Ile, Met, Asn, Gln, and Val
<220> FEATURE:
<221> NAME/KEY: MISC_FEATURE
<222> LOCATION: (18)..(18)
<223> OTHER INFORMATION: X is selected from the group consisting of Ala,
      Asp, Lys, Met, Asn, Gln, Arg, Glu, and Val
<220> FEATURE:
<221> NAME/KEY: MISC_FEATURE
<222> LOCATION: (19)..(19)
<223> OTHER INFORMATION: X is selected from the group consisting of Phe,
      Asp, Asn, and Tyr
<220> FEATURE:
<221> NAME/KEY: MISC_FEATURE
<222> LOCATION: (20)..(20)
<223> OTHER INFORMATION: X is selected from the group consisting of Glu,
      Ala, Asp, Gly, His, Lys, Leu, Met, Asn, Gln, Arg, Ser, Thr, Val,
      and Trp
<220> FEATURE:
<221> NAME/KEY: MISC_FEATURE
<222> LOCATION: (21)..(21)
<223> OTHER INFORMATION: X is selected from the group consisting of Leu,
      Phe, Ile, Met, and Val
<220> FEATURE:
<221> NAME/KEY: MISC_FEATURE
<222> LOCATION: (23)..(23)
<223> OTHER INFORMATION: X is selected from the group consisting of Leu,
      Ile, Met, and Tyr;
<220> FEATURE:
<221> NAME/KEY: MISC_FEATURE
<222> LOCATION: (24)..(24)
<223> OTHER INFORMATION: X is selected from the group consisting of Ser,
      Ala, Gly, and Tyr
<220> FEATURE:
<221> NAME/KEY: MISC_FEATURE
<222> LOCATION: (26)..(30)
<223> OTHER INFORMATION: X is any amino acid
<220> FEATURE:
<221> NAME/KEY: MISC_FEATURE
<222> LOCATION: (31)..(40)
<223> OTHER INFORMATION: X is any amino acid or absent
<220> FEATURE:
<221> NAME/KEY: MISC_FEATURE
<222> LOCATION: (41)..(41)
<223> OTHER INFORMATION: X is selected from the group consisting of Gln,
      Tyr, Phe, Met, Arg, Lys, and Gly
<220> FEATURE:
<221> NAME/KEY: MISC_FEATURE
<222> LOCATION: (42)..(42)
<223> OTHER INFORMATION: X is selected from the group consisting of Tyr,
      Asp, Met, Asn, and Ser
<220> FEATURE:
<221> NAME/KEY: MISC_FEATURE
<222> LOCATION: (43)..(43)
<223> OTHER INFORMATION: X is any amino acid
<220> FEATURE:
<221> NAME/KEY: MISC_FEATURE
<222> LOCATION: (44)..(44)
<223> OTHER INFORMATION: X is selected from the group consisting of Ser,
```

```
              Arg, and Lys
<220> FEATURE:
<221> NAME/KEY: MISC_FEATURE
<222> LOCATION: (45)..(56)
<223> OTHER INFORMATION: amino acids can be absent
<220> FEATURE:
<221> NAME/KEY: MISC_FEATURE
<222> LOCATION: (46)..(46)
<223> OTHER INFORMATION: X is R or K

<400> SEQUENCE: 86

Xaa Ala Ser Thr Arg Gly Ser Gly Arg Pro Trp Xaa Xaa Xaa Xaa
1               5                   10                  15

Xaa Xaa Xaa Xaa Xaa Ala Xaa Xaa Phe Xaa Xaa Xaa Xaa Xaa Xaa
            20                  25                  30

Xaa Xaa Xaa Xaa Xaa Xaa Xaa Xaa Xaa Xaa Xaa Gly Xaa Thr Pro
        35                  40                  45

Glu Glu Val Lys Lys His Tyr Glu
    50                  55

<210> SEQ ID NO 87
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Met or absent
<220> FEATURE:
<221> NAME/KEY: MISC_FEATURE
<222> LOCATION: (12)..(12)
<223> OTHER INFORMATION: X is selected from group consisting of Gly,
      Arg, Lys, and Asp

<400> SEQUENCE: 87

Xaa Ala Ser Thr Arg Gly Ser Gly Arg Pro Trp Xaa
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is R or K

<400> SEQUENCE: 88

Gly Xaa Thr Pro Glu Glu Val Lys Lys His Tyr Glu
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic

<400> SEQUENCE: 89

Phe Ser Glu Asn Leu Ala Phe Glu Leu Ala Leu Ser Phe
1               5                   10

<210> SEQ ID NO 90
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 90

Phe Ser Glu Asn Leu Ala Phe Glu Leu Ala Leu Ala
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic

<400> SEQUENCE: 91

Phe Ser Glu Asn Val Ala Phe Glu Ile Ala Leu Ser Phe
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic

<400> SEQUENCE: 92

Phe Ser Glu Asn Val Ala Phe Glu Ile Ala Leu Ser Phe
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic

<400> SEQUENCE: 93

Phe Arg Glu Asn Ile Ala Phe Glu Ile Ala Leu Tyr Phe
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic

<400> SEQUENCE: 94

Phe Ser Glu Asn Val Ala Phe Glu Ile Ala Leu Ser Phe
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic

<400> SEQUENCE: 95

Phe Ser Glu Asn Ile Ala Phe Glu Leu Ala Leu Tyr Phe
1               5                   10

<210> SEQ ID NO 96
<211> LENGTH: 13
<212> TYPE: PRT
```

```
<213> ORGANISM: Artificial Sequence
<220> FEATURE:
<223> OTHER INFORMATION: Synthetic

<400> SEQUENCE: 96

Phe Ser Glu Asn Val Ala Phe Glu Leu Ala Leu Tyr Phe
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic

<400> SEQUENCE: 97

Phe Ser Glu Asn Ile Ala Phe Glu Leu Ala Leu Tyr Phe
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic

<400> SEQUENCE: 98

Phe Lys Glu Asn Leu Glu Phe Glu Ile Ala Leu Ser Phe
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic

<400> SEQUENCE: 99

Phe Ser Glu Asn Val Ala Phe Glu Ile Ala Leu Ser Phe
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic

<400> SEQUENCE: 100

Phe Ser Glu Asn Val Ala Phe Glu Leu Ala Leu Tyr Phe
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic

<400> SEQUENCE: 101

Phe Ser Glu Asn Val Ala Phe Glu Leu Ala Leu Tyr Phe
1               5                   10

<210> SEQ ID NO 102
<211> LENGTH: 13
<212> TYPE: PRT
<213> ORGANISM: Artificial Sequence
```

<220> FEATURE:
<223> OTHER INFORMATION: Synthetic

<400> SEQUENCE: 102

Phe Ser Glu Asn Val Ala Phe Glu Ile Ala Leu Ser Phe
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Synthetic

<400> SEQUENCE: 103

Phe Ser Glu Asn Val Ala Phe Glu Leu Ala Leu Tyr Phe
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic

<400> SEQUENCE: 104

Phe Ser Glu Asn Val Ala Phe Glu Leu Ala Leu Tyr Phe
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Synthetic

<400> SEQUENCE: 105

Phe Ser Glu Asn Val Ala Phe Glu Leu Ala Leu Tyr Phe
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Synthetic

<400> SEQUENCE: 106

Phe Ser Glu Asn Val Ala Phe Glu Ile Ala Leu Ser Phe
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetic

<400> SEQUENCE: 107

Phe Ser Glu Asn Val Ala Phe Glu Ile Ala Leu Ser Phe
1               5                   10

<210> SEQ ID NO 108
<211> LENGTH: 13
<212> TYPE: PRT
<213> ORGANISM: Artificial Sequence
<220> FEATURE:

<223> OTHER INFORMATION: Synthetic

<400> SEQUENCE: 108

Phe Ser Glu Asn Val Ala Phe Glu Ile Ala Leu Ser Phe
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic

<400> SEQUENCE: 109

Phe Ser Glu Asn Leu Ala Phe Glu Leu Ala Leu Tyr
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic

<400> SEQUENCE: 110

Phe Ser Glu Asn Val Ala Phe Glu Ile Ala Leu Ser Phe
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic

<400> SEQUENCE: 111

Phe Ser Glu Asn Val Ala Phe Glu Ile Ala Leu Ser Phe
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic

<400> SEQUENCE: 112

Phe Ser Glu Asn Val Ala Phe Glu Ile Ala Leu Ser Phe
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Synthetic

<400> SEQUENCE: 113

Phe Ser Glu Asn Ile Ala Phe Glu Ile Ala Leu Ser Phe
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Synthetic

<400> SEQUENCE: 114

Phe Ser Glu Asn Ile Ala Phe Glu Ile Ala Leu Ser Phe
1               5                   10

<210> SEQ ID NO 115
<211> LENGTH: 30
<212> TYPE: PRT
<213> ORGANISM: Artificial Sequence
<220> FEATURE:
<223> OTHER INFORMATION: Synthetic

<400> SEQUENCE: 115

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Synthetic

<400> SEQUENCE: 116

Phe Ser Glu Asn Val Ala Phe Glu Ile Ala Leu Ser Phe Thr Asn Lys
1               5                   10                  15

Asp Thr Pro Asp Arg Trp Lys Lys Val Ala Arg Tyr Val Arg
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Synthetic

<400> SEQUENCE: 117

Phe Ser Glu Asn Val Ala Phe Glu Ile Ala Leu Ser Phe Thr Asn Lys
1               5                   10                  15

Asp Thr Pro Asp Arg Trp Ala Lys Val Ala Arg Tyr Val Arg
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Synthetic

<400> SEQUENCE: 118

Phe Arg Glu Asn Ile Ala Phe Glu Ile Ala Leu Tyr Phe Thr Asn Lys
1               5                   10                  15

Asp Thr Pro Asp Arg Trp Arg Lys Val Ala Arg Tyr Val Lys
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Synthetic

<400> SEQUENCE: 119

Phe Ser Glu Asn Val Ala Phe Glu Ile Ala Leu Ser Phe Thr Asn Lys
1               5                   10                  15

Asp Thr Pro Asp Arg Trp Arg Lys Val Ala Arg Tyr Val Arg
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Synthetic

<400> SEQUENCE: 120

Phe Ser Glu Asn Ile Ala Phe Glu Leu Ala Leu Tyr Phe Thr Asn Lys
1               5                   10                  15

Asp Thr Pro Asp Arg Trp Gly Lys Val Ala Arg Tyr Val Arg
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Synthetic

<400> SEQUENCE: 121

Phe Ser Glu Asn Val Ala Phe Glu Leu Ala Leu Tyr Phe Thr Asn Lys
1               5                   10                  15

Asp Thr Pro Asp Arg Trp Lys Lys Val Ala Arg Tyr Val Lys
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: Synthetic

<400> SEQUENCE: 122

Phe Ser Glu Asn Ile Ala Phe Glu Leu Ala Leu Tyr Phe Thr Asn Lys
1               5                   10                  15

Asp Thr Pro Asp Arg Trp Lys Lys Val Ala Arg Tyr Val Lys
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Synthetic

<400> SEQUENCE: 123

Phe Lys Glu Asn Leu Glu Phe Glu Ile Ala Leu Ser Phe Thr Asn Lys
1               5                   10                  15

Asp Thr Pro Asp Arg Trp Lys Lys Val Ala Tyr Tyr Val Arg
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Synthetic

```
<400> SEQUENCE: 124

Phe Ser Glu Asn Val Ala Phe Glu Ile Ala Leu Ser Phe Thr Asn Lys
1               5                   10                  15

Asp Thr Pro Asp Arg Trp Arg Lys Val Ala Arg Tyr Val Arg
            20                  25                  30

<210> SEQ ID NO 125
<211> LENGTH: 30
<212> TYPE: PRT
<213> ORGANISM: Artificial Sequence
<220> FEATURE:
<223> OTHER INFORMATION: Synthetic

<400> SEQUENCE: 125

Phe Ser Glu Asn Val Ala Phe Glu Leu Ala Leu Tyr Phe Thr Asn Lys
1               5                   10                  15

Asp Thr Pro Asp Arg Trp Thr Lys Val Ala Arg Tyr Val Lys
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Synthetic

<400> SEQUENCE: 126

Phe Ser Glu Asn Val Ala Phe Glu Leu Ala Leu Tyr Phe Thr Asn Lys
1               5                   10                  15

Asp Thr Pro Asp Arg Trp Thr Lys Val Ala Arg Tyr Val Lys
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Synthetic

<400> SEQUENCE: 127

Phe Ser Glu Asn Val Ala Phe Glu Ile Ala Leu Ser Phe Thr Asn Lys
1               5                   10                  15

Asp Thr Pro Asp Arg Trp Arg Lys Val Ala Arg Tyr Val Arg
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Synthetic

<400> SEQUENCE: 128

Phe Ser Glu Asn Val Ala Phe Glu Leu Ala Leu Tyr Phe Thr Asn Lys
1               5                   10                  15

Asp Thr Pro Asp Arg Trp Gly Lys Val Ala Gln Tyr Val Arg
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Synthetic
```

<400> SEQUENCE: 129

Phe Ser Glu Asn Val Ala Phe Glu Leu Ala Leu Tyr Phe Thr Asn Lys
1               5                   10                  15

Asp Thr Pro Asp Arg Trp Ala Lys Val Ala Arg Tyr Val Lys
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Synthetic

<400> SEQUENCE: 130

Phe Ser Glu Asn Val Ala Phe Glu Leu Ala Leu Tyr Phe Thr Asn Lys
1               5                   10                  15

Asp Thr Pro Asp Arg Trp Thr Lys Val Ala Arg Tyr Val Lys
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Synthetic

<400> SEQUENCE: 131

Phe Ser Glu Asn Val Ala Phe Glu Ile Ala Leu Ser Phe Thr Asn Lys
1               5                   10                  15

Asp Thr Pro Asp Arg Trp Arg Lys Val Ala Tyr Tyr Val Arg
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Synthetic

<400> SEQUENCE: 132

Phe Ser Glu Asn Val Ala Phe Glu Ile Ala Leu Ser Phe Thr Asn Lys
1               5                   10                  15

Asp Thr Pro Asp Arg Trp Arg Lys Val Ala Arg Tyr Val Arg
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Synthetic

<400> SEQUENCE: 133

Phe Ser Glu Asn Val Ala Phe Glu Ile Ala Leu Ser Phe Thr Asn Lys
1               5                   10                  15

Asp Thr Pro Asp Arg Trp Ala Lys Val Ala Arg Tyr Val Arg
            20                  25                  30

<210> SEQ ID NO 134
<211> LENGTH: 30
<212> TYPE: PRT
<213> ORGANISM: Artificial Sequence
<220> FEATURE:

<223> OTHER INFORMATION: Synthetic

<400> SEQUENCE: 134

Phe Ser Glu Asn Leu Ala Phe Glu Leu Ala Leu Tyr Phe Thr Asn Lys
1               5                   10                  15

Asp Thr Pro Asp Arg Trp Ala Lys Val Ala Tyr Tyr Val Lys
            20                  25                  30

<210> SEQ ID NO 135
<211> LENGTH: 30
<212> TYPE: PRT
<213> ORGANISM: Artificial Sequence
<220> FEATURE:
<223> OTHER INFORMATION: Synthetic

<400> SEQUENCE: 135

Phe Ser Glu Asn Val Ala Phe Glu Ile Ala Leu Ser Phe Thr Asn Lys
1               5                   10                  15

Asp Thr Pro Asp Arg Trp Lys Lys Val Ala Arg Tyr Val Lys
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Synthetic

<400> SEQUENCE: 136

Phe Ser Glu Asn Val Ala Phe Glu Ile Ala Leu Ser Phe Thr Asn Lys
1               5                   10                  15

Asp Thr Pro Asp Arg Trp Arg Lys Val Ala Arg Tyr Val Arg
            20                  25                  30

<210> SEQ ID NO 137
<211> LENGTH: 30
<212> TYPE: PRT
<213> ORGANISM: Artificial Sequence
<220> FEATURE:
<223> OTHER INFORMATION: Synthetic

<400> SEQUENCE: 137

Phe Ser Glu Asn Val Ala Phe Glu Ile Ala Leu Ser Phe Thr Asn Lys
1               5                   10                  15

Asp Thr Pro Asp Arg Trp Arg Lys Val Ala Arg Tyr Val Arg
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Synthetic

<400> SEQUENCE: 138

Phe Ser Glu Asn Ile Ala Phe Glu Ile Ala Leu Ser Phe Thr Asn Lys
1               5                   10                  15

Asp Thr Pro Asp Arg Trp Lys Lys Val Ala Gln Tyr Val Lys
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Synthetic

<400> SEQUENCE: 139

Phe Ser Glu Asn Ile Ala Phe Glu Ile Ala Leu Ser Phe Thr Asn Lys
1               5                   10                  15

Asp Thr Pro Asp Arg Trp Lys Lys Val Ala Gln Tyr Val Lys
            20                  25                  30

<210> SEQ ID NO 140
<211> LENGTH: 213
<212> TYPE: PRT
<213> ORGANISM: Artificial Sequence
<220> FEATURE:
<223> OTHER INFORMATION: Synthetic

<400> SEQUENCE: 140

Met Ala Glu Thr Lys Asn Phe Thr Asp Leu Val Glu Ala Thr Lys Trp
1               5                   10                  15

Gly Asn Ser Leu Ile Lys Ser Ala Lys Tyr Ser Ser Lys Asp Lys Met
            20                  25                  30

Ala Ile Tyr Asn Tyr Thr Lys Asn Ser Ser Pro Ile Asn Thr Pro Leu
        35                  40                  45

Arg Ser Ala Asn Gly Asp Val Asn Lys Leu Ser Glu Asn Ile Gln Glu
    50                  55                  60

Gln Val Arg Gln Leu Asp Ser Thr Ile Ser Lys Ser Val Thr Pro Asp
65                  70                  75                  80

Ser Val Tyr Val Tyr Arg Leu Leu Asn Leu Asp Tyr Leu Ser Ser Ile
                85                  90                  95

Thr Gly Phe Thr Arg Glu Asp Leu His Met Leu Gln Gln Thr Asn Glu
            100                 105                 110

Gly Gln Tyr Asn Ser Lys Leu Val Leu Trp Leu Asp Phe Leu Met Ser
        115                 120                 125

Asn Arg Ile Tyr Arg Glu Asn Gly Tyr Ser Ser Thr Gln Leu Val Ser
    130                 135                 140

Gly Ala Ala Leu Ala Gly Arg Pro Ile Glu Leu Lys Leu Glu Leu Pro
145                 150                 155                 160

Lys Gly Thr Lys Ala Ala Tyr Ile Asp Ser Lys Glu Leu Thr Ala Tyr
                165                 170                 175

Pro Gly Gln Gln Glu Val Leu Leu Pro Arg Gly Thr Glu Tyr Ala Val
            180                 185                 190

Gly Thr Val Glu Leu Ser Lys Ser Ser Gln Lys Ile Ile Ile Thr Ala
        195                 200                 205

Val Val Phe Lys Lys
    210

<210> SEQ ID NO 141
<211> LENGTH: 13
<212> TYPE: PRT
<213> ORGANISM: Artificial Sequence
<220> FEATURE:
<223> OTHER INFORMATION: Synthetic

<400> SEQUENCE: 141

Phe Ala Glu Asn Leu Ala Phe Glu Leu Ala Leu Ser Phe
1               5                   10

<210> SEQ ID NO 142
<211> LENGTH: 13

```
<212> TYPE: PRT
<213> ORGANISM: Artificial Sequence
<220> FEATURE:
<223> OTHER INFORMATION: Synthetic

<400> SEQUENCE: 142

Phe Gly Glu Asn Leu Ala Phe Glu Leu Ala Leu Ser Phe
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Synthetic

<400> SEQUENCE: 143

Phe Ile Glu Asn Leu Ala Phe Glu Leu Ala Leu Ser Phe
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Synthetic

<400> SEQUENCE: 144

Phe Lys Glu Asn Leu Ala Phe Glu Leu Ala Leu Ser Phe
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Synthetic

<400> SEQUENCE: 145

Phe Arg Glu Asn Leu Ala Phe Glu Leu Ala Leu Ser Phe
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Synthetic

<400> SEQUENCE: 146

Phe Thr Glu Asn Leu Ala Phe Glu Leu Ala Leu Ser Phe
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Synthetic

<400> SEQUENCE: 147

Phe Val Glu Asn Leu Ala Phe Glu Leu Ala Leu Ser Phe
1               5                   10

<210> SEQ ID NO 148
<211> LENGTH: 13
<212> TYPE: PRT
```

```
<213> ORGANISM: Artificial Sequence
<220> FEATURE:
<223> OTHER INFORMATION: Synthetic

<400> SEQUENCE: 148

Phe Ser Glu Asn Ile Ala Phe Glu Leu Ala Leu Ser Phe
1               5                   10

<210> SEQ ID NO 149
<211> LENGTH: 13
<212> TYPE: PRT
<213> ORGANISM: Artificial Sequence
<220> FEATURE:
<223> OTHER INFORMATION: Synthetic

<400> SEQUENCE: 149

Phe Ser Glu Asn Val Ala Phe Glu Leu Ala Leu Ser Phe
1               5                   10

<210> SEQ ID NO 150
<211> LENGTH: 13
<212> TYPE: PRT
<213> ORGANISM: Artificial Sequence
<220> FEATURE:
<223> OTHER INFORMATION: Synthetic

<400> SEQUENCE: 150

Phe Ser Glu Asn Leu Lys Phe Glu Leu Ala Leu Ser Phe
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Synthetic

<400> SEQUENCE: 151

Phe Ser Glu Asn Leu Arg Phe Glu Leu Ala Leu Ser Phe
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic

<400> SEQUENCE: 152

Phe Ser Glu Asn Leu Thr Phe Glu Leu Ala Leu Ser Phe
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Synthetic

<400> SEQUENCE: 153

Phe Ser Glu Asn Leu Ala Phe Ser Leu Ala Leu Ser Phe
1               5                   10

<210> SEQ ID NO 154
<211> LENGTH: 13
<212> TYPE: PRT
<213> ORGANISM: Artificial Sequence
```

<220> FEATURE:
<223> OTHER INFORMATION: Synthetic

<400> SEQUENCE: 154

Phe Ser Glu Asn Leu Ala Phe Glu Leu Ala Leu Tyr Phe
1               5                   10

<210> SEQ ID NO 155
<211> LENGTH: 180
<212> TYPE: PRT
<213> ORGANISM: Artificial Sequence
<220> FEATURE:
<223> OTHER INFORMATION: Synthetic

<400> SEQUENCE: 155

Met Ala Asp Thr Leu Leu Ile Leu Gly Asp Ser Leu Ser Ala Gly Tyr
1               5                   10                  15

Gln Met Leu Ala Glu Phe Ala Trp Pro Phe Leu Leu Asn Lys Lys Trp
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Glu Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Pro Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Gly Ile His Pro Asn Tyr
145                 150                 155                 160

Glu Ala Gln Pro Phe Ile Ala Asp Trp Met Ala Lys Gln Leu Gln Pro
                165                 170                 175

Leu Val Asn His
            180

<210> SEQ ID NO 156
<211> LENGTH: 30
<212> TYPE: PRT
<213> ORGANISM: Artificial Sequence
<220> FEATURE:
<223> OTHER INFORMATION: Synthetic

<400> SEQUENCE: 156

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Arg Tyr Val Ser
            20                  25                  30

<210> SEQ ID NO 157
<211> LENGTH: 30
<212> TYPE: PRT
<213> ORGANISM: Artificial Sequence
<220> FEATURE:
<223> OTHER INFORMATION: Synthetic

<400> SEQUENCE: 157

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Tyr Tyr Val Ser
            20                  25                  30

<210> SEQ ID NO 158
<211> LENGTH: 30
<212> TYPE: PRT
<213> ORGANISM: Artificial Sequence
<220> FEATURE:
<223> OTHER INFORMATION: Synthetic

<400> SEQUENCE: 158

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Lys
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Synthetic

<400> SEQUENCE: 159

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Arg
            20                  25                  30

<210> SEQ ID NO 160
<211> LENGTH: 30
<212> TYPE: PRT
<213> ORGANISM: Artificial Sequence
<220> FEATURE:
<223> OTHER INFORMATION: Synthetic

<400> SEQUENCE: 160

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 161
<211> LENGTH: 30
<212> TYPE: PRT
<213> ORGANISM: Artificial Sequence
<220> FEATURE:
<223> OTHER INFORMATION: Synthetic

<400> SEQUENCE: 161

Phe Ala Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 162
<211> LENGTH: 30
<212> TYPE: PRT
<213> ORGANISM: Artificial Sequence
<220> FEATURE:
<223> OTHER INFORMATION: Synthetic

<400> SEQUENCE: 162

Phe Gly Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 163
<211> LENGTH: 30
<212> TYPE: PRT
<213> ORGANISM: Artificial Sequence
<220> FEATURE:
<223> OTHER INFORMATION: Synthetic

<400> SEQUENCE: 163

Phe Ile Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Synthetic

<400> SEQUENCE: 164

Phe Lys Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 165
<211> LENGTH: 30
<212> TYPE: PRT
<213> ORGANISM: Artificial Sequence
<220> FEATURE:
<223> OTHER INFORMATION: Synthetic

<400> SEQUENCE: 165

Phe Arg Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 166
<211> LENGTH: 30
<212> TYPE: PRT
<213> ORGANISM: Artificial Sequence
<220> FEATURE:
<223> OTHER INFORMATION: Synthetic

<400> SEQUENCE: 166

Phe Thr Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Synthetic

<400> SEQUENCE: 167

Phe Val Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 168
<211> LENGTH: 30
<212> TYPE: PRT
<213> ORGANISM: Artificial Sequence
<220> FEATURE:
<223> OTHER INFORMATION: Synthetic

<400> SEQUENCE: 168

Phe Ser Glu Asn Ile Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Synthetic

<400> SEQUENCE: 169

Phe Ser Glu Asn Val Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 170
<211> LENGTH: 30
<212> TYPE: PRT
<213> ORGANISM: Artificial Sequence
<220> FEATURE:
<223> OTHER INFORMATION: Synthetic

<400> SEQUENCE: 170

Phe Ser Glu Asn Leu Lys Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 171
<211> LENGTH: 30
<212> TYPE: PRT
<213> ORGANISM: Artificial Sequence
<220> FEATURE:
<223> OTHER INFORMATION: Synthetic

<400> SEQUENCE: 171

Phe Ser Glu Asn Leu Arg Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 172
<211> LENGTH: 30
<212> TYPE: PRT
<213> ORGANISM: Artificial Sequence
<220> FEATURE:

<223> OTHER INFORMATION: Synthetic

<400> SEQUENCE: 172

Phe Ser Glu Asn Leu Thr Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 173
<211> LENGTH: 30
<212> TYPE: PRT
<213> ORGANISM: Artificial Sequence
<220> FEATURE:
<223> OTHER INFORMATION: Synthetic

<400> SEQUENCE: 173

Phe Ser Glu Asn Leu Ala Phe Ser Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: Synthetic

<400> SEQUENCE: 174

Phe Ser Glu Asn Leu Ala Phe Glu Leu Ala Leu Tyr Phe Thr Asn Lys
1               5                   10                  15

Asp Thr Pro Asp Arg Trp Ala Lys Val Ala Gln Tyr Val Ser
            20                  25                  30

<210> SEQ ID NO 175
<211> LENGTH: 30
<212> TYPE: PRT
<213> ORGANISM: Artificial Sequence
<220> FEATURE:
<223> OTHER INFORMATION: Synthetic

<400> SEQUENCE: 175

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Ser
            20                  25                  30

<210> SEQ ID NO 176
<211> LENGTH: 30
<212> TYPE: PRT
<213> ORGANISM: Artificial Sequence
<220> FEATURE:
<223> OTHER INFORMATION: Synthetic

<400> SEQUENCE: 176

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Arg Tyr Val Ser
            20                  25                  30

<210> SEQ ID NO 177
<211> LENGTH: 30
<212> TYPE: PRT
<213> ORGANISM: Artificial Sequence
<220> FEATURE:
<223> OTHER INFORMATION: Synthetic

<400> SEQUENCE: 177

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Tyr Tyr Val Ser
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: Synthetic

<400> SEQUENCE: 178

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Lys
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: Synthetic

<400> SEQUENCE: 179

Phe Ser Glu Asn Leu Ala Phe Glu Leu Ala Leu Ser Phe Thr Asn Lys
1               5                   10                  15

Asp Thr Pro Asp Arg Trp Ala Lys Val Ala Gln Tyr Val Arg
            20                  25                  30

<210> SEQ ID NO 180
<211> LENGTH: 95
<212> TYPE: PRT
<213> ORGANISM: Artificial Sequence
<220> FEATURE:
<223> OTHER INFORMATION: Synthetic

<400> SEQUENCE: 180

Met Ala Ser Thr Arg Gly Ser Gly Arg Pro Trp Asp Phe Ser Glu Asn
1               5                   10                  15

Leu Ala Phe Glu Leu Ala Leu Ala Phe Thr Asn Lys Asp Thr Pro Asp
            20                  25                  30

Arg Trp Ala Asn Val Ala Gln Tyr Val Ser Gly Arg Thr Pro Glu Glu
        35                  40                  45

Val Lys Lys His Tyr Glu Ile Leu Val Glu Asp Ile Lys Tyr Ile Glu
    50                  55                  60

Ser Gly Lys Val Pro Phe Pro Asn Tyr Arg Thr Thr Gly Gly Asn Met
65                  70                  75                  80

Lys Thr Asp Glu Lys Arg Phe Arg Asn Leu Lys Ile Arg Leu Glu
                85                  90                  95

<210> SEQ ID NO 181
<211> LENGTH: 95
<212> TYPE: PRT
<213> ORGANISM: Artificial Sequence
<220> FEATURE:
<223> OTHER INFORMATION: Synthetic

<400> SEQUENCE: 181

Met Ala Ser Thr Arg Gly Ser Gly Arg Pro Trp Asp Phe Ser Glu Asn
1               5                   10                  15

Leu Ala Phe Glu Leu Ala Leu Ala Phe Met Asn Lys Asp Thr Pro Asp
            20                  25                  30

Arg Trp Ala Lys Val Ala Gln Tyr Val Ser Gly Arg Thr Pro Glu Glu
        35                  40                  45

Val Lys Lys His Tyr Glu Ile Leu Val Glu Asp Ile Lys Tyr Ile Glu
    50                  55                  60

Ser Gly Lys Val Pro Phe Pro Asn Tyr Arg Thr Gly Gly Asn Met
65                  70                  75                  80

Lys Thr Asp Glu Lys Arg Phe Arg Asn Leu Lys Ile Arg Leu Glu
                85                  90                  95

<210> SEQ ID NO 182
<211> LENGTH: 95
<212> TYPE: PRT
<213> ORGANISM: Artificial Sequence
<220> FEATURE:
<223> OTHER INFORMATION: Synthetic

<400> SEQUENCE: 182

Met Ala Ser Thr Arg Gly Ser Gly Arg Pro Trp Asp Phe Ser Glu Asn
1               5                   10                  15

Leu Ala Phe Glu Leu Ala Leu Ala Phe Thr Asn Lys Asp Thr Pro Asp
            20                  25                  30

Arg Trp Ala Lys Val Ala Gln Tyr Val Ser Gly Arg Thr Pro Glu Glu
        35                  40                  45

Val Lys Lys His Tyr Glu Ile Leu Val Glu Asp Ile Lys Tyr Ile Glu
    50                  55                  60

Ser Gly Lys Val Pro Phe Pro Asn Tyr Arg Thr Gly Gly Asn Met
65                  70                  75                  80

Lys Thr Asp Glu Lys Arg Phe Arg Asn Leu Lys Ile Arg Leu Glu
                85                  90                  95

<210> SEQ ID NO 183
<211> LENGTH: 54
<212> TYPE: PRT
<213> ORGANISM: Artificial Sequence
<220> FEATURE:
<223> OTHER INFORMATION: Synthetic

<400> SEQUENCE: 183

Met Ala Ser Thr Arg Gly Ser Gly Arg Pro Trp Asp Phe Ser Glu Asn
1               5                   10                  15

Leu Ala Phe Glu Leu Ala Leu Ala Phe Thr Asn Lys Asp Thr Pro Asp
            20                  25                  30

Arg Trp Ala Lys Val Ala Gln Tyr Val Ser Gly Arg Thr Pro Glu Glu
        35                  40                  45

Val Lys Lys His Tyr Glu
    50

<210> SEQ ID NO 184
<211> LENGTH: 54
<212> TYPE: PRT
<213> ORGANISM: Artificial Sequence
<220> FEATURE:
<223> OTHER INFORMATION: Synthetic

<400> SEQUENCE: 184

Met Ala Ser Thr Arg Gly Ser Gly Arg Pro Trp Gly Phe Ser Glu Asn
1               5                   10                  15

Leu Ala Phe Glu Leu Ala Leu Ser Phe Thr Asn Lys Asp Thr Pro Asp
                20                  25                  30

Arg Trp Ala Lys Val Ala Gln Tyr Val Ser Gly Arg Thr Pro Glu Glu
            35                  40                  45

Val Lys Lys His Tyr Glu
    50

<210> SEQ ID NO 185
<211> LENGTH: 54
<212> TYPE: PRT
<213> ORGANISM: Artificial Sequence
<220> FEATURE:
<223> OTHER INFORMATION: Synthetic

<400> SEQUENCE: 185

Met Ala Ser Thr Arg Gly Ser Gly Arg Pro Trp Lys Phe Ser Glu Asn
1               5                   10                  15

Leu Ala Phe Glu Leu Ala Leu Ser Phe Thr Asn Lys Asp Thr Pro Asp
                20                  25                  30

Arg Trp Ala Lys Val Ala Gln Tyr Val Ser Gly Arg Thr Pro Glu Glu
            35                  40                  45

Val Lys Lys His Tyr Glu
    50

<210> SEQ ID NO 186
<211> LENGTH: 54
<212> TYPE: PRT
<213> ORGANISM: Artificial Sequence
<220> FEATURE:
<223> OTHER INFORMATION: Synthetic

<400> SEQUENCE: 186

Met Ala Ser Thr Arg Gly Ser Gly Arg Pro Trp Arg Phe Ser Glu Asn
1               5                   10                  15

Leu Ala Phe Glu Leu Ala Leu Ser Phe Thr Asn Lys Asp Thr Pro Asp
                20                  25                  30

Arg Trp Ala Lys Val Ala Gln Tyr Val Ser Gly Arg Thr Pro Glu Glu
            35                  40                  45

Val Lys Lys His Tyr Glu
    50

<210> SEQ ID NO 187
<211> LENGTH: 54
<212> TYPE: PRT
<213> ORGANISM: Artificial Sequence
<220> FEATURE:
<223> OTHER INFORMATION: Synthetic

<400> SEQUENCE: 187

Met Ala Ser Thr Arg Gly Ser Gly Arg Pro Trp Arg Phe Ser Glu Asn
1               5                   10                  15

Val Ala Phe Glu Ile Ala Leu Ser Phe Thr Asn Lys Asp Thr Pro Asp
                20                  25                  30

Arg Trp Lys Lys Val Ala Arg Tyr Val Arg Gly Arg Thr Pro Glu Glu
            35                  40                  45

Val Lys Lys His Tyr Glu
    50

<210> SEQ ID NO 188
<211> LENGTH: 54
<212> TYPE: PRT
<213> ORGANISM: Artificial Sequence
<220> FEATURE:
<223> OTHER INFORMATION: Synthetic

<400> SEQUENCE: 188

```
Met Ala Ser Thr Arg Gly Ser Gly Arg Pro Trp Lys Phe Ser Glu Asn
1               5                   10                  15

Val Ala Phe Glu Ile Ala Leu Ser Phe Thr Asn Lys Asp Thr Pro Asp
                20                  25                  30

Arg Trp Ala Lys Val Ala Arg Tyr Val Arg Gly Arg Thr Pro Glu Glu
            35                  40                  45

Val Lys Lys His Tyr Glu
            50
```

<210> SEQ ID NO 189
<211> LENGTH: 54
<212> TYPE: PRT
<213> ORGANISM: Artificial Sequence
<220> FEATURE:
<223> OTHER INFORMATION: Synthetic

<400> SEQUENCE: 189

```
Met Ala Ser Thr Arg Gly Ser Gly Arg Pro Trp Gly Phe Arg Glu Asn
1               5                   10                  15

Ile Ala Phe Glu Ile Ala Leu Tyr Phe Thr Asn Lys Asp Thr Pro Asp
                20                  25                  30

Arg Trp Arg Lys Val Ala Arg Tyr Val Lys Gly Arg Thr Pro Glu Glu
            35                  40                  45

Val Lys Lys His Tyr Glu
            50
```

<210> SEQ ID NO 190
<211> LENGTH: 54
<212> TYPE: PRT
<213> ORGANISM: Artificial Sequence
<220> FEATURE:
<223> OTHER INFORMATION: Synthetic

<400> SEQUENCE: 190

```
Met Ala Ser Thr Arg Gly Ser Gly Arg Pro Trp Arg Phe Ser Glu Asn
1               5                   10                  15

Val Ala Phe Glu Ile Ala Leu Ser Phe Thr Asn Lys Asp Thr Pro Asp
                20                  25                  30

Arg Trp Arg Lys Val Ala Arg Tyr Val Arg Gly Arg Thr Pro Glu Glu
            35                  40                  45

Val Lys Lys His Tyr Glu
            50
```

<210> SEQ ID NO 191
<211> LENGTH: 54
<212> TYPE: PRT
<213> ORGANISM: Artificial Sequence
<220> FEATURE:
<223> OTHER INFORMATION: Synthetic

<400> SEQUENCE: 191

```
Met Ala Ser Thr Arg Gly Ser Gly Arg Pro Trp Gly Phe Ser Glu Asn
1               5                   10                  15
```

```
Ile Ala Phe Glu Leu Ala Leu Tyr Phe Thr Asn Lys Asp Thr Pro Asp
            20                  25                  30

Arg Trp Gly Lys Val Ala Arg Tyr Val Arg Gly Arg Thr Pro Glu Glu
        35                  40                  45

Val Lys Lys His Tyr Glu
    50

<210> SEQ ID NO 192
<211> LENGTH: 54
<212> TYPE: PRT
<213> ORGANISM: Artificial Sequence
<220> FEATURE:
<223> OTHER INFORMATION: Synthetic

<400> SEQUENCE: 192

Met Ala Ser Thr Arg Gly Ser Gly Arg Pro Trp Lys Phe Ser Glu Asn
1               5                   10                  15

Val Ala Phe Glu Leu Ala Leu Tyr Phe Thr Asn Lys Asp Thr Pro Asp
            20                  25                  30

Arg Trp Lys Lys Val Ala Arg Tyr Val Lys Gly Arg Thr Pro Glu Glu
        35                  40                  45

Val Lys Lys His Tyr Glu
    50

<210> SEQ ID NO 193
<211> LENGTH: 54
<212> TYPE: PRT
<213> ORGANISM: Artificial Sequence
<220> FEATURE:
<223> OTHER INFORMATION: Synthetic

<400> SEQUENCE: 193

Met Ala Ser Thr Arg Gly Ser Gly Arg Pro Trp Lys Phe Ser Glu Asn
1               5                   10                  15

Ile Ala Phe Glu Leu Ala Leu Tyr Phe Thr Asn Lys Asp Thr Pro Asp
            20                  25                  30

Arg Trp Lys Lys Val Ala Arg Tyr Val Lys Gly Arg Thr Pro Glu Glu
        35                  40                  45

Val Lys Lys His Tyr Glu
    50

<210> SEQ ID NO 194
<211> LENGTH: 54
<212> TYPE: PRT
<213> ORGANISM: Artificial Sequence
<220> FEATURE:
<223> OTHER INFORMATION: Synthetic

<400> SEQUENCE: 194

Met Ala Ser Thr Arg Gly Ser Gly Arg Pro Trp Lys Phe Lys Glu Asn
1               5                   10                  15

Leu Glu Phe Glu Ile Ala Leu Ser Phe Thr Asn Lys Asp Thr Pro Asp
            20                  25                  30

Arg Trp Lys Lys Val Ala Tyr Tyr Val Arg Gly Arg Thr Pro Glu Glu
        35                  40                  45

Val Lys Lys His Tyr Glu
    50

<210> SEQ ID NO 195
<211> LENGTH: 56
<212> TYPE: DNA
```

```
<213> ORGANISM: Artificial Sequence
<220> FEATURE:
<223> OTHER INFORMATION: Synthetic

<400> SEQUENCE: 195
agtcactagg tcatatgcat caccatcacc atcacaagga taacaccgtg ccactg        56

<210> SEQ ID NO 196
<211> LENGTH: 54
<212> TYPE: PRT
<213> ORGANISM: Artificial Sequence
<220> FEATURE:
<223> OTHER INFORMATION: Synthetic

<400> SEQUENCE: 196
```

Met Ala Ser Thr Arg Gly Ser Gly Arg Pro Trp Lys Phe Ser Glu Asn
1               5                   10                  15

Val Ala Phe Glu Leu Ala Leu Tyr Phe Thr Asn Lys Asp Thr Pro Asp
            20                  25                  30

Arg Trp Thr Lys Val Ala Arg Tyr Val Lys Gly Arg Thr Pro Glu Glu
        35                  40                  45

Val Lys Lys His Tyr Glu
    50

```
<210> SEQ ID NO 197
<211> LENGTH: 47
<212> TYPE: DNA
<213> ORGANISM: Artificial Sequence
<220> FEATURE:
<223> OTHER INFORMATION: Synthetic

<400> SEQUENCE: 197
agtcactagg taagctttta tttttctgca ctacgcaggg atatttc                   47

<210> SEQ ID NO 198
<211> LENGTH: 54
<212> TYPE: PRT
<213> ORGANISM: Artificial Sequence
<220> FEATURE:
<223> OTHER INFORMATION: Synthetic

<400> SEQUENCE: 198
```

Met Ala Ser Thr Arg Gly Ser Gly Arg Pro Trp Lys Phe Ser Glu Asn
1               5                   10                  15

Val Ala Phe Glu Ile Ala Leu Ser Phe Thr Asn Lys Asp Thr Pro Asp
            20                  25                  30

Arg Trp Arg Lys Val Ala Arg Tyr Val Arg Gly Arg Thr Pro Glu Glu
        35                  40                  45

Val Lys Lys His Tyr Glu
    50

```
<210> SEQ ID NO 199
<211> LENGTH: 54
<212> TYPE: PRT
<213> ORGANISM: Artificial Sequence
<220> FEATURE:
<223> OTHER INFORMATION: Synthetic

<400> SEQUENCE: 199
```

Met Ala Ser Thr Arg Gly Ser Gly Arg Pro Trp Lys Phe Ser Glu Asn
1               5                   10                  15

Val Ala Phe Glu Leu Ala Leu Tyr Phe Thr Asn Lys Asp Thr Pro Asp
            20                  25                  30

Arg Trp Gly Lys Val Ala Gln Tyr Val Arg Gly Arg Thr Pro Glu Glu
         35                  40                  45

Val Lys Lys His Tyr Glu
    50

<210> SEQ ID NO 200
<211> LENGTH: 53
<212> TYPE: PRT
<213> ORGANISM: Artificial Sequence
<220> FEATURE:
<223> OTHER INFORMATION: Synthetic

<400> SEQUENCE: 200

Ala Ser Thr Arg Gly Ser Gly Arg Pro Trp Lys Phe Ser Glu Asn Val
1               5                   10                  15

Ala Phe Glu Leu Ala Leu Tyr Phe Thr Asn Lys Asp Thr Pro Asp Arg
             20                  25                  30

Trp Ala Lys Val Ala Arg Tyr Val Lys Gly Arg Thr Pro Glu Glu Val
         35                  40                  45

Lys Lys His Tyr Glu
    50

<210> SEQ ID NO 201
<211> LENGTH: 454
<212> TYPE: DNA
<213> ORGANISM: Artificial Sequence
<220> FEATURE:
<223> OTHER INFORMATION: Synthetic

<400> SEQUENCE: 201
gacgattgaa ggtagatacc catacgacgt tccagactac gctctgcagg ctagtggtgg    60
aggaggctct ggtggaggcg gtagcggagg cggagggtcg gctagccata tgcacatgtc   120
caatgctatg gatggtcaac aattgaacag attgttattg gaatggatcg gtgcctggga   180
cccttttggt ttgggtaaag atgcttatgm tkwtgaagcc gaarvagttt tamaggcagt   240
atacgmgact ramymtgcat ttgatttggc catgagaatt mwktggatct atrwttttgc   300
ctwtaagaga mmgattcctt tcvyacacgc tcaaaaattg caagaagat tattggaatt    360 gaagcaagct gcatcttcac ctttaccatt ggaactcgag gggggcggat ccgaacaaaa   420
gcttatttct gaagaggact tgtaatagag atct                               454

<210> SEQ ID NO 202
<211> LENGTH: 54
<212> TYPE: PRT
<213> ORGANISM: Artificial Sequence
<220> FEATURE:
<223> OTHER INFORMATION: Synthetic

<400> SEQUENCE: 202

Met Ala Ser Thr Arg Gly Ser Gly Arg Pro Trp Lys Phe Ser Glu Asn
1               5                   10                  15

Val Ala Phe Glu Ile Ala Leu Ser Phe Thr Asn Lys Asp Thr Pro Asp
             20                  25                  30

Arg Trp Arg Lys Val Ala Tyr Tyr Val Arg Gly Arg Thr Pro Glu Glu
         35                  40                  45

Val Lys Lys His Tyr Glu
    50

<210> SEQ ID NO 203

```
<211> LENGTH: 331
<212> TYPE: DNA
<213> ORGANISM: Artificial Sequence
<220> FEATURE:
<223> OTHER INFORMATION: Synthetic

<400> SEQUENCE: 203
gacgattgaa ggtagatacc catacgacgt tccagactac gctctgcagg ctagtggtgg      60
aggaggctct ggtggaggcg gtagcggagg cggagggtcg gctagccata tggcttctac     120
tagaggttct ggtagacctt ggrrgttttar sgaaaatvtt rmgttcgaam ttgctttatm    180
ttttactaac aaagatacac cagacagatg grvgaaggtt gcaydstatg taarsggtag     240
aacacctgaa gaagttaaaa agcattacga actcgagggg ggcggatccg aacaaaagct    300
tatttctgaa gaggacttgt aatagagatc t                                    331

<210> SEQ ID NO 204
<211> LENGTH: 54
<212> TYPE: PRT
<213> ORGANISM: Artificial Sequence
<220> FEATURE:
<223> OTHER INFORMATION: Synthetic

<400> SEQUENCE: 204

Met Ala Ser Thr Arg Gly Ser Gly Arg Pro Trp Arg Phe Ser Glu Asn
1               5                   10                  15

Val Ala Phe Glu Ile Ala Leu Ser Phe Thr Asn Lys Asp Thr Pro Asp
            20                  25                  30

Arg Trp Ala Lys Val Ala Arg Tyr Val Arg Gly Arg Thr Pro Glu Glu
        35                  40                  45

Val Lys Lys His Tyr Glu
    50

<210> SEQ ID NO 205
<211> LENGTH: 54
<212> TYPE: PRT
<213> ORGANISM: Artificial Sequence
<220> FEATURE:
<223> OTHER INFORMATION: Synthetic

<400> SEQUENCE: 205

Met Ala Ser Thr Arg Gly Ser Gly Arg Pro Trp Lys Phe Ser Glu Asn
1               5                   10                  15

Leu Ala Phe Glu Leu Ala Leu Tyr Phe Thr Asn Lys Asp Thr Pro Asp
            20                  25                  30

Arg Trp Ala Lys Val Ala Tyr Tyr Val Lys Gly Arg Thr Pro Glu Glu
        35                  40                  45

Val Lys Lys His Tyr Glu
    50

<210> SEQ ID NO 206
<211> LENGTH: 54
<212> TYPE: PRT
<213> ORGANISM: Artificial Sequence
<220> FEATURE:
<223> OTHER INFORMATION: Synthetic

<400> SEQUENCE: 206

Met Ala Ser Thr Arg Gly Ser Gly Arg Pro Trp Arg Phe Ser Glu Asn
1               5                   10                  15

Val Ala Phe Glu Ile Ala Leu Ser Phe Thr Asn Lys Asp Thr Pro Asp
            20                  25                  30
```

Arg Trp Lys Lys Val Ala Arg Tyr Val Lys Gly Arg Thr Pro Glu Glu
        35                  40                  45

Val Lys Lys His Tyr Glu
    50

<210> SEQ ID NO 207
<211> LENGTH: 54
<212> TYPE: PRT
<213> ORGANISM: Artificial Sequence
<220> FEATURE:
<223> OTHER INFORMATION: Synthetic

<400> SEQUENCE: 207

Met Ala Ser Thr Lys Gly Ser Gly Lys Pro Trp Lys Phe Ser Glu Asn
1               5                   10                  15

Val Ala Phe Glu Ile Ala Leu Ser Phe Thr Asn Lys Asp Thr Pro Asp
            20                  25                  30

Arg Trp Arg Lys Val Ala Arg Tyr Val Arg Gly Lys Thr Pro Glu Glu
        35                  40                  45

Val Lys Lys His Tyr Glu
    50

<210> SEQ ID NO 208

<400> SEQUENCE: 208

000

<210> SEQ ID NO 209
<211> LENGTH: 54
<212> TYPE: PRT
<213> ORGANISM: Artificial Sequence
<220> FEATURE:
<223> OTHER INFORMATION: Synthetic

<400> SEQUENCE: 209

Met Ala Ser Thr Arg Gly Ser Gly Arg Pro Trp Lys Phe Ser Glu Asn
1               5                   10                  15

Ile Ala Phe Glu Ile Ala Leu Ser Phe Thr Asn Lys Asp Thr Pro Asp
            20                  25                  30

Arg Trp Lys Lys Val Ala Gln Tyr Val Lys Gly Arg Thr Pro Glu Glu
        35                  40                  45

Val Lys Lys His Tyr Glu
    50

<210> SEQ ID NO 210

<400> SEQUENCE: 210

000

<210> SEQ ID NO 211
<211> LENGTH: 100
<212> TYPE: PRT
<213> ORGANISM: Artificial Sequence
<220> FEATURE:
<223> OTHER INFORMATION: Synthetic

<400> SEQUENCE: 211

Met Phe Thr Gly Val Ile Ile Lys Gln Gly Cys Leu Leu Lys Gln Gly
1               5                   10                  15

His Thr Arg Lys Asn Trp Ser Val Arg Lys Phe Ile Leu Arg Glu Asp

```
                    20                  25                  30

Pro Ala Tyr Leu His Tyr Tyr Pro Leu Gly Tyr Phe Ser Pro Leu
            35                  40                  45

Gly Ala Ile His Leu Arg Gly Cys Val Val Thr Ser Val Glu Ser Glu
 50                  55                  60

Glu Asn Leu Phe Glu Ile Ile Thr Ala Asp Glu Val His Tyr Phe Leu
 65                  70                  75                  80

Gln Ala Ala Thr Pro Lys Glu Arg Thr Glu Trp Ile Lys Ala Ile Gln
                85                  90                  95

Met Ala Ser Arg
        100

<210> SEQ ID NO 212
<211> LENGTH: 38
<212> TYPE: PRT
<213> ORGANISM: Artificial Sequence
<220> FEATURE:
<223> OTHER INFORMATION: Synthetic

<400> SEQUENCE: 212

Met Val Leu Val Asn Gln Ser His Gln Gly Phe Asn Lys Glu His Thr
 1               5                  10                  15

Ser Lys Met Val Ser Ala Ile Val Leu Tyr Val Leu Leu Ala Ala Ala
                20                  25                  30

Ala His Ser Ala Phe Ala
        35

<210> SEQ ID NO 213
<211> LENGTH: 17
<212> TYPE: PRT
<213> ORGANISM: Artificial Sequence
<220> FEATURE:
<223> OTHER INFORMATION: Synthetic

<400> SEQUENCE: 213

Gly Gly Gly Leu Asn Asp Ile Phe Glu Ala Gln Lys Ile Glu Trp His
 1               5                  10                  15

Glu

<210> SEQ ID NO 214
<211> LENGTH: 454
<212> TYPE: DNA
<213> ORGANISM: Artificial Sequence
<220> FEATURE:
<223> OTHER INFORMATION: Synthetic

<400> SEQUENCE: 214
gacgattgaa ggtagatacc catacgacgt tccagactac gctctgcagg ctagtggtgg      60
aggaggctct ggtggaggcg gtagcggagg cggagggtcg gctagccata tgcacatgtc     120
caatgctatg gatggtcaac aattgaacag attgttattg gaatggatcg gtgcctggga     180
cccttttggt ttgggtaaag atgcttatga cgtcgaagcc gaagctgttt tacaagcagt     240
atacgaaact gaatctgcat tgatttggc catgagaatt atgtggatct atgttttgc       300 cttcaagaga ccaattcctt tcccacacgc tcaaaaattg gcaagaagat tattggaatt     360
gaagcaagct gcatcttcac ctttaccatt ggaactcgag gggggcggat ccgaacaaaa     420
gcttatttct gaagaggact tgtaatagag atct                                 454

<210> SEQ ID NO 215
```

<211> LENGTH: 331
<212> TYPE: DNA
<213> ORGANISM: Artificial Sequence
<220> FEATURE:
<223> OTHER INFORMATION: Synthetic

<400> SEQUENCE: 215

```
gacgattgaa ggtagatacc catacgacgt tccagactac gctctgcagg ctagtggtgg    60
aggaggctct ggtggaggcg gtagcggagg cggagggtcg gctagccata tggcttctac   120
tagaggttct ggtagaccttg ggggtttttc cgaaaatttg gccttcgaat tggctttaag   180
ttttactaac aaagatacac cagacagatg ggctaaggtt gcacaatatg tatctggtag   240
aacacctgaa gaagttaaaa agcattacga actcgagggg ggcggatccg aacaaaagct   300
tatttctgaa gaggacttgt aatagagatc t                                  331
```

<210> SEQ ID NO 216
<211> LENGTH: 49
<212> TYPE: DNA
<213> ORGANISM: Artificial Sequence
<220> FEATURE:
<223> OTHER INFORMATION: Synthetic

<400> SEQUENCE: 216

```
aatgatacgg cgaccaccga gatctacacc ggctagccat atggcttct              49
```

<210> SEQ ID NO 217
<211> LENGTH: 49
<212> TYPE: DNA
<213> ORGANISM: Artificial Sequence
<220> FEATURE:
<223> OTHER INFORMATION: Synthetic

<400> SEQUENCE: 217

```
caagcagaag acggcatacg agatcaaggt cagatccgcc ccctcgag               49
```

<210> SEQ ID NO 218
<211> LENGTH: 49
<212> TYPE: DNA
<213> ORGANISM: Artificial Sequence
<220> FEATURE:
<223> OTHER INFORMATION: Synthetic

<400> SEQUENCE: 218

```
caagcagaag acggcatacg agatacgtac tcgatccgcc ccctcgag               49
```

<210> SEQ ID NO 219
<211> LENGTH: 49
<212> TYPE: DNA
<213> ORGANISM: Artificial Sequence
<220> FEATURE:
<223> OTHER INFORMATION: Synthetic

<400> SEQUENCE: 219

```
caagcagaag acggcatacg agatcttcta aggatccgcc ccctcgag               49
```

<210> SEQ ID NO 220
<211> LENGTH: 49
<212> TYPE: DNA
<213> ORGANISM: Artificial Sequence
<220> FEATURE:
<223> OTHER INFORMATION: Synthetic

<400> SEQUENCE: 220

```
caagcagaag acggcatacg agatactatg acgatccgcc ccctcgag               49
```

<210> SEQ ID NO 221
<211> LENGTH: 49
<212> TYPE: DNA
<213> ORGANISM: Artificial Sequence
<220> FEATURE:
<223> OTHER INFORMATION: Synthetic

<400> SEQUENCE: 221
caagcagaag acggcatacg agatgacgtt aagatccgcc cccctcgag         49

<210> SEQ ID NO 222
<211> LENGTH: 49
<212> TYPE: DNA
<213> ORGANISM: Artificial Sequence
<220> FEATURE:
<223> OTHER INFORMATION: Synthetic

<400> SEQUENCE: 222
caagcagaag acggcatacg agatacaaga tagatccgcc cccctcgag         49

<210> SEQ ID NO 223
<211> LENGTH: 49
<212> TYPE: DNA
<213> ORGANISM: Artificial Sequence
<220> FEATURE:
<223> OTHER INFORMATION: Synthetic

<400> SEQUENCE: 223
caagcagaag acggcatacg agatgactaa gagatccgcc cccctcgag         49

<210> SEQ ID NO 224
<211> LENGTH: 49
<212> TYPE: DNA
<213> ORGANISM: Artificial Sequence
<220> FEATURE:
<223> OTHER INFORMATION: Synthetic

<400> SEQUENCE: 224
caagcagaag acggcatacg agatgtgtct acgatccgcc cccctcgag         49

<210> SEQ ID NO 225
<211> LENGTH: 49
<212> TYPE: DNA
<213> ORGANISM: Artificial Sequence
<220> FEATURE:
<223> OTHER INFORMATION: Synthetic

<400> SEQUENCE: 225
caagcagaag acggcatacg agatttcact aggatccgcc cccctcgag         49

<210> SEQ ID NO 226
<211> LENGTH: 49
<212> TYPE: DNA
<213> ORGANISM: Artificial Sequence
<220> FEATURE:
<223> OTHER INFORMATION: Synthetic

<400> SEQUENCE: 226
caagcagaag acggcatacg agataatcgg atgatccgcc cccctcgag         49

<210> SEQ ID NO 227
<211> LENGTH: 49
<212> TYPE: DNA
<213> ORGANISM: Artificial Sequence
<220> FEATURE:

<223> OTHER INFORMATION: Synthetic

<400> SEQUENCE: 227
caagcagaag acggcatacg agatagtacc gagatccgcc ccctcgag          49

<210> SEQ ID NO 228
<211> LENGTH: 49
<212> TYPE: DNA
<213> ORGANISM: Artificial Sequence
<220> FEATURE:
<223> OTHER INFORMATION: Synthetic

<400> SEQUENCE: 228
caagcagaag acggcatacg agatgcataa ctgatccgcc ccctcgag          49

<210> SEQ ID NO 229
<211> LENGTH: 49
<212> TYPE: DNA
<213> ORGANISM: Artificial Sequence
<220> FEATURE:
<223> OTHER INFORMATION: Synthetic

<400> SEQUENCE: 229
caagcagaag acggcatacg agatctctga ttgatccgcc ccctcgag          49

<210> SEQ ID NO 230
<211> LENGTH: 49
<212> TYPE: DNA
<213> ORGANISM: Artificial Sequence
<220> FEATURE:
<223> OTHER INFORMATION: Synthetic

<400> SEQUENCE: 230
caagcagaag acggcatacg agatgtagca gtgatccgcc ccctcgag          49

<210> SEQ ID NO 231
<211> LENGTH: 49
<212> TYPE: DNA
<213> ORGANISM: Artificial Sequence
<220> FEATURE:
<223> OTHER INFORMATION: Synthetic

<400> SEQUENCE: 231
caagcagaag acggcatacg agatggatca tcgatccgcc ccctcgag          49

<210> SEQ ID NO 232
<211> LENGTH: 49
<212> TYPE: DNA
<213> ORGANISM: Artificial Sequence
<220> FEATURE:
<223> OTHER INFORMATION: Synthetic

<400> SEQUENCE: 232
caagcagaag acggcatacg agatgtgaac gtgatccgcc ccctcgag          49

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
cggctagcca tatggcttct                                          20

```
<210> SEQ ID NO 234
<211> LENGTH: 27
<212> TYPE: DNA
<213> ORGANISM: Artificial Sequence
<220> FEATURE:
<223> OTHER INFORMATION: Synthetic

<400> SEQUENCE: 234
gtgcaacctt agcccatctg tctggtg                                         27

<210> SEQ ID NO 235
<211> LENGTH: 37
<212> TYPE: DNA
<213> ORGANISM: Artificial Sequence
<220> FEATURE:
<223> OTHER INFORMATION: Synthetic

<400> SEQUENCE: 235
ggccttcgaa ttggctttaa gttttactaa caaagat                              37

<210> SEQ ID NO 236
<211> LENGTH: 17
<212> TYPE: DNA
<213> ORGANISM: Artificial Sequence
<220> FEATURE:
<223> OTHER INFORMATION: Synthetic

<400> SEQUENCE: 236
gatccgcccc cctcgag                                                    17

<210> SEQ ID NO 237
<211> LENGTH: 17
<212> TYPE: DNA
<213> ORGANISM: Artificial Sequence
<220> FEATURE:
<223> OTHER INFORMATION: Synthetic

<400> SEQUENCE: 237
ctcgaggggg gcggatc                                                    17

<210> SEQ ID NO 238
<211> LENGTH: 45
<212> TYPE: DNA
<213> ORGANISM: Artificial Sequence
<220> FEATURE:
<223> OTHER INFORMATION: Synthetic

<400> SEQUENCE: 238
aatgatacgg cgaccaccga gatctacacg atcggtgcct gggac                     45

<210> SEQ ID NO 239
<211> LENGTH: 56
<212> TYPE: DNA
<213> ORGANISM: Artificial Sequence
<220> FEATURE:
<223> OTHER INFORMATION: Synthetic

<400> SEQUENCE: 239
caagcagaag acggcatacg agatttgcct cacagcttgc ttcaattcca ataatc         56

<210> SEQ ID NO 240
<211> LENGTH: 56
<212> TYPE: DNA
<213> ORGANISM: Artificial Sequence
<220> FEATURE:
<223> OTHER INFORMATION: Synthetic
```

```
<400> SEQUENCE: 240
caagcagaag acggcatacg agattcgtta gccagcttgc ttcaattcca ataatc      56

<210> SEQ ID NO 241
<211> LENGTH: 56
<212> TYPE: DNA
<213> ORGANISM: Artificial Sequence
<220> FEATURE:
<223> OTHER INFORMATION: Synthetic

<400> SEQUENCE: 241
caagcagaag acggcatacg agattatagt tccagcttgc ttcaattcca ataatc      56

<210> SEQ ID NO 242
<211> LENGTH: 56
<212> TYPE: DNA
<213> ORGANISM: Artificial Sequence
<220> FEATURE:
<223> OTHER INFORMATION: Synthetic

<400> SEQUENCE: 242
caagcagaag acggcatacg agattggcgt atcagcttgc ttcaattcca ataatc      56

<210> SEQ ID NO 243
<211> LENGTH: 56
<212> TYPE: DNA
<213> ORGANISM: Artificial Sequence
<220> FEATURE:
<223> OTHER INFORMATION: Synthetic

<400> SEQUENCE: 243
caagcagaag acggcatacg agattggaca tgcagcttgc ttcaattcca ataatc      56

<210> SEQ ID NO 244
<211> LENGTH: 56
<212> TYPE: DNA
<213> ORGANISM: Artificial Sequence
<220> FEATURE:
<223> OTHER INFORMATION: Synthetic

<400> SEQUENCE: 244
caagcagaag acggcatacg agataggttg ctcagcttgc ttcaattcca ataatc      56

<210> SEQ ID NO 245
<211> LENGTH: 56
<212> TYPE: DNA
<213> ORGANISM: Artificial Sequence
<220> FEATURE:
<223> OTHER INFORMATION: Synthetic

<400> SEQUENCE: 245
caagcagaag acggcatacg agatatatgc tgcagcttgc ttcaattcca ataatc      56

<210> SEQ ID NO 246
<211> LENGTH: 56
<212> TYPE: DNA
<213> ORGANISM: Artificial Sequence
<220> FEATURE:
<223> OTHER INFORMATION: Synthetic

<400> SEQUENCE: 246
caagcagaag acggcatacg agatgtacag tgcagcttgc ttcaattcca ataatc      56

<210> SEQ ID NO 247
<211> LENGTH: 56
```

```
<212> TYPE: DNA
<213> ORGANISM: Artificial Sequence
<220> FEATURE:
<223> OTHER INFORMATION: Synthetic

<400> SEQUENCE: 247
caagcagaag acggcatacg agataatcct gccagcttgc ttcaattcca ataatc      56

<210> SEQ ID NO 248
<211> LENGTH: 56
<212> TYPE: DNA
<213> ORGANISM: Artificial Sequence
<220> FEATURE:
<223> OTHER INFORMATION: Synthetic

<400> SEQUENCE: 248
caagcagaag acggcatacg agatgttata tccagcttgc ttcaattcca ataatc      56

<210> SEQ ID NO 249
<211> LENGTH: 56
<212> TYPE: DNA
<213> ORGANISM: Artificial Sequence
<220> FEATURE:
<223> OTHER INFORMATION: Synthetic

<400> SEQUENCE: 249
caagcagaag acggcatacg agatacacac gtcagcttgc ttcaattcca ataatc      56

<210> SEQ ID NO 250
<211> LENGTH: 56
<212> TYPE: DNA
<213> ORGANISM: Artificial Sequence
<220> FEATURE:
<223> OTHER INFORMATION: Synthetic

<400> SEQUENCE: 250
caagcagaag acggcatacg agatatacga ctcagcttgc ttcaattcca ataatc      56

<210> SEQ ID NO 251
<211> LENGTH: 56
<212> TYPE: DNA
<213> ORGANISM: Artificial Sequence
<220> FEATURE:
<223> OTHER INFORMATION: Synthetic

<400> SEQUENCE: 251
caagcagaag acggcatacg agatatcttc gtcagcttgc ttcaattcca ataatc      56

<210> SEQ ID NO 252
<211> LENGTH: 56
<212> TYPE: DNA
<213> ORGANISM: Artificial Sequence
<220> FEATURE:
<223> OTHER INFORMATION: Synthetic

<400> SEQUENCE: 252
caagcagaag acggcatacg agatacatgt atcagcttgc ttcaattcca ataatc      56

<210> SEQ ID NO 253
<211> LENGTH: 56
<212> TYPE: DNA
<213> ORGANISM: Artificial Sequence
<220> FEATURE:
<223> OTHER INFORMATION: Synthetic

<400> SEQUENCE: 253
```
caagcagaag acggcatacg agattccaca gtcagcttgc ttcaattcca ataatc        56

<210> SEQ ID NO 254
<211> LENGTH: 56
<212> TYPE: DNA
<213> ORGANISM: Artificial Sequence
<220> FEATURE:
<223> OTHER INFORMATION: Synthetic

<400> SEQUENCE: 254
caagcagaag acggcatacg agatcagtct gtcagcttgc ttcaattcca ataatc        56

<210> SEQ ID NO 255
<211> LENGTH: 16
<212> TYPE: DNA
<213> ORGANISM: Artificial Sequence
<220> FEATURE:
<223> OTHER INFORMATION: Synthetic

<400> SEQUENCE: 255
gatcggtgcc tgggac                                                    16

<210> SEQ ID NO 256
<211> LENGTH: 39
<212> TYPE: DNA
<213> ORGANISM: Artificial Sequence
<220> FEATURE:
<223> OTHER INFORMATION: Synthetic

<400> SEQUENCE: 256
tcttgaaggc aaaaacatag atccacataa ttctcatgg                           39

<210> SEQ ID NO 257
<211> LENGTH: 38
<212> TYPE: DNA
<213> ORGANISM: Artificial Sequence
<220> FEATURE:
<223> OTHER INFORMATION: Synthetic

<400> SEQUENCE: 257
acaagcagta tacgaaactg aatctgcatt tgatttgg                            38

<210> SEQ ID NO 258
<211> LENGTH: 24
<212> TYPE: DNA
<213> ORGANISM: Artificial Sequence
<220> FEATURE:
<223> OTHER INFORMATION: Synthetic

<400> SEQUENCE: 258
cagcttgctt caattccaat aatc                                           24

<210> SEQ ID NO 259
<211> LENGTH: 23
<212> TYPE: DNA
<213> ORGANISM: Artificial Sequence
<220> FEATURE:
<223> OTHER INFORMATION: Synthetic

<400> SEQUENCE: 259
gattattgga attgaagcaa gct                                            23

<210> SEQ ID NO 260
<211> LENGTH: 36
<212> TYPE: DNA
<213> ORGANISM: Artificial Sequence
<220> FEATURE:
<223> OTHER INFORMATION: Synthetic

<400> SEQUENCE: 260
ggacaatagc tcgacgattg aaggtagata cccata         36

<210> SEQ ID NO 261
<211> LENGTH: 30
<212> TYPE: DNA
<213> ORGANISM: Artificial Sequence
<220> FEATURE:
<223> OTHER INFORMATION: Synthetic

<400> SEQUENCE: 261
caagtcctct tcagaaataa gcttttgttc         30

<210> SEQ ID NO 262
<211> LENGTH: 27
<212> TYPE: DNA
<213> ORGANISM: Artificial Sequence
<220> FEATURE:
<223> OTHER INFORMATION: Synthetic

<400> SEQUENCE: 262
tggtctaccg gaacctctgg tggatgc         27

<210> SEQ ID NO 263
<211> LENGTH: 30
<212> TYPE: DNA
<213> ORGANISM: Artificial Sequence
<220> FEATURE:
<223> OTHER INFORMATION: Synthetic

<400> SEQUENCE: 263
actcctgaag aagtcaaaaa gcattacgaa         30

<210> SEQ ID NO 264
<211> LENGTH: 24
<212> TYPE: DNA
<213> ORGANISM: Artificial Sequence
<220> FEATURE:
<223> OTHER INFORMATION: Synthetic

<400> SEQUENCE: 264
ttcgtaatgc ttttgactt cttc         24

<210> SEQ ID NO 265
<211> LENGTH: 159
<212> TYPE: DNA
<213> ORGANISM: Artificial Sequence
<220> FEATURE:
<223> OTHER INFORMATION: Synthetic

<400> SEQUENCE: 265
gcatccacca gaggttccgg tagaccatgg rrgttcarsg aaaacvttrm gtttgaamtt         60
gctttgtmtt ttacgaataa ggacacacca gatagatggr vgaaggttgc ayrstatgta        120
arsggtagaa ctcctgaaga agtcaaaaag cattacgaa        159

<210> SEQ ID NO 266
<211> LENGTH: 24
<212> TYPE: DNA
<213> ORGANISM: Artificial Sequence
<220> FEATURE:
<223> OTHER INFORMATION: Synthetic

<400> SEQUENCE: 266
gtcataggca tctttaccca aacc                                          24

<210> SEQ ID NO 267
<211> LENGTH: 21
<212> TYPE: DNA
<213> ORGANISM: Artificial Sequence
<220> FEATURE:
<223> OTHER INFORMATION: Synthetic

<400> SEQUENCE: 267
catgcccaaa agttggctag a                                             21

<210> SEQ ID NO 268
<211> LENGTH: 22
<212> TYPE: DNA
<213> ORGANISM: Artificial Sequence
<220> FEATURE:
<223> OTHER INFORMATION: Synthetic

<400> SEQUENCE: 268
tctagccaac ttttgggcat gt                                            22

<210> SEQ ID NO 269
<211> LENGTH: 165
<212> TYPE: DNA
<213> ORGANISM: Artificial Sequence
<220> FEATURE:
<223> OTHER INFORMATION: Synthetic

<400> SEQUENCE: 269
ccttttggtt tgggtaaaga tgcctatgac kwtgaagccg mtrvagtttt amaggcagta   60
tacgmgactr amymtgcttt tgacttggca atgagaattm wktggatcta trwttttgcc  120
twtaagagam mgattccttt cvyacatgcc caaaagttgg ctaga                  165

<210> SEQ ID NO 270
<211> LENGTH: 93
<212> TYPE: PRT
<213> ORGANISM: Artificial Sequence
<220> FEATURE:
<223> OTHER INFORMATION: Synthetic

<400> SEQUENCE: 270

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Glu Ala Val Leu Gln Ala Val Tyr Glu Thr Glu Ser Ala
        35                  40                  45

Phe Asp Leu Ala Met Arg Ile Met Trp Ile Tyr Ala Phe Ala Phe Asn
    50                  55                  60

Arg Pro Ile Pro Phe Pro His Ala Gln Lys Leu Ala Arg Arg Leu Leu
65                  70                  75                  80

Glu Leu Lys Gln Ala Ala Ser Ser Pro Leu Pro Leu Glu
            85                  90

<210> SEQ ID NO 271
<211> LENGTH: 93
<212> TYPE: PRT
<213> ORGANISM: Artificial Sequence
<220> FEATURE:
<223> OTHER INFORMATION: Synthetic

<400> SEQUENCE: 271

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Glu Ala Val Leu Gln Ala Val Tyr Glu Thr Glu Asp Ala
        35                  40                  45

Phe Asp Leu Ala Met Arg Ile Met Trp Ile Tyr Val Phe Ala Phe Asn
    50                  55                  60

Arg Pro Ile Pro Phe Pro His Ala Gln Lys Leu Ala Arg Arg Leu Leu
65                  70                  75                  80

Glu Leu Lys Gln Ala Ala Ser Ser Pro Leu Pro Leu Glu
                85                  90

<210> SEQ ID NO 272
<211> LENGTH: 93
<212> TYPE: PRT
<213> ORGANISM: Artificial Sequence
<220> FEATURE:
<223> OTHER INFORMATION: Synthetic

<400> SEQUENCE: 272

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Glu Ala Val Leu Gln Ala Val Tyr Glu Thr Glu Ser Ala
        35                  40                  45

Phe Asp Leu Ala Met Arg Ile Met Trp Ile Tyr Val Phe Ala Phe Asn
    50                  55                  60

Arg Pro Ile Pro Phe Pro His Ala Gln Lys Leu Ala Arg Arg Leu Leu
65                  70                  75                  80

Glu Leu Lys Gln Ala Ala Ser Ser Pro Leu Pro Leu Glu
                85                  90

<210> SEQ ID NO 273
<211> LENGTH: 95
<212> TYPE: PRT
<213> ORGANISM: Artificial Sequence
<220> FEATURE:
<223> OTHER INFORMATION: Synthetic

<400> SEQUENCE: 273

Met Ala Ser Thr Arg Gly Ser Gly Arg Pro Trp Asp Phe Ser Glu Asn
1               5                   10                  15

Leu Ala Phe Glu Leu Ala Leu Ala Phe Met Asn Lys Asp Thr Pro Asp
            20                  25                  30

Arg Trp Ala Asn Val Ala Gln Tyr Val Ser Gly Arg Thr Pro Glu Glu
        35                  40                  45

Val Lys Lys His Tyr Glu Ile Leu Val Glu Asp Ile Lys Tyr Ile Glu
    50                  55                  60

Ser Gly Lys Val Pro Phe Pro Asn Tyr Arg Thr Thr Gly Gly Asn Met
65                  70                  75                  80

Lys Thr Asp Glu Lys Arg Phe Arg Asn Leu Lys Ile Arg Leu Glu
                85                  90                  95

<210> SEQ ID NO 274

<211> LENGTH: 605
<212> TYPE: PRT
<213> ORGANISM: Artificial Sequence
<220> FEATURE:
<223> OTHER INFORMATION: Synthetic

<400> SEQUENCE: 274

```
Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Thr Ile Cys Ile Gly
        35                  40                  45

Tyr His Ala Asn Asn Ser Thr Asp Thr Val Asp Thr Val Leu Glu Lys
    50                  55                  60

Asn Val Thr Val Thr His Ser Val Asn Leu Leu Glu Asp Ser His Asn
65                  70                  75                  80

Gly Lys Leu Cys Arg Leu Lys Gly Ile Ala Pro Leu Gln Leu Gly Asn
                85                  90                  95

Cys Ser Val Ala Gly Trp Ile Leu Gly Asn Pro Glu Cys Glu Leu Leu
            100                 105                 110

Ile Ser Arg Glu Ser Trp Ser Tyr Ile Val Glu Lys Pro Asn Pro Glu
        115                 120                 125

Asn Gly Thr Cys Tyr Pro Gly His Phe Ala Asp Tyr Glu Glu Leu Arg
    130                 135                 140

Glu Gln Leu Ser Ser Val Ser Ser Phe Glu Arg Phe Glu Ile Phe Pro
145                 150                 155                 160

Lys Glu Ser Ser Trp Pro Asn His Thr Thr Thr Gly Val Ser Ala Ser
                165                 170                 175

Cys Ser His Asn Gly Glu Ser Ser Phe Tyr Lys Asn Leu Leu Trp Leu
            180                 185                 190

Thr Gly Lys Asn Gly Leu Tyr Pro Asn Leu Ser Lys Ser Tyr Ala Asn
        195                 200                 205

Asn Lys Glu Lys Glu Val Leu Val Leu Trp Gly Val His His Pro Pro
    210                 215                 220

Asn Ile Gly Asp Gln Arg Ala Leu Tyr His Lys Glu Asn Ala Tyr Val
225                 230                 235                 240

Ser Val Val Ser Ser His Tyr Ser Arg Lys Phe Thr Pro Glu Ile Ala
                245                 250                 255

Lys Arg Pro Lys Val Arg Asp Gln Glu Gly Arg Ile Asn Tyr Tyr Trp
            260                 265                 270

Thr Leu Leu Glu Pro Gly Asp Thr Ile Ile Phe Glu Ala Asn Gly Asn
        275                 280                 285

Leu Ile Ala Pro Arg Tyr Ala Phe Ala Leu Ser Arg Gly Phe Gly Ser
    290                 295                 300

Gly Ile Ile Asn Ser Asn Ala Pro Met Asp Glu Cys Asp Ala Lys Cys
305                 310                 315                 320

Gln Thr Pro Gln Gly Ala Ile Asn Ser Ser Leu Pro Phe Gln Asn Val
                325                 330                 335

His Pro Val Thr Ile Gly Glu Cys Pro Lys Tyr Val Arg Ser Ala Lys
            340                 345                 350

Leu Arg Met Val Thr Gly Leu Arg Asn Ile Pro Ser Ile Gln Ser Arg
        355                 360                 365

Gly Leu Phe Gly Ala Ile Ala Gly Phe Ile Glu Gly Gly Trp Thr Gly
    370                 375                 380
```

```
Met Val Asp Gly Trp Tyr Tyr His His Gln Asn Glu Gln Gly Ser
385                 390                 395                 400

Gly Tyr Ala Ala Asp Gln Lys Ser Thr Gln Asn Ala Ile Asn Gly Ile
        405                 410                 415

Thr Asn Lys Val Asn Ser Val Ile Glu Lys Met Asn Thr Gln Phe Thr
            420                 425                 430

Ala Val Gly Lys Glu Phe Asn Lys Leu Glu Arg Arg Met Glu Asn Leu
        435                 440                 445

Asn Lys Lys Val Asp Asp Gly Phe Ile Asp Ile Trp Thr Tyr Asn Ala
    450                 455                 460

Glu Leu Leu Val Leu Leu Glu Asn Glu Arg Thr Leu Asp Phe His Asp
465                 470                 475                 480

Ser Asn Val Lys Asn Leu Tyr Glu Lys Val Lys Ser Gln Leu Lys Asn
                485                 490                 495

Asn Ala Lys Glu Ile Gly Asn Gly Cys Phe Glu Phe Tyr His Lys Cys
            500                 505                 510

Asn Asp Glu Cys Met Glu Ser Val Lys Asn Gly Thr Tyr Asp Tyr Pro
        515                 520                 525

Lys Tyr Ser Glu Glu Ser Lys Leu Asn Arg Glu Lys Ile Asp Ser Gly
    530                 535                 540

Gly Gly Gly Leu Asn Asp Ile Phe Glu Ala Gln Lys Ile Glu Trp His
545                 550                 555                 560

Glu Arg Leu Val Pro Arg Gly Ser Pro Gly Ser Gly Tyr Ile Pro Glu
                565                 570                 575

Ala Pro Arg Asp Gly Gln Ala Tyr Val Arg Lys Asp Gly Glu Trp Val
            580                 585                 590

Leu Leu Ser Thr Phe Leu Gly His His His His His
        595                 600                 605

<210> SEQ ID NO 275
<211> LENGTH: 604
<212> TYPE: PRT
<213> ORGANISM: Artificial Sequence
<220> FEATURE:
<223> OTHER INFORMATION: Synthetic

<400> SEQUENCE: 275

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Gln Ile Cys Ile Gly
        35                  40                  45

Tyr His Ala Asn Asn Ser Thr Glu Lys Val Asp Thr Ile Leu Glu Arg
    50                  55                  60

Asn Val Thr Val Thr His Ala Lys Asp Ile Leu Glu Lys Thr His Asn
65                  70                  75                  80

Gly Lys Leu Cys Lys Leu Asn Gly Ile Pro Pro Leu Glu Leu Gly Asp
                85                  90                  95

Cys Ser Ile Ala Gly Trp Leu Gly Asn Pro Glu Cys Asp Arg Leu
            100                 105                 110

Leu Ser Val Pro Glu Trp Ser Tyr Ile Met Glu Lys Glu Asn Pro Arg
        115                 120                 125

Asp Gly Leu Cys Tyr Pro Gly Ser Phe Asn Asp Tyr Glu Glu Leu Lys
    130                 135                 140
```

```
His Leu Leu Ser Ser Val Lys His Phe Glu Lys Val Lys Ile Leu Pro
145                 150                 155                 160

Lys Asp Arg Trp Thr Gln His Thr Thr Thr Gly Gly Ser Arg Ala Cys
            165                 170                 175

Ala Val Ser Gly Asn Pro Ser Phe Phe Arg Asn Met Val Trp Leu Thr
        180                 185                 190

Glu Lys Gly Ser Asn Tyr Pro Val Ala Lys Gly Ser Tyr Asn Asn Thr
    195                 200                 205

Ser Gly Glu Gln Met Leu Ile Ile Trp Gly Val His His Pro Asn Asp
210                 215                 220

Glu Thr Glu Gln Arg Thr Leu Tyr Gln Asn Val Gly Thr Tyr Val Ser
225                 230                 235                 240

Val Gly Thr Ser Thr Leu Asn Lys Arg Ser Thr Pro Glu Ile Ala Thr
            245                 250                 255

Arg Pro Lys Val Asn Gly Gln Gly Gly Arg Met Glu Phe Ser Trp Thr
        260                 265                 270

Leu Leu Asp Met Trp Asp Thr Ile Asn Phe Glu Ser Thr Gly Asn Leu
    275                 280                 285

Ile Ala Pro Glu Tyr Gly Phe Lys Ile Ser Lys Arg Gly Ser Ser Gly
290                 295                 300

Ile Met Lys Thr Glu Gly Thr Leu Glu Asn Cys Glu Thr Lys Cys Gln
305                 310                 315                 320

Thr Pro Leu Gly Ala Ile Asn Thr Thr Leu Pro Phe His Asn Val His
            325                 330                 335

Pro Leu Thr Ile Gly Glu Cys Pro Lys Tyr Val Lys Ser Glu Lys Leu
        340                 345                 350

Val Leu Ala Thr Gly Leu Arg Asn Val Pro Gln Ile Glu Ser Arg Gly
    355                 360                 365

Leu Phe Gly Ala Ile Ala Gly Phe Ile Glu Gly Gly Trp Gln Gly Met
370                 375                 380

Val Asp Gly Trp Tyr Gly Tyr His His Ser Asn Asp Gln Gly Ser Gly
385                 390                 395                 400

Tyr Ala Ala Asp Lys Glu Ser Thr Gln Lys Ala Phe Asp Gly Ile Thr
            405                 410                 415

Asn Lys Val Asn Ser Val Ile Glu Lys Met Asn Thr Gln Phe Glu Ala
        420                 425                 430

Val Gly Lys Glu Phe Ser Asn Leu Glu Arg Arg Leu Glu Asn Leu Asn
    435                 440                 445

Lys Lys Met Glu Asp Gly Phe Leu Asp Val Trp Thr Tyr Asn Ala Glu
450                 455                 460

Leu Leu Val Leu Met Glu Asn Glu Arg Thr Leu Asp Phe His Asp Ser
465                 470                 475                 480

Asn Val Lys Asn Leu Tyr Asp Lys Val Arg Met Gln Leu Arg Asp Asn
            485                 490                 495

Val Lys Glu Leu Gly Asn Gly Cys Phe Glu Phe Tyr His Lys Cys Asp
        500                 505                 510

Asp Glu Cys Met Asn Ser Val Lys Asn Gly Thr Tyr Asp Tyr Pro Lys
    515                 520                 525

Tyr Glu Glu Glu Ser Lys Leu Asn Arg Asn Glu Ile Lys Ser Gly Gly
530                 535                 540

Gly Gly Leu Asn Asp Ile Phe Glu Ala Gln Lys Ile Glu Trp His Glu
545                 550                 555                 560
```

```
Arg Leu Val Pro Arg Gly Ser Pro Gly Ser Gly Tyr Ile Pro Glu Ala
                565                 570                 575

Pro Arg Asp Gly Gln Ala Tyr Val Arg Lys Asp Gly Glu Trp Val Leu
            580                 585                 590

Leu Ser Thr Phe Leu Gly His His His His His His
            595                 600

<210> SEQ ID NO 276
<211> LENGTH: 600
<212> TYPE: PRT
<213> ORGANISM: Artificial Sequence
<220> FEATURE:
<223> OTHER INFORMATION: Synthetic

<400> SEQUENCE: 276

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Ala Thr Leu Cys Leu Gly
        35                  40                  45

His His Ala Val Pro Asn Gly Thr Leu Val Lys Thr Ile Thr Asp Asp
    50                  55                  60

Gln Ile Glu Val Thr Asn Ala Thr Glu Leu Val Gln Ser Ser Ser Thr
65                  70                  75                  80

Gly Lys Ile Cys Asn Asn Pro His Arg Ile Leu Asp Gly Ile Asp Cys
                85                  90                  95

Thr Leu Ile Asp Ala Leu Leu Gly Asp Pro His Cys Asp Val Phe Gln
            100                 105                 110

Asn Glu Thr Trp Asp Leu Phe Val Glu Arg Ser Lys Ala Phe Ser Asn
        115                 120                 125

Cys Tyr Pro Tyr Asp Val Pro Asp Tyr Ala Ser Leu Arg Ser Leu Val
    130                 135                 140

Ala Ser Ser Gly Thr Leu Glu Phe Ile Thr Glu Gly Phe Thr Trp Thr
145                 150                 155                 160

Gly Val Thr Gln Asn Gly Gly Ser Asn Ala Cys Lys Arg Gly Pro Gly
                165                 170                 175

Ser Gly Phe Phe Ser Arg Leu Asn Trp Leu Thr Lys Ser Gly Ser Thr
            180                 185                 190

Tyr Pro Val Leu Asn Val Thr Met Pro Asn Asn Asp Asn Phe Asp Lys
        195                 200                 205

Leu Tyr Ile Trp Gly Val His His Pro Ser Thr Asn Gln Glu Gln Thr
    210                 215                 220

Ser Leu Tyr Val Gln Ala Ser Gly Arg Val Thr Val Ser Thr Arg Arg
225                 230                 235                 240

Ser Gln Gln Thr Ile Ile Pro Asn Ile Gly Ser Arg Pro Trp Val Arg
                245                 250                 255

Gly Leu Ser Ser Arg Ile Ser Ile Tyr Trp Thr Ile Val Lys Pro Gly
            260                 265                 270

Asp Val Leu Val Ile Asn Ser Asn Gly Asn Leu Ile Ala Pro Arg Gly
        275                 280                 285

Tyr Phe Lys Met Arg Thr Gly Lys Ser Ser Ile Met Arg Ser Asp Ala
    290                 295                 300

Pro Ile Asp Thr Cys Ile Ser Glu Cys Ile Thr Pro Asn Gly Ser Ile
305                 310                 315                 320
```

Pro Asn Asp Lys Pro Phe Gln Asn Val Asn Lys Ile Thr Tyr Gly Ala
            325                 330                 335

Cys Pro Lys Tyr Val Lys Gln Asn Thr Leu Lys Leu Ala Thr Gly Met
        340                 345                 350

Arg Asn Val Pro Glu Lys Gln Thr Arg Gly Leu Phe Gly Ala Ile Ala
            355                 360                 365

Gly Phe Ile Glu Asn Gly Trp Glu Gly Met Ile Asp Gly Trp Tyr Gly
370                 375                 380

Phe Arg His Gln Asn Ser Glu Gly Thr Gly Gln Ala Ala Asp Leu Lys
385                 390                 395                 400

Ser Thr Gln Ala Ala Ile Asp Gln Ile Asn Gly Lys Leu Asn Arg Val
                405                 410                 415

Ile Glu Lys Thr Asn Glu Lys Phe His Gln Ile Glu Lys Glu Phe Ser
            420                 425                 430

Glu Val Glu Gly Arg Ile Gln Asp Leu Glu Lys Tyr Val Glu Asp Thr
        435                 440                 445

Lys Ile Asp Leu Trp Ser Tyr Asn Ala Glu Leu Leu Val Ala Leu Glu
450                 455                 460

Asn Gln His Thr Ile Asp Leu Thr Asp Ser Glu Met Asn Lys Leu Phe
465                 470                 475                 480

Glu Lys Thr Gly Arg Gln Leu Arg Glu Asn Ala Glu Asp Met Gly Asn
                485                 490                 495

Gly Cys Phe Lys Ile Tyr His Lys Cys Asp Asn Ala Cys Ile Glu Ser
            500                 505                 510

Ile Arg Asn Gly Thr Tyr Asp His Asp Val Tyr Arg Asp Glu Ala Leu
        515                 520                 525

Asn Asn Arg Phe Gln Ile Lys Gly Val Ser Gly Gly Gly Leu Asn
530                 535                 540

Asp Ile Phe Glu Ala Gln Lys Ile Glu Trp His Glu Arg Leu Val Pro
545                 550                 555                 560

Arg Gly Ser Pro Gly Ser Gly Tyr Ile Pro Glu Ala Pro Arg Asp Gly
                565                 570                 575

Gln Ala Tyr Val Arg Lys Asp Gly Glu Trp Val Leu Leu Ser Thr Phe
            580                 585                 590

Leu Gly His His His His His His
        595                 600

<210> SEQ ID NO 277
<211> LENGTH: 325
<212> TYPE: PRT
<213> ORGANISM: Artificial Sequence
<220> FEATURE:
<223> OTHER INFORMATION: Synthetic

<400> SEQUENCE: 277

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Pro Val Ile Cys Met Gly
        35                  40                  45

His His Ala Val Ala Asn Gly Thr Met Val Lys Thr Leu Ala Asp Asp
    50                  55                  60

Gln Val Glu Val Val Thr Ala Gln Glu Leu Val Glu Ser Gln Asn Leu
65                  70                  75                  80

Pro Glu Leu Cys Pro Ser Pro Leu Arg Leu Val Asp Gly Gln Thr Cys
            85                  90                  95

Asp Ile Ile Asn Gly Ala Leu Gly Ser Pro Gly Cys Asp His Leu Asn
            100                 105                 110

Gly Ala Glu Trp Asp Val Phe Ile Glu Arg Pro Asn Ala Val Asp Thr
            115                 120                 125

Cys Tyr Pro Phe Asp Val Pro Glu Tyr Gln Ser Leu Arg Ser Ile Leu
            130                 135                 140

Ala Asn Asn Gly Lys Phe Glu Phe Ile Ala Glu Phe Gln Trp Asn
145                 150                 155                 160

Thr Val Lys Gln Asn Gly Lys Ser Gly Ala Cys Lys Arg Ala Asn Val
            165                 170                 175

Asn Asp Phe Phe Asn Arg Leu Asn Trp Leu Val Lys Ser Asp Gly Asn
            180                 185                 190

Ala Tyr Pro Leu Gln Asn Leu Thr Lys Ile Asn Asn Gly Asp Tyr Ala
            195                 200                 205

Arg Leu Tyr Ile Trp Gly Val His His Pro Ser Thr Asp Thr Glu Gln
            210                 215                 220

Thr Asn Leu Tyr Lys Asn Asn Pro Gly Arg Val Thr Val Ser Thr Lys
225                 230                 235                 240

Thr Ser Gln Thr Ser Val Val Pro Asn Ile Gly Ser Arg Pro Leu Val
            245                 250                 255

Arg Gly Gln Ser Gly Arg Val Ser Phe Tyr Trp Thr Ile Val Glu Pro
            260                 265                 270

Gly Asp Leu Ile Val Phe Asn Thr Ile Gly Asn Leu Ile Ala Pro Arg
            275                 280                 285

Gly His Tyr Lys Leu Asn Asn Gln Lys Lys Ser Thr Ile Leu Asn Thr
            290                 295                 300

Ala Ile Pro Ile Gly Ser Cys Val Ser Lys Cys His Thr Asp Lys Gly
305                 310                 315                 320

Ser Leu Ser Thr Thr
            325

<210> SEQ ID NO 278
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is D, I or P
<220> FEATURE:
<221> NAME/KEY: MISC_FEATURE
<222> LOCATION: (4)..(4)
<223> OTHER INFORMATION: X is Q or P
<220> FEATURE:
<221> NAME/KEY: MISC_FEATURE
<222> LOCATION: (15)..(15)
<223> OTHER INFORMATION: X is Q or L

<400> SEQUENCE: 278

Xaa His Ala Xaa Lys Leu Ala Arg Arg Leu Leu Glu Leu Lys Xaa Ala
1               5                   10                  15

Ala Ser Ser Pro Leu Pro
            20

<210> SEQ ID NO 279
<211> LENGTH: 46

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (36)..(36)
<223> OTHER INFORMATION: X is A or D
<220> FEATURE:
<221> NAME/KEY: MISC_FEATURE
<222> LOCATION: (40)..(40)
<223> OTHER INFORMATION: X is Q or K
<220> FEATURE:
<221> NAME/KEY: MISC_FEATURE
<222> LOCATION: (44)..(44)
<223> OTHER INFORMATION: X is E or A

<400> SEQUENCE: 279

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Phe Glu Ala Xaa Glu Val Leu Xaa Ala Val Tyr Xaa Thr Glu
        35                  40                  45

<210> SEQ ID NO 280
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is M or is absent

<400> SEQUENCE: 280

Xaa Ala Ser Thr Arg Gly Ser Gly Arg Pro Trp Asn
1               5                   10

<210> SEQ ID NO 281
<211> LENGTH: 17
<212> TYPE: PRT
<213> ORGANISM: Artificial Sequence
<220> FEATURE:
<223> OTHER INFORMATION: Synthetic

<400> SEQUENCE: 281

His Ala Phe Asp Leu Ala Met Arg Ile His Trp Ile Tyr Asn Phe Ala
1               5                   10                  15

Phe

<210> SEQ ID NO 282
<211> LENGTH: 17
<212> TYPE: PRT
<213> ORGANISM: Artificial Sequence
<220> FEATURE:
<223> OTHER INFORMATION: Synthetic

<400> SEQUENCE: 282

Ser Ala Phe Asp Leu Ala Met Arg Ile Met Trp Ile Tyr Val Phe Ala
1               5                   10                  15

Tyr

<210> SEQ ID NO 283
<211> LENGTH: 17
<212> TYPE: PRT
```

<213> ORGANISM: Artificial Sequence
<220> FEATURE:
<223> OTHER INFORMATION: Synthetic

<400> SEQUENCE: 283

His Ala Phe Asp Leu Ala Met Arg Ile Met Trp Ile Tyr Val Phe Ala
1               5                   10                  15

Tyr

<210> SEQ ID NO 284
<211> LENGTH: 23
<212> TYPE: PRT
<213> ORGANISM: Artificial Sequence
<220> FEATURE:
<223> OTHER INFORMATION: Synthetic

<400> SEQUENCE: 284

His Ala Phe Asp Leu Ala Met Arg Ile His Trp Ile Tyr Asn Phe Ala
1               5                   10                  15

Phe Lys Arg Lys Ile Pro Phe
            20

<210> SEQ ID NO 285
<211> LENGTH: 38
<212> TYPE: PRT
<213> ORGANISM: Artificial Sequence
<220> FEATURE:
<223> OTHER INFORMATION: Synthetic

<400> SEQUENCE: 285

Tyr Glu Ala Ala Glu Val Leu Lys Ala Val Tyr Glu Thr Glu Ser Ala
1               5                   10                  15

Phe Asp Leu Ala Met Arg Ile His Trp Ile Tyr Asn Phe Ala Phe Lys
            20                  25                  30

Arg Pro Ile Pro Phe Pro
        35

<210> SEQ ID NO 286
<211> LENGTH: 38
<212> TYPE: PRT
<213> ORGANISM: Artificial Sequence
<220> FEATURE:
<223> OTHER INFORMATION: Synthetic

<400> SEQUENCE: 286

Asp Glu Ala Ala Arg Val Leu Lys Ala Val Tyr Glu Thr Asp Ser Ala
1               5                   10                  15

Phe Asp Leu Ala Met Arg Ile His Trp Ile Tyr Asn Phe Ala Phe Lys
            20                  25                  30

Arg Pro Ile Pro Phe Pro
        35

<210> SEQ ID NO 287
<211> LENGTH: 38
<212> TYPE: PRT
<213> ORGANISM: Artificial Sequence
<220> FEATURE:
<223> OTHER INFORMATION: Synthetic

<400> SEQUENCE: 287

Tyr Glu Ala Asp Glu Val Leu Lys Ala Val Tyr Glu Thr Asn Ser Ala
1               5                   10                  15

Phe Asp Leu Ala Met Arg Ile His Trp Ile Tyr Asn Phe Ala Phe Lys

```
                20                  25                  30

Arg Pro Ile Pro Phe Pro
        35

<210> SEQ ID NO 288
<211> LENGTH: 37
<212> TYPE: PRT
<213> ORGANISM: Artificial Sequence
<220> FEATURE:
<223> OTHER INFORMATION: Synthetic

<400> SEQUENCE: 288

Val Glu Ala Ala Arg Val Leu Gln Ala Val Tyr Glu Thr Asn Ser Ala
1               5                   10                  15

Phe Asp Leu Ala Met Arg Ile Trp Ile Tyr Asn Phe Ala Phe Lys Arg
            20                  25                  30

Pro Ile Pro Phe Pro
        35

<210> SEQ ID NO 289
<211> LENGTH: 38
<212> TYPE: PRT
<213> ORGANISM: Artificial Sequence
<220> FEATURE:
<223> OTHER INFORMATION: Synthetic

<400> SEQUENCE: 289

Val Glu Ala Asp Lys Val Leu Gln Ala Val Tyr Glu Thr Asn Ser Ala
1               5                   10                  15

Phe Asp Leu Ala Met Arg Ile His Trp Ile Tyr Asn Phe Ala Phe Lys
            20                  25                  30

Arg Pro Ile Pro Phe Pro
        35

<210> SEQ ID NO 290
<211> LENGTH: 38
<212> TYPE: PRT
<213> ORGANISM: Artificial Sequence
<220> FEATURE:
<223> OTHER INFORMATION: Synthetic

<400> SEQUENCE: 290

Val Glu Ala Asp Ala Val Leu Lys Ala Val Tyr Ala Thr Asn Ser Ala
1               5                   10                  15

Phe Asp Leu Ala Met Arg Ile His Trp Ile Tyr Asn Phe Ala Phe Lys
            20                  25                  30

Arg Pro Ile Pro Phe Pro
        35

<210> SEQ ID NO 291
<211> LENGTH: 38
<212> TYPE: PRT
<213> ORGANISM: Artificial Sequence
<220> FEATURE:
<223> OTHER INFORMATION: Synthetic

<400> SEQUENCE: 291

Tyr Glu Ala Ala Glu Val Leu Lys Ala Val Tyr Glu Thr Glu His Ala
1               5                   10                  15

Phe Asp Leu Ala Met Arg Ile His Trp Ile Tyr Asn Phe Ala Phe Lys
            20                  25                  30

Arg Pro Ile Pro Phe Pro
```

<210> SEQ ID NO 292
<211> LENGTH: 38
<212> TYPE: PRT
<213> ORGANISM: Artificial Sequence
<220> FEATURE:
<223> OTHER INFORMATION: Synthetic

<400> SEQUENCE: 292

Tyr Glu Ala Ala Glu Val Leu Glu Ala Val Tyr Glu Thr Glu Ser Ala
1               5                   10                  15

Phe Asp Leu Ala Met Arg Ile His Trp Ile Tyr Asn Phe Ala Phe Lys
            20                  25                  30

Arg Pro Ile Pro Phe Pro
        35

<210> SEQ ID NO 293
<211> LENGTH: 38
<212> TYPE: PRT
<213> ORGANISM: Artificial Sequence
<220> FEATURE:
<223> OTHER INFORMATION: Synthetic

<400> SEQUENCE: 293

Tyr Glu Ala Ala Glu Val Leu Lys Ala Val Tyr Glu Thr Glu Ser Ala
1               5                   10                  15

Phe Asp Leu Ala Met Arg Ile His Trp Ile Tyr Asn Phe Ala Phe Lys
            20                  25                  30

Arg Pro Ile Pro Phe Pro
        35

<210> SEQ ID NO 294
<211> LENGTH: 94
<212> TYPE: PRT
<213> ORGANISM: Artificial Sequence
<220> FEATURE:
<223> OTHER INFORMATION: Synthetic

<400> SEQUENCE: 294

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Tyr Glu Ala Ala Glu Val Leu Lys Ala Val Tyr Glu Thr Glu Ser Ala
            35                  40                  45

Phe Asp Leu Ala Met Arg Ile His Trp Ile Tyr Asn Phe Ala Phe Lys
        50                  55                  60

Arg Pro Ile Pro Phe Pro His Ala Gln Lys Leu Ala Arg Arg Leu
65                  70                  75                  80

Leu Glu Leu Lys Gln Ala Ala Ser Ser Pro Leu Pro Leu Glu
                85                  90

<210> SEQ ID NO 295
<211> LENGTH: 94
<212> TYPE: PRT
<213> ORGANISM: Artificial Sequence
<220> FEATURE:
<223> OTHER INFORMATION: Synthetic

<400> SEQUENCE: 295

Met Ser Asn Ala Met Asp Gly Gln Gln Leu Asn Arg Leu Leu Leu Glu

```
 1               5                   10                  15
Trp Ile Gly Ala Trp Asp Pro Phe Gly Leu Gly Lys Asp Ala Tyr Asp
            20                  25                  30

Asp Glu Ala Ala Arg Val Leu Lys Ala Val Tyr Glu Thr Asp Ser Ala
            35                  40                  45

Phe Asp Leu Ala Met Arg Ile His Trp Ile Tyr Asn Phe Ala Phe Lys
            50                  55                  60

Arg Pro Ile Pro Phe Pro Pro His Ala Gln Lys Leu Ala Arg Arg Leu
65                  70                  75                  80

Leu Glu Leu Lys Gln Ala Ala Ser Ser Pro Leu Pro Leu Glu
                85                  90

<210> SEQ ID NO 296
<211> LENGTH: 94
<212> TYPE: PRT
<213> ORGANISM: Artificial Sequence
<220> FEATURE:
<223> OTHER INFORMATION: Synthetic

<400> SEQUENCE: 296

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Tyr Glu Ala Asp Glu Val Leu Lys Ala Val Tyr Glu Thr Asn Ser Ala
            35                  40                  45

Phe Asp Leu Ala Met Arg Ile His Trp Ile Tyr Asn Phe Ala Phe Lys
            50                  55                  60

Arg Pro Ile Pro Phe Pro Pro His Ala Gln Lys Leu Ala Arg Arg Leu
65                  70                  75                  80

Leu Glu Leu Lys Gln Ala Ala Ser Ser Pro Leu Pro Leu Glu
                85                  90

<210> SEQ ID NO 297
<211> LENGTH: 93
<212> TYPE: PRT
<213> ORGANISM: Artificial Sequence
<220> FEATURE:
<223> OTHER INFORMATION: Synthetic

<400> SEQUENCE: 297

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Ala Arg Val Leu Gln Ala Val Tyr Glu Thr Asn Ser Ala
            35                  40                  45

Phe Asp Leu Ala Met Arg Ile Trp Ile Tyr Asn Phe Ala Phe Lys Arg
            50                  55                  60

Pro Ile Pro Phe Pro Pro His Ala Gln Lys Leu Ala Arg Arg Leu Leu
65                  70                  75                  80

Glu Leu Lys Gln Ala Ala Ser Ser Pro Leu Pro Leu Glu
                85                  90

<210> SEQ ID NO 298
<211> LENGTH: 94
<212> TYPE: PRT
<213> ORGANISM: Artificial Sequence
<220> FEATURE:
```

<223> OTHER INFORMATION: Synthetic

<400> SEQUENCE: 298

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Asp Lys Val Leu Gln Ala Val Tyr Glu Thr Asn Ser Ala
        35                  40                  45

Phe Asp Leu Ala Met Arg Ile His Trp Ile Tyr Asn Phe Ala Phe Lys
    50                  55                  60

Arg Pro Ile Pro Phe Pro Pro His Ala Gln Lys Leu Ala Arg Arg Leu
65                  70                  75                  80

Leu Glu Leu Lys Gln Ala Ala Ser Ser Pro Leu Pro Leu Glu
                85                  90

<210> SEQ ID NO 299
<211> LENGTH: 94
<212> TYPE: PRT
<213> ORGANISM: Artificial Sequence
<220> FEATURE:
<223> OTHER INFORMATION: Synthetic

<400> SEQUENCE: 299

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Val Glu Ala Asp Ala Val Leu Lys Ala Val Tyr Ala Thr Asn Ser Ala
        35                  40                  45

Phe Asp Leu Ala Met Arg Ile His Trp Ile Tyr Asn Phe Ala Phe Lys
    50                  55                  60

Arg Pro Ile Pro Phe Pro Pro His Ala Gln Lys Leu Ala Arg Arg Leu
65                  70                  75                  80

Leu Glu Leu Lys Gln Ala Ala Ser Ser Pro Leu Pro Leu Glu
                85                  90

<210> SEQ ID NO 300
<211> LENGTH: 94
<212> TYPE: PRT
<213> ORGANISM: Artificial Sequence
<220> FEATURE:
<223> OTHER INFORMATION: Synthetic

<400> SEQUENCE: 300

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Tyr Glu Ala Ala Glu Val Leu Lys Ala Val Tyr Glu Thr Glu His Ala
        35                  40                  45

Phe Asp Leu Ala Met Arg Ile His Trp Ile Tyr Asn Phe Ala Phe Lys
    50                  55                  60

Arg Pro Ile Pro Phe Pro Pro His Ala Gln Lys Leu Ala Arg Arg Leu
65                  70                  75                  80

Leu Glu Leu Lys Gln Ala Ala Ser Ser Pro Leu Pro Leu Glu
                85                  90

```
<210> SEQ ID NO 301
<211> LENGTH: 94
<212> TYPE: PRT
<213> ORGANISM: Artificial Sequence
<220> FEATURE:
<223> OTHER INFORMATION: Synthetic

<400> SEQUENCE: 301

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Tyr Glu Ala Ala Glu Val Leu Glu Ala Val Tyr Glu Thr Glu Ser Ala
        35                  40                  45

Phe Asp Leu Ala Met Arg Ile His Trp Ile Tyr Asn Phe Ala Phe Lys
    50                  55                  60

Arg Pro Ile Pro Phe Pro Pro His Ala Gln Lys Leu Ala Arg Arg Leu
65                  70                  75                  80

Leu Glu Leu Lys Gln Ala Ala Ser Ser Pro Leu Pro Leu Glu
                85                  90

<210> SEQ ID NO 302
<211> LENGTH: 94
<212> TYPE: PRT
<213> ORGANISM: Artificial Sequence
<220> FEATURE:
<223> OTHER INFORMATION: Synthetic

<400> SEQUENCE: 302

Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
            20                  25                  30

Tyr Glu Ala Ala Glu Val Leu Lys Ala Val Tyr Glu Thr Glu Ser Ala
        35                  40                  45

Phe Asp Leu Ala Met Arg Ile His Trp Ile Tyr Asn Phe Ala Phe Lys
    50                  55                  60

Arg Pro Ile Pro Phe Pro Pro His Ala Gln Lys Leu Ala Arg Arg Leu
65                  70                  75                  80

Leu Glu Leu Lys Gln Ala Ala Ser Ser Pro Leu Pro Leu Glu
                85                  90

<210> SEQ ID NO 303
<211> LENGTH: 13
<212> TYPE: PRT
<213> ORGANISM: Artificial Sequence
<220> FEATURE:
<223> OTHER INFORMATION: Synthetic

<400> SEQUENCE: 303

Phe Ser Glu Asn Val Ala Phe Glu Leu Ala Leu Tyr Phe
1               5                   10

<210> SEQ ID NO 304
<211> LENGTH: 13
<212> TYPE: PRT
<213> ORGANISM: Artificial Sequence
<220> FEATURE:
<223> OTHER INFORMATION: Synthetic

<400> SEQUENCE: 304

Phe Ser Glu Asn Val Ala Phe Glu Ile Ala Leu Ser Phe
```

```
1               5                   10
```

<210> SEQ ID NO 305
<211> LENGTH: 13
<212> TYPE: PRT
<213> ORGANISM: Artificial Sequence
<220> FEATURE:
<223> OTHER INFORMATION: Synthetic

<400> SEQUENCE: 305

```
Phe Ser Glu Asn Ile Ala Phe Glu Ile Ala Leu Ser Phe
1               5                   10
```

<210> SEQ ID NO 306
<211> LENGTH: 13
<212> TYPE: PRT
<213> ORGANISM: Artificial Sequence
<220> FEATURE:
<223> OTHER INFORMATION: Synthetic

<400> SEQUENCE: 306

```
Phe Ser Glu Asn Val Ala Phe Glu Ile Ala Leu Ser Phe
1               5                   10
```

<210> SEQ ID NO 307
<211> LENGTH: 13
<212> TYPE: PRT
<213> ORGANISM: Artificial Sequence
<220> FEATURE:
<223> OTHER INFORMATION: Synthetic

<400> SEQUENCE: 307

```
Phe Ser Glu Asn Ile Ala Phe Glu Leu Ala Leu Ser Phe
1               5                   10
```

<210> SEQ ID NO 308
<211> LENGTH: 13
<212> TYPE: PRT
<213> ORGANISM: Artificial Sequence
<220> FEATURE:
<223> OTHER INFORMATION: Synthetic

<400> SEQUENCE: 308

```
Phe Ser Glu Asn Ile Ala Phe Glu Leu Ala Leu Tyr Phe
1               5                   10
```

<210> SEQ ID NO 309
<211> LENGTH: 13
<212> TYPE: PRT
<213> ORGANISM: Artificial Sequence
<220> FEATURE:
<223> OTHER INFORMATION: Synthetic

<400> SEQUENCE: 309

```
Phe Ser Glu Asn Leu Ala Phe Glu Leu Ala Leu Ser Phe
1               5                   10
```

<210> SEQ ID NO 310
<211> LENGTH: 31
<212> TYPE: PRT
<213> ORGANISM: Artificial Sequence
<220> FEATURE:
<223> OTHER INFORMATION: Synthetic

<400> SEQUENCE: 310

```
Lys Phe Ser Glu Asn Val Ala Phe Glu Leu Ala Leu Tyr Phe Thr Asn
1               5                   10                  15
```

Lys Asp Thr Pro Asp Arg Trp Ala Lys Val Ala Arg Tyr Val Lys
            20                  25                  30

<210> SEQ ID NO 311
<211> LENGTH: 31
<212> TYPE: PRT
<213> ORGANISM: Artificial Sequence
<220> FEATURE:
<223> OTHER INFORMATION: Synthetic

<400> SEQUENCE: 311

Arg Phe Ser Glu Asn Val Ala Phe Glu Ile Ala Leu Ser Phe Thr Asn
1               5                   10                  15

Lys Asp Thr Pro Asp Arg Trp Arg Lys Val Ala Arg Tyr Val Arg
            20                  25                  30

<210> SEQ ID NO 312
<211> LENGTH: 31
<212> TYPE: PRT
<213> ORGANISM: Artificial Sequence
<220> FEATURE:
<223> OTHER INFORMATION: Synthetic

<400> SEQUENCE: 312

Lys Phe Ser Glu Asn Val Ala Phe Glu Ile Ala Leu Ser Phe Thr Asn
1               5                   10                  15

Lys Asp Thr Pro Asp Arg Trp Lys Lys Val Ala Arg Tyr Val Arg
            20                  25                  30

<210> SEQ ID NO 313
<211> LENGTH: 31
<212> TYPE: PRT
<213> ORGANISM: Artificial Sequence
<220> FEATURE:
<223> OTHER INFORMATION: Synthetic

<400> SEQUENCE: 313

Lys Phe Ser Glu Asn Val Ala Phe Glu Ile Ala Leu Ser Phe Thr Asn
1               5                   10                  15

Lys Asp Thr Pro Asp Arg Trp Thr Lys Val Ala Arg Tyr Val Arg
            20                  25                  30

<210> SEQ ID NO 314
<211> LENGTH: 31
<212> TYPE: PRT
<213> ORGANISM: Artificial Sequence
<220> FEATURE:
<223> OTHER INFORMATION: Synthetic

<400> SEQUENCE: 314

Lys Phe Ser Glu Asn Val Ala Phe Glu Ile Ala Leu Ser Phe Thr Asn
1               5                   10                  15

Lys Asp Thr Pro Asp Arg Trp Ala Lys Val Ala Tyr Tyr Val Arg
            20                  25                  30

<210> SEQ ID NO 315
<211> LENGTH: 31
<212> TYPE: PRT
<213> ORGANISM: Artificial Sequence
<220> FEATURE:
<223> OTHER INFORMATION: Synthetic

<400> SEQUENCE: 315

Lys Phe Ser Glu Asn Ile Ala Phe Glu Ile Ala Leu Ser Phe Thr Asn

```
1               5                   10                  15
Lys Asp Thr Pro Asp Arg Trp Lys Lys Val Ala Ser Tyr Val Lys
            20                  25                  30

<210> SEQ ID NO 316
<211> LENGTH: 31
<212> TYPE: PRT
<213> ORGANISM: Artificial Sequence
<220> FEATURE:
<223> OTHER INFORMATION: Synthetic

<400> SEQUENCE: 316

Lys Phe Ser Glu Asn Ile Ala Phe Glu Ile Ala Leu Ser Phe Thr Asn
1               5                   10                  15
Lys Asp Thr Pro Asp Arg Trp Lys Lys Val Ala Pro Tyr Val Lys
            20                  25                  30

<210> SEQ ID NO 317
<211> LENGTH: 31
<212> TYPE: PRT
<213> ORGANISM: Artificial Sequence
<220> FEATURE:
<223> OTHER INFORMATION: Synthetic

<400> SEQUENCE: 317

Lys Phe Ser Glu Asn Ile Ala Phe Glu Ile Ala Leu Ser Phe Thr Asn
1               5                   10                  15
Lys Asp Thr Pro Asp Arg Trp Lys Lys Val Ala Tyr Tyr Val Lys
            20                  25                  30

<210> SEQ ID NO 318
<211> LENGTH: 31
<212> TYPE: PRT
<213> ORGANISM: Artificial Sequence
<220> FEATURE:
<223> OTHER INFORMATION: Synthetic

<400> SEQUENCE: 318

Arg Phe Ser Glu Asn Val Ala Phe Glu Ile Ala Leu Ser Phe Thr Asn
1               5                   10                  15
Lys Asp Thr Pro Asp Arg Trp Arg Lys Val Ala Arg Tyr Val Arg
            20                  25                  30

<210> SEQ ID NO 319
<211> LENGTH: 31
<212> TYPE: PRT
<213> ORGANISM: Artificial Sequence
<220> FEATURE:
<223> OTHER INFORMATION: Synthetic

<400> SEQUENCE: 319

Arg Phe Ser Glu Asn Val Ala Phe Glu Ile Ala Leu Ser Phe Thr Asn
1               5                   10                  15
Lys Asp Thr Pro Asp Arg Trp Ala Lys Val Ala Tyr Tyr Val Arg
            20                  25                  30

<210> SEQ ID NO 320
<211> LENGTH: 31
<212> TYPE: PRT
<213> ORGANISM: Artificial Sequence
<220> FEATURE:
<223> OTHER INFORMATION: Synthetic

<400> SEQUENCE: 320
```

-continued

Lys Phe Ser Glu Asn Val Ala Phe Glu Ile Ala Leu Ser Phe Thr Asn
1               5                   10                  15

Lys Asp Thr Pro Asp Arg Trp Ala Lys Val Ala Tyr Tyr Val Arg
                20                  25                  30

<210> SEQ ID NO 321
<211> LENGTH: 31
<212> TYPE: PRT
<213> ORGANISM: Artificial Sequence
<220> FEATURE:
<223> OTHER INFORMATION: Synthetic

<400> SEQUENCE: 321

Asn Phe Ser Glu Asn Ile Ala Phe Glu Leu Ala Leu Ser Phe Thr Asn
1               5                   10                  15

Lys Asp Thr Pro Asp Arg Trp Lys Lys Val Ala Arg Tyr Val Lys
                20                  25                  30

<210> SEQ ID NO 322
<211> LENGTH: 31
<212> TYPE: PRT
<213> ORGANISM: Artificial Sequence
<220> FEATURE:
<223> OTHER INFORMATION: Synthetic

<400> SEQUENCE: 322

Lys Phe Ser Glu Asn Ile Ala Phe Glu Leu Ala Leu Tyr Phe Thr Asn
1               5                   10                  15

Lys Asp Thr Pro Asp Arg Trp Lys Lys Val Ala Arg Tyr Val Lys
                20                  25                  30

<210> SEQ ID NO 323
<211> LENGTH: 31
<212> TYPE: PRT
<213> ORGANISM: Artificial Sequence
<220> FEATURE:
<223> OTHER INFORMATION: Synthetic

<400> SEQUENCE: 323

Arg Phe Ser Glu Asn Leu Ala Phe Glu Leu Ala Leu Ser Phe Thr Asn
1               5                   10                  15

Lys Asp Thr Pro Asp Arg Trp Arg Lys Val Ala Gln Tyr Val Arg
                20                  25                  30

<210> SEQ ID NO 324
<211> LENGTH: 54
<212> TYPE: PRT
<213> ORGANISM: Artificial Sequence
<220> FEATURE:
<223> OTHER INFORMATION: Synthetic

<400> SEQUENCE: 324

Met Ala Ser Thr Arg Gly Ser Gly Arg Pro Trp Lys Phe Ser Glu Asn
1               5                   10                  15

Val Ala Phe Glu Leu Ala Leu Tyr Phe Thr Asn Lys Asp Thr Pro Asp
                20                  25                  30

Arg Trp Ala Lys Val Ala Arg Tyr Val Lys Gly Arg Thr Pro Glu Glu
            35                  40                  45

Val Lys Lys His Tyr Glu
    50

<210> SEQ ID NO 325
<211> LENGTH: 54

```
<212> TYPE: PRT
<213> ORGANISM: Artificial Sequence
<220> FEATURE:
<223> OTHER INFORMATION: Synthetic

<400> SEQUENCE: 325

Met Ala Ser Thr Arg Gly Ser Gly Arg Pro Trp Arg Phe Ser Glu Asn
1               5                   10                  15

Val Ala Phe Glu Ile Ala Leu Ser Phe Thr Asn Lys Asp Thr Pro Asp
                20                  25                  30

Arg Trp Arg Lys Val Ala Arg Tyr Val Arg Gly Arg Thr Pro Glu Glu
            35                  40                  45

Val Lys Lys His Tyr Glu
        50

<210> SEQ ID NO 326
<211> LENGTH: 54
<212> TYPE: PRT
<213> ORGANISM: Artificial Sequence
<220> FEATURE:
<223> OTHER INFORMATION: Synthetic

<400> SEQUENCE: 326

Met Ala Ser Thr Arg Gly Ser Gly Arg Pro Trp Lys Phe Ser Glu Asn
1               5                   10                  15

Val Ala Phe Glu Ile Ala Leu Ser Phe Thr Asn Lys Asp Thr Pro Asp
                20                  25                  30

Arg Trp Lys Lys Val Ala Arg Tyr Val Arg Gly Arg Thr Pro Glu Glu
            35                  40                  45

Val Lys Lys His Tyr Glu
        50

<210> SEQ ID NO 327
<211> LENGTH: 54
<212> TYPE: PRT
<213> ORGANISM: Artificial Sequence
<220> FEATURE:
<223> OTHER INFORMATION: Synthetic

<400> SEQUENCE: 327

Met Ala Ser Thr Arg Gly Ser Gly Arg Pro Trp Lys Phe Ser Glu Asn
1               5                   10                  15

Val Ala Phe Glu Ile Ala Leu Ser Phe Thr Asn Lys Asp Thr Pro Asp
                20                  25                  30

Arg Trp Thr Lys Val Ala Arg Tyr Val Arg Gly Arg Thr Pro Glu Glu
            35                  40                  45

Val Lys Lys His Tyr Glu
        50

<210> SEQ ID NO 328
<211> LENGTH: 54
<212> TYPE: PRT
<213> ORGANISM: Artificial Sequence
<220> FEATURE:
<223> OTHER INFORMATION: Synthetic

<400> SEQUENCE: 328

Met Ala Ser Thr Arg Gly Ser Gly Arg Pro Trp Lys Phe Ser Glu Asn
1               5                   10                  15

Val Ala Phe Glu Ile Ala Leu Ser Phe Thr Asn Lys Asp Thr Pro Asp
                20                  25                  30
```

```
Arg Trp Ala Lys Val Ala Tyr Tyr Val Arg Gly Arg Thr Pro Glu Glu
         35                  40                  45

Val Lys Lys His Tyr Glu
    50
```

<210> SEQ ID NO 329
<211> LENGTH: 54
<212> TYPE: PRT
<213> ORGANISM: Artificial Sequence
<220> FEATURE:
<223> OTHER INFORMATION: Synthetic

<400> SEQUENCE: 329

```
Met Ala Ser Thr Arg Gly Ser Gly Arg Pro Trp Lys Phe Ser Glu Asn
1               5                   10                  15

Ile Ala Phe Glu Ile Ala Leu Ser Phe Thr Asn Lys Asp Thr Pro Asp
            20                  25                  30

Arg Trp Lys Lys Val Ala Ser Tyr Val Lys Gly Arg Thr Pro Glu Glu
         35                  40                  45

Val Lys Lys His Tyr Glu
    50
```

<210> SEQ ID NO 330
<211> LENGTH: 54
<212> TYPE: PRT
<213> ORGANISM: Artificial Sequence
<220> FEATURE:
<223> OTHER INFORMATION: Synthetic

<400> SEQUENCE: 330

```
Met Ala Ser Thr Arg Gly Ser Gly Arg Pro Trp Lys Phe Ser Glu Asn
1               5                   10                  15

Ile Ala Phe Glu Ile Ala Leu Ser Phe Thr Asn Lys Asp Thr Pro Asp
            20                  25                  30

Arg Trp Lys Lys Val Ala Pro Tyr Val Lys Gly Arg Thr Pro Glu Glu
         35                  40                  45

Val Lys Lys His Tyr Glu
    50
```

<210> SEQ ID NO 331
<211> LENGTH: 54
<212> TYPE: PRT
<213> ORGANISM: Artificial Sequence
<220> FEATURE:
<223> OTHER INFORMATION: Synthetic

<400> SEQUENCE: 331

```
Met Ala Ser Thr Arg Gly Ser Gly Arg Pro Trp Lys Phe Ser Glu Asn
1               5                   10                  15

Ile Ala Phe Glu Ile Ala Leu Ser Phe Thr Asn Lys Asp Thr Pro Asp
            20                  25                  30

Arg Trp Lys Lys Val Ala Tyr Tyr Val Lys Gly Arg Thr Pro Glu Glu
         35                  40                  45

Val Lys Lys His Tyr Glu
    50
```

<210> SEQ ID NO 332
<211> LENGTH: 54
<212> TYPE: PRT
<213> ORGANISM: Artificial Sequence
<220> FEATURE:
<223> OTHER INFORMATION: Synthetic

<400> SEQUENCE: 332

Met Ala Ser Thr Arg Gly Ser Gly Arg Pro Trp Arg Phe Ser Glu Asn
1               5                   10                  15

Val Ala Phe Glu Ile Ala Leu Ser Phe Thr Asn Lys Asp Thr Pro Asp
            20                  25                  30

Arg Trp Arg Lys Val Ala Arg Tyr Val Arg Gly Arg Thr Pro Glu Glu
        35                  40                  45

Val Lys Lys His Tyr Glu
    50

<210> SEQ ID NO 333
<211> LENGTH: 54
<212> TYPE: PRT
<213> ORGANISM: Artificial Sequence
<220> FEATURE:
<223> OTHER INFORMATION: Synthetic

<400> SEQUENCE: 333

Met Ala Ser Thr Arg Gly Ser Gly Arg Pro Trp Arg Phe Ser Glu Asn
1               5                   10                  15

Val Ala Phe Glu Ile Ala Leu Ser Phe Thr Asn Lys Asp Thr Pro Asp
            20                  25                  30

Arg Trp Ala Lys Val Ala Tyr Tyr Val Arg Gly Arg Thr Pro Glu Glu
        35                  40                  45

Val Lys Lys His Tyr Glu
    50

<210> SEQ ID NO 334
<211> LENGTH: 54
<212> TYPE: PRT
<213> ORGANISM: Artificial Sequence
<220> FEATURE:
<223> OTHER INFORMATION: Synthetic

<400> SEQUENCE: 334

Met Ala Ser Thr Arg Gly Ser Gly Arg Pro Trp Lys Phe Ser Glu Asn
1               5                   10                  15

Val Ala Phe Glu Ile Ala Leu Ser Phe Thr Asn Lys Asp Thr Pro Asp
            20                  25                  30

Arg Trp Ala Lys Val Ala Tyr Tyr Val Arg Gly Arg Thr Pro Glu Glu
        35                  40                  45

Val Lys Lys His Tyr Glu
    50

<210> SEQ ID NO 335
<211> LENGTH: 54
<212> TYPE: PRT
<213> ORGANISM: Artificial Sequence
<220> FEATURE:
<223> OTHER INFORMATION: Synthetic

<400> SEQUENCE: 335

Met Ala Ser Thr Arg Gly Ser Gly Arg Pro Trp Asn Phe Ser Glu Asn
1               5                   10                  15

Ile Ala Phe Glu Leu Ala Leu Ser Phe Thr Asn Lys Asp Thr Pro Asp
            20                  25                  30

Arg Trp Lys Lys Val Ala Arg Tyr Val Lys Gly Arg Thr Pro Glu Glu
        35                  40                  45

Val Lys Lys His Tyr Glu

```
<210> SEQ ID NO 336
<211> LENGTH: 54
<212> TYPE: PRT
<213> ORGANISM: Artificial Sequence
<220> FEATURE:
<223> OTHER INFORMATION: Synthetic

<400> SEQUENCE: 336

Met Ala Ser Thr Arg Gly Ser Gly Arg Pro Trp Lys Phe Ser Glu Asn
1               5                   10                  15

Ile Ala Phe Glu Leu Ala Leu Tyr Phe Thr Asn Lys Asp Thr Pro Asp
            20                  25                  30

Arg Trp Lys Lys Val Ala Arg Tyr Val Lys Gly Arg Thr Pro Glu Glu
        35                  40                  45

Val Lys Lys His Tyr Glu
    50

<210> SEQ ID NO 337
<211> LENGTH: 54
<212> TYPE: PRT
<213> ORGANISM: Artificial Sequence
<220> FEATURE:
<223> OTHER INFORMATION: Synthetic

<400> SEQUENCE: 337

Met Ala Ser Thr Arg Gly Ser Gly Arg Pro Trp Arg Phe Ser Glu Asn
1               5                   10                  15

Leu Ala Phe Glu Leu Ala Leu Ser Phe Thr Asn Lys Asp Thr Pro Asp
            20                  25                  30

Arg Trp Arg Lys Val Ala Gln Tyr Val Arg Gly Arg Thr Pro Glu Glu
        35                  40                  45

Val Lys Lys His Tyr Glu
    50

<210> SEQ ID NO 338
<211> LENGTH: 54
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: X is G, K or R
<220> FEATURE:
<221> NAME/KEY: MISC_FEATURE
<222> LOCATION: (35)..(35)
<223> OTHER INFORMATION: X is A, K, R, T, or G
<220> FEATURE:
<221> NAME/KEY: MISC_FEATURE
<222> LOCATION: (39)..(39)
<223> OTHER INFORMATION: X is Q, Y or R
<220> FEATURE:
<221> NAME/KEY: MISC_FEATURE
<222> LOCATION: (42)..(42)
<223> OTHER INFORMATION: X is S, K or R

<400> SEQUENCE: 338

Met Ala Ser Thr Arg Gly Ser Gly Arg Pro Trp Xaa Phe Ser Glu Asn
1               5                   10                  15

Leu Ala Phe Glu Leu Ala Leu Ser Phe Thr Asn Lys Asp Thr Pro Asp
            20                  25                  30

Arg Trp Xaa Lys Val Ala Xaa Tyr Val Xaa Gly Arg Thr Pro Glu Glu
```

```
            35                  40                  45
Val Lys Lys His Tyr Glu
    50

<210> SEQ ID NO 339
<211> LENGTH: 604
<212> TYPE: PRT
<213> ORGANISM: Artificial Sequence
<220> FEATURE:
<223> OTHER INFORMATION: Synthetic

<400> SEQUENCE: 339

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Gln Ile Cys Ile Gly
        35                  40                  45

Tyr His Ala Asn Asn Ser Thr Glu Lys Val Asp Thr Ile Leu Glu Arg
    50                  55                  60

Asn Val Thr Val Thr His Ala Lys Asp Ile Leu Glu Lys Thr His Asn
65                  70                  75                  80

Gly Lys Leu Cys Lys Leu Asn Gly Ile Pro Pro Leu Glu Leu Gly Asp
                85                  90                  95

Cys Ser Ile Ala Gly Trp Leu Leu Gly Asn Pro Glu Cys Asp Arg Leu
            100                 105                 110

Leu Ser Val Pro Glu Trp Ser Tyr Ile Met Glu Lys Glu Asn Pro Arg
        115                 120                 125

Asn Gly Leu Cys Tyr Pro Gly Ser Phe Asn Asp Tyr Glu Glu Leu Lys
    130                 135                 140

His Leu Leu Ser Ser Val Lys His Phe Glu Lys Val Lys Ile Leu Pro
145                 150                 155                 160

Lys Asp Arg Trp Thr Gln His Thr Thr Thr Gly Gly Ser Gln Ala Cys
                165                 170                 175

Ala Val Ser Gly Asn Pro Ser Phe Phe Arg Asn Met Val Trp Leu Thr
            180                 185                 190

Lys Lys Gly Ser Asp Tyr Pro Val Ala Lys Gly Ser Tyr Asn Asn Thr
        195                 200                 205

Ser Gly Glu Gln Met Leu Ile Ile Trp Gly Val His His Pro Ile Asp
    210                 215                 220

Glu Thr Glu Gln Arg Thr Leu Tyr Gln Asn Val Gly Thr Tyr Val Ser
225                 230                 235                 240

Val Gly Thr Ser Thr Leu Asn Lys Arg Ser Thr Pro Glu Ile Ala Thr
                245                 250                 255

Arg Pro Lys Val Asn Gly Leu Gly Ser Arg Met Glu Phe Ser Trp Thr
            260                 265                 270

Leu Leu Asp Met Trp Asp Thr Ile Asn Phe Glu Ser Thr Gly Asn Leu
        275                 280                 285

Ile Ala Pro Glu Tyr Gly Phe Lys Ile Ser Lys Arg Gly Ser Ser Gly
    290                 295                 300

Ile Met Lys Thr Glu Gly Thr Leu Glu Asn Cys Glu Thr Lys Cys Gln
305                 310                 315                 320

Thr Pro Leu Gly Ala Ile Asn Thr Thr Leu Pro Phe His Asn Val His
                325                 330                 335

Pro Leu Thr Ile Gly Glu Cys Pro Lys Tyr Val Lys Ser Glu Lys Leu
```

Val Leu Ala Thr Gly Leu Arg Asn Val Pro Gln Ile Glu Ser Arg Gly
                355                 360                 365

Leu Phe Gly Ala Ile Ala Gly Phe Ile Glu Gly Trp Gln Gly Met
    370                 375                 380

Val Asp Gly Trp Tyr Gly Tyr His His Ser Asn Asp Gln Gly Ser Gly
385                 390                 395                 400

Tyr Ala Ala Asp Lys Glu Ser Thr Gln Lys Ala Phe Asp Gly Ile Thr
                405                 410                 415

Asn Lys Val Asn Ser Val Ile Glu Lys Met Asn Thr Gln Phe Glu Ala
            420                 425                 430

Val Gly Lys Glu Phe Gly Asn Leu Glu Arg Arg Leu Glu Asn Leu Asn
        435                 440                 445

Lys Lys Met Glu Asp Gly Phe Leu Asp Val Trp Thr Tyr Asn Ala Glu
    450                 455                 460

Leu Leu Val Leu Met Glu Asn Glu Arg Thr Leu Asp Phe His Asp Ser
465                 470                 475                 480

Asn Val Lys Asn Leu Tyr Asp Lys Val Arg Met Gln Leu Arg Asp Asn
                485                 490                 495

Val Lys Glu Leu Gly Asn Gly Cys Phe Glu Phe Tyr His Lys Cys Asp
            500                 505                 510

Asp Glu Cys Met Asn Ser Val Lys Asn Gly Thr Tyr Asp Tyr Pro Lys
        515                 520                 525

Tyr Glu Glu Glu Ser Lys Leu Asn Arg Asn Glu Ile Lys Ser Gly Gly
    530                 535                 540

Gly Gly Leu Asn Asp Ile Phe Glu Ala Gln Lys Ile Glu Trp His Glu
545                 550                 555                 560

Arg Leu Val Pro Arg Gly Ser Pro Gly Ser Gly Tyr Ile Pro Glu Ala
                565                 570                 575

Pro Arg Asp Gly Gln Ala Tyr Val Arg Lys Asp Gly Glu Trp Val Leu
            580                 585                 590

Leu Ser Thr Phe Leu Gly His His His His His His
        595                 600

<210> SEQ ID NO 340
<211> LENGTH: 609
<212> TYPE: PRT
<213> ORGANISM: Artificial Sequence
<220> FEATURE:
<223> OTHER INFORMATION: Synthetic

<400> SEQUENCE: 340

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Gln Ile Cys Ile Gly
        35                  40                  45

Tyr His Ala Asn Asn Ser Thr Glu Gln Val Asp Thr Ile Met Glu Lys
    50                  55                  60

Asn Val Thr Val Thr His Ala Gln Asp Ile Leu Glu Lys Lys His Asn
65                  70                  75                  80

Gly Lys Leu Cys Asp Leu Asp Gly Val Lys Pro Leu Ile Leu Arg Asp
                85                  90                  95

Cys Ser Val Ala Gly Trp Leu Leu Gly Asn Pro Met Cys Asp Glu Phe

```
                100             105             110
Ile Asn Val Pro Glu Trp Ser Tyr Ile Val Glu Lys Ala Asn Pro Val
            115             120             125

Asn Asp Leu Cys Tyr Pro Gly Asp Phe Asn Asp Tyr Glu Glu Leu Lys
            130             135             140

His Leu Leu Ser Arg Ile Asn His Phe Glu Lys Ile Gln Ile Ile Pro
145             150             155             160

Lys Ser Ser Trp Ser Ser His Glu Ala Ser Leu Gly Val Ser Ser Ala
            165             170             175

Cys Pro Tyr Gln Gly Lys Ser Ser Phe Phe Arg Asn Val Val Trp Leu
            180             185             190

Ile Lys Lys Asn Ser Thr Tyr Pro Thr Ile Lys Arg Ser Tyr Asn Asn
            195             200             205

Thr Asn Gln Glu Asp Leu Leu Val Leu Trp Gly Ile His His Pro Asn
            210             215             220

Asp Ala Ala Glu Gln Thr Lys Leu Tyr Gln Asn Pro Thr Thr Tyr Ile
225             230             235             240

Ser Val Gly Thr Ser Thr Leu Asn Gln Arg Leu Val Pro Arg Ile Ala
            245             250             255

Thr Arg Ser Lys Val Asn Gly Gln Ser Gly Arg Met Glu Phe Phe Trp
            260             265             270

Thr Ile Leu Lys Pro Asn Asp Ala Ile Asn Phe Glu Ser Asn Gly Asn
            275             280             285

Phe Ile Ala Pro Glu Tyr Ala Tyr Lys Ile Val Lys Lys Gly Asp Ser
            290             295             300

Thr Ile Met Lys Ser Glu Leu Glu Tyr Gly Asn Cys Asn Thr Lys Cys
305             310             315             320

Gln Thr Pro Met Gly Ala Ile Asn Ser Ser Met Pro Phe His Asn Ile
            325             330             335

His Pro Leu Thr Ile Gly Glu Cys Pro Lys Tyr Val Lys Ser Asn Arg
            340             345             350

Leu Val Leu Ala Thr Gly Leu Arg Asn Ser Pro Gln Arg Glu Arg Arg
            355             360             365

Arg Lys Lys Arg Gly Leu Phe Gly Ala Ile Ala Gly Phe Ile Glu Gly
            370             375             380

Gly Trp Gln Gly Met Val Asp Gly Trp Tyr Gly Tyr His His Ser Asn
385             390             395             400

Glu Gln Gly Ser Gly Tyr Ala Ala Asp Lys Glu Ser Thr Gln Lys Ala
            405             410             415

Ile Asp Gly Val Thr Asn Lys Val Asn Ser Ile Ile Asp Lys Met Asn
            420             425             430

Thr Gln Phe Glu Ala Val Gly Arg Glu Phe Asn Asn Leu Glu Arg Arg
            435             440             445

Ile Glu Asn Leu Asn Lys Lys Met Glu Asp Gly Phe Leu Asp Val Trp
450             455             460

Thr Tyr Asn Ala Glu Leu Leu Val Leu Met Glu Asn Glu Arg Thr Leu
465             470             475             480

Asp Phe His Asp Ser Asn Val Lys Asn Leu Tyr Asp Lys Val Arg Leu
            485             490             495

Gln Leu Arg Asp Asn Ala Lys Glu Leu Gly Asn Gly Cys Phe Glu Phe
            500             505             510

Tyr His Lys Cys Asp Asn Glu Cys Met Glu Ser Val Arg Asn Gly Thr
            515             520             525
```

-continued

```
Tyr Asp Tyr Pro Gln Tyr Ser Glu Glu Ala Arg Leu Lys Arg Glu Glu
        530                 535                 540

Ile Ser Ser Gly Gly Gly Gly Leu Asn Asp Ile Phe Glu Ala Gln Lys
545                 550                 555                 560

Ile Glu Trp His Glu Arg Leu Val Pro Arg Gly Ser Pro Gly Ser Gly
                565                 570                 575

Tyr Ile Pro Glu Ala Pro Arg Asp Gly Gln Ala Tyr Val Arg Lys Asp
        580                 585                 590

Gly Glu Trp Val Leu Leu Ser Thr Phe Leu Gly His His His His
                595                 600                 605

His

<210> SEQ ID NO 341
<211> LENGTH: 609
<212> TYPE: PRT
<213> ORGANISM: Artificial Sequence
<220> FEATURE:
<223> OTHER INFORMATION: Synthetic

<400> SEQUENCE: 341

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro Gly Asp Gln Ile Cys Ile Gly
            35                  40                  45

Tyr His Ala Asn Asn Ser Thr Glu Gln Val Asp Thr Ile Met Glu Lys
        50                  55                  60

Asn Val Thr Val Thr His Ala Gln Asp Ile Leu Glu Lys Thr His Asn
65                  70                  75                  80

Gly Lys Leu Cys Asp Leu Asp Gly Val Lys Pro Leu Ile Leu Arg Asp
                85                  90                  95

Cys Ser Val Ala Gly Trp Leu Leu Gly Asn Pro Met Cys Asp Glu Phe
            100                 105                 110

Ile Asn Val Pro Glu Trp Ser Tyr Ile Val Glu Lys Ala Asn Pro Thr
        115                 120                 125

Asn Asp Leu Cys Tyr Pro Gly Ser Phe Asn Asp Tyr Glu Glu Leu Lys
    130                 135                 140

His Leu Leu Ser Arg Ile Asn His Phe Glu Lys Ile Gln Ile Ile Pro
145                 150                 155                 160

Lys Ser Ser Trp Ser Asp His Glu Ala Ser Ser Gly Val Ser Ser Ala
                165                 170                 175

Cys Pro Tyr Leu Gly Ser Pro Ser Phe Phe Arg Asn Val Val Trp Leu
            180                 185                 190

Ile Lys Lys Asn Ser Thr Tyr Pro Thr Ile Lys Lys Ser Tyr Asn Asn
        195                 200                 205

Thr Asn Gln Glu Asp Leu Leu Val Leu Trp Gly Ile His His Pro Asn
    210                 215                 220

Asp Ala Ala Glu Gln Thr Arg Leu Tyr Gln Asn Pro Thr Thr Tyr Ile
225                 230                 235                 240

Ser Ile Gly Thr Ser Thr Leu Asn Gln Arg Leu Val Pro Lys Ile Ala
                245                 250                 255

Thr Arg Ser Lys Val Asn Gly Gln Ser Gly Arg Met Glu Phe Phe Trp
            260                 265                 270
```

```
Thr Ile Leu Lys Pro Asn Asp Ala Ile Asn Phe Glu Ser Asn Gly Asn
            275                 280                 285

Phe Ile Ala Pro Glu Tyr Ala Tyr Lys Ile Val Lys Lys Gly Asp Ser
        290                 295                 300

Ala Ile Met Lys Ser Glu Leu Glu Tyr Gly Asn Cys Asn Thr Lys Cys
305                 310                 315                 320

Gln Thr Pro Met Gly Ala Ile Asn Ser Ser Met Pro Phe His Asn Ile
                325                 330                 335

His Pro Leu Thr Ile Gly Glu Cys Pro Lys Tyr Val Lys Ser Asn Arg
            340                 345                 350

Leu Val Leu Ala Thr Gly Leu Arg Asn Ser Pro Gln Arg Glu Ser Arg
        355                 360                 365

Arg Lys Lys Arg Gly Leu Phe Gly Ala Ile Ala Gly Phe Ile Glu Gly
370                 375                 380

Gly Trp Gln Gly Met Val Asp Gly Trp Tyr Gly Tyr His His Ser Asn
385                 390                 395                 400

Glu Gln Gly Ser Gly Tyr Ala Ala Asp Lys Glu Ser Thr Gln Lys Ala
                405                 410                 415

Ile Asp Gly Val Thr Asn Lys Val Asn Ser Ile Ile Asp Lys Met Asn
            420                 425                 430

Thr Gln Phe Glu Ala Val Gly Arg Glu Phe Asn Asn Leu Glu Arg Arg
        435                 440                 445

Ile Glu Asn Leu Asn Lys Lys Met Glu Asp Gly Phe Leu Asp Val Trp
450                 455                 460

Thr Tyr Asn Ala Glu Leu Leu Val Leu Met Glu Asn Glu Arg Thr Leu
465                 470                 475                 480

Asp Phe His Asp Ser Asn Val Lys Asn Leu Tyr Asp Lys Val Arg Leu
                485                 490                 495

Gln Leu Arg Asp Asn Ala Lys Glu Leu Gly Asn Gly Cys Phe Glu Phe
            500                 505                 510

Tyr His Lys Cys Asp Asn Glu Cys Met Glu Ser Ile Arg Asn Gly Thr
        515                 520                 525

Tyr Asn Tyr Pro Gln Tyr Ser Glu Glu Ala Arg Leu Lys Arg Glu Glu
530                 535                 540

Ile Ser Ser Gly Gly Gly Gly Leu Asn Asp Ile Phe Glu Ala Gln Lys
545                 550                 555                 560

Ile Glu Trp His Glu Arg Leu Val Pro Arg Gly Ser Pro Gly Ser Gly
                565                 570                 575

Tyr Ile Pro Glu Ala Pro Arg Asp Gly Gln Ala Tyr Val Arg Lys Asp
            580                 585                 590

Gly Glu Trp Val Leu Leu Ser Thr Phe Leu Gly His His His His
        595                 600                 605
His
```

<210> SEQ ID NO 342
<211> LENGTH: 610
<212> TYPE: PRT
<213> ORGANISM: Artificial Sequence
<220> FEATURE:
<223> OTHER INFORMATION: Synthetic

<400> SEQUENCE: 342

```
Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
```

-continued

```
                 20                  25                  30
Ala His Ser Ala Phe Ala Ala Asp Pro Gly Asp Lys Ile Cys Ile Gly
             35                  40                  45

Tyr His Ala Asn Asn Ser Thr Thr Gln Val Asp Thr Ile Leu Glu Lys
 50                  55                  60

Asn Val Thr Val Thr His Ser Val Glu Leu Leu Glu Ser Gln Lys Glu
 65                  70                  75                  80

Glu Arg Phe Cys Arg Val Leu Asn Lys Thr Pro Leu Asp Leu Lys Gly
             85                  90                  95

Cys Thr Ile Glu Gly Trp Ile Leu Gly Asn Pro Gln Cys Asp Ile Leu
            100                 105                 110

Leu Gly Asp Gln Ser Trp Ser Tyr Ile Val Glu Arg Pro Gly Ala Gln
            115                 120                 125

Asn Gly Ile Cys Tyr Pro Gly Val Leu Asn Glu Val Glu Glu Leu Lys
            130                 135                 140

Ala Phe Ile Gly Ser Gly Glu Lys Val Gln Arg Phe Glu Met Phe Pro
145                 150                 155                 160

Lys Ser Thr Trp Thr Gly Val Asp Thr Asn Ser Gly Val Thr Arg Ala
                165                 170                 175

Cys Pro Tyr Thr Thr Ser Gly Ser Ser Phe Tyr Arg Asn Leu Leu Trp
                180                 185                 190

Ile Ile Lys Thr Arg Ser Ala Ala Tyr Pro Val Ile Lys Gly Thr Tyr
                195                 200                 205

Asn Asn Thr Gly Ser Gln Pro Ile Leu Tyr Phe Trp Gly Val His His
            210                 215                 220

Pro Pro Asn Thr Asp Glu Gln Asn Thr Leu Tyr Gly Ser Gly Asp Arg
225                 230                 235                 240

Tyr Val Arg Met Gly Thr Glu Ser Met Asn Phe Ala Lys Ser Pro Glu
                245                 250                 255

Ile Ala Ala Arg Pro Ala Val Asn Gly Gln Arg Gly Arg Ile Asp Tyr
                260                 265                 270

Tyr Trp Ser Val Leu Lys Pro Gly Glu Thr Leu Asn Val Glu Ser Asn
                275                 280                 285

Gly Asn Leu Ile Ala Pro Trp Tyr Ala Tyr Lys Phe Thr Ser Ser Asn
            290                 295                 300

Asn Lys Gly Ala Ile Phe Lys Ser Asn Leu Pro Ile Glu Asn Cys Asp
305                 310                 315                 320

Ala Val Cys Gln Thr Val Ala Gly Ala Leu Lys Thr Asn Lys Thr Phe
                325                 330                 335

Gln Asn Val Ser Pro Leu Trp Ile Gly Glu Cys Pro Lys Tyr Val Lys
                340                 345                 350

Ser Glu Ser Leu Arg Leu Ala Thr Gly Leu Arg Asn Val Pro Gln Ala
                355                 360                 365

Glu Thr Arg Gly Leu Phe Gly Ala Ile Ala Gly Phe Ile Glu Gly Gly
                370                 375                 380

Trp Thr Gly Met Ile Asp Gly Trp Tyr Gly Tyr His His Glu Asn Ser
385                 390                 395                 400

Gln Gly Ser Gly Tyr Ala Ala Asp Lys Glu Ser Thr Gln Lys Ala Ile
                405                 410                 415

Asp Gly Ile Thr Asn Lys Val Asn Ser Ile Ile Asp Lys Met Asn Thr
                420                 425                 430

Gln Phe Glu Ala Val Glu His Glu Phe Ser Asn Leu Glu Arg Arg Ile
                435                 440                 445
```

```
Asp Asn Leu Asn Lys Arg Met Glu Asp Gly Phe Leu Asp Val Trp Thr
            450                 455                 460
Tyr Asn Ala Glu Leu Leu Val Leu Leu Glu Asn Glu Arg Thr Leu Asp
465                 470                 475                 480
Leu His Asp Ala Asn Val Lys Asn Leu Tyr Glu Lys Val Lys Ser Gln
                485                 490                 495
Leu Arg Asp Asn Ala Lys Asp Leu Gly Asn Gly Cys Phe Glu Phe Trp
                500                 505                 510
His Lys Cys Asp Asp Glu Cys Ile Asn Ser Val Lys Asn Gly Thr Tyr
            515                 520                 525
Asp Tyr Pro Lys Tyr Gln Asp Glu Ser Lys Leu Asn Arg Gln Glu Ile
            530                 535                 540
Asp Ser Val Ser Gly Gly Gly Leu Asn Asp Ile Phe Glu Ala Gln
545                 550                 555                 560
Lys Ile Glu Trp His Glu Arg Leu Val Pro Arg Gly Ser Pro Gly Ser
                565                 570                 575
Gly Tyr Ile Pro Glu Ala Pro Arg Asp Gly Gln Ala Tyr Val Arg Lys
                580                 585                 590
Asp Gly Glu Trp Val Leu Leu Ser Thr Phe Leu Gly His His His
            595                 600                 605
His His
    610

<210> SEQ ID NO 343
<211> LENGTH: 601
<212> TYPE: PRT
<213> ORGANISM: Artificial Sequence
<220> FEATURE:
<223> OTHER INFORMATION: Synthetic

<400> SEQUENCE: 343

Met Val Leu Val Asn Gln Ser His Gln Gly Phe Asn Lys Glu His Thr
1               5                   10                  15
Ser Lys Met Val Ser Ala Ile Val Leu Tyr Val Leu Leu Ala Ala Ala
                20                  25                  30
Ala His Ser Ala Phe Ala Ala Asp Pro Gly Asp Lys Ile Cys Ile Gly
            35                  40                  45
Tyr Gln Ser Thr Asn Ser Thr Glu Thr Val Asp Thr Leu Thr Glu Ser
        50                  55                  60
Asn Val Pro Val Thr His Thr Lys Glu Leu Leu His Thr Glu His Asn
65                  70                  75                  80
Gly Met Leu Cys Ala Thr Asp Leu Gly His Pro Leu Ile Leu Asp Thr
                85                  90                  95
Cys Thr Ile Glu Gly Leu Ile Tyr Gly Asn Pro Ser Cys Asp Ile Leu
            100                 105                 110
Leu Gly Gly Lys Glu Trp Ser Tyr Ile Val Glu Arg Ser Ser Ala Val
        115                 120                 125
Asn Gly Met Cys Tyr Pro Gly Asn Val Glu Asn Leu Glu Glu Leu Arg
130                 135                 140
Ser Leu Phe Ser Ser Ala Lys Ser Tyr Lys Arg Ile Gln Ile Phe Pro
145                 150                 155                 160
Asp Lys Thr Trp Asn Val Thr Tyr Ser Gly Thr Ser Arg Ala Cys Ser
                165                 170                 175
Asn Ser Phe Tyr Arg Ser Met Arg Trp Leu Thr His Lys Ser Asn Ser
            180                 185                 190
```

Tyr Pro Phe Gln Asn Ala His Tyr Thr Asn Asn Glu Arg Glu Asn Ile
            195                 200                 205

Leu Phe Met Trp Gly Ile His His Pro Pro Thr Thr Asp Thr Glu Gln Thr
210                 215                 220

Asp Leu Tyr Lys Asn Ala Asp Thr Thr Thr Ser Val Thr Thr Glu Asp
225                 230                 235                 240

Ile Asn Arg Thr Phe Lys Pro Val Ile Gly Pro Arg Pro Leu Val Asn
                245                 250                 255

Gly Gln Gln Gly Arg Ile Asp Tyr Tyr Trp Ser Val Leu Lys Pro Gly
                260                 265                 270

Gln Thr Leu Arg Ile Arg Ser Asn Gly Asn Leu Ile Ala Pro Trp Tyr
            275                 280                 285

Gly His Val Leu Thr Gly Glu Ser His Gly Arg Ile Leu Lys Thr Asp
            290                 295                 300

Leu Asn Asn Gly Asn Cys Val Val Gln Cys Gln Thr Glu Lys Gly Gly
305                 310                 315                 320

Leu Asn Thr Thr Leu Pro Phe His Asn Ile Ser Lys Tyr Ala Phe Gly
                325                 330                 335

Asn Cys Pro Lys Tyr Val Gly Val Lys Ser Leu Lys Leu Ala Val Gly
            340                 345                 350

Leu Arg Asn Val Pro Ala Val Ser Ser Arg Gly Leu Phe Gly Ala Ile
            355                 360                 365

Ala Gly Phe Ile Glu Gly Gly Trp Pro Gly Leu Val Ala Gly Trp Tyr
            370                 375                 380

Gly Phe Gln His Ser Asn Asp Gln Gly Val Gly Met Ala Ala Asp Lys
385                 390                 395                 400

Gly Ser Thr Gln Lys Ala Ile Asp Lys Ile Thr Ser Lys Val Asn Asn
                405                 410                 415

Ile Ile Asp Lys Met Asn Lys Gln Tyr Glu Val Ile Asp His Glu Phe
                420                 425                 430

Asn Glu Leu Glu Ala Arg Leu Asn Met Ile Asn Asn Lys Ile Asp Asp
            435                 440                 445

Gln Ile Gln Asp Ile Trp Ala Tyr Asn Ala Glu Leu Leu Val Leu Leu
450                 455                 460

Glu Asn Gln Lys Thr Leu Asp Glu His Asp Ala Asn Val Asn Asn Leu
465                 470                 475                 480

Tyr Asn Lys Val Lys Arg Ala Leu Gly Ser Asn Ala Val Glu Asp Gly
                485                 490                 495

Asn Gly Cys Phe Glu Leu Tyr His Lys Cys Asp Asp Gln Cys Met Glu
            500                 505                 510

Thr Ile Arg Asn Gly Thr Tyr Asp Arg Gln Lys Tyr Gln Glu Glu Ser
            515                 520                 525

Arg Leu Glu Arg Gln Lys Ile Glu Gly Val Ser Gly Gly Gly Gly Leu
            530                 535                 540

Asn Asp Ile Phe Glu Ala Gln Lys Ile Glu Trp His Glu Arg Leu Val
545                 550                 555                 560

Pro Arg Gly Ser Pro Gly Ser Gly Tyr Ile Pro Glu Ala Pro Arg Asp
                565                 570                 575

Gly Gln Ala Tyr Val Arg Lys Asp Gly Glu Trp Val Leu Leu Ser Thr
            580                 585                 590

Phe Leu Gly His His His His His His
            595                 600

<210> SEQ ID NO 344
<211> LENGTH: 606
<212> TYPE: PRT
<213> ORGANISM: Artificial Sequence
<220> FEATURE:
<223> OTHER INFORMATION: Synthetic

<400> SEQUENCE: 344

```
Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Thr Ile Cys Val Gly
        35                  40                  45

Tyr His Ala Asn Asn Ser Thr Asp Thr Val Thr Val Leu Glu Lys
    50                  55                  60

Asn Val Thr Val Thr His Ser Val Asn Leu Leu Glu Asp Ser His Asn
65                  70                  75                  80

Gly Lys Leu Cys Ser Leu Asn Gly Ile Ala Pro Leu Gln Leu Gly Lys
                85                  90                  95

Cys Asn Val Ala Gly Trp Leu Leu Gly Asn Pro Glu Cys Asp Leu Leu
            100                 105                 110

Leu Thr Ala Asn Ser Trp Ser Tyr Ile Ile Glu Thr Ser Asn Ser Glu
        115                 120                 125

Asn Gly Thr Cys Tyr Pro Gly Glu Phe Ile Asp Tyr Glu Glu Leu Arg
    130                 135                 140

Glu Gln Leu Ser Ser Ile Ser Ser Phe Glu Lys Phe Glu Ile Phe Pro
145                 150                 155                 160

Lys Ala Ser Ser Trp Pro Asn His Glu Thr Thr Lys Gly Val Thr Ala
                165                 170                 175

Ala Cys Ser Tyr Ser Gly Ala Ser Ser Phe Tyr Arg Asn Leu Leu Trp
            180                 185                 190

Ile Thr Lys Lys Gly Thr Ser Tyr Pro Lys Leu Ser Lys Ser Tyr Thr
        195                 200                 205

Asn Asn Lys Gly Lys Glu Val Leu Val Leu Trp Gly Val His His Pro
    210                 215                 220

Pro Ser Val Ser Glu Gln Gln Ser Leu Tyr Gln Asn Ala Asp Ala Tyr
225                 230                 235                 240

Val Ser Val Gly Ser Ser Lys Tyr Asn Arg Arg Phe Ala Pro Glu Ile
                245                 250                 255

Ala Ala Arg Pro Glu Val Arg Gly Gln Ala Gly Arg Met Asn Tyr Tyr
            260                 265                 270

Trp Thr Leu Leu Asp Gln Gly Asp Thr Ile Thr Phe Glu Ala Thr Gly
        275                 280                 285

Asn Leu Ile Ala Pro Trp Tyr Ala Phe Ala Leu Asn Lys Gly Ser Asp
    290                 295                 300

Ser Gly Ile Ile Thr Ser Asp Ala Pro Val His Asn Cys Asp Thr Arg
305                 310                 315                 320

Cys Gln Thr Pro His Gly Ala Leu Asn Ser Ser Leu Pro Phe Gln Asn
                325                 330                 335

Val His Pro Ile Thr Ile Gly Glu Cys Pro Lys Tyr Val Lys Ser Thr
            340                 345                 350

Lys Leu Arg Met Ala Thr Gly Leu Arg Asn Val Pro Ser Ile Gln Ser
        355                 360                 365
```

```
Arg Gly Leu Phe Gly Ala Ile Ala Gly Phe Ile Glu Gly Gly Trp Thr
    370                 375                 380

Gly Met Ile Asp Gly Trp Tyr Gly Tyr His His Gln Asn Glu Gln Gly
385                 390                 395                 400

Ser Gly Tyr Ala Ala Asp Gln Lys Ser Thr Gln Asn Ala Ile Asp Gly
                405                 410                 415

Ile Thr Asn Lys Val Asn Ser Val Ile Glu Lys Met Asn Thr Gln Phe
            420                 425                 430

Thr Ala Val Gly Lys Glu Phe Asn Asn Leu Glu Arg Arg Ile Glu Asn
        435                 440                 445

Leu Asn Lys Lys Val Asp Asp Gly Phe Leu Asp Val Trp Thr Tyr Asn
    450                 455                 460

Ala Glu Leu Leu Val Leu Leu Glu Asn Glu Arg Thr Leu Asp Phe His
465                 470                 475                 480

Asp Ser Asn Val Arg Asn Leu Tyr Glu Lys Val Lys Ser Gln Leu Arg
                485                 490                 495

Asn Asn Ala Lys Glu Ile Gly Asn Gly Cys Phe Glu Phe Tyr His Lys
            500                 505                 510

Cys Asp Asp Glu Cys Met Glu Ser Val Lys Asn Gly Thr Tyr Asp Tyr
        515                 520                 525

Pro Lys Tyr Ser Glu Glu Ser Lys Leu Asn Arg Glu Glu Ile Asp Ser
    530                 535                 540

Gly Gly Gly Gly Leu Asn Asp Ile Phe Glu Ala Gln Lys Ile Glu Trp
545                 550                 555                 560

His Glu Arg Leu Val Pro Arg Gly Ser Pro Gly Ser Gly Tyr Ile Pro
                565                 570                 575

Glu Ala Pro Arg Asp Gly Gln Ala Tyr Val Arg Lys Asp Gly Glu Trp
            580                 585                 590

Val Leu Leu Ser Thr Phe Leu Gly His His His His His
    595                 600                 605

<210> SEQ ID NO 345
<211> LENGTH: 606
<212> TYPE: PRT
<213> ORGANISM: Artificial Sequence
<220> FEATURE:
<223> OTHER INFORMATION: Synthetic

<400> SEQUENCE: 345

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Arg Ile Cys Val Gly
        35                  40                  45

Tyr Leu Ser Thr Asn Ser Ser Glu Arg Val Asp Thr Leu Leu Glu Asn
    50                  55                  60

Gly Val Pro Val Thr Ser Ser Ile Asp Leu Ile Glu Thr Asn His Thr
65                  70                  75                  80

Gly Thr Tyr Cys Ser Leu Asn Gly Val Ser Pro Val His Leu Gly Asp
                85                  90                  95

Cys Ser Phe Glu Gly Trp Ile Val Gly Asn Pro Ala Cys Thr Ser Asn
            100                 105                 110

Phe Gly Ile Arg Glu Trp Ser Tyr Leu Ile Glu Asp Pro Ala Ala Pro
        115                 120                 125
```

```
His Gly Leu Cys Tyr Pro Gly Glu Leu Asn Asn Gly Glu Leu Arg
    130                 135                 140

His Leu Phe Ser Gly Ile Arg Ser Phe Ser Arg Thr Glu Leu Ile Pro
145                 150                 155                 160

Pro Thr Ser Trp Gly Glu Val Leu Asp Gly Thr Thr Ser Ala Cys Arg
                165                 170                 175

Asp Asn Thr Gly Thr Asn Ser Phe Tyr Arg Asn Leu Val Trp Phe Ile
            180                 185                 190

Lys Lys Asn Asn Arg Tyr Pro Val Ile Ser Lys Thr Tyr Asn Asn Thr
                195                 200                 205

Thr Gly Arg Asp Val Leu Val Leu Trp Gly Ile His His Pro Val Ser
    210                 215                 220

Val Asp Glu Thr Lys Thr Leu Tyr Val Asn Ser Asp Pro Tyr Thr Leu
225                 230                 235                 240

Val Ser Thr Lys Ser Trp Ser Glu Lys Tyr Lys Leu Glu Thr Gly Val
                245                 250                 255

Arg Pro Gly Tyr Asn Gly Gln Arg Ser Trp Met Lys Ile Tyr Trp Ser
            260                 265                 270

Leu Ile His Pro Gly Glu Met Ile Thr Phe Glu Ser Asn Gly Gly Phe
    275                 280                 285

Leu Ala Pro Arg Tyr Gly Tyr Ile Ile Glu Glu Tyr Gly Lys Gly Arg
    290                 295                 300

Ile Phe Gln Ser Arg Ile Arg Met Ser Arg Cys Asn Thr Lys Cys Gln
305                 310                 315                 320

Thr Ser Val Gly Gly Ile Asn Thr Asn Arg Thr Phe Gln Asn Ile Asp
                325                 330                 335

Lys Asn Ala Leu Gly Asp Cys Pro Lys Tyr Ile Lys Ser Gly Gln Leu
            340                 345                 350

Lys Leu Ala Thr Gly Leu Arg Asn Val Pro Ala Ile Ser Asn Arg Gly
    355                 360                 365

Leu Phe Gly Ala Ile Ala Gly Phe Ile Glu Gly Gly Trp Pro Gly Leu
    370                 375                 380

Ile Asn Gly Trp Tyr Gly Phe Gln His Gln Asn Glu Gln Gly Thr Gly
385                 390                 395                 400

Ile Ala Ala Asp Lys Glu Ser Thr Gln Lys Ala Ile Asp Gln Ile Thr
                405                 410                 415

Thr Lys Ile Asn Asn Ile Ile Asp Lys Met Asn Gly Asn Tyr Asp Ser
            420                 425                 430

Ile Arg Gly Glu Phe Asn Gln Val Glu Lys Arg Ile Asn Met Leu Ala
    435                 440                 445

Asp Arg Ile Asp Asp Ala Val Thr Asp Ile Trp Ser Tyr Asn Ala Lys
    450                 455                 460

Leu Leu Val Leu Leu Glu Asn Asp Lys Thr Leu Asp Met His Asp Ala
465                 470                 475                 480

Asn Val Lys Asn Leu His Glu Gln Val Arg Arg Glu Leu Lys Asp Asn
                485                 490                 495

Ala Ile Asp Glu Gly Asn Gly Cys Phe Glu Leu Leu His Lys Cys Asn
            500                 505                 510

Asp Ser Cys Met Glu Thr Ile Arg Asn Gly Thr Tyr Asp His Thr Glu
            515                 520                 525

Tyr Ala Glu Glu Ser Lys Leu Lys Arg Gln Glu Ile Asp Gly Ile Ser
    530                 535                 540

Gly Gly Gly Gly Leu Asn Asp Ile Phe Glu Ala Gln Lys Ile Glu Trp
```

His Glu Arg Leu Val Pro Arg Gly Ser Pro Gly Ser Gly Tyr Ile Pro
545                 550                 555                 560

Glu Ala Pro Arg Asp Gly Gln Ala Tyr Val Arg Lys Asp Gly Glu Trp
            565                 570                 575

Val Leu Leu Ser Thr Phe Leu Gly His His His His His His
        580                 585                 590
                595                 600                 605

<210> SEQ ID NO 346
<211> LENGTH: 604
<212> TYPE: PRT
<213> ORGANISM: Artificial Sequence
<220> FEATURE:
<223> OTHER INFORMATION: Synthetic

<400> SEQUENCE: 346

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Lys Ile Cys Ile Gly
        35                  40                  45

Tyr Leu Ser Asn Asn Ser Thr Asp Thr Val Asp Thr Leu Thr Glu Asn
    50                  55                  60

Gly Val Pro Val Thr Ser Ser Ile Asp Leu Val Glu Thr Asn His Thr
65                  70                  75                  80

Gly Thr Tyr Cys Ser Leu Asn Gly Val Ser Pro Ile His Leu Gly Asp
            85                  90                  95

Cys Ser Phe Glu Gly Trp Ile Val Gly Asn Pro Ser Cys Ala Ser Asn
        100                 105                 110

Ile Asn Ile Arg Glu Trp Ser Tyr Leu Ile Glu Asp Pro Asn Ala Pro
    115                 120                 125

His Lys Leu Cys Phe Pro Gly Glu Val Asp Asn Asn Gly Glu Leu Arg
130                 135                 140

His Leu Phe Ser Gly Val Asn Ser Phe Ser Arg Thr Glu Leu Ile Pro
145                 150                 155                 160

Pro Ser Lys Trp Gly Asp Ile Leu Glu Gly Thr Thr Ala Ser Cys Gln
            165                 170                 175

Asn Arg Gly Ala Asn Ser Phe Tyr Arg Asn Leu Ile Trp Leu Val Asn
        180                 185                 190

Lys Leu Asn Lys Tyr Pro Val Val Lys Gly Glu Tyr Asn Asn Thr Thr
    195                 200                 205

Gly Arg Asp Val Leu Val Leu Trp Gly Ile His His Pro Asp Thr Glu
210                 215                 220

Ala Thr Ala Asn Lys Leu Tyr Val Asn Lys Asn Pro Tyr Thr Leu Val
225                 230                 235                 240

Ser Thr Lys Glu Trp Ser Arg Arg Tyr Glu Leu Glu Ile Gly Thr Arg
            245                 250                 255

Ile Gly Asp Gly Gln Arg Ser Trp Met Lys Ile Tyr Trp His Leu Met
        260                 265                 270

His Pro Gly Glu Arg Ile Thr Phe Glu Ser Ser Gly Leu Leu Ala
    275                 280                 285

Pro Arg Tyr Gly Tyr Ile Ile Glu Lys Tyr Gly Thr Gly Arg Ile Phe
290                 295                 300

Gln Ser Gly Val Arg Leu Ala Lys Cys Asn Thr Lys Cys Gln Thr Ser

```
                305                 310                 315                 320
            Met Gly Gly Ile Asn Thr Asn Lys Thr Phe Gln Asn Ile Glu Arg Asn
                            325                 330                 335

Ala Leu Gly Asp Cys Pro Lys Tyr Ile Lys Ser Gly Gln Leu Lys Leu
                            340                 345                 350

Ala Thr Gly Leu Arg Asn Val Pro Ser Ile Val Glu Arg Gly Leu Phe
                            355                 360                 365

Gly Ala Ile Ala Gly Phe Ile Glu Gly Gly Trp Pro Gly Leu Ile Asn
                            370                 375                 380

Gly Trp Tyr Gly Phe Gln His Gln Asn Glu Gln Gly Thr Gly Ile Ala
            385                 390                 395                 400

Ala Asp Lys Thr Ser Thr Gln Lys Ala Ile Asn Glu Ile Thr Thr Lys
                            405                 410                 415

Ile Asn Asn Ile Ile Glu Lys Met Asn Gly Asn Tyr Asp Ser Ile Arg
                            420                 425                 430

Gly Glu Phe Asn Gln Val Glu Lys Arg Ile Asn Met Ile Ala Asp Arg
                            435                 440                 445

Val Asp Asp Ala Val Thr Asp Ile Trp Ser Tyr Asn Ala Lys Leu Leu
                            450                 455                 460

Val Leu Ile Glu Asn Asp Arg Thr Leu Asp Leu His Asp Ala Asn Val
            465                 470                 475                 480

Arg Asn Leu His Glu Gln Ile Lys Arg Ala Leu Lys Asp Asn Ala Ile
                            485                 490                 495

Asp Glu Gly Asp Gly Cys Phe Ser Ile Leu His Lys Cys Asn Asp Ser
                            500                 505                 510

Cys Met Glu Thr Ile Arg Asn Gly Thr Tyr Asn His Glu Asp Tyr Lys
                            515                 520                 525

Glu Glu Ser Gln Leu Lys Arg Gln Glu Ile Glu Gly Ile Ser Gly Gly
                            530                 535                 540

Gly Gly Leu Asn Asp Ile Phe Glu Ala Gln Lys Ile Glu Trp His Glu
            545                 550                 555                 560

Arg Leu Val Pro Arg Gly Ser Pro Gly Ser Gly Tyr Ile Pro Glu Ala
                            565                 570                 575

Pro Arg Asp Gly Gln Ala Tyr Val Arg Lys Asp Gly Glu Trp Val Leu
                            580                 585                 590

Leu Ser Thr Phe Leu Gly His His His His His
                            595                 600

<210> SEQ ID NO 347
<211> LENGTH: 604
<212> TYPE: PRT
<213> ORGANISM: Artificial Sequence
<220> FEATURE:
<223> OTHER INFORMATION: Synthetic

<400> SEQUENCE: 347

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro Gly Asp Lys Ile Cys Leu Gly
                35                  40                  45

His His Ala Val Ser Asn Gly Thr Lys Val Asn Thr Leu Thr Glu Arg
                50                  55                  60

Gly Val Glu Val Val Asn Ala Thr Glu Thr Val Glu Arg Thr Asn Val
```

```
            65                  70                  75                  80
Pro Arg Ile Cys Ser Lys Gly Lys Arg Thr Val Asp Leu Gly Gln Cys
                    85                  90                  95
Gly Leu Leu Gly Thr Ile Thr Gly Pro Pro Gln Cys Asp Gln Phe Leu
                100                 105                 110
Glu Phe Ser Ala Asp Leu Ile Ile Glu Arg Arg Glu Gly Ser Asp Val
                115                 120                 125
Cys Tyr Pro Gly Lys Phe Val Asn Glu Ala Leu Arg Gln Ile Leu
130                 135                 140
Arg Glu Ser Gly Gly Ile Asp Lys Glu Thr Met Gly Phe Thr Tyr Ser
145                 150                 155                 160
Gly Ile Arg Thr Asn Gly Thr Thr Ser Ala Cys Arg Arg Ser Gly Ser
                    165                 170                 175
Ser Phe Tyr Ala Glu Met Lys Trp Leu Leu Ser Asn Thr Asp Asn Ala
                180                 185                 190
Ala Phe Pro Gln Met Thr Lys Ser Tyr Lys Asn Thr Arg Lys Asp Pro
                195                 200                 205
Ala Leu Ile Ile Trp Gly Ile His His Ser Gly Ser Thr Thr Glu Gln
210                 215                 220
Thr Lys Leu Tyr Gly Ser Gly Asn Lys Leu Ile Thr Val Gly Ser Ser
225                 230                 235                 240
Asn Tyr Gln Gln Ser Phe Val Pro Ser Pro Gly Ala Arg Pro Gln Val
                245                 250                 255
Asn Gly Gln Ser Gly Arg Ile Asp Phe His Trp Leu Ile Leu Asn Pro
                260                 265                 270
Asn Asp Thr Val Thr Phe Ser Phe Asn Gly Ala Phe Ile Ala Leu Asp
                275                 280                 285
Arg Ala Ser Phe Leu Arg Gly Lys Ser Met Gly Ile Gln Ser Glu Val
                290                 295                 300
Gln Val Asp Ala Asn Cys Glu Gly Asp Cys Tyr His Ser Gly Gly Thr
305                 310                 315                 320
Ile Ile Ser Asn Leu Pro Phe Gln Asn Ile Asn Ser Arg Ala Val Gly
                325                 330                 335
Lys Cys Pro Arg Tyr Val Lys Gln Glu Ser Leu Leu Leu Ala Thr Gly
                340                 345                 350
Met Lys Asn Val Pro Glu Ile Pro Lys Arg Arg Arg Gly Leu Phe
                355                 360                 365
Gly Ala Ile Ala Gly Phe Ile Glu Asn Gly Trp Glu Gly Leu Ile Asp
                370                 375                 380
Gly Trp Tyr Gly Phe Arg His Gln Asn Ala Gln Gly Glu Gly Thr Ala
385                 390                 395                 400
Ala Asp Tyr Lys Ser Thr Gln Ser Ala Ile Asp Gln Ile Thr Gly Lys
                    405                 410                 415
Leu Asn Arg Leu Ile Glu Lys Thr Asn Gln Gln Phe Glu Leu Ile Asp
                420                 425                 430
Asn Glu Phe Thr Glu Val Glu Arg Gln Ile Gly Asn Val Ile Asn Trp
                435                 440                 445
Thr Arg Asp Ser Met Thr Glu Val Trp Ser Tyr Asn Ala Glu Leu Leu
                450                 455                 460
Val Ala Met Glu Asn Gln His Thr Ile Asp Leu Ala Asp Ser Glu Met
465                 470                 475                 480
Asn Lys Leu Tyr Glu Arg Val Lys Arg Gln Leu Arg Glu Asn Ala Glu
                    485                 490                 495
```

```
Glu Asp Gly Thr Gly Cys Phe Glu Ile Phe His Lys Cys Asp Asp
                500                 505                 510

Cys Met Ala Ser Ile Arg Asn Asn Thr Tyr Asp His Ser Lys Tyr Arg
        515                 520                 525

Glu Glu Ala Ile Gln Asn Arg Ile Gln Ile Asp Pro Val Ser Gly Gly
    530                 535                 540

Gly Gly Leu Asn Asp Ile Phe Glu Ala Gln Lys Ile Glu Trp His Glu
545                 550                 555                 560

Arg Leu Val Pro Arg Gly Ser Pro Gly Ser Gly Tyr Ile Pro Glu Ala
                565                 570                 575

Pro Arg Asp Gly Gln Ala Tyr Val Arg Lys Asp Gly Trp Val Leu
                580                 585                 590

Leu Ser Thr Phe Leu Gly His His His His His His
                595                 600
```

<210> SEQ ID NO 348
<211> LENGTH: 604
<212> TYPE: PRT
<213> ORGANISM: Artificial Sequence
<220> FEATURE:
<223> OTHER INFORMATION: Synthetic

<400> SEQUENCE: 348

```
Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro Gly Asp Arg Ile Cys Leu Gly
            35                  40                  45

His His Ala Val Ala Asn Gly Thr Ile Val Lys Thr Leu Thr Asn Glu
        50                  55                  60

Gln Glu Glu Val Thr Asn Ala Thr Glu Thr Val Glu Ser Thr Asn Leu
65                  70                  75                  80

Asn Lys Leu Cys Met Lys Gly Arg Ser Tyr Lys Asp Leu Gly Asn Cys
                85                  90                  95

His Pro Val Gly Met Leu Ile Gly Thr Pro Val Cys Asp Pro His Leu
                100                 105                 110

Thr Gly Thr Trp Asp Thr Leu Ile Glu Arg Glu Asn Ala Ile Ala His
            115                 120                 125

Cys Tyr Pro Gly Ala Thr Ile Asn Glu Glu Ala Leu Arg Gln Lys Ile
        130                 135                 140

Met Glu Ser Gly Gly Ile Ser Lys Met Ser Thr Gly Phe Thr Tyr Gly
145                 150                 155                 160

Ser Ser Ile Asn Ser Ala Gly Thr Thr Lys Ala Cys Met Arg Asn Gly
                165                 170                 175

Gly Asp Ser Phe Tyr Ala Glu Leu Lys Trp Leu Val Ser Lys Thr Lys
                180                 185                 190

Gly Gln Asn Phe Pro Gln Thr Thr Asn Thr Tyr Arg Asn Thr Asp Thr
            195                 200                 205

Ala Glu His Leu Ile Ile Trp Gly Ile His His Pro Ser Ser Thr Gln
        210                 215                 220

Glu Lys Asn Asp Leu Tyr Gly Thr Gln Ser Leu Ser Ile Ser Val Glu
225                 230                 235                 240

Ser Ser Thr Tyr Gln Asn Asn Phe Val Pro Val Val Gly Ala Arg Pro
                245                 250                 255
```

Gln Val Asn Gly Gln Ser Gly Arg Ile Asp Phe His Trp Thr Leu Val
            260                 265                 270

Gln Pro Gly Asp Asn Ile Thr Phe Ser His Asn Gly Leu Ile Ala
            275                 280                 285

Pro Ser Arg Val Ser Lys Leu Thr Gly Arg Gly Leu Gly Ile Gln Ser
290                 295                 300

Glu Ala Leu Ile Asp Asn Ser Cys Glu Ser Lys Cys Phe Trp Arg Gly
305                 310                 315                 320

Gly Ser Ile Asn Thr Lys Leu Pro Phe Gln Asn Leu Ser Pro Arg Thr
            325                 330                 335

Val Gly Gln Cys Pro Lys Tyr Val Asn Gln Arg Ser Leu Leu Ala
            340                 345                 350

Thr Gly Met Arg Asn Val Pro Glu Val Val Gln Gly Arg Gly Leu Phe
            355                 360                 365

Gly Ala Ile Ala Gly Phe Ile Glu Asn Gly Trp Glu Gly Met Val Asp
370                 375                 380

Gly Trp Tyr Gly Phe Arg His Gln Asn Ala Gln Gly Thr Gly Gln Ala
385                 390                 395                 400

Ala Asp Tyr Lys Ser Thr Gln Ala Ala Ile Asp Gln Ile Thr Gly Lys
            405                 410                 415

Leu Asn Arg Leu Ile Glu Lys Thr Asn Thr Glu Phe Glu Ser Ile Glu
            420                 425                 430

Ser Glu Phe Ser Glu Thr Glu His Gln Ile Gly Asn Val Ile Asn Trp
            435                 440                 445

Thr Lys Asp Ser Ile Thr Asp Ile Trp Thr Tyr Gln Ala Glu Leu Leu
450                 455                 460

Val Ala Met Glu Asn Gln His Thr Ile Asp Met Ala Asp Ser Glu Met
465                 470                 475                 480

Leu Asn Leu Tyr Glu Arg Val Arg Lys Gln Leu Arg Gln Asn Ala Glu
            485                 490                 495

Glu Asp Gly Lys Gly Cys Phe Glu Ile Tyr His Thr Cys Asp Asp Ser
            500                 505                 510

Cys Met Glu Ser Ile Arg Asn Asn Thr Tyr Asp His Ser Gln Tyr Arg
            515                 520                 525

Glu Glu Ala Leu Leu Asn Arg Leu Asn Ile Asn Ser Val Ser Gly Gly
530                 535                 540

Gly Gly Leu Asn Asp Ile Phe Glu Ala Gln Lys Ile Glu Trp His Glu
545                 550                 555                 560

Arg Leu Val Pro Arg Gly Ser Pro Gly Ser Gly Tyr Ile Pro Glu Ala
            565                 570                 575

Pro Arg Asp Gly Gln Ala Tyr Val Arg Lys Asp Gly Trp Val Leu
            580                 585                 590

Leu Ser Thr Phe Leu Gly His His His His His
            595                 600

<210> SEQ ID NO 349
<211> LENGTH: 602
<212> TYPE: PRT
<213> ORGANISM: Artificial Sequence
<220> FEATURE:
<223> OTHER INFORMATION: Synthetic

<400> SEQUENCE: 349

Met Val Leu Val Asn Gln Ser His Gln Gly Phe Asn Lys Glu His Thr
1               5                   10                  15

```
Ser Lys Met Val Ser Ala Ile Val Leu Tyr Val Leu Ala Ala Ala
         20                  25                  30

Ala His Ser Ala Phe Ala Ala Asp Pro Gly Pro Ile Ile Cys Leu Gly
         35                  40                  45

His His Ala Val Glu Asn Gly Thr Ser Val Lys Thr Leu Thr Asp Asn
 50                  55                  60

His Val Glu Val Val Ser Ala Lys Glu Leu Val Glu Thr Asn His Thr
 65                  70                  75                  80

Asp Glu Leu Cys Pro Ser Pro Leu Lys Leu Val Asp Gly Gln Asp Cys
                 85                  90                  95

Asp Leu Ile Asn Gly Ala Leu Gly Ser Pro Gly Cys Asp Arg Leu Gln
                100                 105                 110

Asp Thr Thr Trp Asp Val Phe Ile Glu Arg Pro Thr Ala Val Asp Thr
            115                 120                 125

Cys Tyr Pro Phe Asp Val Pro Asp Tyr Gln Ser Leu Arg Ser Ile Leu
130                 135                 140

Ala Ser Ser Gly Ser Leu Glu Phe Ile Ala Glu Gln Phe Thr Trp Asn
145                 150                 155                 160

Gly Val Lys Val Asp Gly Ser Ser Ala Cys Leu Arg Gly Gly Arg
                165                 170                 175

Asn Ser Phe Phe Ser Arg Leu Asn Trp Leu Thr Lys Ala Thr Asn Gly
            180                 185                 190

Asn Tyr Gly Pro Ile Asn Val Thr Lys Glu Asn Thr Gly Ser Tyr Val
        195                 200                 205

Arg Leu Tyr Leu Trp Gly Val His His Pro Ser Ser Asp Asn Glu Gln
    210                 215                 220

Thr Asp Leu Tyr Lys Val Ala Thr Gly Arg Val Thr Val Ser Thr Arg
225                 230                 235                 240

Ser Asp Gln Ile Ser Ile Val Pro Asn Ile Gly Ser Arg Pro Arg Val
                245                 250                 255

Arg Asn Gln Ser Gly Arg Ile Ser Ile Tyr Trp Thr Leu Val Asn Pro
                260                 265                 270

Gly Asp Ser Ile Ile Phe Asn Ser Ile Gly Asn Leu Ile Ala Pro Arg
            275                 280                 285

Gly His Tyr Lys Ile Ser Lys Ser Thr Lys Ser Thr Val Leu Lys Ser
        290                 295                 300

Asp Lys Arg Ile Gly Ser Cys Thr Ser Pro Cys Leu Thr Asp Lys Gly
305                 310                 315                 320

Ser Ile Gln Ser Asp Lys Pro Phe Gln Asn Val Ser Arg Ile Ala Ile
                325                 330                 335

Gly Asn Cys Pro Lys Tyr Val Lys Gln Gly Ser Leu Met Leu Ala Thr
            340                 345                 350

Gly Met Arg Asn Ile Pro Gly Lys Gln Ala Lys Gly Leu Phe Gly Ala
        355                 360                 365

Ile Ala Gly Phe Ile Glu Asn Gly Trp Gln Gly Leu Ile Asp Gly Trp
    370                 375                 380

Tyr Gly Phe Arg His Gln Asn Ala Glu Gly Thr Gly Thr Ala Ala Asp
385                 390                 395                 400

Leu Lys Ser Thr Gln Ala Ala Ile Asp Gln Ile Asn Gly Lys Leu Asn
                405                 410                 415

Arg Leu Ile Glu Lys Thr Asn Glu Lys Tyr His Gln Ile Glu Lys Glu
            420                 425                 430
```

```
Phe Glu Gln Val Glu Gly Arg Ile Gln Asp Leu Glu Lys Tyr Val Glu
            435                 440                 445

Asp Thr Lys Ile Asp Leu Trp Ser Tyr Asn Ala Glu Leu Leu Val Ala
450                 455                 460

Leu Glu Asn Gln His Thr Ile Asp Val Thr Asp Ser Glu Met Asn Lys
465                 470                 475                 480

Leu Phe Glu Arg Val Arg Arg Gln Leu Arg Glu Asn Ala Glu Asp Gln
                485                 490                 495

Gly Asn Gly Cys Phe Glu Ile Phe His Gln Cys Asp Asn Asn Cys Ile
            500                 505                 510

Glu Ser Ile Arg Asn Gly Thr Tyr Asp His Asn Ile Tyr Arg Asp Glu
        515                 520                 525

Ala Ile Asn Asn Arg Ile Lys Ile Asn Pro Val Ser Gly Gly Gly Gly
    530                 535                 540

Leu Asn Asp Ile Phe Glu Ala Gln Lys Ile Glu Trp His Glu Arg Leu
545                 550                 555                 560

Val Pro Arg Gly Ser Pro Gly Ser Gly Tyr Ile Pro Glu Ala Pro Arg
                565                 570                 575

Asp Gly Gln Ala Tyr Val Arg Lys Asp Gly Glu Trp Val Leu Leu Ser
            580                 585                 590

Thr Phe Leu Gly His His His His His His
            595                 600
```

```
<210> SEQ ID NO 350
<211> LENGTH: 612
<212> TYPE: PRT
<213> ORGANISM: Artificial Sequence
<220> FEATURE:
<223> OTHER INFORMATION: Synthetic

<400> SEQUENCE: 350

Met Val Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro Gly Asp Lys Ile Cys Leu Gly
            35                  40                  45

His His Ala Val Ala Asn Gly Thr Lys Val Asn Thr Leu Thr Glu Arg
    50                  55                  60

Gly Val Glu Val Val Asn Ala Thr Glu Thr Val Glu Ile Thr Gly Ile
65                  70                  75                  80

Asp Lys Val Cys Thr Lys Gly Lys Lys Ala Val Asp Leu Gly Ser Cys
                85                  90                  95

Gly Ile Leu Gly Thr Ile Ile Gly Pro Pro Gln Cys Asp Leu His Leu
            100                 105                 110

Glu Phe Lys Ala Asp Leu Ile Ile Glu Arg Arg Asn Ser Ser Asp Ile
        115                 120                 125

Cys Tyr Pro Gly Arg Phe Thr Asn Glu Glu Ala Leu Arg Gln Ile Ile
    130                 135                 140

Arg Glu Ser Gly Gly Ile Asp Lys Glu Ser Met Gly Phe Arg Tyr Ser
145                 150                 155                 160

Gly Ile Arg Thr Asp Gly Ala Thr Ser Ala Cys Lys Arg Thr Val Ser
                165                 170                 175

Ser Phe Tyr Ser Glu Met Lys Trp Leu Ser Ser Ser Met Asn Asn Gln
            180                 185                 190
```

```
Val Phe Pro Gln Leu Asn Gln Thr Tyr Arg Asn Thr Arg Lys Glu Pro
        195                 200                 205

Ala Leu Ile Val Trp Gly Val His His Ser Ser Ser Leu Asp Glu Gln
    210                 215                 220

Asn Lys Leu Tyr Gly Thr Gly Asn Lys Leu Ile Thr Val Gly Ser Ser
225                 230                 235                 240

Lys Tyr Gln Gln Ser Phe Ser Pro Ser Pro Gly Ala Arg Pro Lys Val
                245                 250                 255

Asn Gly Gln Ala Gly Arg Ile Asp Phe His Trp Met Leu Leu Asp Pro
                260                 265                 270

Gly Asp Thr Val Thr Phe Thr Phe Asn Gly Ala Phe Ile Ala Pro Asp
            275                 280                 285

Arg Ala Thr Phe Leu Arg Ser Asn Ala Pro Ser Gly Ile Glu Tyr Asn
        290                 295                 300

Gly Lys Ser Leu Gly Ile Gln Ser Asp Ala Gln Ile Asp Glu Ser Cys
305                 310                 315                 320

Glu Gly Glu Cys Phe Tyr Ser Gly Gly Thr Ile Asn Ser Pro Leu Pro
                325                 330                 335

Phe Gln Asn Ile Asp Ser Arg Ala Val Gly Lys Cys Pro Arg Tyr Val
                340                 345                 350

Lys Gln Ser Ser Leu Pro Leu Ala Leu Gly Met Lys Asn Val Pro Glu
            355                 360                 365

Lys Ile Arg Thr Arg Gly Leu Phe Gly Ala Ile Ala Gly Phe Ile Glu
        370                 375                 380

Asn Gly Trp Glu Gly Leu Ile Asp Gly Trp Tyr Gly Phe Arg His Gln
385                 390                 395                 400

Asn Ala Gln Gly Gln Gly Thr Ala Ala Asp Tyr Lys Ser Thr Gln Ala
                405                 410                 415

Ala Ile Asp Gln Ile Thr Gly Lys Leu Asn Arg Leu Ile Glu Lys Thr
                420                 425                 430

Asn Lys Gln Phe Glu Leu Ile Asp Asn Glu Phe Thr Glu Val Glu Gln
            435                 440                 445

Gln Ile Gly Asn Val Ile Asn Trp Thr Arg Asp Ser Leu Thr Glu Ile
        450                 455                 460

Trp Ser Tyr Asn Ala Glu Leu Leu Val Ala Met Glu Asn Gln His Thr
465                 470                 475                 480

Ile Asp Leu Ala Asp Ser Glu Met Asn Lys Leu Tyr Glu Arg Val Arg
                485                 490                 495

Arg Gln Leu Arg Glu Asn Ala Glu Glu Asp Gly Thr Gly Cys Phe Glu
                500                 505                 510

Ile Phe His Arg Cys Asp Asp Gln Cys Met Glu Ser Ile Arg Asn Asn
            515                 520                 525

Thr Tyr Asn His Thr Glu Tyr Arg Gln Glu Ala Leu Gln Asn Arg Ile
        530                 535                 540

Met Ile Asn Pro Val Ser Gly Gly Gly Leu Asn Asp Ile Phe Glu
545                 550                 555                 560

Ala Gln Lys Ile Glu Trp His Glu Arg Leu Val Pro Arg Gly Ser Pro
                565                 570                 575

Gly Ser Gly Tyr Ile Pro Glu Ala Pro Arg Asp Gly Gln Ala Tyr Val
                580                 585                 590

Arg Lys Asp Gly Glu Trp Val Leu Leu Ser Thr Phe Leu Gly His His
            595                 600                 605

His His His His
```

<210> SEQ ID NO 351
<211> LENGTH: 23
<212> TYPE: PRT
<213> ORGANISM: Artificial Sequence
<220> FEATURE:
<223> OTHER INFORMATION: Synthetic

<400> SEQUENCE: 351

```
Ser Ala Phe Asp Leu Ala Met Arg Ile Met Trp Ile Tyr Val Phe Ala
1               5                   10                  15

Tyr Asn Arg Pro Ile Pro Phe
            20
```

<210> SEQ ID NO 352
<211> LENGTH: 23
<212> TYPE: PRT
<213> ORGANISM: Artificial Sequence
<220> FEATURE:
<223> OTHER INFORMATION: Synthetic

<400> SEQUENCE: 352

```
Ser Ala Phe Asp Leu Ala Met Arg Ile Met Trp Ile Tyr Val Phe Ala
1               5                   10                  15

Tyr Lys Arg Pro Ile Pro Phe
            20
```

<210> SEQ ID NO 353
<211> LENGTH: 93
<212> TYPE: PRT
<213> ORGANISM: Artificial Sequence
<220> FEATURE:
<223> OTHER INFORMATION: Synthetic

<400> SEQUENCE: 353

```
Met Ser Asn Ala Met Asp Gly Gln Gln Leu Asn Arg Leu Leu Leu Glu
1               5                   10                  15

Trp Ile Gly Ala Trp Asp Pro Phe Gly Leu Gly Lys Asp Ala Tyr Asp
                20                  25                  30

Val Glu Ala Glu Ala Val Leu Gln Ala Val Tyr Glu Thr Glu Ser Ala
            35                  40                  45

Phe Asp Leu Ala Met Arg Ile Met Trp Ile Tyr Val Phe Ala Tyr Lys
        50                  55                  60

Arg Pro Ile Pro Phe Pro His Ala Gln Lys Leu Ala Arg Arg Leu Leu
65                  70                  75                  80

Glu Leu Lys Gln Ala Ala Ser Ser Pro Leu Pro Leu Glu
                85                  90
```

<210> SEQ ID NO 354
<211> LENGTH: 93
<212> TYPE: PRT
<213> ORGANISM: Artificial Sequence
<220> FEATURE:
<223> OTHER INFORMATION: Synthetic

<400> SEQUENCE: 354

```
Met Ser Asn Ala Met Asp Gly Gln Gln Leu Asn Arg Leu Leu Leu Glu
1               5                   10                  15
```

-continued

```
Trp Ile Gly Ala Trp Asp Pro Phe Gly Leu Gly Lys Asp Ala Tyr Asp
            20              25              30

Val Glu Ala Glu Ala Val Leu Gln Ala Val Tyr Glu Thr Glu Ser Ala
        35              40              45

Phe Asp Leu Ala Met Arg Ile Met Trp Ile Tyr Val Phe Ala Tyr Asn
    50              55              60

Arg Pro Ile Pro Phe Ser His Ala Gln Lys Leu Ala Arg Arg Leu Leu
65              70              75              80

Glu Leu Lys Gln Ala Ala Ser Ser Pro Leu Pro Leu Glu
            85              90
```

POLYPEPTIDES FOR TREATING AND/OR LIMITING INFLUENZA INFECTION

CROSS-REFERENCE

This application is a U.S. National Phase of International Application No. PCT/US2013/030311, filed Mar. 12, 2013, which claims priority to U.S. Provisional Application No. 61/610,311, filed Mar. 13, 2012, the disclosures of which are hereby incorporated by reference in their entireties.

STATEMENT OF GOVERNMENT SUPPORT

This invention was made with government support under grant number 5P41RR011823-15 awarded by National Institutes of Health and grant number HR0011-08-0085 awarded by Defense Advanced Research Projects Agency and grant number HDTRA1-10-1-0040 awarded by Defense Threat Reduction Agency. The government has certain rights in the invention.

BACKGROUND

Influenza virus is a member of Orthomyxoviridae family. There are three subtypes of influenza viruses designated A, B, and C. The influenza virion contains a segmented negative-sense RNA genome, encoding, among other proteins, hemagglutinin (HA) and neuraminidase (NA). Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA2 protein undergoes conformational changes that lead to fusion of viral and cell membranes and virus uncoating and M2-mediated release of M1 proteins from nucleocapsid-associated ribonucleoproteins (RNPs), which migrate into the cell nucleus for viral RNA synthesis. Antibodies to HA proteins prevent virus infection by neutralizing virus infectivity.

Influenza presents a serious public-health challenge and new therapies are needed to combat viruses that are resistant to existing antivirals or escape neutralization by the immune system.

SUMMARY OF THE INVENTION

In a first aspect, the present invention provides polypeptides comprising or consisting of an amino acid sequence according to general formula I R1-R2-Phe-R3-R4-R5-R6-R7-R8-R9-R10-R11-R12-R13-R14-R15-R16-X1-R17 (SEQ ID NO: 2), wherein R1 is selected from the group consisting of Ser, Ala, Phe, His, Lys, Met, Asn, Gln, Thr, Val, Tyr, and Asp;

R2 can be any amino acid;

R3 is selected from the group consisting of Asp, Ala, Glu, Gly, Asn, Pro, Ser, and Tyr;

R4 is selected from the group consisting of Leu and Phe;

R5 can be any amino acid;

R6 is selected from the group consisting of Met, Phe, His, Ile, Leu, Gln, and Thr;

R7 is selected from the group consisting of Arg, Gly, Lys, Gln, and Thr;

R8 is selected from the group consisting of Ile, Asn, Gln, Val, and Trp;

R9 is selected from the group consisting of Met, Gly, Ile, Lys, Leu, Asn, Arg, Ser, Thr, Val, His, and Tyr;

R10 is selected from the group consisting of Trp and Phe;

R11 is selected from the group consisting of Ile, Phe, Ser, Thr, and Val;

R12 is selected from the group consisting of Tyr, Cys, Asp, Phe, His, Asn, and Ser;

R13 is selected from the group consisting of Val, Ala, Phe, Ile, Leu, Asn, Gln, Thr, and Tyr;

R14 is selected from the group consisting of Phe, Glu, and Leu;

R15 is selected from the group consisting of Ala, Gly, Lys, Arg, and Ser;

R16 is selected from the group consisting of Phe, Cys, His, Lys, Leu, Met, Asn, Gln, Arg, Thr, Val, Trp, and Tyr.

X1 is comprises the amino acid sequence Z1-Arg-Z2-Ile-Pro (SEQ ID NO: 3), wherein Z1 is Lys or Asn, and Z2 is selected from the group consisting of Lys, Pro, Gln, and Thr; and R17 is Phe or Tyr.

In one embodiment, Z2 is Gln. In another embodiment, general formula I is A1-R1-R2-Phe-R3-R4-R5-R6-R7-R8-R9-R10-R11-R12-R13-R14-R15-R16-X1-R17-B1 (SEQ ID NO: 4), wherein one or both of A1 and B1 are present, and wherein A1 comprises the amino acid sequence: MSNAMDGQQLNRLLLEWIGAWDPFGLGKDAYD(D/V/Y/F)EA(A/D)(A/K/R/E)VL(Q/K)AVY(E/A)T(N/D/E) (SEQ ID NO: 5); and B1 comprises the amino acid sequence (L/A/V/D/I/P)HA(Q/P)KLARRLLELK(Q/L)AASSPLP (SEQ ID NO: 6). In one further embodiment, A1 is present and comprises the amino acid sequence MSNAMDGQQLNRLLLEWIGAWDPFGLGKDAYD(F)EA(A/D)(E)VL(Q/K)AVY(E/A)T(E) (SEQ ID NO: 279). In a further embodiment, B1 is present and comprises the amino acid sequence (D/I/P)HA(Q/P)KLARRLLELK(Q/L)AASSPLP (SEQ ID NO: 278).

In another embodiment, the present invention provides polypeptides comprising or consisting of an amino acid sequence according to general formula II R1-R2-R3-R4-R5-R6-R7-R8-R9-Ala-R10-R11-Phe-X1-R12-R13-X2-R14 (SEQ ID NO: 84), wherein R1 is selected from the group consisting of Phe and Val;

R2 is selected from the group consisting of Ser, Ala, Phe, Gly, Ile, Lys, Leu, Met, Asn, Pro, Gln, Arg, Thr, and Val;

R3 is selected from the group consisting of Glu, and Asp;

R4 is selected from the group consisting of Asn, His, Ile, Lys, Leu, Met, Arg, Ser, and Thr;

R5 is selected from the group consisting of Leu, Phe, Ile, Met, Asn, Gln, and Val;

R6 is selected from the group consisting of Ala, Asp, Lys, Met, Asn, Gln, Arg, Glu, and Val;

R7 is selected from the group consisting of Phe, Asp, Asn, and Tyr;

R8 is selected from the group consisting of Glu, Ala, Asp, Gly, His, Lys, Leu, Met, Asn, Gln, Arg, Ser, Thr, Val, and Trp;

R9 is selected from the group consisting of Leu, Phe, Ile, Met, and Val;

R10 is selected from the group consisting of Leu, Ile, Met, and Tyr; and

R11 is selected from the group consisting of Ser, Ala, Gly, and Tyr;

X1 is 5-15 amino acids in length, wherein each position can be any amino acid;

R12 is selected from the group consisting of Gln, Tyr, Phe, Met, Arg, Lys, Ser, and Gly;

R13 is selected from the group consisting of Tyr, Asp, Met, Asn, and Ser;

X2 is any amino acid; and R14 is selected from the group consisting of Ser, Arg, and Lys.

In one embodiment, R12 is Ser. In another embodiment, general formula II is A1-R1-R2-R3-R4-R5-R6-R7-R8-R9-Ala-R10-R11-Phe-X1-R12-R13-X2-R14-B1 (SEQ ID NO: 86), wherein at least one of A1 and B1 are present, and wherein:

A1 comprises the amino acid sequence: Z1-ASTRGS-GRPW-Z2 (SEQ ID NO: 87), wherein Z1 is absent or is Met, and Z2 is selected from group consisting of Gly, Arg, Lys, Asp, and Asn, and B1 comprises the amino acid sequence G-Z1-TPEEVKKHYE (SEQ ID NO: 88), where Z1 is R or K. In a further embodiment, A1 is present and comprises the amino acid sequence Z1-ASTRGSGRPWN (SEQ ID NO: 280).

In a third aspect, the present invention provides isolated nucleic acids encoding the polypeptide of any embodiment of the invention. In a fourth aspect, the present invention provides recombinant expression vectors comprising the nucleic acid of the third aspect of the invention, operatively linked to a suitable control sequence. In a fifth aspect, the present invention provides recombinant host cells comprising the recombinant expression vectors of the fourth aspect of the invention. In a sixth aspect, the present invention provides antibodies that selectively bind to the polypeptides of the invention.

In a seventh aspect, the present invention provides pharmaceutical compositions, comprising one or more polypeptides according of the invention and a pharmaceutically acceptable carrier.

In an eighth aspect, the present invention provides methods for treating and/or limiting an influenza infection, comprising administering to a subject in need thereof a therapeutically effective amount of one or more polypeptides of the invention, salts thereof, conjugates thereof, or pharmaceutical compositions thereof, to treat and/or limit the influenza infection.

In a ninth aspect, the present invention provides methods for diagnosing an influenza infection, or monitoring progression of an influenza infection, comprising (a) contacting a biological sample from a subject suspected of having an influenza infection with a diagnostically effective amount of one or more polypeptides of the invention under conditions suitable for binding of the polypeptide to a viral HA protein present in the sample; and (b) detecting polypeptide-viral HA binding complexes, where the presence of such binding complexes indicates that the subject has an influenza infection, or provides a measure progression of an influenza infection.

In a tenth aspect, the present invention provides methods for identifying candidate influenza vaccines, comprising (a) contacting test compounds with a polypeptide of the present invention under conditions suitable for polypeptide binding;

(b) removing unbound test compounds; and (c) identifying those test compounds that bind to the polypeptide of the invention, wherein such test compounds are candidate influenza vaccines.

In an eleventh aspect, the present invention provides methods for identifying candidate compounds for treating, limiting, and/or diagnosing influenza infection, comprising (a) contacting an influenza HA protein with (i) test compounds and (ii) a polypeptide of the present invention, under conditions suitable for binding of the HA protein to the polypeptide of the present invention; and (b) identifying those test compounds that outcompete the polypeptide for binding to the HA protein, wherein such test compounds are candidate compounds for treating, limiting, and/or diagnosing influenza infection.

DETAILED DESCRIPTION OF THE INVENTION

Figure 1:
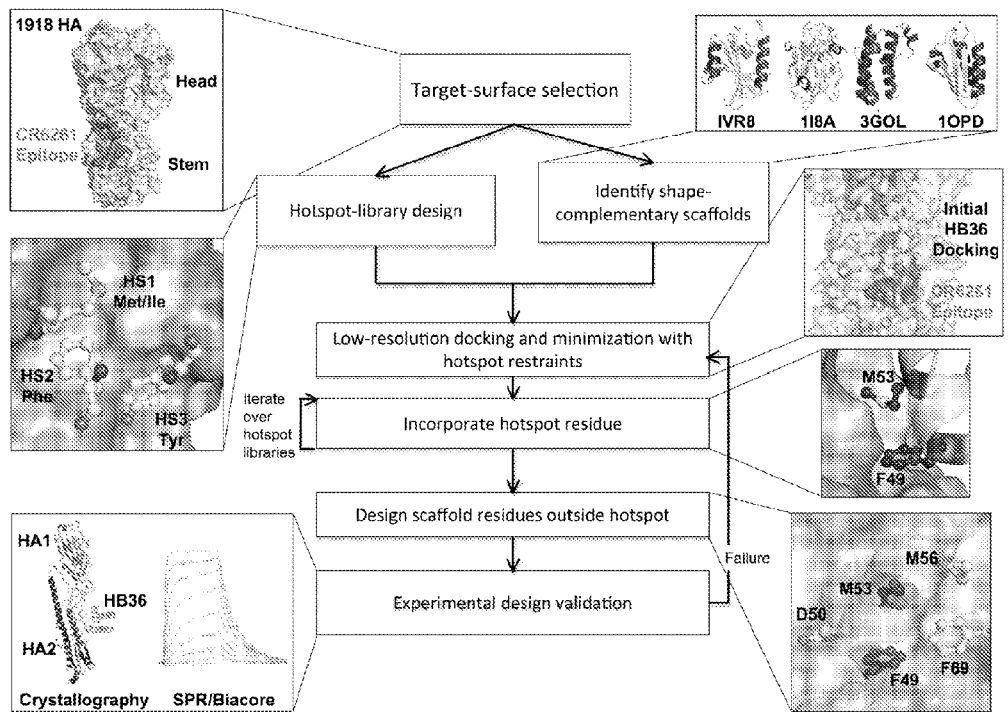
FIG. 1. Overview of the design process. The flow chart illustrates key steps in the design process for novel binding proteins, with thumbnails illustrating each step in the creation of binders that target the stem of the 1918 HA.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2nd Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides polypeptides comprising an amino acid sequence according to general formula I R1-R2-Phe-R3-R4-R5-R6-R7-R8-R9-R10-R11-R12-R13-R14-R15-R16 (SEQ ID NO: 1), wherein R1 is selected from the group consisting of Ser, Ala, Phe, His, Lys, Met, Asn, Gln, Thr, Val, Tyr, and Asp;

R2 can be any amino acid;

R3 is selected from the group consisting of Asp, Ala, Glu, Gly, Asn, Pro, Ser, and Tyr;

R4 is selected from the group consisting of Leu and Phe;

R5 can be any amino acid;

R6 is selected from the group consisting of Met, Phe, His, Ile, Leu, Gln, and Thr;

R7 is selected from the group consisting of Arg, Gly, Lys, Gln, and Thr;

R8 is selected from the group consisting of Ile, Asn, Gln, Val, and Trp;

R9 is selected from the group consisting of Met, Gly, Ile, Lys, Leu, Asn, Arg, Ser, Thr, Val, His, and Tyr;

R10 is selected from the group consisting of Trp and Phe;

R11 is selected from the group consisting of Ile, Phe, Ser, Thr, and Val;

R12 is selected from the group consisting of Tyr, Cys, Asp, Phe, His, Asn, and Ser;

R13 is selected from the group consisting of Val, Ala, Phe, Ile, Leu, Asn, Gln, Thr, and Tyr;

R14 is selected from the group consisting of Phe, Glu, and Leu;

R15 is selected from the group consisting of Ala, Gly, Lys, Arg, and Ser; and

R16 is selected from the group consisting of Phe, Cys, His, Lys, Leu, Met, Asn, Gln, Arg, Thr, Val, Trp, and Tyr.

In one embodiment, general formula I is R1-R2-Phe-R3-R4-R5-R6-R7-R8-R9-R10-R11-R12-R13-R14-R15-R16-X1-R17 (SEQ ID NO: 2), wherein R1 through R16 are as defined above, and wherein X1 is 4-8 amino acids in length, wherein each position can be any amino acid; and R17 is Phe or Tyr.

In various embodiments, X1 is 4, 5, 6, 7, or 8 amino acids in length. In another embodiment, X1 comprises the amino acid sequence Z1-Arg-Z2-Ile-Pro (SEQ ID NO: 3), wherein Z1 is Lys or Asn, and Z2 is selected from the group consisting of Lys, Pro, Gln, and Thr. In one specific embodiment, Z2 is Gln.

In another embodiment, that can be combined with any other embodiments herein, general formula I is A1-R1-R2-Phe-R3-R4-R5-R6-R7-R8-R9-R10-R11-R12-R13-R14-R15-R16-X1-R17-B1 (SEQ ID NO: 4), wherein R1 through R17 and X1 are as defined above, wherein A1 and/or B1 are optionally present, and wherein A1 comprises the amino acid sequence: MSNAMDGQQLNRLLLEWIGAWDPFGLGKDAYD(D/V/Y/F)EA(A/D)(A/K/R/E)VL(Q/K)AVY(E/A)T(N/D/E) (SEQ ID NO: 5); and B1 comprises the amino acid sequence (L/A/V/D/I/P)HA (Q/P)KLARRLLELK(Q/L)AASSPLP (SEQ ID NO: 6). The inventors have discovered that polypeptides comprising or consisting of the amino acid sequence of general formula I (derived from HB36.4, as described in more detail in the attached) form helices that recognize and are strong binders to Influenza A hemagglutinin ("HA"), such as influenza viruses of phylogenetic group I, preferably influenza A viruses comprising HA of the H1 or H5 subtype. Thus, the polypeptides can be used, for example, to treat and/or limit development of an influenza infection. In one embodiment, A1 is present and comprises the amino acid sequence MSNAMDGQQLNRLLLEWIGAWDPFGLGKDAYD(F)EA(A/D)(E)VL(Q/K)AVY(E/A)T(E) (SEQ ID NO: 279). In another embodiment, B1 is present and comprises the amino acid sequence (D/I/P)HA(Q/P)KLARRLLELK(Q/L)AASS-PLP (SEQ ID NO: 278).

In one embodiment, the polypeptide comprises the polypeptide SAFDLAMRIMWIYVFAF (SEQ ID NO:7), SAFDLAMRIMWIYVFAFKRPIPF (SEQ ID NO:8), or a variant including 1, 2, 3, 4, 5, 6, 7, 8, 9, 10, or more variant positions or SEQ ID NOS. 7 or 8 according to any embodiment of general formula I. In other exemplary embodiments, the polypeptide comprises or consists of a polypeptide selected from the group consisting of (scaffold derived from noted in parentheses):

(HB36.2) (SEQ ID NO: 9)
DAFDLAMRIMWIYVFAFNRPIPF;

(HB36.2) (SEQ ID NO: 10)
DAFDLAMRIMWIYVFAF;

(HB36.3) (SEQ ID NO: 11)
SAFDLAMRIMWIYVFAFNRPIPF;

(HB36.3 and HB36.4) (SEQ ID NO: 7)
SAFDLAMRIMWIYVFAF;

(HB36.4) (SEQ ID NO: 8)
SAFDLAMRIMWIYVFAFKRPIPF;

>HB36.4_s4_E03 (SEQ ID NO: 15)
HAFDLAMRIHWIYVFAF;

(SEQ ID NO: 16)
HAFDLAMRIHWIYVFAFKRKIPF;

>HB36.4_s4_E05 (SEQ ID NO: 17)
SAFDLAMRIIWIYVFAY;

(SEQ ID NO: 18)
SAFDLAMRIIWIYVFAYKRKIPF;

>HB36.4_s4_E06 (SEQ ID NO: 19)
SAFDLAMRINWIYVFAF;

(SEQ ID NO: 20)
SAFDLAMRINWIYVFAFKRPIPF;

>HB36.4_s4_E07 (SEQ ID NO: 21)
SAFDLAMRINWIYVFAF;

(SEQ ID NO: 22)
SAFDLAMRINWIYVFAFKRKIPF;

>HB36.4_s4_E08 (SEQ ID NO: 23)
SAFDLAMTIHWIYNFAF;

(SEQ ID NO: 24)
SAFDLAMTIHWIYNFAFKRKIPF;

>HB36.4_s4_E09 (SEQ ID NO: 25)
SAFDLAMRINWIYVFAF;

(SEQ ID NO: 26)
SAFDLAMRINWIYVFAFKRTIPF;

>HB36.4_s4_E10 (SEQ ID NO: 27)
SAFDLAMRIHWIYIFAF;

(SEQ ID NO: 28)
SAFDLAMRIHWIYIFAFKRPIPF;

>HB36.4_s4_E11 (SEQ ID NO: 29)
SAFDLAMRIHWIYNFAF;

(SEQ ID NO: 30)
SAFDLAMRIHWIYNFAFKRKIPF;

>HB36.4_s4_E12 (SEQ ID NO: 31)
SAFDLAMRIHWIYNFAY;

(SEQ ID NO: 32)
SAFDLAMRIHWIYNFAYKRTIPF;

>HB36.4_s4_E13 (SEQ ID NO: 33)
SAFDLAMRIHWIYNFAF;

(SEQ ID NO: 34)
SAFDLAMRIHWIYNFAFKRKIPF;

>HB36.4_s4_E14 (SEQ ID NO: 35)
SAFDLAMRIHWIYIFAF;

(SEQ ID NO: 36)
SAFDLAMRIHWIYIFAFKRTIPF;

>HB36.4_s4_E17 (SEQ ID NO: 37)
SAFDLAMRIHWIYNFAF;

(SEQ ID NO: 38)
SAFDLAMRIHWIYNFAFKRKIPF;

>HB36.4_s4_E18 (SEQ ID NO: 39)
SAFDLAMKIHWIYNFAF;

(SEQ ID NO: 40)
SAFDLAMKIHWIYNFAFKRTIPF;

>HB36.4_s4_E19 (SEQ ID NO: 41)
SAFDLAMKIHWIYIFAF;

(SEQ ID NO: 42)
SAFDLAMKIHWIYIFAFKRTIPF;

(SEQ ID NO: 44)
HAFDLAMRIMWIYVFAF;

(SEQ ID NO: 45)
SAFDLAMKIMWIYVFAF;

(SEQ ID NO: 46)
SAFDLAMRIHWIYVFAF;

(SEQ ID NO: 47)
SAFDLAMRINWIYVFAF;

(SEQ ID NO: 48)
SAFDLAMRIYWIYVFAF;

-continued

SAFDLAMRIMWIYFFAF; (SEQ ID NO: 49)

SAFDLAMRIMWIYLFAF; (SEQ ID NO: 50)

SAFDLAMRIMWIYTFAF; (SEQ ID NO: 51)

SAFDLAMRIMWIYNFAF; (SEQ ID NO: 52)

SAFDLAMRIMWIYVFAW; (SEQ ID NO: 53)

HAFDLAMRIMWIYVFAFKRPIPF; (SEQ ID NO: 55)

SAFDLAMKIMWIYVFAFKRPIPF; (SEQ ID NO: 56)

SAFDLAMRIHWIYVFAFKRPIPF; (SEQ ID NO: 57)

SAFDLAMRINWIYVFAFKRPIPF; (SEQ ID NO: 58)

SAFDLAMRIYWIYVFAFKRPIPF; (SEQ ID NO: 59)

SAFDLAMRIMWIYFFAFKRPIPF; (SEQ ID NO: 60)

SAFDLAMRIMWIYLFAFKRPIPF; (SEQ ID NO: 61)

SAFDLAMRIMWIYTFAFKRPIPF; (SEQ ID NO: 62)

SAFDLAMRIMWIYNFAFKRPIPF; (SEQ ID NO: 63)

SAFDLAMRIMWIYVFAWKRPIPF; (SEQ ID NO: 64)

>HB36.4 (SEQ ID NO: 65)
(Asp47Ser, Ala60Val, Asn64Lys)
MSNAMDGQQLNRLLLEWIGAWDPFGLGKDAYDVEAEAVLQAVYETESAFD

LAMRIMWIYVFAFKRPIPFPHAQKLARRLLELKQAASSPLPLE;

>HB36.1 (Asp47Ser) (SEQ ID NO: 66)
MSNAMDGQQLNRLLLEWIGAWDPFGLGKDAYDVEAEAVLQAVYETESAFD

LAMRIMWIYAFAFNRPIPFSHAQKLARRLLELKQAASSPLPLE;

>HB36.2 (Ala60Val) (SEQ ID NO: 67)
MSNAMDGQQLNRLLLEWIGAWDPFGLGKDAYDVEAEAVLQAVYETEDAFD

LAMRIMWIYVFAFNRPIPFSHAQKLARRLLELKQAASSPLPLE;

>HB36.3 (Asp47Ser, Ala60Val) (SEQ ID NO: 68)
MSNAMDGQQLNRLLLEWIGAWDPFGLGKDAYDVEAEAVLQAVYETESAFD

LAMRIMWIYVFAFNRPIPFSHAQKLARRLLELKQAASSPLPLE;

>HB36.4_s4_E03 (SEQ ID NO: 69)
MSNAMDGQQLNRLLLEWIGAWDPFGLGKDAYDDEAAAVLQAVYETNHAFD

LAMRIHWIYVFAFKRKIPFLHAQKLARRLLELKQAASSPLP;

>HB36.4_s4_E05 (SEQ ID NO: 70)
MSNAMDGQQLNRLLLEWIGAWDPFGLGKDAYDVEAAAVLKAVYATNSAFD

LAMRIIWIYVFAYKRKIPFAHAQKLARRLLELKQAASSPLP;

>HB36.4_s4_E06 (SEQ ID NO: 71)
MSNAMDGQQLNRLLLEWIGAWDPFGLGKDAYDFEADKVLQAVYETNSAFD

LAMRINWIYVFAFKRPIPFVHAQKLARRLLELKQAASSPLP;

>HB36.4_s4_E07 (SEQ ID NO: 72)
MSNAMDGQQLNRLLLEWIGAWDPFGLGKDAYDVEAAAVLKAVYETNSAFD

LAMRINWIYVFAFKRKIPFAHAQKLARRLLELKQAASSPLP;

>HB36.4_s4_E08 (SEQ ID NO: 73)
MSNAMDGQQLNRLLLEWIGAWDPFGLGKDAYDVEADKVLQAVYDTNSAFD

LAMTIHWIYNFAFKRKIPFLHAPKLARRLLELKLAASSPLP;

>HB36.4_s4_E09 (SEQ ID NO: 74)
MSNAMDGQQLNRLLLEWIGAWDPFGLGKDAYDDEADRVLQAVYETNSAFD

LAMRINWIYVFAFKRTIPFAHAQKLARRLLELKQAASSPLP;

>HB36.4_s4_E10 (SEQ ID NO: 75)
MSNAMDGQQLNRLLLEWIGAWDPFGLGKDAYDYEADKVLQAVYETNSAFD

LAMRIHWIYIFAFKRPIPFVHAQKLARRLLELKQAASSPLP;

>HB36.4_s4_E11 (SEQ ID NO: 76)
MSNAMDGQQLNRLLLEWIGAWDPFGLGKDAYDVEADAVLKAVYETNSAFD

LAMRIHWIYNFAFKRKIPFVHAQKLARRLLELKQAASSPLP;

>HB36.4_s4_E12 (SEQ ID NO: 77)
MSNAMDGQQLNRLLLEWIGAWDPFGLGKDAYDDEADKVLQAVYATNSAFD

LAMRIHWIYNFAYKRTIPFVHAQKLARRLLELKQAASSPLP;

>HB36.4_s4_E13 (SEQ ID NO: 78)
MSNAMDGQQLNRLLLEWIGAWDPFGLGKDAYDDEAARVLKAVYATDSAFD

LAMRIHWIYNFAFKRKIPFLHAQKLARRLLELKQAASSPLP;

>HB36.4_s4_E14 (SEQ ID NO: 79)
MSNAMDGQQLNRLLLEWIGAWDPFGLGKDAYDVEADKVLQAVYATNSAFD

LAMRIHWIYIFAFKRTIPFIHAQKLARRLLELKQAASSPLP;

>HB36.4_s4_E17 (SEQ ID NO: 80)
MSNAMDGQQLNRLLLEWIGAWDPFGLGKDAYDYEADEVLKAVYATNSAFD

LAMRIHWIYNFAFKRKIPFTHAQKLARRLLELKQAASSPLP;

>HB36.4_s4_E18 (SEQ ID NO: 81)
MSNAMDGQQLNRLLLEWIGAWDPFGLGKDAYDVEAAKVLKAVYETNSAFD

LAMKIHWIYNFAFKRTIPFVHAQKLARRLLELKQAASSPLPLE;

>HB36.4_s4_E19 (SEQ ID NO: 82)
MSNAMDGQQLNRLLLEWIGAWDPFGLGKDAYDVEADKVLQAVYATNSAFD

LAMKIHWIYIFAFKRTIPFIHAQKLARRLLELKQAASSPLP;

E14 (SEQ ID NO: 33)
SAFDLAMRIHWIYNFAF;

E20 (SEQ ID NO: 281)
HAFDLAMRIHWIYNFAF;

36.5 (SEQ ID NO: 33)
SAFDLAMRIHWIYNFAF;

(SEQ ID NO. 282)
SAFDLAMRIMWIYVFAY;

(SEQ ID NO: 283)
HAFDLAMRIMWIYVFAY;

E14 (SEQ ID NO: 30)
SAFDLAMRIHWIYNFAFKRKIPF;

E20 (SEQ ID NO: 284)
HAFDLAMRIHWIYNFAFKRKIPF;

36.5 (SEQ ID NO: 30)
SAFDLAMRIHWIYNFAFKRKIPF;

-continued

E14: (SEQ ID NO: 285)
(33Y)EA(36A)(37E)VL(40K)AVY(44E)T(46E)SAFDLAMRIHWI

YNFAFKRPIPFP;

E15: (SEQ ID NO: 286)
(33D)EA(36A)(37R)VL(40K)AVY(44E)T(46D)SAFDLAMRIHWI

YNFAFKRPIPFP;

E16: (SEQ ID NO: 287)
(33Y)EA(36D)(37E)VL(40K)AVY(44E)T(46N)SAFDLAMRIHWI

YNFAFKRPIPFP;

E17: (SEQ ID NO: 288)
(33V)EA(36A)(37R)VL(40Q)AVY(44E)T(46N)SAFDLAMRI-WI

YNFAFKRPIPFP;

E18: (SEQ ID NO: 289)
(33V)EA(36D)(37K)VL(40Q)AVY(44E)T(46N)SAFDLAMRIHWI

YNFAFKRPIPFP;

E19: (SEQ ID NO: 290)
(33V)EA(36D)(37A)VL(40K)AVY(44A)T(46N)SAFDLAMRIHWI

YNFAFKRPIPFP;

E20: (SEQ ID NO: 291)
(33Y)EA(36A)(37E)VL(40K)AVY(44E)T(46E)HAFDLAMRIHWI

YNFAFKRPIPFP;

36.5: (SEQ ID NO: 292)
(33Y)EA(36A)(37E)VL(40E)AVY(44E)T(46E)SAFDLAMRIHWI

YNFAFKRPIPFP;

Best: (SEQ ID NO: 293)
(33Y)EA(36A)(37E)VL(40K)AVY(44E)T(46E)SAFDLAMRIHWI

YNFAFKRPIPFP;

E14: (SEQ ID NO: 294)
MSNAMDGQQLNRLLLEWIGAWDPFGLGKDAYD(33Y)EA(36A)(37E)

VL(40K)AVY(44E)T(46E)SAFDLAMRIHWIYNFAFKRPIPFPPHAQ

KLARRLLELKQAASSPLPLE;

E15: (SEQ ID NO: 295)
MSNAMDGQQLNRLLLEWIGAWDPFGLGKDAYD(33D)EA(36A)(37R)

VL(40K)AVY(44E)T(46D)SAFDLAMRIHWIYNFAFKRPIPFPPHAQ

KLARRLLELKQAASSPLPLE;

E16: (SEQ ID NO: 296)
MSNAMDGQQLNRLLLEWIGAWDPFGLGKDAYD(33Y)EA(36D)(37E)

VL(40K)AVY(44E)T(46N)SAFDLAMRIHWIYNFAFKRPIPFPPHAQ

KLARRLLELKQAASSPLPLE;

E17: (SEQ ID NO: 297)
MSNAMDGQQLNRLLLEWIGAWDPFGLGKDAYD(33V)EA(36A)(37R)

VL(40Q)AVY(44E)T(46N)SAFDLAMRI-WIYNFAFKRPIPFPPHAQ

KLARRLLELKQAASSPLPLE

E18: (SEQ ID NO: 298)
MSNAMDGQQLNRLLLEWIGAWDPFGLGKDAYD(33V)EA(36D)(37K)

VL(40Q)AVY(44E)T(46N)SAFDLAMRIHWIYNFAFKRPIPFPPHAQ

KLARRLLELKQAASSPLPLE;

E19: (SEQ ID NO: 299)
MSNAMDGQQLNRLLLEWIGAWDPFGLGKDAYD(33V)EA(36D)(37A)

VL(40K)AVY(44A)T(46N)SAFDLAMRIHWIYNFAFKRPIPFPPHAQ

KLARRLLELKQAASSPLPLE;

E20: (SEQ ID NO: 300)
MSNAMDGQQLNRLLLEWIGAWDPFGLGKDAYD(33Y)EA(36A)(37E)

VL(40K)AVY(44E)T(46E)HAFDLAMRIHWIYNFAFKRPIPFPPHAQ

KLARRLLELKQAASSPLPLE 36.5: (SEQ ID NO: 301)
MSNAMDGQQLNRLLLEWIGAWDPFGLGKDAYD(33Y)EA(36A)(37E)

VL(40E)AVY(44E)T(46E)SAFDLAMRIHWIYNFAFKRPIPFPPHAQ

KLARRLLELKQAASSPLPLE;
and

Best: (SEQ ID NO: 302)
MSNAMDGQQLNRLLLEWIGAWDPFGLGKDAYD(33Y)EA(36A)(37E)

VL(40K)AVY(44E)T(46E)SAFDLAMRIHWIYNFAFKRPIPFPPHAQ

KLARRLLELKQAASSPLPLE.

In various preferred embodiments, HB36.4 (SAFDLAMRIMWIYVFAF (SEQ ID NO: 7)) is modified such that one or more of the following is true: R1 is His; R7 is Lys; R9 is Tyr, Asn, or His; R13 is Phe, Leu, Thr, or Asn; and R16 is Trp. In another embodiment, R10 is Trp. In a further embodiment, R2 and/or R5 is Ala. In a further embodiment, R17 is Phe.

As will be appreciated by those of skill in the art, these are just exemplary polypeptides falling under the scope of the claim. The table below provides per position allowable substitutions on an HB36.4 scaffold.

HB36.4:
(1) Central helix recognition motif from Serine 47-Phenylalanine 63 (SAFDLAMRIMWIYVFAF (SEQ ID NO: 7)); Also Phe 69 outside of that recognition motif (MSNAMDGQQLNRLLLEWIGAWDPFGLGKDAYDVEAEAVLQAVYETESAF DLAMRIMWIYVFAFKRPIPFPHAQKLARRLLELKQAASSPLPLE (SEQ ID NO: 65))
(2) Allowable positions were determined from yeast display selections of HB36.4 variants to SC1918/H1 HA coupled to deep sequencing (see attached for further details). The threshold was no more than 80% depletion in the frequency of a given mutant in the selection library after two selection sorts by FACS. Positions listed in bold font indicate positions that make contact with the HA surface.

TABLE 1

Allowable substitutions on an HB36.4 scaffold

| Position | HB36.4 Residue | Allowable |
| --- | --- | --- |
| 47 R1 | Ser | ala, phe, his, lys, met, asn, gln, thr, val, tyr, asp |
| 48 R2 | Ala | All Amino Acids |
| 49 | Phe | Phe |
| 50 R3 | Asp | Ala, Glu, Gly, Asn, Pro, Ser, Tyr |
| 51 R4 | Leu | Phe |
| 52 R5 | Ala | All amino acids |
| 53 R6 | Met | Phe, His, Ile, Leu, Gln, Thr |
| 54 R7 | Arg | gly, lys, gln, thr |
| 55 R8 | Ile | asn, gln, val, trp |
| 56 R9 | Met | Gly, Ile, Lys, Leu, Asn, Arg, Ser, Thr, Val, Tyr, His |
| 57 R10 | Trp | Phe |
| 58 R11 | Ile | phe, ser, thr, val |

TABLE 1-continued

Allowable substitutions on an HB36.4 scaffold

| Position | HB36.4 Residue | Allowable |
|---|---|---|
| 59 R12 | Tyr | cys, asp, phe, his, asn, ser |
| 60 R13 | Val | Ala, Phe, Ile, Leu, Asn, Gln, Thr, Tyr |
| 61 R14 | Phe | Glu, Leu |
| 62 R15 | Ala | gly, lys, arg, ser |
| 63 R16 | Phe | cys, his, lys, leu, met, asn, gln, arg, thr, val, trp, tyr |
| 69 R17 | Phe | Tyr |

The table below shows where single point mutants from HB36.4 (SAFDLAMRIMWIYVFAF (SEQ ID NO: 7)) are shown to result in increased binding affinity. Thus, in other embodiments, the polypeptide comprises amino acid substitutions relative to HB36.4 as follows (singly or in combination):

TABLE 2

HB36.4 point mutations that show increased binding affinity

| Position | HB36.4 Residue | Increased Affinity |
|---|---|---|
| 47 R1 | Ser | His |
| 54 R7 | Arg | Lys |
| 56 R9 | Met | His, Asn, Tyr |
| 60 R13 | Val | Phe, Leu, Thr, Asn |
| 63 R16 | Phe | Trp, Tyr |

All of these embodiments can be combined with any other embodiment, unless the context clearly dictates otherwise.

In a second aspect, the present invention provides polypeptides comprising an amino acid sequence according to general formula II R1-R2-R3-R4-R5-R6-R7-R8-R9-Ala-R10-R11-Phe (SEQ ID NO: 83), wherein R1 is selected from the group consisting of Phe and Val;
R2 is selected from the group consisting of Ser, Ala, Phe, Gly, Ile, Lys, Leu, Met, Asn, Pro, Gln, Arg, Thr, and Val;
R3 is selected from the group consisting of Glu, and Asp;
R4 is selected from the group consisting of Asn, His, Ile, Lys, Leu, Met, Arg, Ser, and Thr;
R5 is selected from the group consisting of Leu, Phe, Ile, Met, Asn, Gln, and Val;
R6 is selected from the group consisting of Ala, Asp, Lys, Met, Asn, Gln, Arg, Glu, and Val;
R7 is selected from the group consisting of Phe, Asp, Asn, and Tyr;
R8 is selected from the group consisting of Glu, Ala, Asp, Gly, His, Lys, Leu, Met, Asn, Gln, Arg, Ser, Thr, Val, and Trp;
R9 is selected from the group consisting of Leu, Phe, Ile, Met, and Val;
R10 is selected from the group consisting of Leu, Ile, Met, and Tyr; and
R11 is selected from the group consisting of Ser, Ala, Gly, and Tyr;

In one embodiment, general formula II is R1-R2-R3-R4-R5-R6-R7-R8-R9-Ala-R10-R11-Phe-X1-R12-R13-X2-R14 (SEQ ID NO: 84), wherein R1 through R11 are as defined above, and wherein X1 is 5-15 amino acids in length, wherein each position can be any amino acid;
R12 is selected from the group consisting of Gln, Tyr, Phe, Met, Arg, Lys, Ser, and Gly;
R13 is selected from the group consisting of Tyr, Asp, Met, Asn, and Ser;
X2 is any amino acid; and
R14 is selected from the group consisting of Ser, Arg, and Lys.

In one specific embodiment, R12 is Ser.

In various embodiments, X1 is 5, 6, 7, 8, 9, 10, 11, 12, 13, 14, or 15 amino acids in length. In another embodiment, X1 comprises the amino acid sequence TNKDTPDRW-Z1-KVA (SEQ ID NO: 85) where Z1 is Ala, Lys, Arg, Gly, or Thr.

In another embodiment, that can be combined with any other embodiments herein, general formula II is A1-R1-R2-R3-R4-R5-R6-R7-R8-R9-Ala-R10-R11-Phe-X1-R12-R13-X2-R14-B1 (SEQ ID NO: 86), wherein R1 through R14 and X1 are as defined above, wherein A1 and/or B1 are optionally present, and wherein:

A1 comprises the amino acid sequence: Z1-ASTRGS-GRPW-Z2 (SEQ ID NO: 87), wherein Z1 is absent or is Met, and Z2 is selected from group consisting of Gly, Arg, Lys, Asp, and Asn, and B1 comprises the amino acid sequence G-Z1-TPEEVKKHYE (SEQ ID NO: 88), where Z1 is R or K. In one specific embodiment, A1 is present and comprises or consists of the amino acid sequence: Z1-ASTRGSGRPWN (SEQ ID NO. 280).

The inventors have discovered that polypeptides comprising the amino acid sequence of general formula II (derived from HB80.3, as described in more detail herein) form helices that recognize and are strong binders to Influenza A hemagglutinin. Thus, the polypeptides can be used, for example, to treat and/or limit development of an influenza infection.

In one embodiment, the polypeptide comprises the peptide FSENLAFELALSF (SEQ ID NO: 89), or a variant including 1, 2, 3, 4, 5, 6, 7, 8, 9, 10, or more variant positions of FSENLAFELALSF (SEQ ID NO: 89) according to general formula II. In other embodiments, the polypeptide comprises amino acid substitutions relative to HB80.3 as follows (singly or in combination)

| Position | HB80.3 Residue | Increased Affinity |
|---|---|---|
| 12 R-1 | Gly | Lys/Arg |
| 14 R2 | Ser | Lys/Arg |
| 17 R5 | Leu | Val/Ile |
| 18 R6 | Ala | Thr/Lys |
| 21 R9 | Leu | Ile |
| 24 R12 | Ser | Tyr |
| 39 | Gln | Arg/Tyr |
| 42 | Ser | Lys/Arg |

In other exemplary embodiments, the polypeptide comprises or consists of a polypeptide selected from the group consisting of

```
                                    (SEQ ID NO: 90)
FSENLAFELALA;

>HB80.3_s4_E81:                     (SEQ ID NO: 91)
FSENVAFEIALSF;

>HB80.3_s4_E82:                     (SEQ ID NO: 92)
FSENVAFEIALSF;

>HB80.3_s4_E83:                     (SEQ ID NO: 93)
FRENIAFEIALYF;
```

-continued

>HB80.3_s4_E84: (SEQ ID NO: 94)
FSENVAFEIALSF;

>HB80.3_s4_E85: (SEQ ID NO: 95)
FSENIAFELALYF;

>HB80.3_s4_E86: (SEQ ID NO: 96)
FSENVAFELALYF;

>HB80.3_s4_E87: (SEQ ID NO: 97)
FSENIAFELALYF;

>HB80.3_s4_E88: (SEQ ID NO: 98)
FKENLEFEIALSF;

>HB80.3_s4_E89: (SEQ ID NO: 99)
FSENVAFEIALSF;

>HB80.3_s4_E90: (SEQ ID NO: 100)
FSENVAFELALYF;

>HB80.3_s4_E91: (SEQ ID NO: 101)
FSENVAFELALYF;

>HB80.3_s4_E92: (SEQ ID NO: 102)
FSENVAFEIALSF;

>HB80.3_s4_E93: (SEQ ID NO: 103)
FSENVAFELALYF;

>HB80.3_s4_E94: (SEQ ID NO: 104)
FSENVAFELALYF;

>HB80.3_s4_E95: (SEQ ID NO: 105)
FSENVAFELALYF;

>HB80.3_s4_E96: (SEQ ID NO: 106)
FSENVAFEIALSF;

>HB80.3_s4_E97: (SEQ ID NO: 107)
FSENVAFEIALSF;

>HB80.3_s4_E98: (SEQ ID NO: 108)
FSENVAFEIALSF;

>HB80.3_s4_E99: (SEQ ID NO: 109)
FSENLAFELALYF;

>HB80.3_s4_E100: (SEQ ID NO: 110)
FSENVAFEIALSF;

>HB80.3_s5_E01: (SEQ ID NO: 111)
FSENVAFEIALSF;

>HB80.3_s5_E04: (SEQ ID NO: 112)
FSENVAFEIALSF;

>HB80.3_02: (SEQ ID NO: 113)
FSENIAFEIALSF;

>HB80.3_16: (SEQ ID NO: 114)
FSENIAFEIALSF;

>HB 80.3(Asp12Gly, (SEQ ID NO: 115)
Ala24Ser, Met26Thr, Asn36Lys, Delta54-95)
FSENLAFELALSFTNKDTPDRWAKVAQYVS;

>HB80.3_s4_E81: (SEQ ID NO: 116)
FSENVAFEIALSFTNKDTPDRWKKVARYVR;

>HB80.3_s4_E82: (SEQ ID NO: 117)
FSENVAFEIALSFTNKDTPDRWAKVARYVR;

>HB80.3_s4_E83: (SEQ ID NO: 118)
FRENIAFEIALYFTNKDTPDRWRKVARYVK;

>HB80.3_s4_E84: (SEQ ID NO: 119)
FSENVAFEIALSFTNKDTPDRWRKVARYVR;

>HB80.3_s4_E85: (SEQ ID NO: 120)
FSENIAFELALYFTNKDTPDRWGKVARYVR;

>HB80.3_s4_E86: (SEQ ID NO: 121)
FSENVAFELALYFTNKDTPDRWKKVARYVK;

>HB80.3_s4_E87: (SEQ ID NO: 122)
FSENIAFELALYFTNKDTPDRWKKVARYVK;

>HB80.3_s4_E88: (SEQ ID NO: 123)
FKENLEFEIALSFTNKDTPDRWKKVAYYVR;

>HB80.3_s4_E89: (SEQ ID NO: 124)
FSENVAFEIALSFTNKDTPDRWRKVARYVR;

>HB80.3_s4_E90: (SEQ ID NO: 125)
FSENVAFELALYFTNKDTPDRWTKVARYVK;

>HB80.3_s4_E91: (SEQ ID NO: 126)
FSENVAFELALYFTNKDTPDRWTKVARYVK;

>HB80.3_s4_E92: (SEQ ID NO: 127)
FSENVAFEIALSFTNKDTPDRWRKVARYVR;

>HB80.3_s4_E93: (SEQ ID NO: 128)
FSENVAFELALYFTNKDTPDRWGKVAQYVR;

>HB80.3_s4_E94: (SEQ ID NO: 129)
FSENVAFELALYFTNKDTPDRWAKVARYVK;

>HB80.3_s4_E95: (SEQ ID NO: 130)
FSENVAFELALYFTNKDTPDRWTKVARYVK;

>HB80.3_s4_E96: (SEQ ID NO: 131)
FSENVAFEIALSFTNKDTPDRWRKVAYYVR;

>HB80.3_s4_E97: (SEQ ID NO: 132)
FSENVAFEIALSFTNKDTPDRWRKVARYVR;

>HB80.3_s4_E98: (SEQ ID NO: 133)
FSENVAFEIALSFTNKDTPDRWAKVARYVR;

>HB80.3_s4_E99: (SEQ ID NO: 134)
FSENLAFELALYFTNKDTPDRWAKVAYYVK;

>HB80.3_s4_E100: (SEQ ID NO: 135)
FSENVAFEIALSFTNKDTPDRWKKVARYVK;

>HB80.3_s5_E01: (SEQ ID NO: 136)
FSENVAFEIALSFTNKDTPDRWRKVARYVR;

>HB80.3_s5_E04: (SEQ ID NO: 137)
FSENVAFEIALSFTNKDTPDRWRKVARYVR;

>HB80.3_02: (SEQ ID NO: 138)
FSENIAFEIALSFTNKDTPDRWKKVAQYVK;

>HB80.3_16: (SEQ ID NO: 139)
FSENIAFEIALSFTNKDTPDRWKKVAQYVK;

(SEQ ID NO: 141)
FAENLAFELALSF;

(SEQ ID NO: 142)
FGENLAFELALSF;

(SEQ ID NO: 143)
FIENLAFELALSF;

(SEQ ID NO: 144)
FKENLAFELALSF;

(SEQ ID NO: 145)
FRENLAFELALSF;

(SEQ ID NO: 146)
FTENLAFELALSF;

(SEQ ID NO: 147)
FVENLAFELALSF;

FSENIAFELALSF; (SEQ ID NO: 148)

FSENVAFELALSF; (SEQ ID NO: 149)

FSENLKFELALSF; (SEQ ID NO: 150)

FSENLRFELALSF; (SEQ ID NO: 151)

FSENLTFELALSF; (SEQ ID NO: 152)

FSENLAFSLALSF; (SEQ ID NO: 153)

FSENLAFELALYF; (SEQ ID NO: 154)

FSENLAFELALSFTNKDTPDRWAKVARYVS; (SEQ ID NO: 156)

FSENLAFELALSFTNKDTPDRWAKVAYYVS; (SEQ ID NO: 157)

FSENLAFELALSFTNKDTPDRWAKVAQYVK; (SEQ ID NO: 158)

FSENLAFELALSFTNKDTPDRWAKVAQYVR; (SEQ ID NO: 159)

FSENLAFELALSFTNKDTPDRWAKVAQYVS; (SEQ ID NO: 160)

FAENLAFELALSFTNKDTPDRWAKVAQYVS; (SEQ ID NO: 161)

FGENLAFELALSFTNKDTPDRWAKVAQYVS; (SEQ ID NO: 162)

FIENLAFELALSFTNKDTPDRWAKVAQYVS; (SEQ ID NO: 163)

FKENLAFELALSFTNKDTPDRWAKVAQYVS; (SEQ ID NO: 164)

FRENLAFELALSFTNKDTPDRWAKVAQYVS; (SEQ ID NO: 165)

FTENLAFELALSFTNKDTPDRWAKVAQYVS; (SEQ ID NO: 166)

FVENLAFELALSFTNKDTPDRWAKVAQYVS; (SEQ ID NO: 167)

FSENIAFELALSFTNKDTPDRWAKVAQYVS; (SEQ ID NO: 168)

FSENVAFELALSFTNKDTPDRWAKVAQYVS; (SEQ ID NO: 169)

FSENLKFELALSFTNKDTPDRWAKVAQYVS; (SEQ ID NO: 170)

FSENLRFELALSFTNKDTPDRWAKVAQYVS; (SEQ ID NO: 171)

FSENLTFELALSFTNKDTPDRWAKVAQYVS; (SEQ ID NO: 172)

FSENLAFSLALSFTNKDTPDRWAKVAQYVS; (SEQ ID NO: 173)

FSENLAFELALYFTNKDTPDRWAKVAQYVS; (SEQ ID NO: 174)

FSENLAFELALSFTNKDTPDRWAKVAQYVS; (SEQ ID NO: 175)

FSENLAFELALSFTNKDTPDRWAKVARYVS; (SEQ ID NO: 176)

FSENLAFELALSFTNKDTPDRWAKVAYYVS; (SEQ ID NO: 177)

FSENLAFELALSFTNKDTPDRWAKVAQYVK; (SEQ ID NO: 178)

FSENLAFELALSFTNKDTPDRWAKVAQYVR; (SEQ ID NO: 179)

>HB80 Met26Thr (SEQ ID NO: 180)
MASTRGSGRPWDFSENLAFELALAFTNKDTPDRWANVAQYVSGRTPEEVK
KHYEILVEDIKYIESGKVPFPNYRTTGGNMKTDEKRFRNLKIRLE;

>HB80 Asn36Lys (SEQ ID NO: 181)
MASTRGSGRPWDFSENLAFELALAFMNKDTPDRWAKVAQYVSGRTPEEVK
KHYEILVEDIKYIESGKVPFPNYRTTGGNMKTDEKRFRNLKIRLE;

>HB80.1 (SEQ ID NO: 182)
(Met26Thr, Asn36Lys)
MASTRGSGRPWDFSENLAFELALAFTNKDTPDRWAKVAQYVSGRTPEEVK
KHYEILVEDIKYIESGKVPFPNYRTTGGNMKTDEKRFRNLKIRLE;

>HB80.2 (SEQ ID NO: 183)
(Met26Thr, Asn36Lys, Delta54-95)
MASTRGSGRPWDFSENLAFELALAFTNKDTPDRWAKVAQYVSGRTPEEVK
KHYE >HB80.3(Asp12Gly, (SEQ ID NO: 184)
Ala24Ser, Met26Thr, Asn36Lys, Delta54-95)
MASTRGSGRPWGFSENLAFELALSFTNKDTPDRWAKVAQYVSGRTPEEVK
KHYE;

(SEQ ID NO: 185)
MASTRGSGRPWKFSENLAFELALSFTNKDTPDRWAKVAQYVSGRTPEEVK
KHYE;

(SEQ ID NO: 186)
MASTRGSGRPWRFSENLAFELALSFTNKDTPDRWAKVAQYVSGRTPEEVK
KHYE;

>HB80.3_s4_E81 (SEQ ID NO: 187)
MASTRGSGRPWRFSENVAFEIALSFTNKDTPDRWKKVARYVRGRTPEEVK
KHYE;

>HB80.3_s4_E82 (SEQ ID NO: 188)
MASTRGSGRPWKFSENVAFEIALSFTNKDTPDRWAKVARYVRGRTPEEVK
KHYE;

>HB80.3_s4_E83 (SEQ ID NO: 189)
MASTRGSGRPWGFRENIAFEIALYFTNKDTPDRWRKVARYVKGRTPEEVK
KHYE;

>HB80.3_s4_E84 (SEQ ID NO: 190)
MASTRGSGRPWRFSENVAFEIALSFTNKDTPDRWRKVARYVKGRTPEEVK
KHYE;

>HB80.3_s4_E85 (SEQ ID NO: 191)
MASTRGSGRPWGFSENIAFELALYFTNKDTPDRWGKVARYVRGRTPEEVK
KHYE;

>HB80.3_s4_E86 (SEQ ID NO: 192)
MASTRGSGRPWKFSENVAFELALYFTNKDTPDRWKKVARYVKGRTPEEVK

```
>HB80.3_s4_E87                              (SEQ ID NO: 193)
MASTRGSGRPWKFSENIAFELALYFTNKDTPDRWKKVARYVKGRTPEEVK

KHYE;

>HB80.3_s4_E88                              (SEQ ID NO: 194)

MASTRGSGRPWKFKENLEFEIALSFTNKDTPDRWKKVAYYVRGRTPEEVK

KHYE;

>HB80.3_s4_E90                              (SEQ ID NO: 196)
MASTRGSGRPWKFSENVAFELALYFTNKDTPDRWTKVARYVKGRTPEEVK

KHYE;

>HB80.3_s4_E92                              (SEQ ID NO: 198)
MASTRGSGRPWKFSENVAFEIALSFTNKDTPDRWRKVARYVRGRTPEEVK

KHYE;

>HB80.3_s4_E93                              (SEQ ID NO: 199)
MASTRGSGRPWKFSENVAFELALYFTNKDTPDRWGKVAQYVRGRTPEEVK

KHYE;

>HB80.3_s4_E94                              (SEQ ID NO: 200)
ASTRGSGRPWKFSENVAFELALYFTNKDTPDRWAKVARYVKGRTPEEVKK

HYE;

>HB80.3_s4_E96                              (SEQ ID NO: 202)
MASTRGSGRPWKFSENVAFEIALSFTNKDTPDRWRKVAYYVRGRTPEEVK

KHYE;

>HB80.3_s4_E98                              (SEQ ID NO: 204)
MASTRGSGRPWRFSENVAFEIALSFTNKDTPDRWAKVARYVRGRTPEEVK

KHYE;

>HB80.3_s4_E99                              (SEQ ID NO: 205)
MASTRGSGRPWKFSENLAFELALYFTNKDTPDRWAKVAYYVRGRTPEEVK

KHYE;

>HB80.3_s4_E100                             (SEQ ID NO: 206)
MASTRGSGRPWRFSENVAFEIALSFTNKDTPDRWKKVARYVRGRTPEEVK

KHYE;

>HB80.3_s5_E01                              (SEQ ID NO: 207)
MASTKGSGKPWKFSENVAFEIALSFTNKDTPDRWRKVARYVRGKTPEEVK

KHYE;

>HB80.30_2                                  (SEQ ID NO: 209)
MASTRGSGRPWKFSENIAFEIALSFTNKDTPDRWKKVAQYVKGRTPEEVK

KHYE;

E05:                                        (SEQ ID NO: 303)
FSENVAFELALYF;

E14:                                        (SEQ ID NO: 304)
FSENVAFEIALSF;

E23:                                        (SEQ ID NO: 305)
FSENVAFEIALSF;

E26:                                        (SEQ ID NO: 306)
FSENVAFEIALSF;

E29:                                        (SEQ ID NO: 307)
FSENLAFELALSF;

E30:                                        (SEQ ID NO: 308)
FSENVAFELALYF;

E31:                                        (SEQ ID NO: 309)
FSENLAFELALSF;

E05:                                        (SEQ ID NO: 310)
KFSENVAFELALYFTNKDTPDRWAKVARYVK;

E14:                                        (SEQ ID NO: 311)
RFSENVAFEIALSFTNKDTPDRWRKVARYVR;

E20;                                        (SEQ ID NO: 312)
KFSENVAFEIALSFTNKDTPDRWKKVARYVK;

E21:                                        (SEQ ID NO: 313)
KFSENVAFEIALSFTNKDTPDRWTKVARYVR;

E22:                                        (SEQ ID NO: 314)
KFSENVAFEIALSFTNKDTPDRWAKVAYYVR;

E23:                                        (SEQ ID NO: 315)
KFSENIAFEIALSFTNKDTPDRWKKVASYVK;

E24:                                        (SEQ ID NO: 316)
KFSENIAFEIALSFTNKDTPDRWKKVAPYVK;

E25:                                        (SEQ ID NO: 317)
KFSENIAFEIALSFTNKDTPDRWKKVAYYVK;

E26:                                        (SEQ ID NO: 318)
RFSENVAFEIALSFTNKDTPDRWRKVARYVR;

E27:                                        (SEQ ID NO: 319)
RFSENVAFEIALSFTNKDTPDRWAKVAYYVR;

E28:                                        (SEQ ID NO: 320)
KFSENVAFEIALSFTNKDTPDRWAKVAYYVR;

E29:                                        (SEQ ID NO: 321)
NFSENIAFEIALSFTNKDTPDRWKKVARYVK;

E30:                                        (SEQ ID NO: 322)
KFSENIAFELALYFTNKDTPDRWKKVARYVK;

E31:                                        (SEQ ID NO: 323)
RFSENLAFELALSFTNKDTPDRWRKVAQYVR;

E05:                                        (SEQ ID NO: 324)
MASTRGSGRPWKFSENVAFELALYFTNKDTPDRWAKVARYVKGRTPEEVK

KHYE;

E14:                                        (SEQ ID NO: 325)
MASTRGSGRPWRFSENVAFEIALSFTNKDTPDRWRKVARYVRGRTPEEVK

KHYE;

E20;                                        (SEQ ID NO: 326)
MASTRGSGRPWKFSENVAFEIALSFTNKDTPDRWKKVARYVRGRTPEEVK

KHYE;

E21:                                        (SEQ ID NO: 327)
MASTRGSGRPWKFSENVAFEIALSFTNKDTPDRWTKVARYVRGRTPEEVK

KHYE;

E22:                                        (SEQ ID NO: 328)
MASTRGSGRPWKFSENVAFEIALSFTNKDTPDRWAKVAYYVRGRTPEEVK

KHYE;

E23:                                        (SEQ ID NO: 329)
MASTRGSGRPWKFSENIAFEIALSFTNKDTPDRWKKVASYVKGRTPEEVK

KHYE;

E24:                                        (SEQ ID NO: 330)
MASTRGSGRPWKFSENIAFEIALSFTNKDTPDRWKKVAPYVKGRTPEEVK

KHYE;
```

-continued

E25: (SEQ ID NO: 331)
MASTRGSGRPWKFSENIAFEIALSFTNKDTPDRWKKVAYYVKGRTPEEVK
KHYE;

E26: (SEQ ID NO: 332)
MASTRGSGRPWRFSENVAFEIALSFTNKDTPDRWRKVARYVRGRTPEEVK
KHYE;

E27: (SEQ ID NO: 333)
MASTRGSGRPWRFSENVAFEIALSFTNKDTPDRWAKVAYYVRGRTPEEVK
KHYE;

E28: (SEQ ID NO: 334)
MASTRGSGRPWKFSENVAFEIALSFTNKDTPDRWAKVAYYVRGRTPEEVK
KHYE;

E29: (SEQ ID NO: 335)
MASTRGSGRPWNFSENIAFELALSFTNKDTPDRWKKVARYVKGRTPEEVK
KHYE;

E30: (SEQ ID NO: 336)
MASTRGSGRPWKFSENIAFELALYFTNKDTPDRWKKVARYVKGRTPEEVK
KHYE;

E31: (SEQ ID NO: 337)
MASTRGSGRPWRFSENLAFELALSFTNKDTPDRWRKVAQYVRGRTPEEVK
KHYE;
and (SEQ ID NO: 338)
MASTRGSGRPW(G/K/R)FSENLAFELALSFTNKDTPDRW(A/K/R/T/

G)KVA(Q/Y/R)YV(S/K/R)GRTPEEVKKHYE.

As will be appreciated by those of skill in the art, these are just exemplary polypeptides falling under the scope of the claim. The table below provides per position allowable substitutions on an HB80.3 scaffold.

(1) Central helix recognition motif from Phenylalanine 13-Phenylalanine 25; Also Tyrosine 40 that is outside of that recognition motif.

(SEQ ID NO: 184)
(MASTRGSGRPWGFSENLAFELALSFTNKDTPDRWAKVAQYVSGRTPEEV

KKHYE)

Allowable positions were determined from yeast display selections of HB80.3 variants to SC1918/H1 HA coupled to deep sequencing (see attached for further details). The threshold was no more than 80% depletion in the frequency of a given mutant in the selection library after two selection sorts by FACS. Positions listed in bold font indicate positions that make contact with the HA surface.

TABLE 3

Allowable substitutions on an HB80.3 scaffold

| Position | HB80.3 Residue | Allowable |
|---|---|---|
| 12 | Gly | Lys, Arg |
| 13 R1 | Phe | Val |
| 14 R2 | Ser | Ala, Phe, Gly, Ile, Lys, Leu, Met, Asn, Pro, Gln, Arg, Thr, Val |
| 15 R3 | Glu | Asp |
| 16 R4 | Asn | His, Ile, Lys, Leu, Met, Arg, Ser, Thr |
| 17 R5 | Leu | Phe, Ile, Met, Asn, Gln, Val |

TABLE 3-continued

Allowable substitutions on an HB80.3 scaffold

| Position | HB80.3 Residue | Allowable |
|---|---|---|
| 18 R6 | Ala | Asp, Lys, Met, Asn, Gln, Arg, Val |
| 19 R7 | Phe | Asp, Asn, Tyr |
| 20 R8 | Glu | Ala, Asp, Gly, His, Lys, Leu, Met, Asn, Gln, Arg, Ser, Thr, Val, Trp |
| 21 R9 | Leu | Phe, Ile, Met, Val |
| 22 | Ala | Ala |
| 23 R10 | Leu | Ile, Met, Tyr |
| 24 R11 | Ser | Ala, Gly, Tyr |
| 25 | Phe | Phe |
| 35 | Ala | Lys, Arg, Thr, Gly |
| 39 R12 | Gln | Tyr, Phe, Met, Arg, Lys, Gly |
| 40 R13 | Tyr | Asp, Met, Asn, Ser |
| 42 R14 | Ser | Arg, Lys |

The table below shows where single point mutants from HB80.3 are shown to result in increased binding affinity. Thus, in other embodiments, the polypeptide comprises amino acid substitutions relative to HB80.3 as follows (singly or in combination).

TABLE 4

HB80.3 point mutations that show increased binding affinity

| Position | HB80.3 Residue | Increased Affinity |
|---|---|---|
| 12 | Gly | Lys, Arg |
| 14 R2 | Ser | Ala, Gly, Ile, Lys, Arg, Thr, Val, Asn |
| 17 R5 | Leu | Ile, Val |
| 18 R6 | Ala | Lys, Arg |
| 20 R8 | Glu | Ser |
| 21 R9 | Leu | Ile |
| 24 R11 | Ser | Tyr |
| 35 | Ala | Lys, Arg |
| 39 | Gln | Tyr, Arg |
| 42 | Ser | Lys, Arg |

In various preferred embodiments, HB80.3 (FSENLAFELALSF (SEQ ID NO: 89)) is modified such that one or more of the following is true: R2 is Ala, Gly, Ile, Lys, Arg, Thr, or Val; R5 is Ile or Val; R6 is Lys or Arg; R8 is Ser; R9 is Ile; and/or R11 is Tyr.

All of these embodiments can be combined with any other embodiment, unless the context clearly dictates otherwise.

In a third aspect, the invention provides polypeptides comprising or consisting of a polypeptide selected from the group consisting of

>HB3 (SEQ ID NO: 155)
MADTLLILGDSLSAGYQMLAEFAWPFLLNKKWSKTSVVNASISGDTSQQG

LARLPALLKQHQPRWVLVELGGNDGLEGFQPQQTEQTLRQILQDVKAANA

EPLLMQIRPPANYGRRYNEAFSAIYPKLAKEFDVPLLPFFMEEVYLKPQW

MQDDGIHPNYEAQPFIADWMAKQLQPLVNH;

>HB54 (SEQ ID NO: 140)
MAETKNFTDLVEATKWGNSLIKSAKYSSKDKMAIYNYTKNSSPINTPLRS

ANGDVNKLSENIQEQVRQLDSTISKSVTPDSVYVYRLLNLDYLSSITGFT

```
-continued
REDLHMLQQTNEGQYNSKLVLWLDFLMSNRIYRENGYSSTQLVSGAALAG

RPIELKLELPKGTKAAYIDSKELTAYPGQQEVLLPRGTEYAVGTVELSKS

SQKIIITAVVFKK;
and

>HB78                                           (SEQ ID NO: 211)
MFTGVIIKQGCLLKQGHTRKNWSVRKFILREDPAYLHYYYPLGYFSPLGA

IHLRGCVVTSVESEENLFEIITADEVHYFLQAATPKERTEWIKAIQMAS

R.
```

Each of these polypeptides form helices that recognize and are strong binders to Influenza A hemagglutinin. Thus, the polypeptides can be used, for example, to treat and/or limit development of an influenza infection In a fourth aspect, the present invention provides a polypeptide comprising or consisting of any helix coming from a peptide or a protein that docks and binds against the HA epitope recognized by the polypeptides of the invention. In one embodiment, the helix is 15-17 residues in length, similar to the HB36.4 and HB80.3 helices disclosed above As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or noncovalent as is understood by those of skill in the art.

In a further embodiment, the polypeptides of any embodiment of any aspect of the invention may further comprise a tag, such as a detectable moiety or therapeutic agent. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used diagnostically to, for example, assess if a subject has been infected with influenza virus or monitor the development or progression of an influenza virus infection as part of a clinical testing procedure to, e.g., determine the efficacy of a given treatment regimen. However, they may also be used for other detection and/or analytical and/or diagnostic purposes. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis/diagnosis techniques and/or methods used such as immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples preferred tags are enzymes that catalyze production and local deposition of a detectable product. Enzymes typically conjugated to polypeptides to permit their immunohistochemical visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. The polypeptides can be labeled using colloidal gold or they can be labeled with radioisotopes, such as $^{33}$P, $^{32}$P, $^{35}$S, $^{3}$H, and $^{125}$I. Polypeptides of the invention can be attached to radionuclides directly or indirectly via a chelating agent by methods well known in the art.

When the polypeptides of the invention are used for flow cytometric detections, scanning laser cytometric detections, or fluorescent immunoassays, the tag may comprise, for example, a fluorophore. A wide variety of fluorophores useful for fluorescently labeling the polypeptides of the invention are known to the skilled artisan. When the polypeptides are used for in vivo diagnostic use, the tag can comprise, for example, magnetic resonance imaging (MRI) contrast agents, such as gadolinium diethylenetriaminepentaacetic acid, to ultrasound contrast agents or to X-ray contrast agents, or by radioisotopic labeling.

The polypeptides of the invention can also be attached to solid supports, which are particularly useful for in vitro assays or purification of influenza virus or HA protein. Such solid supports might be porous or nonporous, planar or nonplanar and include, but are not limited to, glass, cellulose, polyacrylamide, nylon, polystyrene, polyvinyl chloride or polypropylene supports. The polypeptides can also, for example, usefully be conjugated to filtration media, such as NHS-activated Sepharose or CNBr-activated Sepharose for purposes of affinity chromatography. They can also usefully be attached to paramagnetic microspheres, typically by biotin-streptavidin interaction. The microspheres can be used for isolation of influenza virus or HA protein from a sample containing influenza virus or HA protein. As another example, the polypeptides of the invention can usefully be attached to the surface of a microtiter plate for ELISA.

The polypeptides of the invention can be fused to marker sequences to facilitate purification. Examples include, but are not limited to, the hexa-histidine tag, the myc tag or the flag tag.

The polypeptides of the invention can be conjugated to an antigen recognized by the immune system of a subject to which the polypeptide is administered. Conjugation methods for attaching the antigens and polypeptide are well known in the art and include, but are not limited to, the use of cross-linking agents. The polypeptide will bind to the influenza virus HA protein and the antigen will initiate a T-cell attack on the conjugate that will facilitate destruction of the influenza virus.

In another embodiment of any aspect herein, the present invention provides retro-inverso polypeptides corresponding to the polypeptides of the invention. Retro-inverso polypeptides of the invention comprise or consist of D-amino acids assembled in a reverse order from that of L-sequence polypeptide versions of the polypeptides disclosed above, thus maintaining the overall topology of the polypeptide, and maintaining HA binding.

In a fifth aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a sixth aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a seventh aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In an eighth aspect, the present invention provides antibodies that selectively bind to the polypeptides of the invention. The antibodies can be polyclonal, monoclonal antibodies, humanized antibodies, and fragments thereof, and can be made using techniques known to those of skill in the art. As used herein, "selectively bind" means preferential binding of the antibody to the polypeptide of the invention, as opposed to one or more other biological molecules, structures, cells, tissues, etc., as is well understood by those of skill in the art.

In a ninth aspect, the present invention provides pharmaceutical compositions, comprising one or more polypeptides of the invention and a pharmaceutically acceptable carrier. The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides may be the sole active agent in the pharmaceutical composition, or the composition may further comprise one or more other active agents suitable for an intended use, including but not limited to anti-HA and anti-NA antibodies.

In a tenth aspect, the present invention provides methods for treating and/or limiting an influenza infection, comprising administering to a subject in need thereof a therapeutically effective amount of one or more polypeptides of the invention, salts thereof, conjugates thereof, or pharmaceutical compositions thereof, to treat and/or limit the influenza infection. When the method comprises treating an influenza infection, the one or more polypeptides are administered to a subject that has already been infected with the influenza virus, and/or who is suffering from symptoms (including but not limited to chills, fever, sore throat, muscle pains, coughing, weakness, fatigue, and general discomfort) indicating that the subject is likely to have been infected with the influenza virus. As used herein, "treat" or "treating" means accomplishing one or more of the following: (a) reducing influenza viral titer in the subject; (b) limiting any increase of influenza viral titer in the subject; (c) reducing the severity of flu symptoms; (d) limiting or preventing development of flu symptoms after infection; (e) inhibiting worsening of flu symptoms; (f) limiting or preventing recurrence of flu symptoms in subjects that were previously symptomatic for influenza infection.

When the method comprises limiting an influenza infection, the one or more polypeptides are administered prophylactically to a subject that is not known to have been infected, but may be at risk of exposure to the influenza virus. As used herein, "limiting" means to limit influenza infection in subjects at risk of influenza infection. Given the nature of seasonal influenza outbreaks, virtually all subjects are at risk of exposure, at least at certain times of the year. Groups at particularly high risk include children under age 18, adults over the age of 65, and individuals suffering from one or more of asthma, diabetes, heart disease, or any type of immunodeficiency.

The methods of the invention can be used to treat any individual infected with influenza virus, including but not limited to influenza virus A, influenza virus B, and influenza virus C. The methods are preferably used to treat influenza A virus infections caused by influenza A viruses of phylogenetic group I, in particular comprising HA of the H1 or H5 subtype.

As used herein, a "therapeutically effective amount" refers to an amount of the polypeptide that is effective for treating and/or limiting influenza infection. The polypeptides are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In certain embodiments, the polypeptides of the invention neutralize influenza virus infectivity. While not being limited by any mechanism of action, neutralizing activity may be achieved by inhibiting fusion of the influenza virus and the membrane of the targeted cell, including a membrane of an intracellular compartment, such as an endosome. The polypeptides of the invention were designed to target an HA epitope that is absent in HA post-conformational change. Since the HA protein conformational change leads to fusion of the viral and cell membrane, polypeptide binding to the HA protein in its pre-fusion form may prevent fusion. In various embodiments, the polypeptides of the invention prevent influenza virus from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by influenza virus in the absence of the polypeptides. Neutralization can, for instance, be measured as described in "Laboratory techniques in influenza," edited by F.-X. Meslin, M. M. Kaplan and H. Koprowski (1996), 4th edition, Chapters 15-17, World Health Organization, Geneva.

The polypeptides according to the invention can bind to the HA protein with any suitable affinity constant ($K_d$ value) that provides therapeutic or prophylactic benefit. In various embodiments, the $K_d$ value is lower than $0.2*10^{-4}$ M, $1.0*10^{-5}$M, $1.0*10^{-6}$M, $1.0*10^{-7}$M, $1.0*10^{-8}$M, $1.0*10^{-9}$M, $1.0*10^{-10}$M, $1.0*10^{-11}$M, or $1.0*10^{-12}$M. Affinity constants can for instance be measured using surface plasmon resonance, i.e., an optical phenomenon that allows for the analysis of real-time biospecific interactions by detection of alterations in protein concentrations within a biosensor matrix, for example, using the BIACORE system (Pharmacia Biosensor AB, Uppsala, Sweden).

In a eleventh aspect, the present invention provides methods for diagnosing an influenza infection, or monitoring progression of an influenza infection, comprising
  (a) contacting a biological sample from a subject suspected of having an influenza infection with a diagnostically effective amount of one or more polypeptides of the invention under conditions suitable for binding of the polypeptide to a viral HA protein present in the sample;
  (b) removing unbound polypeptide and/or sample; and
  (c) detecting polypeptide-viral HA binding complexes, where the presence of such binding complexes indicates that the subject has an influenza infection, or provides a measure progression of an influenza infection.

The methods of this aspect of the invention can be used to more accurately identify patients that may be suffering from an influenza infection and to thus provide more informed determination of treatment options by an attending caregiver. Individuals at risk of an influenza infection are as described above. The methods can also be used to monitor progression of an influenza infection; in this embodiment, the subject is known to be infected, and the methods can be used, for example, as a data point for an attending caregiver to determine whether to initiate, modify, or continue a particular course of therapy, such as treatment with neuraminidase or M2 protein inhibitors.

The biological sample may be any suitable biological sample including, but not limited to blood, serum, nasal secretions, tissue or other biological material from a subject at risk of infection.

The sample may first be manipulated to make it more suitable for the method of detection. "Manipulation" includes, but is not limited to treating the sample in such a way that any influenza virus in the sample will disintegrate into antigenic components such as proteins, polypeptides or other antigenic fragments. The polypeptides of the invention are contacted with the sample under conditions which allow the formation of an complex between the human polypeptides and influenza virus or antigenic components thereof that may be present in the sample. The formation of such complexes, if any, indicating the presence of influenza virus in the sample, is then detected and measured by suitable means. Such methods include, but are not limited to homogeneous and heterogeneous binding immunoassays, such as radioimmunoassays (RIA), ELISA, immunofluorescence, immunohistochemistry, FACS, BIACORE and Western blot analyses. Suitable conditions to promote binding of the test compounds to one or more polypeptide of the invention can be determined by those of skill in the art, based on the teachings herein.

The polypeptides of the invention for use in this aspect may comprise a conjugate as disclosed above, to provide a tag useful for any detection technique suitable for a given assay. The tag used will depend on the specific detection/analysis/diagnosis techniques and/or methods used. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape. In one embodiment, conditions are selected to identify test compounds that bind to the polypeptide of the invention with a $K_d$ value lower than $0.2*10^{-4}$ M, $1.0*10^{-5}$M, $1.0*10^{-6}$M, $1.0*10^{-7}$M, $1.0*10^{-8}$M, $1.0*10^{-9}$M, $1.0*10^{-10}$M, $1.0*10^{-11}$M, or $1.0*10^{-12}$M.

In a twelfth aspect, the present invention provides methods for identifying candidate influenza vaccines, comprising
 (a) contacting test compounds with a polypeptide of the present invention under conditions suitable for polypeptide binding; and
 (b) identifying those test compounds that bind to the polypeptide of the invention, wherein such test compounds are candidate influenza vaccines.

As discussed above, the polypeptides of the present invention were designed to target an HA epitope that is absent in HA post-conformational change. Thus, the polypeptides of the invention can be viewed as specific binders to an HA epitope, similar to antibody binding to a specific epitope. Vaccines can be produced, for example, by selecting small molecules (ie: mimotopes) that bind to an antibody specific to a viral epitope. Thus, the present methods involve substituting one or more polypeptides of the present invention for the antibody in such assay to identify candidate influenza vaccines.

Suitable conditions to promote binding of the test compounds to one or more polypeptide of the invention can be determined by those of skill in the art, based on the teachings herein. The polypeptides of the invention for use in this aspect may comprise a conjugate as disclosed above, to provide a tag useful for any detection technique suitable for a given assay. The tag used will depend on the specific detection/analysis/diagnosis techniques and/or methods used, as discussed above. The methods may be carried in solution, or the polypeptide(s) of the invention may be bound or attached to a carrier or substrate, as discussed above. Based on the teachings herein, it is within the level of skill in the art to determine specific conditions for the various types of diagnostic assays disclosed in this aspect of the invention. In one embodiment, conditions are selected to identify test compounds that bind to the polypeptide of the invention with a $K_d$ value lower than $0.2*10^{-4}$ M, $1.0*10^{-5}$M, $1.0*10^{-6}$M, $1.0*10^{-7}$M, $1.0*10^{-8}$M, $1.0*10^{-9}$M, $1.0*10^{-10}$M, $1.0*10^{-11}$M, or $1.0*10^{-12}$M.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be produced by any suitable means, such as chemical synthesis. The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

In a thirteenth aspect, the present invention provides methods for identifying candidate compounds for treating, limiting, and/or diagnosing influenza infection, comprising (a) contacting an influenza HA protein with (i) test compounds and (ii) a polypeptide of the present invention, under conditions suitable for binding of the HA protein to the polypeptide of the present invention; and (b) identifying those test compounds that outcompete the polypeptide for binding to the HA protein, wherein such test compounds are candidate compounds for treating, limiting, and/or diagnosing influenza infection.

In this aspect, the methods identify test compounds that compete with the polypeptides of the invention for binding to HA, and thus such candidate compounds may be useful in any of the other methods of the invention disclosed herein. Any suitable test compound can be used, as disclosed above in the eleventh aspect of the invention.

In general, competitive inhibition is measured by means of an assay, wherein an HA composition is admixed with the polypeptide(s) of the invention and the test compounds to be screened. In one embodiment, the test compounds to be screened are present in excess. Protocols based upon ELISAs are suitable for use in such competition studies. In certain embodiments, one may pre-mix the polypeptide(s) of the invention with varying amounts of test compounds to be screened (e.g., 1:10, 1:20, 1:30, 1:40, 1:50, 1:60, 1:70, 1:80, 1:90 or 1:100) for a period of time prior to applying to the HA composition. In other embodiments, the polypeptide(s) of the invention and varying amounts of test compounds to be screened are admixed during exposure to the HA composition. Any suitable detection means can be used binding. In one embodiment, the polypeptide(s) of the invention are tagged for detection, as discussed above. In this embodiment, the detectable label will decrease in the presence of competitive test compounds. The reactivity of the (labeled) polypeptide of the invention in the absence of test compound could serve as one suitable control. Preferably, competitive test compounds will, when present in excess, inhibit specific binding of the polypeptide(s) of the invention to HA by at least 10%, preferably by at least 25%, more preferably by at least 50%, and most preferably by at least 75% to 90% or even greater.

Exemplary conditions for HA binding studies can be carried out as disclosed in the examples that follow.

All of these aspects/embodiments disclosed herein can be combined with any other aspect/embodiment, unless the context clearly dictates otherwise.

Example 1

Design of Proteins for Binding to Influenza Hemagglutinin

Abstract

We describe a general computational method for designing proteins that bind a surface patch of interest on a target macromolecule. Favorable interactions between disembodied amino-acid residues and the target surface are identified and used to anchor de novo designed interfaces. The method was used to design proteins that bind a conserved surface patch on the stem of the influenza hemagglutinin (HA) from the 1918 H1N1 pandemic virus. After affinity maturation, two of the designed proteins, HB36 and HB80, bind H1 and H5 HAs with low-nanomolar affinity. Further, HB80 inhibits the HA fusogenic conformational changes induced at low pH. The crystal structure of HB36 in complex with 1918/H1 HA revealed that the actual binding interface is nearly identical to that in the computational design model. Such designed proteins may be useful for both diagnostics and therapeutics.

Introduction

Molecular recognition is central to biology, and high-affinity binding proteins, such as antibodies, are invaluable for both diagnostics and therapeutics (1). Current methods for producing antibodies and other proteins that bind a protein of interest involve screening of large numbers of variants generated by the immune system or by library construction (2). The computer-based design of high-affinity binding proteins is a fundamental test of the current understanding of the physical-chemical basis of molecular recognition and, if successful, would be a powerful complement to current library-based screening methods since it would allow targeting of specific patches on a protein surface. Recent advances in computational design of protein interactions have yielded switches in interaction specificity (3), methods to generate modest-affinity complexes (4, 5), two-sided design of a novel protein interface (6), and design of a high-affinity interaction by grafting known key residues onto an unrelated protein scaffold (7). However, the capability to target an arbitrarily selected protein surface has remained elusive.

Influenza presents a serious public-health challenge and new therapies are needed to combat viruses that are resistant to existing antivirals (8) or escape neutralization by the immune system. Hemagglutinin (HA) is a prime candidate for drug development as it is the major player in viral invasion of cells lining the respiratory tract. While most antibodies bind to the rapidly varying head region of HA, recently two antibodies, CR6261 and F10, were structurally characterized (9, 10) that bind to a region on the HA stem, which is conserved among all group 1 influenza strains (11). Here, we describe a computational method for designing protein-protein interactions de novo, and use the method to design high-affinity binders to the conserved stem region on influenza HA.

Computational Design Method

In devising the computational design strategy, we considered features common to dissociable protein complexes. During protein complex formation, proteins bury on average ~1,600 $Å^2$ of solvent-exposed surface area (12). Interfaces typically contain several residues that make highly optimized van der Waals, hydrogen bonding, and electrostatic interactions with the partner protein; these interaction hotspots contribute a large fraction of the binding energy (13).

Our strategy thus centers on the design of interfaces that have both high shape complementarity and a core region of highly optimized, hotspot-like residue interactions. We engineer high-affinity interactions and high shape complementarity into scaffold proteins in two steps (see FIG. 1): (i) disembodied amino-acid residues are computationally docked or positioned against the target surface to identify energetically favorable configurations with the target surface; and (ii) shape-complementary configurations of scaffold proteins are computed that incorporate the key residues.

Design of HA-Binding Proteins

The surface on the stem of HA recognized by neutralizing antibodies consists of a hydrophobic groove that is flanked by two loops that place severe steric constraints on binding to the epitope (FIG. 2A-B) (14). In the first step of our design protocol (FIG. 1), the disembodied residues found through computational docking cluster into three regions (HS1, HS2, and HS3; FIG. 1). In HS1, a Phe side chain forms an energetically favorable aromatic-stacking interaction with Trp21 on chain 2 of the HA (HA2) (HA residue numbering corresponds to the H3 subtype sequence-numbering convention). In HS2, the nonpolar residues Ile, Leu, Met, Phe, and Val, make favorable van der Waals interactions with both the hydrophobic groove and HS1 (FIG. 1). In HS3, a Tyr side chain forms a hydrogen bond to Asp18 on HA2 and van der Waals interactions with the A-helix on HA2. The Tyr in HS3 resembles the conformation of a Tyr residue observed on the antibody in the structure of the HA and CR6261 Fab complex; the HS1 and HS2 interactions are not found in the antibody structures (9, 10, 15).

Figure 3:
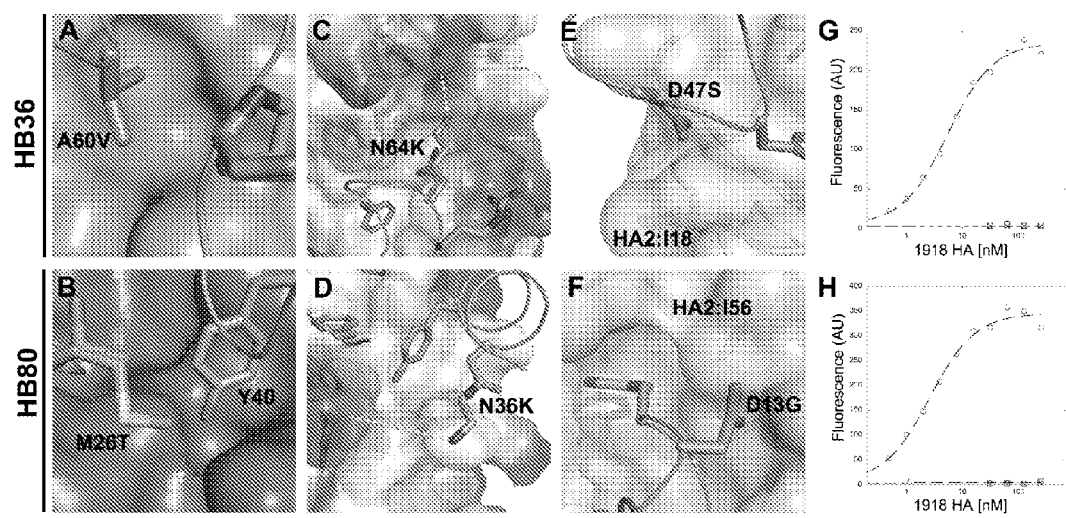
FIG. 3 Affinity maturation. Substitutions that increase the affinity of the original designs can be classified as deficiencies in modeling the (A and B) repulsive interactions HB36 Ala60Val (A), HB80 Met26Thr (B); (C and D) electrostatics HB36 Asn64Lys (C), HB80 Asn36Lys (D); (E and F) and solvation HB36 Asp47Ser (E), HB80 Asp12Gly (F). Binding titrations of HB36.4 (G) and HB80.3 (H) to SC1918/H1 HA as measured by yeast surface display. Circles represent the affinity-matured design, Squares the scaffold protein from which the design is derived, and crosses represent the design in the presence of 750 nM inhibitory CR6261 Fab.

In the second step, we searched a set of 865 protein structures selected for ease of experimental manipulation (16) for scaffolds capable of supporting the disembodied hotspot residues and shape complementary to the stem region. Each scaffold protein was docked against the stem region using the feature-matching algorithm PATCHDOCK™ (17), identifying hundreds of compatible binding modes for each scaffold (260,000 in total). These coarse-grained binding modes were then refined using ROSETTADOCK™ (18) with a potential function that favored configurations that maximized the compatibility of the scaffold protein backbone with as many hotspot residues as possible. Next, residues from the hotspot-residue libraries were incorporated on the scaffold. First, for each Phe conformation in HS1, scaffold residues with backbone atoms within 4 Å of the hotspot residue were identified. For each of these candidate positions, the scaffold protein was placed to coincide with the backbone of the hotspot, the residue was modeled explicitly, and the rigid-body orientation was minimized. If no steric clashes were observed and the Phe was in contact with Trp21 and Thr41 of HA2 (FIG. 2B), the placement of the first hotspot was deemed successful; otherwise, another HS1 Phe conformation was selected and the process was repeated. For each success with HS1, nonpolar residues were incorporated at positions in the scaffold protein, from which the HS2 interactions could be realized, and the remainder of the scaffold protein surface was then redesigned using ROSETTADESIGN™ (19).

Designing proteins also containing HS3 interactions was more challenging due to the large number of combinations of residue placements to be considered. To generate designs containing all three hotspot regions, we started by superimposing the scaffold protein on the backbone of the Tyr residue in HS3 (as for the Phe HS1 residue above). We then searched for two positions on the scaffold protein that were nearest to residues in HS1 and HS2 and were best aligned to them. These positions were then simultaneously designed to Phe in the case of HS1 and to nonpolar residues in the case of HS2. ROSETTADESIGN™ (19) was then used to redesign the remainder of the interface on the scaffold protein, allowing sequence changes within a distance of 10 Å of the HA.

Experimental and Structural Characterization

A total 51 designs using the two hotspot-residue concept and 37 using the three-residue concept were selected for testing. The designs are derived from 79 different protein scaffolds and differ from the scaffold by on average 11 mutations. Genes encoding the designs were synthesized, cloned into a yeast-display vector, and transformed into yeast strain EBY100 (20, 21). Upon induction, the designed protein is displayed on the cell surface as a fusion between an adhesion subunit of the Aga2p yeast protein and a C-terminal c-myc tag. Cells expressing designs were incubated with 1 uM of biotinylated SC1918/H1 (A/South Carolina/1/1918 (H1N1)) HA ectodomain, washed, and dual-labeled with phycoerythrin-conjugated streptavidin and fluorescein-conjugated anti-c-myc antibody. Binding was measured by flow cytometry with the two fluorescent tags allowing simultaneous interrogation of binding to HA and surface display of the design.

73 designs were surface-displayed, and 2 showed reproducible binding activity towards the HA stem region (22)(for models, see FIG. 2C-F). One design, HA Binder 36 (HB36) used the two-residue hotspot, and bound to the HA with an apparent dissociation constant ($K_d$) of 200 nM (23)(FIG. 2G, FIG. 6. The starting scaffold, Structural Genomics target APC36109, a protein of unknown function from *B. stearothermophilus* (PDB entry 1U84), did not bind HA (FIG. 6), indicating that binding is mediated by the designed surface on HB36. A second design, HB80, used the three-residue hotspot and bound HA only weakly (FIG. 2H). The scaffold from which this design was derived, the MYB domain of the RAD transcription factor from *A. Majus* (PDB code: 2CJJ) (24), again did not bind the HA (FIG. 7).

In the computational models of the two designs (FIG. 2C-F), the hotspot residues are buttressed by a concentric arrangement of hydrophobic residues with an outer ring of polar and charged residues as often observed in native protein-protein interfaces. Both designs present a row of hydrophobic residues on a helix that fits into the HA hydrophobic groove. The complexes each bury approximately 1,550 $Å^2$ surface area (total), close to the mean value for dissociable protein interactions (12) and slightly larger than the total surface area buried by each of the two neutralizing antibodies (9, 10). The helical binding modes in these designs are very different from the loop-based binding observed in the antibody-bound structures.

Affinity Maturation

The computational design protocol is far from perfect; the energy function that guides design contains numerous approximations (25) and conformational sampling is incomplete. We used affinity maturation to identify shortcomings in the design protocol. Libraries of HB36 and HB80 variants were generated by single site-saturation mutagenesis at the interface, or by error-prone PCR (epPCR), and subjected to two rounds of selection for binding to HA using yeast-surface display (21, 24).

For both designed binders, the selections converged on a small number of substitutions that increase affinity and provide insight into how to improve the underlying energy function. Among the key contributions to the energetics of macromolecular interactions are short-range repulsive interactions due to atomic overlaps, electrostatic interactions between charged and polar atoms, and the elimination of favorable interactions with solvent (desolvation). The affinity-increasing substitutions point to how each of these contributions can be better modeled in the initial design calculations.

Repulsive Interactions:

For HB36, substitution of Ala60 with the isosteres Thr/Val increased the apparent binding affinity 25-fold (apparent $K_d$'s for all design variants are listed in Table 5).

TABLE 5

Dissociation constants ($K_d$) for binding of design variants to SC1918 HA

| Design | $K_d$ [nM]* |
|---|---|
| 1U84 (HB36 Scaffold) | NB (NB) |
| HB36 | 200 (>2000) |
| HB36 Asp47Ser | 5 |
| HA36 Ala60Val | 8 |
| HB36.3 (HB36 Asp47Ser, Ala60Val) | 4 (29) |
| HB36.4 (HB36 Asp47Ser, Ala60Val, Asn64Lys) | 4 (22) |
| 2CJJ (HB80 Scaffold) | NB |
| HB80 | >5000 |
| HB80 Met26Thr | 100 |
| HB80 Asn36Lys | 300 |
| HB80 Met26Thr Asn36Lys | 7.5 |
| HB80 Δ54-95, Met26Thr, Asn36Lys | 5 |
| HB80.3 (HB80 Δ54-95, Asp12Gly, Ala24Ser, Met26Thr, Asn36Lys) | 3 (38) |

*$K_d$ was determined using yeast surface display titrations.
Number in parentheses indicates $K_d$ determined by SPR.
NB, no binding.

These substitutions fill a void between the designed protein and the HA surface, but were not included in the original design because they were disfavored by steric clashes within HB36 (FIG. 3A). Backbone minimization, however, readily relieved these clashes resulting in higher predicted affinity for the substitutions. For HB80, a Met26Thr mutation significantly increased binding compared to the starting design. Modeling showed that Met26 disfavored the conformation of the Tyr hotspot residue, rationalizing the substitution to a smaller residue (FIG. 3B). More direct incorporation of backbone minimization in the design algorithm should allow identification of such favorable interactions from the start, whereas insuring that hotspot residues are fully relaxed in the design would eliminate unfavorable interactions.

Electrostatics:

In HB36, the substitution to Lys at position 64 places a complementary charge adjacent to an acidic pocket on HA near the conserved stem region (FIG. 3C); in HB80, an Asn36Lys substitution positions a positive charge 6.5 Å from the negative Asp18 on HA2 (FIG. 3D). These substitutions all enhance electrostatic complementarity in the complex. The lysines were not selected in the design calculations because the magnitudes of surface-electrostatic interactions between atoms outside of hydrogen-bonding range are largely reduced; improvement of the electrostatic model would evidently allow design of higher-affinity binders from the start.

Desolvation:

In HB36, 8 different substitutions at Asp47 increased apparent affinity by over an order of magnitude compared to the original design (Table 6); the highest-affinity substitution was Asp47Ser that increased binding affinity circa 40-fold. The design of an unfavorable charged group in this position likely stems from underestimation of the energetic cost of desolvating Asp47 by the aliphatic Ile18 on HA2 (FIG. 3E); the substitutions remedy this error by replacing the Asp with residues that are less costly to desolvate upon binding. In HB80, an Asp12Gly substitution relieves the desolvation by the neighboring Ile56 on HA2 (FIG. 3F). With improvements in the solvation model, the deleterious Asp residues would not be present in starting designs.

TABLE 6

Selected mutations at Asp47 of HB36 design that increased binding affinity >10-fold relative to original design.

| Clone | Mutation(s) | Approx Binding Affinity* |
|---|---|---|
| C1 | D47S | +++ |
| C3 | D47H | +++ |
| C4 | D47H, P70S | +++ |
| D3 | D47N, G7S | ++ |
| E1 | D47Y, G19C | ++ |
| A2 | D47L, P68L, P70L | ++ |
| A4 | D47R, P70L | ++ |
| B6 | D47W | ++ |
| B3 | D47R | + |
| B2 | D47E | + |

*Approximate binding affinity by 5-pt yeast titration.

+++, $K_d$ ~2-5 nM ++ 5-15 nM, + 15-40 nM

Figure 8:
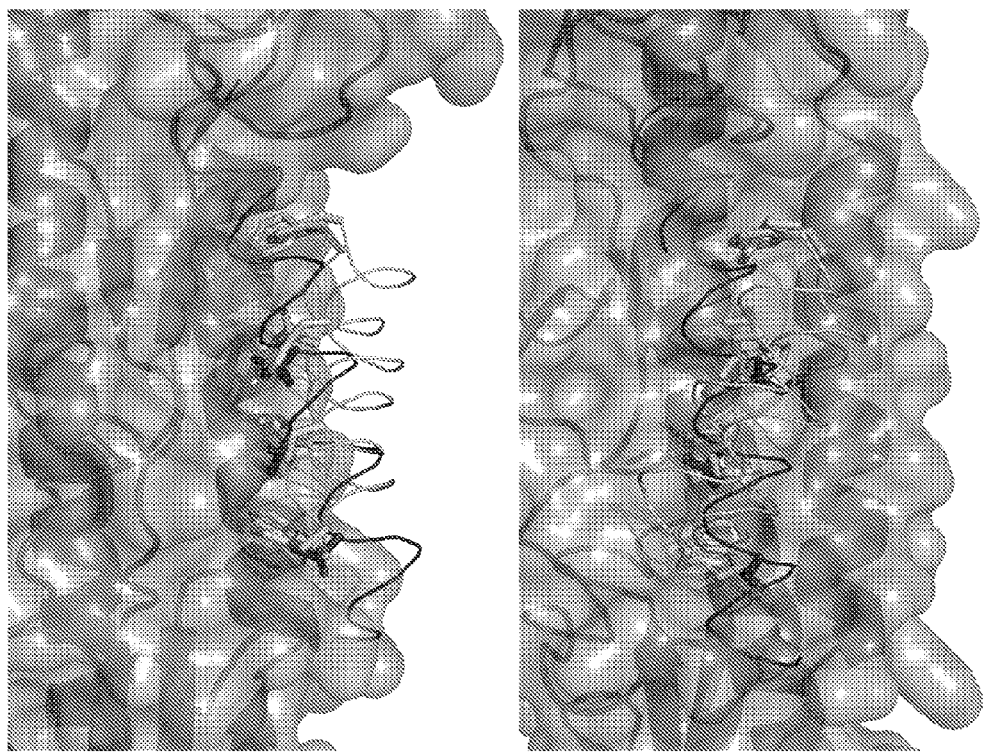
FIG. 8. Truncation after position 54 on HB80 M26T N36K increases mean surface display. FITC intensity histograms of (a.) HB80 M26T N36K and (b.) HB80 M26T N36K Δ54-95. In both cases, gray lines represent unlabeled cells, while black lines represent cells labeled with anti-cmyc FITC.
Figure 8:
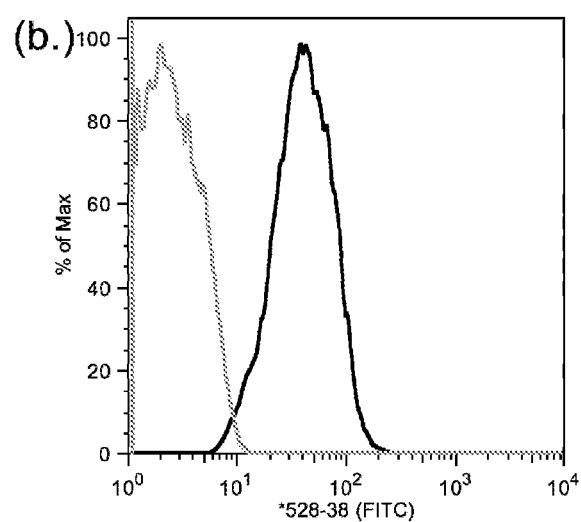

The favorable substitutions were combined and the proteins were expressed with a His-tag in *E. coli* and purified by nickel affinity and size-exclusion chromatography. The variant HB36.3, incorporating the Asp47Ser and Ala60Val substitutions, bound to SC1918/H1 HA as confirmed by surface plasmon resonance (SPR;), ELISA, and co-elution on a size-exclusion column (data not shown). The HB36.4 variant, which incorporates Asp47Ser, Ala60Val, and Asn64Lys, bound to SC1918/H1 HA with a dissociation constant measured by SPR of 22 nM and an off-rate of $7 \cdot 10^{-3}$ s$^{-1}$ (Table 7). Co-incubation with an excess of CR6261 Fab abolished binding to the HA (FIG. 3G), consistent with HB36.4 binding in close proximity to the same stem epitope on the HA. For the HB80 design, the combination of the affinity-increasing mutations reduced surface expression on yeast, indicative of poor stability. Therefore, we excised a C-terminal stretch (Δ54-95) greatly boosting surface expression of the design with no significant loss of binding affinity (FIG. 8). HB80.3, which incorporates the truncation as well as the Asp12Gly, Ala24Ser, Met26Thr, and Asn36Lys substitutions, has a $K_d$=38 nM with off-rate of $4 \cdot 10^{-2}$ s$^{-1}$ by SPR. As with HB36.4, co-incubating HA with the CR6261 Fab completely abolished binding to HB80.3 (FIG. 3H), consistent with the designed binding mode.

TABLE 7

Affinity and kinetic binding constants for specified design variants. All measurements were recorded using surface plasmon resonance. Numbers in parentheses indicate error associated with the measurement.

| Design Variant | $K_d$ [nM] | $k_{on}$ [M$^{-1}$s$^{-1}$] | $k_{off}$ [s$^{-1}$] |
|---|---|---|---|
| HB36.3 (D47S, A60V) | 29.0 ± 0.6 | 1.2 ± 0.1e6 | 3.5 ± 0.3e2 |
| HB36.4 (D47S, A60V, N64K) | 22.3 ± 0.9 | 3.2 ± 0.2e5 | 7 ± 1e3 |
| HB80.3 (D12G, A24S, M26T, N36K) | 38 ± 2 | 1.0 ± 0.2e6 | 3.9 ± 0.8e2 |

Figure 9:
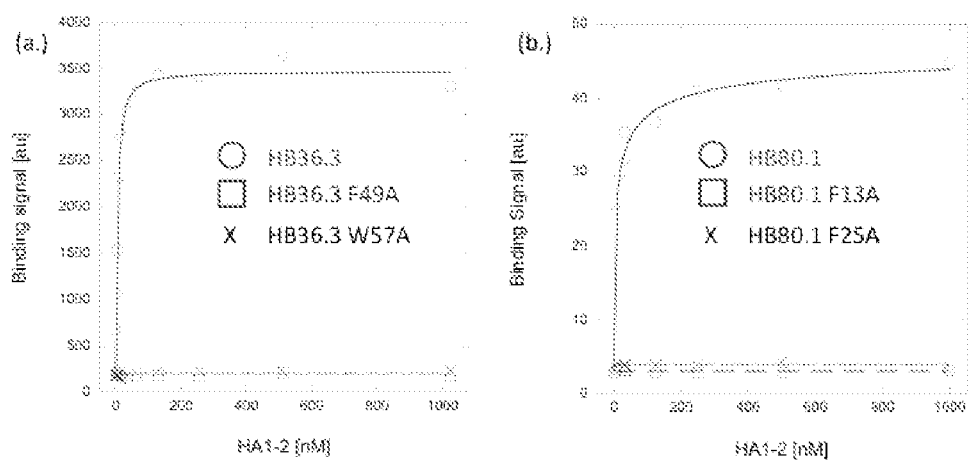
FIG. 9. Alanine scanning mutagenesis of key residues at the designed interface of HB36.3 (a.) and HB80.1 (b.) completely abrogating binding. Binding was measured by yeast surface display titrations FIG. 10. Yeast display titrations of designs to H1 & H5 HA subtypes show heterosubtypic binding of (A.) HB36.4 & (B.) HB80.3 design variants. For both panels, circles are binding titrations of SC/1918/H1 HA and squares the titration data for VN/2004/H5 HA.

Site-directed alanine mutagenesis of several core positions on each affinity-matured design partially or completely knocked out HA binding (Table 8, FIG. 9) supporting the computational model of the designed interfaces (26). Furthermore, no mutations were uncovered during selection for higher affinity that were inconsistent with the designed binding modes.

TABLE 8

Summary of alanine scanning mutagenesis of key residues at the interface of HB36 and HA80. Binding was measured by yeast surface display titrations on two separate days. NB marks no binding at 1 μM HA. ΔΔG was computed from the change in $K_d$ relative to HB36.3 at the assay temperature of 294 K.

| Construct | $K_d$ [nM] | ΔΔG [kcal/mol] |
|---|---|---|
| HB36.3 (D47S, A60V) | 5.0 ± 0.5 | — |
| HB36.3 F49A | NB | >3.4 |
| HB36.3 M53A | 115 ± 35 | 1.8 ± 0.2 |
| HB36.3 W57A | NB | >3.4 |
| H80.1 (M26T, N36K) | 7.5 ± 1.0 | — |
| HB80.1 F13A | NB | >2.9 |
| HB80.1 F25A | NB | >2.9 |
| HB80.1 Y40A | 140 ± 20 | 1.7 ± 0.2 |

Crystal Structure of the HB36.3-SC1918 HA Complex

Figure 4:
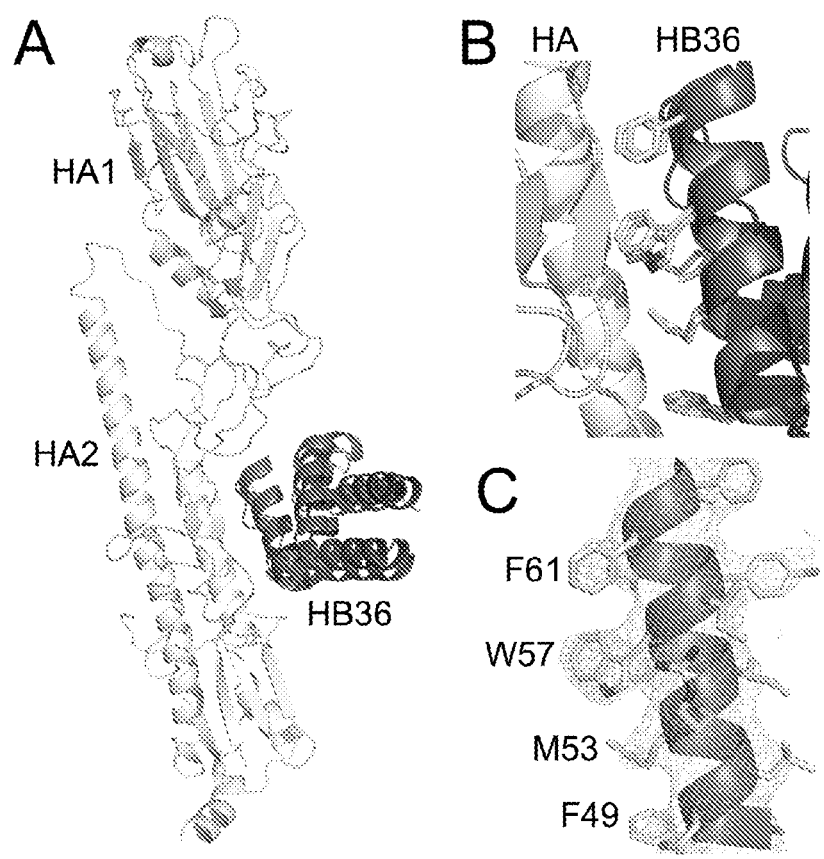
FIG. 4 Crystal structure of HB36.3-SC1918/H1 complex validates the precision of the computational design. (A) Superposition of the crystal structure of HB36.3-SC1918/H1 complex and the computational design reveals good agreement in the position of the main recognition helix, with a slight rotation of the rest of the protein domain. Superposition was performed using the HA2 subunits. For clarity, only the HA from the crystal structure is depicted here (the HA used for superposition of the design, which is essentially identical to the crystal structure, was omitted). (B) Close up of the SC1918 HA-HB36.3 interface, highlighting the close agreement between the design and the crystal structure. The main recognition helix is oriented approximately as in (A). (C) Unbiased 2Fo-Fc (gray mesh, contoured at 1σ) and Fo-Fc (dark mesh, contoured at 3σ) electron-density maps for the main recognition helix of HB36.3. The helix is oriented as in (B), with key contact residues of the left face of the helix in this view labeled (the right surface faces and interacts with the core of the HB36.3 protein). Significant density was observed for most of the large side chains at the interface with HA, including F49, M53, W57, F61, and F69 (not visible in this view). While side chains are shown here to illustrate their agreement with the experimental electron density, maps were calculated after initial refinement of an HA-HB36.3 model with the following side chains truncated to alanine (no prior refinement with side chains present): F49, M53, M56, W57, F61, and F69.

The crystal structure of HB36.3 in complex with the SC1918 HA ectodomain was determined to 3.1 Å resolution. After molecular replacement using only the 1918/H1 HA structure as the search model (approximately 86% of the protein mass in the crystal asymmetric unit), clear electron density was observed for HB36.3 near the target surface in the HA stem region into which HB36.3 could be unambiguously placed. The orientation was essentially identical to the designed binding mode, with the modified surface of the main recognition helix packed in the hydrophobic groove on HA (FIG. 4A). To obtain unbiased density for the designed side chains, the native structure from which HB36.3 was derived (PDB entry: 1U86) was manually fit into the electron-density maps and contact side chains were pruned back to their β-carbon. After crystallographic refinement, electron density became apparent for the side chains of most of the contact residues on HB36.3, allowing the predominant rotamers to be assigned for Phe49, Trp57, Phe61, and Phe69. This unbiased density clearly shows that these four hydrophobic side chains are all positioned as in the designed model (FIG. 4B). The Met53 side chain is consistent with the design model (FIG. 4C), although other rotamers could also be fit to the map. For Met56, only very weak side-chain density was observed. Overall, the crystal structure is in excellent agreement with the designed interface, with no significant deviations at any of the contact positions.

Given the quite low (2 out of the 73 surface displayed proteins) design success rate and starting affinities, the atomic-level agreement between the designed and experimentally determined HB36.3-SC1918 HA complex is very encouraging and suggests that, despite their shortcomings, the current energy function and design methodology capture essential features of protein-protein interactions.

Cross-Reactivity and Inhibitory Activity

Figure 10:
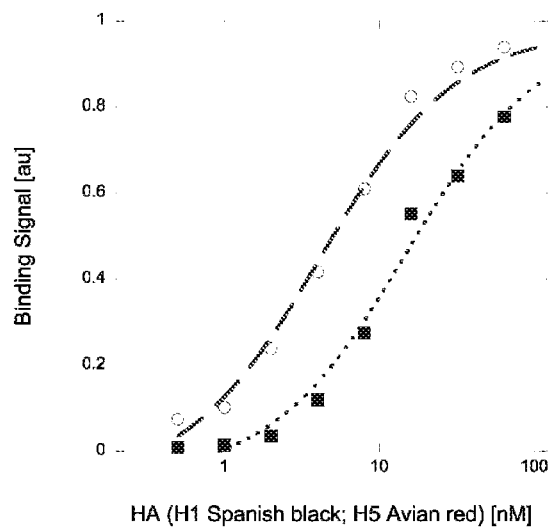
Figure 10:
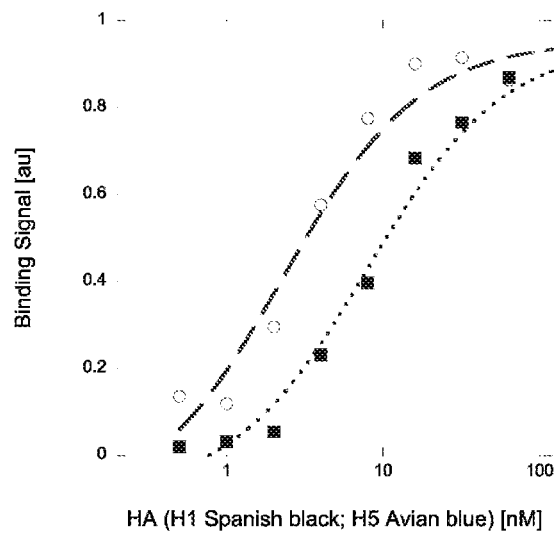

The surface contacted by HB36.3 is accessible and highly conserved in the HAs of most group 1 influenza viruses, suggesting that it may be capable of binding not only other H1 HAs, but also other HA subtypes. Indeed, binding of HB36.3 to A/South Carolina/1/1918(H1N1) and A/WSN/1933 (H1N1) is readily detectable in solution by gel filtration (data not shown), as well as high-affinity binding of HB36.4 to A/Vietnam/1203/2004 H5 subtype by yeast display (FIG. 10).

Figure 5:
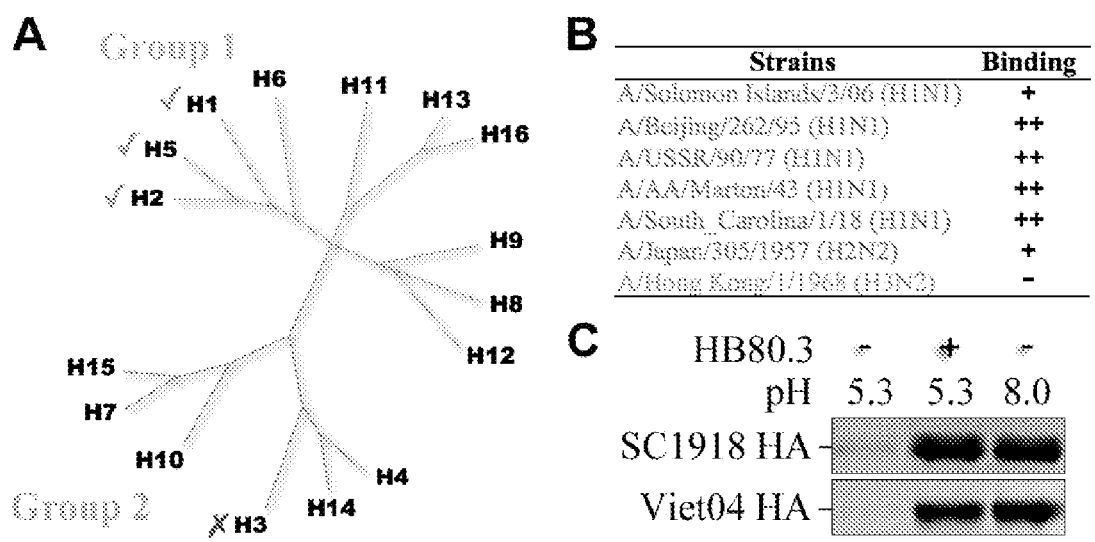
FIG. 5. HB80.3 binds and inhibits multiple HA subtypes. (A) Phylogenetic tree depicting the relationship between the 16 influenza A hemagglutinin subtypes. These subtypes can be divided into two main lineages, groups 1 and 2. CR6261 has broad activity against group 1 viruses. HB80.3 has a similar cross-reactivity profile and binds multiple group 1 subtypes, including H1 and H5. (B) Binding data for HB80.3 and CR6261 Fab against a panel of HAs. "+", "++", and "+++" indicate relative degree of binding (approximately $10^{-7}$, $10^{-8}$, and $10^{-9}$ M, respectively), while "−" indicates no detectable binding at the highest concentration tested (100 nM). (C) HB80.3 inhibits the pH-induced conformational changes that drive membrane fusion. Exposure to low pH converts 1918 H1 HA (top panel) and the Viet04 H5 HA to a protease susceptible state (lane 1), while HAs maintained at neutral pH are highly resistant to trypsin (lane 3). Pre-incubation of HB80.3 with H1 and H5 prevents pH-induced conformational changes and retains the HAs in the protease-resistant, pre-fusion state (lane 2).
Figure 6:
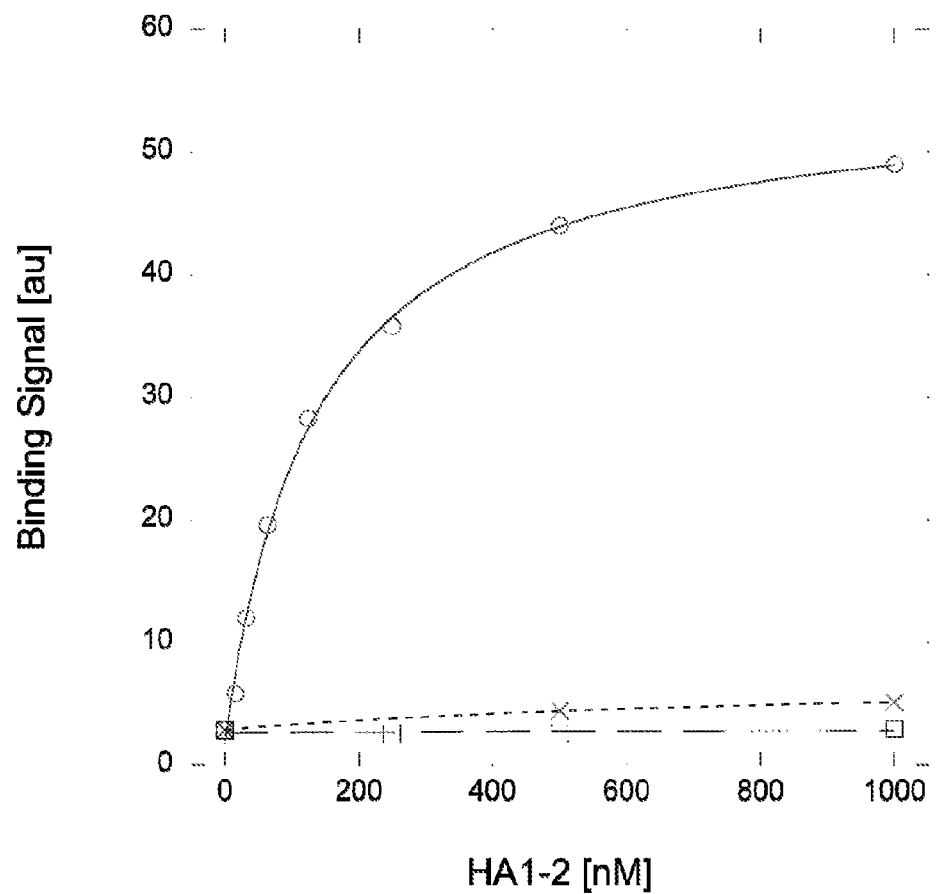
FIG. 6. Binding titrations of HB36 to SC1918/H1 HA as measured by yeast surface display. Circles represent the computational design, squares the scaffold protein from which the design is derived, and crosses represent the design in the presence of 1.5 uM inhibitory CR6261 Fab.
Figure 7:
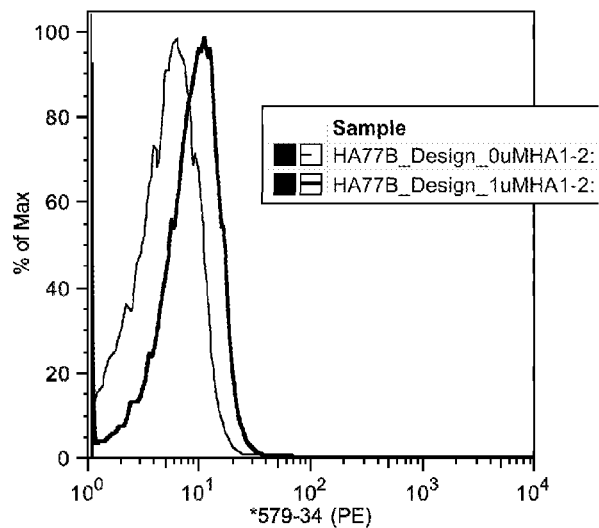
FIG. 7. Phycoerythrin (PE) intensity histograms for (a.) HB80 design and (b.) the scaffold the design was derived from (PDB code 2CJJ). Dashed lines represent the population of yeast cells displaying the design in the absence and dark lines the presence of 1 uM H1 HA.
Figure 7:
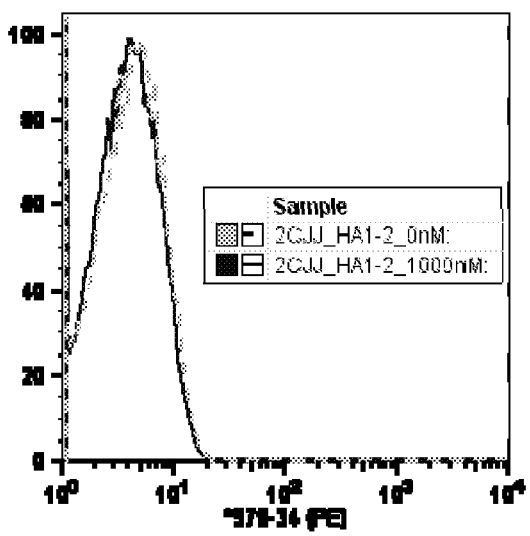

While a crystal structure of HB80 in complex with HA has not been obtained, the mutational data and the antibody-competition results suggest that HB80 also binds to the designed target surface, overlapping with HB36 and CR6261. Consequently, HB80.3 is also expected to be highly cross-reactive and binds with high affinity to A/Vietnam/1203/2004 H5 HA (FIG. 10), and to H1, H2, H5, and H6 subtypes by biolayer interferometry (FIGS. 5A,B). Overall, the pattern of HB80 binding mirrors that of CR6261 and binds most of the group 1 HAs tested, with no detectable binding to group 2 HAs.

Figure 11:
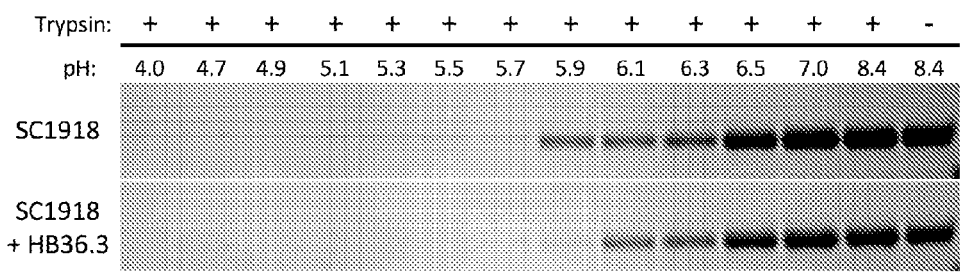
FIG. 11. Protease susceptibility-inhibition assay for HB36.3 against the SC1918/H1 HA. (A) The upper panel shows the effect of various pH treatments and trypsin digestion on SC1918 HA alone. Most of the HA is converted to the protease-susceptible, post-fusion conformation below pH~6.0-6.5. The lower panel shows the identical assay for the HB36.3-SC1918 complex (saturated with HB36.3 and purified by gel filtration prior to the experiment; approximately 1:1 molar ratio of HB36.3 to HA). Presence of pre-bound HB36.3 in the reactions is unable to block the conversion of HA to the protease-resistant state. (B) Assay carried out under conditions identical those used for HB80.3 as presented in FIG. 5C (approximately 10:1 molar ratio of HB36.3 to HA). HB36.3 has no protective effect under these conditions.
Figure 11:
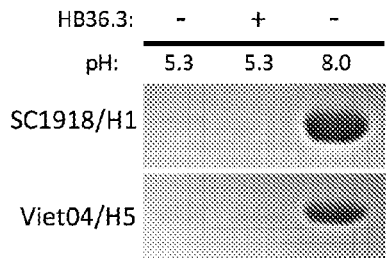

Antibody CR6261 inhibits influenza virus replication by blocking the pH-induced refolding of HA, which drives fusion of the viral envelope with the endosomal membrane of the host cell. Given extensive overlap between the HB80.3 and CR6261 binding sites and its high affinity for SC1918 HA, it seemed plausible that HB80.3 would also block this conformational change. Indeed, HB80.3 inhibits the pH-induced conformational changes in both H1 and H5 HAs (FIG. 5C, FIG. 11)(10), suggesting that this design may possess virus-neutralizing activity against multiple influenza subtypes (27).

REFERENCES AND NOTES FOR EXAMPLE 1

1. H. Ledford, *Nature* 455, 437 (2008).
2. R. A. Lerner, *Angew Chem Int Ed Engl* 45, 8106 (2006).
3. T. Kortemme et al., *Nat. Struct. Mol. Biol.* 11, 371 (2004).
4. R. K. Jha et al., *J Mol Biol* 400, 257 (2010).
5. P. S. Huang, J. J. Love, S. L. Mayo, *Protein Sci* 16, 2770 (2007).
6. J. Karanicolas et al., *Mol. Cell* in press, (2011).
7. S. Liu et al., *Proc Natl Acad Sci USA* 104, 5330 (2007).
8. E. Bautista et al., *N Engl J Med* 362, 1708 (2010).
9. J. Sui et a, *Nat Struct Mol Biol* 16, 265 (2009).
10. D. C. Ekiert et al., *Science* 324, 246 (2009).
11. Group 1 includes 10 of the 16 HA subtypes: H1, H2, H5, H6, H8, H9, H11, H12, H13, and H16. Group 2 includes the remaining 6 subtypes: H3, H4, H7, H10, H14, and H15.
12. L. Lo Conte, C. Chothia, J. Janin, *J Mol Biol* 285, 2177 (1999).
13. T. Clackson, J. A. Wells, *Science* 267, 383 (1995).
14. M. G. Rossmann, *J Biol Chem* 264, 14587 (1989).
15. The other hotspot residues (HS1 and HS2) differed from the sidechains observed in the crystal structures in their conformation or identity. Each hotspot residue was further diversified by constructing all conformations, the terminal atoms of which coincided with those modeled above. For instance, for HS3, these consisted of all Tyr conformations that matched the position of the aromatic ring and hydrogen bond. This diversification step produced a 'fan' of backbone positions for each residue in the hotspot libraries.
16. Proteins in the scaffold set contained no disulfides, were expressed in *E. coli*, and were predicted to form monomers (see Supplemental Information).
17. D. Schneidman-Duhovny, Y. Inbar, R. Nussinov, H. J. Wolfson, *Nucleic Acids Res* 33, W363 (2005).
18. J. J. Gray et al., *J Mol Biol* 331, 281 (2003).
19. B. Kuhlman et al., *Science* 302, 1364 (2003).
20. J. Chen, J. J. Skehel, D. C. Wiley, *Proc Natl Acad Sci USA* 96, 8967 (1999).
21. G. Chao et al., *Nat Protoc* 1, 755 (2006).
22. A third design HB35 bound HA at apparent low $\mu$M affinity; however, binding was only partially abolished upon co-incubation of HA with the CR6261 Fab, indicating of at most partial contact with the target surface on the stem region of HA, and so this design was eliminated from further consideration. A handful of other designs bound HA albeit weakly and with incomplete reproducibility.
23. We recorded dissociation constants using two main methods: by titration of HA against yeast surface-displayed designs, and by fitting both kinetic and equilibrium measurements using surface plasmon resonance. As there is a discrepancy in determining Kd's between the methods, measurements derived from yeast surface-display titrations are listed as apparent Kd and should be viewed qualitatively.
24. C. E. Stevenson et al., *Proteins* 65, 1041 (2006).
25. R. Das, D. Baker, *Annu Rev Biochem* 77, 363 (2008).
26. The alanine-scan mutations were as follows: for HB36.3, Phe49, Met53, and Trp57; for HB80.1 Phe13, Phe25, and Tyr40 (Table S4 and supplemental results).
27. HB36.4 was not able to block the pH-induced conformational changes in the H1 HA under identical assay conditions, even though HB36.4 and HB80.3 have very similar dissociation constants and kinetic off-rates at pH 7.5 (FIG. 11).
28. Computational designs were generated on resources generously provided by participants of Rosetta@Home and the Argonne National Leadership Computing Facility. X-ray diffraction datasets were collected at the Stanford Synchrotron Radiation Lightsource beamline 9-2 and at the Advanced Photon Source beamline 231D-B (GM/CA-CAT). Coordinates and structure factors were deposited in the Protein Data Bank (PDB) as entry 3R2X.

Supporting Material

Computational Design Methodology

FIG. 1 provides a flowchart overview of the approach. This method is a generalization of a recently described approach for two-sided design of pairs of interacting proteins (S1). In that method surfaces of an ankyrin-repeat protein and a target protein were simultaneously mutated to introduce a hotspot region buttressed by a periphery of compatible interactions. The hotspot region in that method comprised aromatic residues that formed intermolecular hydrogen bonds. Our approach does not make any assumptions about the nature of the hotspot or the scaffold protein. We generate a hotspot region consisting of high-affinity interacting residues of all types and incorporate them into a variety of scaffold proteins. These generalizations allow us to design binders of potentially any protein surface.

Generating Hotspot Residues

Individual residues were docked against the target surface on influenza A/SC/1918/H1 hemagglutinin (hereafter referred to as HA) using ROSETTADOCK™ (S2) starting from the structure of HA bound to the antibody fragment (Fab) CR6261(S3). We positioned the hydrophobic residues Leu, Val, Ile, Phe, Trp, Met, and Tyr against the surface of HA near Trp21 on HA2 (H3 HA sequencing numbering as in Protein Data Bank (PDB) entry 3GBN). Only conformations of the Phe were able to form satisfactory contacts with the surface, whereas the other residues either left small voids or buried polar atoms. Two dominant conformations of Phe were selected that were roughly 60° rotated relative to one another with respect to the center of the aromatic ring as hotspot residue 1 (HS1) (FIG. 1).

To compute the position of the second hotspot residue (HS2), we docked the same set of hydrophobic residues against the HA surface with the two major Phe conformations from HS1 placed to ensure that the residues that are selected form energetically favorable interactions with HA, as well as with HS1. This search yielded low-energy placements of Leu, Val, Ile, Phe, and Met for HS2.

Third, the Tyr, Asn, and Gln residues were docked against the HA2 A-helix region spanning Thr41 (FIG. 1) again including the Phe HS1 residues. We required each docked residue to form a hydrogen bond to the backbone carbonyl of Asp 19 on HA2. Only a single dominant orientation for a Tyr was identified that formed the requisite hydrogen bond, did not bury polar groups at the interface, and formed favorable van der Waals contacts with the A helix (FIG. 1).

All of the conformations identified by ROSETTADOCK™ were diversified by generating inverse rotamers starting from their side-chain atoms nearest to the HA surface. These inverse rotamers were expanded to include rotamers one standard deviation away from the base rotamers in the Dunbrack library (S4) with the ROSETTA™ commandline flags—ex1-ex2.

A Set of Scaffold Proteins

We selected a set of 865 proteins from the PDB in March 2009 according to the following criteria: they contained no disulfides, RNA, or DNA molecules, were solved by X-ray crystallography at a resolution better than 2.5 Å, are reported to have been expressed in *E. coli*, are predicted to be monomeric by the Protein Quaternary Structure server(S5), and contain a single polypeptide chain of between 80 and 250 amino acids. The list was pruned at 70% sequence identity. Each structure was refined in the ROSETTA™ forcefield by full side-chain repacking and minimization.

Low-Resolution Docking of Scaffold Proteins Against the Target Epitope

To obtain high shape-complementary configurations of the scaffold protein with respect to HA we used the PATCHDOCK™ feature-matching algorithm (S6). Constraints were used to prune conformations of each scaffold protein that do not interact with Trp21 and Thr41 on HA2. The surviving conformations were clustered at 4 Å root-mean-square deviation (RMSD). PATCHDOCK™ was run with default parameters.

Backbone Restraints

The hotspot-residue libraries are used to identify configurations of the scaffold protein with respect to HA that may accommodate the placement of these hotspot residues. Each hotspot residue computed in the library implies an approximate location for a position on the scaffold protein and an orientation for the Cα-Cβ and the C-N vectors. For each hotspot residue h and each scaffold position i, we formulate scoring restraints $R_i^h$ to bias conformational sampling to configurations that would favor the placement of the hotspot residues:

$$R_i^h = \min[0, (\Delta G_h + k/n(\breve{\beta}_i - \breve{\beta}_h))[(\breve{\beta}_h - \breve{\alpha}_h) \cdot (\breve{\beta}_i - \breve{\alpha}_i)][(\breve{C}_h - \breve{N}_h) \cdot (\breve{C}_i - \breve{N}_i)]] \quad (Eq.\ 1)$$

where $\Delta G_h$ is the computed binding energy for hotspot residue h, is always negative and was chosen to be −3 in all design trajectories; β, α, C, and N, are the coordinates of the Cβ, Cα, C, and N atoms; k (the spring constant) is arbitrarily set to 0.5; min is the minimum function ensuring that the restraint is negative or zero; the quantities within the square brackets are the dot products of the relevant vectors; and $n = \|\breve{\beta}_h - \breve{\alpha}_h\|\|\breve{\beta}_i - \breve{\alpha}_i\|\|\breve{C}_h - \breve{N}_h\|\|\breve{C}_i - \breve{N}_i\|$ is a normalization constant.

This form of the restraint function reaches a minimum when the distance between the Cβ of the hotspot residue and a position on the scaffold is 0 and the Cα-Cβ and C-N vectors are matched. Thus, a given restraint is best satisfied when a potential grafting position on the scaffold is perfectly aligned with a pre-computed hotspot residue. If the orientation of either of the two vectors of position i with respect to hotspot h is more than 90°, then $R_i^h$ is set to 0. A library of n hotspot residues thus implies n restraints. Each residue i is then assigned the smallest of these n restraints:

$$R_i = \min_h(R_i^h) \quad (Eq.\ 2)$$

Equation 2 then assigns the minimal restraint to each amino-acid position i on the scaffold, so that each scaffold position is affected only by the most appropriate hotspot restraint at any given time during conformational search.

Since only the locations of the Cβ and the backbone atoms are required in evaluating Equation 2, the restraints can be computed efficiently during low-resolution Monte-Carlo based docking of the scaffold protein with respect to the HA surface. Importantly, the restraints can be used during minimization as Equation 1 is readily differentiable.

Hotspot-Residue Placement

We used two different protocols to design scaffolds that incorporate the computed hotspots. The more restrictive design strategy incorporated three hotspot residues (Tyr for HS3, Phe for HS1, and a nonpolar residue for HS2); the less restrictive one incorporated two (Phe for HS1 and a nonpolar residue for HS2). We developed three methods for hotspot-residue placement for use in the different stages of design. Each starts with the configuration of the scaffold protein obtained from hotspot-residue guided docking and minimization with one of the hotspot-residue libraries. Except for Gly, Pro and disulfide-linked cysteines, interfacial residues on the scaffold protein within 10 Å from the target protein were reduced to alanine to increase the chances of accommodating the hotspot residues.

Method 1: Placement of the Scaffold onto an Idealized Hotspot Residue

The residues within the hotspot-residue libraries define configurations that are optimal for realizing the hotspot interaction. For a given interfacial scaffold position, we iterate over each of the nearby hotspot residues in the library and rotate and translate the scaffold protein so as to align it perfectly with the rotamer of the hotspot residue. Scaffold positions, for which the Cβ atoms are farther than 4.0 Å from the relevant hotspot residue or whose C-N or Cα-Cβ vectors are misaligned with the hotspot residues by more than 60°, are triaged to avoid compromising the initial, high shape complementary configuration of the two partners. We then minimize the rigid-body orientation and the side-chain degrees of freedom of the placed hotspot residue in a reduced forcefield that only considers the punitive energy terms for van der Waals clashes and rotameric energies. If the energy of the placed hotspot residue is higher than 1.0 Rosetta energy unit (R.e.u.), we discard this placement.

In the context of the two-residue hotspot designs, we used this strategy to place the hotspot residue Phe (HS1) on the scaffold proteins. In the case of the three-residue designs, we used this strategy to place the Tyr (HS3).

Method 2: Placement of a Hotspot Residue onto a Scaffold Position

For each interfacial scaffold position, we minimize the configuration of the scaffold protein with respect to the target in the context of a single restraint (Eq. 1) derived from the hotspot residue. All other parameters and cutoffs are as in the previous section. We used this strategy to place HS2 in the two-residue hotspot designs.

Method 3: Simultaneous Placement of Multiple Hotspot Residues

For each hotspot-residue library, we identify a position on the scaffold protein that produces the most favorable restraint score as defined by Equation 1 compared to the remainder of the hotspot-residue libraries. Each such scaffold position is then coupled to the appropriate hotspot-residue library. If not all hotspot-residue libraries are matched to different scaffold positions, the configuration of the scaffold with respect to the target is discarded. Upon success, we simultaneously redesign the identities of the relevant scaffold positions to those amino-acid identities contained in their matched hotspot-residue libraries. Since only a handful of positions are designed in this scheme and the identities of the designed residues are limited based on the relevant hotspot-residue library, the addition of off-rotameric conformations into the design step is computationally affordable. We used this scheme to place HS1 and HS2 in the three-residue hotspot designs.

Intensified Conformational Search in the Design of Scaffolds Incorporating the Three-Residue Hotspot Preliminary trials using the three-residue placement approach (incorporating HS1-3) revealed that this combination of residues implies constraints on scaffold proteins that are very rarely met by proteins in the scaffold set. To increase the chances of identifying scaffolds that may incorporate the three-residue hotspot, we used a protocol that intensified the search in terms of both the backbone conformation of the scaffold proteins and their rigid-body orientations. This intensification was made possible by the computational-efficiency gains provided by the simultaneous-placement method.

For each scaffold, placement of the scaffold on the Tyr HS3 residue was attempted and was deemed successful if the Tyr hotspot residue's energy did not surpass 1 R.e.u. and the Tyr formed a hydrogen bond with the Asp19 backbone carbonyl. We next conducted 4 trials of rigid-body docking followed by simultaneous placement (of HS1-2). During simultaneous hotspot-residue placement, backbone minimization and backrub (S7) were conducted to increase the chances of successful placement. In retrospect, backbone remodeling is likely to have contributed little to the success of the placement of the hotspot residues on HB80 as the backbone of this redesigned protein does not show significant differences from the starting wildtype structure.

Redesign of Residues Outside of the Hotspot

Following the successful placement of residues from all hotspot-residue libraries, scaffold positions that are at most 10 Å from the target protein are redesigned using ROSETTA-DESIGN™ (S8), while the target protein side chains are allowed to repack. Gly, Pro and disulfide-linked cysteines are left as in the wildtype sequence. Three iterations of redesign and minimization were used to increase the likelihood that higher-affinity interactions are found, starting with a soft-repulsive potential, and gradually increasing the repulsive terms. The last design step uses the default all-atom forcefield with high weights on the steric clashes and rotameric strain to ensure that the designed residues do not assume high-energy conformations.

During these design simulations, the side chains of the placed hotspot residues are biased towards the coordinates of the idealized hotspot residues as present in the hotspot-residue library (similar to the implementation in ref (S9)). This bias is implemented as harmonic coordinate restraints, typically on three atoms that define the functional group of the side chain, in effect pulling the placed hotspot residue's functional group towards its idealized position with respect to the target protein. For example, these atoms would be the three carbon atoms at the root of Tyr and Phe aromatic rings. To ensure that the placed residues are stable in their position on the scaffold, all restraints are gradually removed during the simulation and the last packing and minimization step is carried out in the absence of restraints.

Each resulting model is automatically filtered according to computed binding energy (S10), buried surface area, and shape complementarity (S11). Complexes that were predicted to have binding energies of more than −15 R.e.u., surface areas of less than 1000 Å$^2$, or shape-complementarity scores less than 0.65, were eliminated. At this stage, designs were reviewed manually, and a subset was selected for more rigorous evaluation. After the subsequently described modifications in the designs, some of the designs had statistics that failed these filters. While both HB36 (binding energy=−24, Sc=0.66, buried surface area=1620 Å$^2$) and HB80 (binding energy=−19, Sc=0.72, buried surface area=1580 Å$^2$) passed these filters, other designs with comparable statistics did not.

Minimizing the Number of Residue Changes at the Interface

For each design that passed the abovementioned filters, the contribution of each amino-acid substitution at the interface is assessed by singly reverting residues to their wild-type identities and testing the effects of the reversion on the computed binding energy. If the difference in binding energy between the designed residue and the reverted one is less than 0.5 R.e.u. in favor of the design, then the position is reverted to its wild-type identity.

A report of all residue changes was produced and each suggestion was reviewed manually. At this stage of manual review, additional mutations were introduced. These typically involve the introduction or removal of peripheral charges to better complement the charged surface of HA and did not routinely involve more than 5 substitutions per design.

An additional means of minimizing changes to the sequence of the original scaffold consisted of introducing sequence restraints during all stages of design. Briefly, mutations from the wildtype sequence were penalized according to their distance in the BLOSUM62 matrix (S12). The weight on these sequence restraints was set to 0.2.

Binding-Energy Calculations

In keeping with ref. (S10), the binding energy was defined as the difference between the total system energy in the bound and unbound states. In each state, interface residues were allowed to repack. For numerical stability, binding-energy calculations were repeated three times and the average taken.

Shape Complementarity

Shape complementarity was computed using the CCP4 package v.6.0.2 (S13) using the sc program.

Experimental Characterization
Expression and Purification of BirA

E. coli biotin ligase (BirA enzyme) was expressed and purified in a manner similar to previous reports (S14), but with an N-terminal His tag. The birA gene was amplified from an E. coli colony (wild-type strain MG1655) using primers DE389 (5'-agtcactaggtcatatgcatcaccatcaccatcacaaggataacaccgtgccactg-3' (SEQ ID NO: 195)) and DE390 (5'-agtcactaggtaagcttttatttttctgcactacgcagggatatttc-3' (SEQ ID NO: 197)). The PCR product was digested with NdeI and HindIII and ligated into similarly digested pET21a, yielding pDCE095. This vector was transformed into BL21 (DE3) cells for protein expression.

BL21(DE3)/pDCE095 cells were grown in shake flasks in low salt LB medium at 37° C. to an OD (600 nm) of ~0.7, then shifted to 23° C. and induced with the addition of IPTG (isopropyl-beta-D-thiogalactopyranoside) to a final concentration of 1 mM. The culture was incubated at 23° C. for ~16 hours after induction, then harvested by centrifugation (3000 g, 10 minutes). The pellet from a 1 L culture was resuspended in 50-100 mL of lysis buffer (50 mM Tris pH 8.0, 300 mM potassium chloride, 10 mM imidazole pH 8.0, with Roche EDTA-free protease inhibitor cocktail tablet) and the cells were lysed and homogenized by two passes through an EMULSIFLEX™ C-3 cell disruptor (15kPSI). After clearing the lysates by centrifugation (25,000 g, ~1 hour), the supernatant was incubated with NiNTA resin (Qiagen), washed with excess lysis buffer, and bound proteins were eluted (with 50 mM Tris pH 8.0, 300 mM potassium chloride, 250 mM imidazole pH 8.0). After concentrating and buffer exchanging into 50 mM potassium phosphate, pH6.5, 5% glycerol, 0.1 mM dithiothreitol (DTT), the BirA was loaded onto a MonoQ column (GE Healthcare) and eluted with a linear gradient of 0-1M potassium chloride. BirA containing fractions were pooled, concentrated, and subjected to gel filtration. The final yield of BirA protein was approximately 10 mg/L and >95% pure as assessed by SDS-PAGE. Purified BirA protein was concentrated to 5 mg/mL in 50 mM Tris, pH 7.5, 200 mM potassium chloride, 5% glycerol, aliquoted, snap frozen in liquid nitrogen, and stored at −80° C.

Cloning, Expression and Purification of Hemagglutinins

Based on H3 numbering, cDNAs corresponding to residues 11-329 (HA1) and 1-176 (HA2) of the influenza A hemagglutinin (HA) were fused to an N-terminal gp67 signal peptide (amino acid sequence: MVLVNQSHQGFNKEHTSKMVSAIVLYVLLAAAAHSAFA (SEQ ID NO: 212)) and to a C-terminal trimerization domain and His-tag by overlap PCR, essentially as previously described (S3). The trimerization domain and His-tag were separated from the HA ectodomain by a thrombin cleavage site. For biotinylated HAs, a BirA target biotinylation site (amino-acid sequence: GGGLNDIFEAQKIEWHE (SEQ ID NO: 213)) was inserted between the HA and the thrombin site. The resulting PCR products were digested with SfiI, and inserted into a custom baculovirus transfer vector, pDCE198. Recombinant bacmids were generated using the Bac-to-Bac system (Invitrogen) and viruses were rescued by transfecting purified bacmid DNA into Sf9 cells using Cellfectin II (Invitrogen). HA proteins were produced by infecting suspension cultures of Hi5 cells (Invitrogen) with recombinant baculovirus at an MOI of 5-10 and incubating at 28° C. shaking at 110 RPM. After 72 hours, the cultures were clarified by two rounds of centrifugation at 2000 g and 10,000 g at 4° C. The supernatant, containing secreted, soluble HA was concentrated and buffer exchanged into 1×PBS, pH 7.4. After metal affinity chromatography using Ni-NTA resin, HAs were modified and purified further as required for specific purposes (see following sections). At this stage, yields typically varied from 1-10 mg/L, depending upon the HA isolate.

Biotinylation and Purification of HAs for Affinity Maturation and Binding Studies After Ni-NTA purification, HAs with C-terminal biotinylation tags were concentrated down to ~2-5 mg/mL total protein. The HAs were biotinylated by the addition of 25 ug BirA enzyme/mg total protein, in a buffer of the following composition: 100 mM Tris pH 8.0, 10 mM ATP, 10 mM MgOAc, 50 uM biotin, with less than 50 mM NaCl. The biotinylation reactions were incubated at 37° C. for 1-2 hours. At this point, some HAs were digested with trypsin (New England Biolabs, 5 mU trypsin per mg HA, 16 hours at 17° C.) to generate the fusion competent HA1/HA2 form, while the majority were kept undigested as HA0. Biotinylated HAs were purified by size-exclusion chromatography, and concentrated down to ~5-20 mg/mL.

Expression and Purification of CR6261 Fab

Genes coding for the Fab region of the CR6261 heavy and light chains were synthesized (Mr. Gene), fused to the gp67 signal peptide and a C-terminal His tag by overlap PCR, and cloned into pFastBacDual (Invitrogen) for expression in baculovirus. Virus production methods, protein expression in High5 cells, harvesting, and Ni-NTA purification was essentially as described above for HA. CR6261 Fab was further purified by protein G affinity chromatography (elution in glycine buffer, pH 2.7); cation exchange chromatography (MonoS resin, sodium acetate, pH 5.0, with a linear gradient from 0-500 mM NaCl); and gel filtration (10 mM Tris, pH8.0, 150 mM NaCl). The final yield was approximately 15 mg/L.

Binder Screening Methodology

Designed binding proteins were tested for binding using yeast-surface display (S15). Yeast codon-optimized genes encoding designs were custom ordered from Genscript (Piscataway, N.J.) and subcloned between NdeI/XhoI sites in an in-house yeast display plasmid named PETCON™. PETCON™ is the original yeast display plasmid pCTCON(S16) with the following modifications: (a) a frameshift mutation in the CD20 encoding region; (b) a NdeI restriction site immediately downstream of the NheI site; and (c) a XhoI-Gly$_2$ spacer sequence immediately upstream of the BamHI restriction site. The full sequence is available upon request. Binding studies were done essentially as described (S15) using 1 μM of a biotinylated SC/1918/H1 HA1-2 ectodomain, except where noted otherwise. Secondary labels were anti-cmyc FITC (Miltenyi Biotec, Auburn, Calif.) to monitor design surface expression and streptavidin-phycoerythrin (Invitrogen, Carlsbad, Calif.) to monitor binding of the biotinylated antigen. Binding signal was quantified as the mean phycoerythrin fluorescence of the displaying population of cells using a 488 nm laser for excitation and a 575 nm band pass filter for emission (appropriately compensated) using either a Cytopeia inFlux Cell Sorter or an Accuri C6 flow cytometer.

The positive control for binding was CR6261 scFv Phe54Ala. The CR6261 scFv was constructed by a (Gly$_4$Ser)$_3$ linker joining the heavy to the light variable region using the DNA encoding CR6261 Fab (S17) as a template. The scFv was further amplified to include recombination sites for integration into pETCON between the NdeI/XhoI restriction sites. The Phe54Ala and all other point mutations were introduced by the method of Kunkel (S18).

Affinity Maturation

HB36 Round 1: First-generation libraries were constructed from the designed HB36 gene by error-prone PCR (epPCR) on the entire amino-acid coding segment or through single site-saturation mutagenesis at 22 out of the 27 residues that are modeled as being within 10 Å from HA. In this and other cases, epPCR was done using a Stratagene GENEMORPH™ II random mutagenesis kit (Agilent, CA) and site-saturation mutagenesis by the method of Kunkel (S19). The total library size was 3e5. We carried these libraries through 2 sorts of yeast display selection, with cells labeled at 50 nM HA1-2 for sort 1 and 10 nM for sort 2. Asp47X and Ala60Val/Thr mutations were recovered that improved affinity >10-fold. The best combination was used for the start of Round 2, and was HB36 Asp47Ser Ala60Val (HB36.3).

HB36 Round 2: Second-generation libraries were constructed from HB36.3 gene using epPCR at 2±1 mutations per gene. A total of 4 yeast display sorts were taken on a library size of 5.4e6. For the 1$^{st}$ sort, cells were labeled with 5 nM HA1-2 and gated to collect the top 5% of the population. For the second and third sorts, cells were labeled with 10 nM HA1-2 and then thoroughly washed with phosphate buffer saline with 1 mg/mL Fraction V bovine serum albumin (Sigma, St. Louis, Mo.). Cells were then incubated at 22° C. with 1 μM of soluble HB36.3 for 40 min. A 4$^{th}$ sort was taken with an off-rate incubation of 60 min. All clones selected from this round included the mutation Asn64Lys.

HB80 Round 1: First-generation libraries were constructed from the designed HB80 gene by epPCR using a mutational load of 2±1 mutations per gene. A library of 1.6e6 transformants was subjected to selection using a labeling concentration of 1 μM HA1-2 and three total sorts. We recovered mutations Met26Val/Thr and Asn36Lys, each of which improved affinity >10-fold. A gene encoding a combination of these mutations HB80 Met26Thr Asn36Lys and a truncation after position 54 (named HB80.2) was the starting sequence for the next round of selection.

HB80 Round 2: Starting with the HB80.2 gene, an epPCR library with a mutational load of 2±1 mutations per gene was transformed into yeast, yielding 2e4 transformants. Cells were labeled with HA1-2 at 3 nM (sort 1), and 5 nM (sorts 2&3) and gated to collect the top 4-5% of cells. All clones selected had a Asp12Gly or a Ala24Ser mutation.

Protein-Design Expression and Purification

Genes encoding the designs were subcloned (NdeI/XhoI) in a pET29b expression vector (EMD, Gibbstown, N.J.) and transformed into *E. coli* ROSETTA™ (DE3) chemically competent cells. Protein expression was induced using the autoinduction method of Studier (S20). After expression for 24 h at 18° C., cells were pelleted, resuspended into buffer FIBS (20 mM Hepes, 150 mM NaCl pH 7.4), and sonicated to release cell lysate. Following clarification by centrifugation, supernatant was applied to a Nickel column for purification. Proteins were eluted by step elution at 250 mM imidazole in HBS. Size exclusion chromatography on a Superdex75 column was used as a finishing purification step into HBS buffer.

Surface-Plasmon Resonance (SPR) Data and Analysis

All SPR data were recorded on a Biacore model 2000 (Biacore, Uppsula, Sweden). A streptavidin (SA)-coated chip (Biacore) was coated with 200 or 400 response units (RU) of biotinylated SC/1918/H1 HA1-2 ectodomain. A blank flow cell and a flow cell coated with 200 RU biotinylated lysozyme were used as negative controls. 150 μL of designed protein at a flowrate of 50 μL/min with a dissociation time of 900 s was used throughout. At least 8 varying concentrations of protein were used to determine kinetic and equilibrium fits. Binding kinetics were evaluated using a 1:1 Langmuir binding model. Proteins were in buffer HBS with 0.1%(v/v) P20 surfactant and 0.5 mg/mL carboxymethyl dextran sodium salt (Biacore, Uppsula, Sweden) to minimize nonspecific adsorption onto the SA chip. Scrubber-2 software (see web site cores.utah.edu/interaction/) was used to fit the data globally using standard double background subtracted values.

Binder Cross-Reactivity Studies by Biolayer Interferometry

Binding of HB80.3 and CR6261 Fab to a panel of representative HA isolates was assayed by biolayer interferometry using an OCTET RED™ instrument (ForteBio, Inc.). Biolayer interferometry is conceptually similar to surface plasmon resonance experiments in that a protein of interest is immobilized on a surface and then exposed to potential binding partners in solution. The binding of analytes to the immobilized protein changes the optical properties of the biosensors, leading to a shift in the wavelength of light reflected off the binding surface. This shift in wavelength can be measured in real-time, allowing the measurement of association and dissociation rates and, therefore, $K_d$. Biotinylated HAs, purified as described above, were used for these measurements. HAs at ~10-50 μg/mL in 1× kinetics buffer (1×PBS, pH 7.4, 0.01% BSA, and 0.002% Tween 20) were loaded onto streptavidin coated biosensors and incubated with varying concentrations of HB80.3 or CR6261 Fab in solution. All binding data were collected at 25° C. The experiments comprised 5 steps: 1. Baseline acquisition (60 s); 2. HA loading onto sensor (180 s); 3. Second baseline acquisition (180 s); 4. Association of the designed binder for the measurement of $k_{on}$ (180 s); and 5. Dissociation of the binder for the measurement of $k_{off}$ (180 s). 4-6 concentrations of each binder were used, with the highest concentration being 100 nM. Baseline and dissociation steps were carried out in buffer only. The sequences of all proteins used in this work are available in FASTA format as Table 10 below.

Expression and Purification of HB36.3 for Crystallization

ROSETTA™ 2 (BL21/DE3) cells carrying the pET29a-HB36.3 construct were grown in shake flasks in low salt LB medium to an $OD_{600}$ of ~0.7 at 37° C., then shifted to 18° C. and induced by the addition of 1 mM IPTG. Cultures were incubated overnight at 18° C. for protein expression, then harvested by centrifugation (3000 g, 10 minutes). The pellet from a 1 L culture was resuspended in 50-100 mL of lysis buffer (50 mM Tris pH 8.0, 300 mM NaCl, 10 mM imidazole pH 8.0, with Roche EDTA-free protease inhibitor cocktail tablet) and the cells were lysed and homogenized by two passes through an EMULSIFLEX™ C-3 cell disruptor (15kPSI). After clearing the lysates by centrifugation (25,000 g, ~1 hour), the supernatant was incubated with NiNTA resin (Qiagen), washed with excess lysis buffer, and bound proteins were eluted (with 50 mM Tris pH 8.0, 300 mM NaCl, 250 mM imidazole pH 8.0). The eluted material was buffer exchanged into 10 mM Tris pH8.0, 50 mM NaCl, loaded onto a MONOQ™ anion exchange column, and eluted with a linear gradient from 50-500 mM NaCl. Peak fractions containing HB36.3 were pooled and subjected to gel filtration. HB36.3 eluted as an apparent dimer when loaded at high concentrations (~10 mg/mL), but eluted as a monomer when loaded at lower concentrations (<1 mg/mL), and the two forms were in rapid equilibrium. Fractions containing HB36.3 were pooled and concentrated to ~5 mg/mL.

Isolation of HB36.3-SC1918/H1 HA Complex for Crystallization

Following Ni-NTA purification, SC1918 HA was digested with trypsin (New England Biolabs, 5 mU trypsin per mg HA, 16 hours at 17° C.) to produce uniformly cleaved (HA1/HA2), and to remove the trimerization domain and His-tag. After quenching the digests with 2 mM PMSF, the digested material was purified by anion exchange chromatography (10 mM Tris, pH 8.0, 50-1M NaCl) and size exclusion chromatography (10 mM Tris, pH 8.0, 150 mM NaCl).

To prepare the HB36.3/SC1918 complex for crystallization, excess HB36.3 (approximately 5 HB36.3 molecules per HA trimer) was mixed with purified SC1918 HA in 10 mM Tris pH 8.0, 150 mM NaCl at ~2 mg/mL. The mixtures were incubated overnight at 4° C. to allow complex formation. Saturated complexes were then purified from unbound HB36.3 by gel filtration.

Crystallization and Structure Determination of the HB36.3-SC1918/H1 Complex

Gel filtration fractions containing the HB36.3-SC1918/H1 HA complex were concentrated to ~10 mg/mL in 10 mM Tris, pH 8.0 and 50 mM NaCl. Initial crystallization trials were set up using the automated Rigaku CRYSTALMATION™ robotic system at the Joint Center for Structural Genomics (web site JCSG.org). Several hits were obtained, with the most promising candidates grown in ~10% PEG8000 near pH 7. Optimization of these conditions resulted in diffraction quality crystals. The crystals used for data collection were grown by the sitting drop, vapor diffusion method with a reservoir solution (100 uL) containing 10% PEG8000, 200 mM magnesium chloride, and 100 mM Tris pH 7.0. Drops consisting of 100 nL protein+100 nL precipitant were set up at 4° C., and crystals appeared within 7-14 days. The resulting crystals were cryoprotected by soaking in well solution supplemented with increasing concentrations of ethylene glycol (5% steps, 5 min/step), to a final concentration of 25%, then flash cooled and stored in liquid nitrogen until data collection.

Diffraction data for the HB36.3-SC1918/H1 complex were collected at the Advanced Photon Source (APS) General Medicine/Cancer Institutes-Collaborative Access Team (GM/CA-CAT) beamline 23ID-D at the Argonne National Laboratory. The data were indexed in R32, integrated using HKL2000 (HKL Research) and scaled using XPREP™ (Bruker). The structure was solved by molecular replacement to 3.10 Å resolution using PHASER™ (S21). An unpublished, 1.8 Å resolution structure of the 1918 HA was used as the initial search model and a single protomer was found in the asymmetric unit. Examination of the maps at this stage revealed clear positive electron density around the membrane distal end of HA consistent with the expected location and orientation of HB36.3. Attempts to place HB36.3 by molecular replacement using PHASER™ were unsuccessful (using various search models derived from PDB code 1U84). However, phasing using the HA only (~85% of the mass in the asymmetric unit) yielded maps with continuous density for HB36.3, including key side-chain features. This phasing model allowed HB36.3 to be fitted into the maps manually and unambiguously. Rigid-body and restrained refinement (including TLS refinement, with one group for HAL one for HA2, and one for HB36.3) were carried out in PHENIX™ (S22). Between rounds of refinement, the model was built and adjusted using COOT™ (S23). The insect cells used for protein expression produce fully glycosylated HA, and additional electron density was observed for glycans at all 5 predicted glycosylation sites (NX(S/T) motifs) on the HA. A total of 5 sugar residues were built at 2 of these sites (at the remaining three sites, density was too weak or ambiguous to allow accurate model building). The high redundancy of the relatively weak data aided in obtaining relatively good quality electron density maps at this moderate resolution that were readily interpretable, particularly around the HB36.1-HA interface (see FIG. 4C), despite high apparent $R_{sym}$ and B-values(S24).

Structural Analyses

Hydrogen bonds and van der Waals contacts between HB36.3 and SC1918/H1 HA were calculated using HBPLUS™ (S25) and CONTACSYM™ (S26), respectively. Surface area burial was analyzed with ROSETTA™ (S27). MACPYMOL™ (DeLano Scientific) (S28) was used to render structure figures and for general manipulations. The final coordinates were validated using the JCSG quality control server (v2.7), which includes MOLPROBITY™ (S29).

Protease Susceptibility Assay

Each reaction contained ~2.5 μg HA or ~5 μg binder-HA complex and 1% dodecyl-maltoside (to prevent aggregation of the post-fusion HA). Reactions were set up at room temperature and the pH was lowered by adding 100 mM buffer to all samples except controls. Sodium acetate was used for pH ranges 4.9 to 6.1, PIPES buffer for pH 6.2 to 7.4 and Tris for pH 7.5 and above. Reactions were thoroughly mixed, centrifuged at >12,000 g for 30 seconds and allowed to incubate at 37° C. for one hour. After incubation, reactions were equilibrated to room temperature and the pH was neutralized by addition of 200 mM Tris, pH 8.5. Trypsin was added to all samples except controls, at a final ratio of 1:25 for the SC1918/H1 reactions, and 1:50 for the Viet04/H5 reactions. SC1918/H1 and Viet04/H5 samples were digested overnight (18 hours) at 37° C. and 17° C., respectively. Reactions were quenched by addition of non-reducing SDS buffer and were boiled for ~2 min. Samples were analyzed by SDS-PAGE.

Limitations of Initial Binding Screen; Other Potential Binders

One important component in the recovery of active binders from our design set is the choice of screening system. We chose the yeast surface-display assay as our screen because the system allows rapid testing of many designs, there was minimal non-specific adsorption of the biotinylated hemagglutinin (at 1 μM) on the yeast surface (low background), and the screen could be readily reconfigured to select for higher-affinity variants. While it has been reported that binding dissociation constants are roughly equivalent between yeast display titrations and in vitro measurements (S30), we noted approximately 10-fold weaker affinity for in vitro SPR measurements as compared to the yeast surface display titrations. Although there may be many reasons for the discrepancies between measurements (e.g. non-specific lectin adsorption increasing the local HA concentration), we suspect that the major contribution to increased affinity on yeast is avidity effects between the trimeric ectodomain of hemagglutinin used for binding studies and the thousands of copies of designs displayed on the surface. Given the test concentration of 1 μM HA, we estimate that we were able to detect binding for designs that displayed on the surface of yeast with an in vitro $K_d$<25 μM.

Another important parameter blocking the recovery of active designs is the dissociation rate of the HA-design complex. During affinity maturation of the HB36 & HB80 designs, we noted a marked increase in the mean phycoerythrin fluorescence (PE) signal at binding saturation for several variants, controlling for mean surface display of the design variants (data not shown). This increase in PE signal correlated with slower in vitro off-rates. Extrapolating the off-rate to the limit of binding detection by PE signal, we estimate that the yeast display system can detect binders with $k_{off}$<10 $s^{-1}$.

Thus our yeast display screen can recover from our design set all binders that surface display with an in vitro $K_d$<25 uM and a $k_{off}$<10 $s^{-1}$. Several designs showed weak binding activity in this screen; and include HB3, HB54, and HB78 (amino acid sequences are available in Table 9, below).

On the Usefulness of De Novo Design in Generating Specific Binders

As de novo design of protein interactions may find many uses, it is instructive to note the effort required to isolate the HA binders reported here. A number of technical advances coalesced to facilitate this research, including the availability of highly parallel computing, of yeast cell-surface display as a tool for fast screening and affinity maturation of binding proteins, the low cost of gene synthesis, and the ability to custom-order plasmids from commercial sources. For a typical de novo design goal, we estimate that a hundred thousand CPU hours would be sufficient to generate several dozen candidates for experimental testing. The yeast-display format used here removes the laborious steps needed for purifying each design and allows fast screening and affinity maturation.

While in this case two antibody-bound structures were available, the method made minimal use of information contained in these antibodies, with only a single hotspot residue in HB80 (the Tyr of HS3) coinciding with a residue on the antibodies. Only the structure of H1 HA was essential for the design process. The hemagglutinin target surface is very apolar, enabling the design of high-affinity interactions. It remains to be seen whether this methodology could be used to target more polar protein surfaces.

The Importance of a Diverse Set of Protein Scaffolds for De Novo Design

Figure 2:
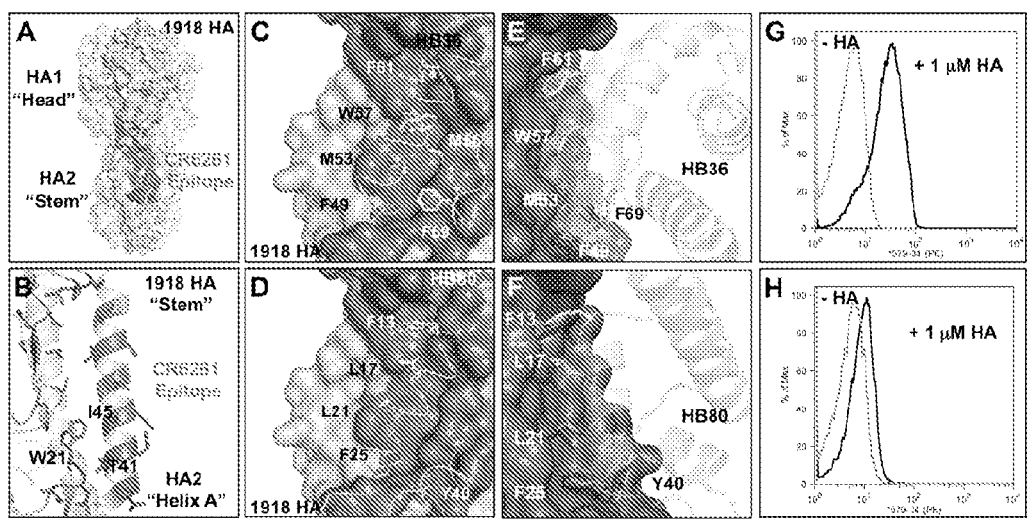
FIG. 2. Design of HB36 and HB80, targeting the stem of the 1918 HA. (A) Surface representation of the trimeric HA structure (PDB 3R2X) from the 1918 pandemic virus. Broadly neutralizing antibody CR6261 binds a highly conserved epitope in the stem region, close to the viral membrane (bottom). (B) Enlarged view of the CR6261 epitope, with CR6261 contact residues depicted as sticks. This target site on HA contains a groove lined by multiple hydrophobic residues. Loops on either side of this hydrophobic groove (above and below) constrain access to this region. Key residues on HA2 are noted in one-letter code. (C and D) Front view of the designed interaction between HB36 (C) and HB80 (D) and the target site on HA. HA is rotated approximately 60° relative to FIG. 2A. HB36 and HB80 residues are depicted as sticks, with hotspot residues noted (F49 and M53 for HB36 and L21, F25, and Y40 for HB80). For clarity, the non-contacting regions from the designs have been omitted. (E and F) Further details of the designed interactions of HB36 (E) and HB80 (F) with 1918/H1 HA. (G and H) Initial binding data for HB36 (G) and HB80 (H) designs (before affinity maturation). When incubated with 1 uM 1918 HA, yeast displaying the two designed proteins show an increase in fluorescent phycoerythrin signal (x-axis) compared to the absence of 1918 HA.

The use of diverse protein folds was a crucial element in the success of the design method. Binding to the hydrophobic target site on HA is highly constrained due to flanking polar and charged loops and residues (FIG. 1). The backbones of both HB36 and HB80 are exquisitely suited to this site with helices that sequester their backbone polar groups from interacting with the apolar surface of HA, while the rest of the redesigned proteins form little if any interactions with the flanking HA regions (FIGS. 1 & 2). The diversity of protein scaffolds available in the PDB has, therefore, been key to this design procedure. Nearly 40% of the proteins in the scaffold set were solved as part of the NIH NIGMS Protein Structure Initiative (PSI; web site is nigms.nih.gov/Initiatives/PSI/) and HB36 was derived from a PSI target protein of unknown function (APC36109 from *B. stearothermophilus*, PDB entry 1U84). While the utility to molecular biology of structures of relatively small, bacterial proteins of sometimes unknown function has been hotly debated by some (S31-33), we note that a previously unanticipated benefit of these structures is that they may open the road to the design of new protein functions.

Comparison of the Designed Proteins with Post-Fusion HA

Interestingly, the structure of post-fusion hemagglutinin (S34) reveals a helix bound to the hydrophobic region in the stem in a manner that is reminiscent of the main recognition helices observed in HB36 and HB80 although different in crucial details. The post-fusion structure shows significant rearrangement of the target epitope compared to the pre-fusion form, with the two loops that flank the hydrophobic surface moving away, providing unimpeded access to it. Against this surface, a helical segment from HA2 docks, burying the hydrophobic surface on the stem region. Although several hydrophobic chemical groups from this HA2 helix overlay on similar groups in the two designed binders, the angular orientation of the HA2 helix, its length, and the identities of other residues preclude its use as a template from which to generate binders to the pre-fusion form. We nevertheless find this coarse similarity to be intriguingly suggestive of the phenomenon of structural mimicry (S35), whereby evolutionarily unrelated proteins present similar chemical groups for binding to certain target epitopes.

TABLE 9

FASTA sequences of active designs and design variants

```
>HB36.1 (Asp47Ser)                          (SEQ ID NO: 270)
MSNAMDGQQLNRLLLEWIGAWDPFGLGKDAYDVEAEAVLQAVYETESAFD

LAMRIMWIYAFAFNRPIPFPHAQKLARRLLELKQAASSPLPLE

>HB36.2 (Ala60Val)                          (SEQ ID NO: 271)
MSNAMDGQQLNRLLLEWIGAWDPFGLGKDAYDVEAEAVLQAVYETEDAFD

LAMRIMWIYVFAFNRPIPFPHAQKLARRLLELKQAASSPLPLE

>HB36.3 (Asp47Ser,                          (SEQ ID NO: 272)
Ala60Val)
MSNAMDGQQLNRLLLEWIGAWDPFGLGKDAYDVEAEAVLQAVYETESAFD

LAMRIMWIYVFAFNRPIPFPHAQKLARRLLELKQAASSPLPLE

>HB36.4 (Asp47Ser,                           (SEQ ID NO: 65)
Ala60Val, Asn64Lys)
MSNAMDGQQLNRLLLEWIGAWDPFGLGKDAYDVEAEAVLQAVYETESAFD

LAMRIMWIYVFAFKRPIPFPHAQKLARRLLELKQAASSPLPLE

>HB80                                       (SEQ ID NO: 273)
MASTRGSGRPWDFSENLAFELALAFMNKDTPDRWANVAQYVSGRTPEEVK

KHYEILVEDIKYIESGKVPFPNYRTTGGNMKTDEKRFRNLKIRLE

>HB80 Met26Thr                              (SEQ ID NO: 180)
MASTRGSGRPWDFSENLAFELALAFTNKDTPDRWANVAQYVSGRTPEEVK

KHYEILVEDIKYIESGKVPFPNYRTTGGNMKTDEKRFRNLKIRLE

>HB80 Asn36Lys                              (SEQ ID NO: 181)
MASTRGSGRPWDFSENLAFELALAFMNKDTPDRWAKVAQYVSGRTPEEVK

KHYEILVEDIKYIESGKVPFPNYRTTGGNMKTDEKRFRNLKIRLE

>HB80.1 (Met26Thr,                          (SEQ ID NO: 182)
                                                 Asn36Lys)
MASTRGSGRPWDFSENLAFELALAFTNKDTPDRWAKVAQYVSGRTPEEVK

KHYEILVEDIKYIESGKVPFPNYRTTGGNMKTDEKRFRNLKIRLE

>HB80.2 (Met26Thr,                          (SEQ ID NO: 183)
                                    Asn36Lys, Delta54-95)
MASTRGSGRPWDFSENLAFELALAFTNKDTPDRWAKVAQYVSGRTPEEVK

KHYE

>HB80.3 (Asp12Gly,                          (SEQ ID NO: 184)
Ala24Ser, Met26Thr, Asn36Lys, Delta54-95)
MASTRGSGRPWGFSENLAFELALSFTNKDTPDRWAKVAQYVSGRTPEEVK

KHYE

>HB3                                        (SEQ ID NO: 155)
MADTLLILGDSLSAGYQMLAEFAWPFLLNKKWSKTSVVNASISGDTSQQG

LARLPALLKQHQPRWVLVELGGNDGLEGFQPQQTEQTLRQILQDVKAANA

EPLLMQIRPPANYGRRYNEAFSAIYPKLAKEFDVPLLPFFMEEVYLKPQW

MQDDGIHPNYEAQPFIADWMAKQLQPLVNH

>HB54                                       (SEQ ID NO: 140)
MAETKNFTDLVEATKWGNSLIKSAKYSSKDKMAIYNYTKNSSPINTPLRS

ANGDVNKLSENIQEQVRQLDSTISKSVTPDSVYVYRLLNLDYLSSITGFT

REDLHMLQQTNEGQYNSKLVLWLDFLMSNRIYRENGYSSTQLVSGAALAG

RPIELKLELPKGTKAAYIDSKELTAYPGQQEVLLPRGTEYAVGTVELSKS

SQKIIITAVVFKK
```

TABLE 9-continued

FASTA sequences of active designs
and design variants

>HB78 (SEQ ID NO: 211)
MFTGVIIKQGCLLKQGHTRKNWSVRKFILREDPAYLHYYYPLGYFSPLGA

IHLRGCVVTSVESEENLFEIITADEVHYFLQAATPKERTEWIKAIQMASR

TABLE 10

Sequences of HAs used in binding studies.
The sequences listed below represent the full-
length
ORF as cloned in the baculovirus transfer vector.
Most of the N-terminal signal peptide
MVLVNQSHQGFNKEHTSKMVSAIVLYVLLAAAAHSAFA
(SEQ ID NO: 212)) is presumably removed
during secretion, leaving four non-native
residues (ADPG) at the N-terminus of HA1.
The C-terminal biotinylation site, trimerization
domain, and His tag are retained on all.

>A/South Carolina/1/1918(H1N1) (SEQ ID NO: 12)
MVLVNQSHQGFNKEHTSKMVSAIVLYVLLAAAAHSAFAADPGDTICIGYH

ANNSTDTVDTVLEKNVTVTHSVNLLEDSHNGKLCKLKGIAPLQLGKCNIA

GWLLGNPECDLLLTASSWSYIVETSNSENGTCYPGDFIDYEELREQLSSV

SSFEKFEIFPKTSSWPNHETTKGVTAACSYAGASSFYRNLLWLTKKGSSY

PKLSKSYVNNKGKEVLVLWGVHHPPTGTDQQSLYQNADAYVSVGSSKYNR

RFTPEIAARPKVRDQAGRMNYYWTLLEPGDTITFEATGNLIAPWYAFALN

RGSGSGIITSDAPVHDCNTKCQTPHGAINSSLPFQNIHPVTIGECPKYVR

STKLRMATGLRNIPSIQSRGLFGAIAGFIEGGWTGMIDGWYGYHHQNEQG

SGYAADQKSTQNAIDGITNKVNSVIEKMNTQFTAVGKEFNNLERRIENLN

KKVDDGFLDIWTYNAELLVLLENERTLDFHDSNVRNLYEKVKSQLKNNAK

EIGNGCFEFYHKCDDACMESVRNGTYDYPKYSEESKLNREEIDGVSGGGG

LNDIFEAQKIEWHERLVPRGSPGSGYIPEAPRDGQAYVRKDGEWVLLSTF

LGHHHHHH

>A/WSN/1933(H1N1) (SEQ ID NO: 13)
MVLVNQSHQGFNKEHTSKMVSAIVLYVLLAAAAHSAFAADPGDTICIGYH

ANNSTDTVDTIFEKNVAVTHSVNLLEDRHNGKLCKLKGIAPLQLGKCNIT

GWLLGNPECDSLLPARSWSYIVETPNSENGACYPGDFIDYEELREQLSSV

SSLERFEIFPKESSWPNHTFNGVTVSCSHRGKSSFYRNLLWLTKKGDSYP

KLTNSYVNNKGKEVLVLWGVHHPSSSDEQQSLYSNGNAYVSVASSNYNRR

FTPEIAARPKVKDQHGRMNYYWTLLEPGDTIIFEATGNLIAPWYAFALSR

GFESGIITSNASMHECNTKCQTPQGSINSNLPFQNIHPVTIGECPKYVRS

TKLRMVTGLRNIPSIQYRGLFGAIAGFIEGGWTGMIDGWYGYHHQNEQGS

GYAADQKSTQNAINGITNKVNSIIEKMNTQFTAVGKEFNNLEKRMENLNK

KVDDGFLDIWTYNAELLVLLENERTLDFHDLNVKNLYEKVKSQLKNNAKE

IGNGCFEFYHKCDNECMESVRNGTYDYPKYSEESKLNREKIDGVSGGGGL

NDIFEAQKIEWHERLVPRGSPGSGYIPEAPRDGQAYVRKDGEWVLLSTFL

GHHHHHH

TABLE 10-continued

Sequences of HAs used in binding studies.
The sequences listed below represent the full-
length
ORF as cloned in the baculovirus transfer vector.
Most of the N-terminal signal peptide
MVLVNQSHQGFNKEHTSKMVSAIVLYVLLAAAAHSAFA
(SEQ ID NO: 212)) is presumably removed
during secretion, leaving four non-native
residues (ADPG) at the N-terminus of HA1.
The C-terminal biotinylation site, trimerization
domain, and His tag are retained on all.

>A/AA/Marton/1943(H1N1) (SEQ ID NO: 14)
MVLVNQSHQGFNKEHTSKMVSAIVLYVLLAAAAHSAFAADPGDTICIGYH

ANNSTDTVDTVLEKNVTVTHSVNLLEDSHNGKLCRLKGIAPLQLGKCNIA

GWILGNPECESLLSERSWSYIVETPNSENGTCYPGDFIDYEELREQLSSV

SSFERFEIFSKESSWPKHNTTRGVTAACSHAGKSSFYRNLLWLTEKDGSY

PNLNNSYVNKKGKEVLVLWGVHHPSNIKDQQTLYQKENAYVSVSSNYNR

RFTPEIAERPKVRGQAGRMNYYWTLLKPGDTIMFEANGNLIAPWYAFALS

RGFGSGIITSNASMHECDTKCQTPQGAINSSLPFQNIHPVTIGECPKYVR

STKLRMVTGLRNIPSIQSRGLFGAIAGFIEGGWTGMIDGWYGYHHQNEQG

SGYAADQKSTQNAINGITNKVNSVIEKMNTQFTAVGKEFNNLEKRMENLN

KKVDDGFLDIWTYNAELLVLLENERTLDFHDSNVKNLYEKVKNQLRNNAK

EIGNGCFEFYHKCNNECMESVKNGTYDYPKYSEESKLNREKIDSGGGGLN

DIFEAQKIEWHERLVPRGSPGSGYIPEAPRDGQAYVRKDGEWVLLSTFLG

HHHHHH

>A/USSR/90/1977(H1N1) (SEQ ID NO: 43)
MVLVNQSHQGFNKEHTSKMVSAIVLYVLLAAAAHSAFAADPGDTICIGYH

ANNSTDTVDTVLEKNVTVTHSVNLLEDSHNGKLCRLKGIAPLQLGKCNIA

GWILGNPECESLFSKKSWSYIAETPNSENGTCYPGYFADYEELREQLSSV

SSFERFEIFPKERSWPKHNVTRGVTASCSHKGKSSFYRNLLWLTEKNGSY

PNLSKSYVNNKEKEVLVLWGVHHPSNIEDQKTIYRKENAYVSVSSNYNR

RFTPEIAERPKVRGQAGRINYYWTLLEPGDTIIFEANGNLIAPWHAFALN

RGFGSGIITSNASMDECDTKCQTPQGAINSSLPFQNIHPVTIGECPKYVR

STKLRMVTGLRNIPSIQSRGLFGAIAGFIEGGWTGMIDGWYGYHHQNEQG

SGYAADQKSTQNAINGITNKVNSVIEKMNTQFTAVGKEFNKLEKRMENLN

KKVDDGFLDIWTYNAELLVLLENERTLDFHDSNVKNLYEKVKSQLKNNAK

EIGNGCFEFYHKCNNECMESVKNGTYDYPKYSEESKLNREKIDSGGGGLN

DIFEAQKIEWHERLVPRGSPGSGYIPEAPRDGQAYVRKDGEWVLLSTFLG

HHHHHH

>A/Beijing/262/1995(H1N1) (SEQ ID NO: 54)
MVLVNQSHQGFNKEHTSKMVSAIVLYVLLAAAAHSAFAADPGDTICIGYH

ANNSTDTVDTVLEKNVTVTHSVNLLEDSHNGKLCRLKGIAPLQLGNCSVA

GWILGNPECESLISKESWSYIVETPNPENGTCYPGYFADYEELREQLSSV

SSFERFEIFPKESSWPNHTVTGVTASCSHNGKSSFYRNLLWLTEKNGLYP

NLSNSYVNNKEKEVLVLWGVHHPSNIGVQRAIYHTENAYVSVVSSHYSRR

FTPEIAKRPKVRGQEGRINYYWTLLEPGDTIIFEANGNLIAPWYAFALSR

GFGSGIITSNAPMNECDAKCQTPQGAINSSLPFQNVHPVTIGECPKYVRS

TABLE 10-continued

Sequences of HAs used in binding studies.
The sequences listed below represent the full-length
ORF as cloned in the baculovirus transfer vector.
Most of the N-terminal signal peptide
MVLVNQSHQGFNKEHTSKMVSAIVLYVLLAAAAHSAFA
(SEQ ID NO: 212)) is presumably removed
during secretion, leaving four non-native
residues (ADPG) at the N-terminus of HA1.
The C-terminal biotinylation site, trimerization
domain, and His tag are retained on all.

TKLRMVTGLRNIPSIQSRGLFGAIAGFIEGGWTGMMDGWYGYHHQNEQGS

GYAADQKSTQNAINGITNKVNSVIEKMNTQFTAVGKEFNKLERRMENLNK

KVDDGFLDIWTYNAELLVLLENERTLDFHDSNVKNLYEKVKSQLKNNAKE

IGNGCFEFYHKCNNECMESVKNGTYDYPKYSEESKLNREKIDSGGGGLND

IFEAQKIEWHERLVPRGSPGSGYIPEAPRDGQAYVRKDGEWVLLSTFLGH

HHHHH

>A/Solomon Islands/3/2006(H1N1)  (SEQ ID NO: 274)
MVLVNQSHQGFNKEHTSKMVSAIVLYVLLAAAAHSAFAADPGDTICIGYH

ANNSTDTVDTVLEKNVTVTHSVNLLEDSHNGKLCRLKGIAPLQLGNCSVA

GWILGNPECELLISRESWSYIVEKPNPENGTCYPGHFADYEELREQLSSV

SSFERFEIFPKESSWPNHTTTGVSASCSHNGESSFYKNLLWLTGKNGLYP

NLSKSYANNKEKEVLVLWGVHHPPNIGDQRALYHKENAYVSVVSSHYSRK

FTPEIAKRPKVRDQEGRINYYWTLLEPGDTIIFEANGNLIAPRYAFALSR

GFGSGIINSNAPMDECDAKCQTPQGAINSSLPFQNVHPVTIGECPKYVRS

AKLRMVTGLRNIPSIQSRGLFGAIAGFIEGGWTGMVDGWYGYHHQNEQGS

GYAADQKSTQNAINGITNKVNSVIEKMNTQFTAVGKEFNKLERRMENLNK

KVDDGFIDIWTYNAELLVLLENERTLDFHDSNVKNLYEKVKSQLKNNAKE

IGNGCFEFYHKCNDECMESVKNGTYDYPKYSEESKLNREKIDSGGGGLND

IFEAQKIEWHERLVPRGSPGSGYIPEAPRDGQAYVRKDGEWVLLSTFLGH

HHHHH

>A/Japan/305/1957(H2N2)  (SEQ ID NO: 275)
MVLVNQSHQGFNKEHTSKMVSAIVLYVLLAAAAHSAFAADPGDQICIGYH

ANNSTEKVDTILERNVTVTHAKDILEKTHNGKLCKLNGIPPLELGDCSIA

GWLLGNPECDRLLSVPEWSYIMEKENPRDGLCYPGSFNDYEELKHLLSSV

KHFEKVKILPKDRWTQHTTTGGSRACAVSGNPSFFRNMVWLTEKGSNYPV

AKGSYNNTSGEQMLIIWGVHHPNDETEQRTLYQNVGTYVSVGTSTLNKRS

TPEIATRPKVNGQGGRMEFSWTLLDMWDTINFESTGNLIAPEYGFKISKR

GSSGIMKTEGTLENCETKCQTPLGAINTTLPFHNVHPLTIGECPKYVKSE

KLVLATGLRNVPQIESRGLFGAIAGFIEGGWQGMVDGWYGYHHSNDQSG

YAADKESTQKAFDGITNKVNSVIEKMNTQFEAVGKEFSNLERRLENLNKK

MEDGFLDVWTYNAELLVLMENERTLDFHDSNVKNLYDKVRMQLRDNVKEL

GNGCFEFYHKCDDECMNSVKNGTYDYPKYEEESKLNRNEIKSGGGGLNDI

FEAQKIEWHERLVPRGSPGSGYIPEAPRDGQAYVRKDGEWVLLSTFLGHH

HHHH

>A/Hong Kong/1/1968(H3N2)  (SEQ ID NO: 276)
MVLVNQSHQGFNKEHTSKMVSAIVLYVLLAAAAHSAFAADPGATLCLGHH

AVPNGTLVKTITDDQIEVTNATELVQSSSTGKICNNPHRILDGIDCTLID

ALLGDPHCDVFQNETWDLFVERSKAFSNCYPYDVPDYASLRSLVASSGTL

EFITEGFTWTGVTQNGGSNACKRGPGSGFFSRLNWLTKSGSTYPVLNVTM

PNNDNFDKLYIWGVHHPSTNQEQTSLYVQASGRVTVSTRRSQQTIIPNIG

SRPWVRGLSSRISIYWTIVKPGDVLVINSNGNLIAPRGYFKMRTGKSSIM

RSDAPIDTCISECITPNGSIPNDKPFQNVNKITYGACPKYVKQNTLKLAT

GMRNVPEKQTRGLFGAIAGFIENGWEGMIDGWYGFRHQNSEGTGQAADLK

STQAAIDQINGKLNRVIEKTNEKFHQIEKEFSEVEGRIQDLEKYVEDTKI

DLWSYNAELLVALENQHTIDLTDSEMNKLFEKTGRQLRENAEDMGNGCFK

IYHKCDNACIESIRNGTYDHDVYRDEALNNRFQIKGVSGGGGLNDIFEAQ

KIEWHERLVPRGSPGSGYIPEAPRDGQAYVRKDGEWVLLSTFLGHHHHHH

>A/duck/Czechoslovakia/1956 (H4N6)  (SEQ ID NO: 277)
MVLVNQSHQGFNKEHTSKMVSAIVLYVLLAAAAHSAFAADPGPVICMGHH

AVANGTMVKTLADDQVEVVTAQELVESQNLPELCPSPLRLVDGQTCDIIN

GALGSPGCDHLNGAEWDVFIERPNAVDTCYPFDVPEYQSLRSILANNGKF

EFIAEEFQWNTVKQNGKSGACKRANVNDFFNRLNWLVKSDGNAYPLQNLT

KINNGDYARLYIWGVHHPSTDTEQTNLYKNNPGRVTVSTKTSQTSVVPNI

GSRPLVRGQSGRVSFYWTIVEPGDLIVFNTIGNLIAPRGHYKLNNQKKST

ILNTAIPIGSCVSKCHTDKGSLSTT

>A/Adachi/2/1957 (H2N2)  (SEQ ID NO: 339)
MVLVNQSHQGFNKEHTSKMVSAIVLYVLLAAAAHSAFAADPGDQICIGYH

ANNSTEKVDTILERNVTVTHAKDILEKTHNGKLCKLNGIPPLELGDCSIA

GWLLGNPECDRLLSVPEWSYIMEKENPRNGLCYPGSFNDYEELKHLLSSV

KHFEKVKILPKDRWTQHTTTGGSQACAVSGNPSFFRNMVWLTKKGSDYPV

AKGSYNNTSGEQMLIIWGVHHPIDETEQRTLYQNVGTYVSVGTSTLNKRS

TPEIATRPKVNGLGSRMEFSWTLLDMWDTINFESTGNLIAPEYGFKISKR

GSSGIMKTEGTLENCETKCQTPLGAINTTLPFHNVHPLTIGECPKYVKSE

KLVLATGLRNVPQIESRGLFGAIAGFIEGGWQGMVDGWYGYHHSNDQSG

YAADKESTQKAFDGITNKVNSVIEKMNTQFEAVGKEFGNLERRLENLNKK

MEDGFLDVWTYNAELLVLMENERTLDFHDSNVKNLYDKVRMQLRDNVKEL

GNGCFEFYHKCDDECMNSVKNGTYDYPKYEEESKLNRNEIKSGGGGLNDI

FEAQKIEWHERLVPRGSPGSGYIPEAPRDGQAYVRKDGEWVLLSTFLGHH

HHHH

TABLE 10-continued

Sequences of HAs used in binding studies.
The sequences listed below represent the full-length
ORF as cloned in the baculovirus transfer vector.
Most of the N-terminal signal peptide
MVLVNQSHQGFNKEHTSKMVSAIVLYVLLAAAAHSAFA
(SEQ ID NO: 212)) is presumably removed
during secretion, leaving four non-native
residues (ADPG) at the N-terminus of HA1.
The C-terminal biotinylation site, trimerization
domain, and His tag are retained on all.

>A/Vietnam/1203/2004 (H5N1)   (SEQ ID NO: 340)
MVLVNQSHQGFNKEHTSKMVSAIVLYVLLAAAAHSAFAADPGDQICIGYH

ANNSTEQVDTIMEKNVTVTHAQDILEKKHNGKLCDLDGVKPLILRDCSVA

GWLLGNPMCDEFINVPEWSYIVEKANPVNDLCYPGDFNDYEELKHLLSRI

NHFEKIQIIPKSSWSSHEASLGVSSACPYQGKSSFFRNVVWLIKKNSTYP

TIKRSYNNTNQEDLLVLWGIHHPNDAAEQTKLYQNPTTYISVGTSTLNQR

LVPRIATRSKVNGQSGRMEFFWTILKPNDAINFESNGNFIAPEYAYKIVK

KGDSTIMKSELEYGNCNTKCQTPMGAINSSMPFHNIHPLTIGECPKYVKS

NRLVLATGLRNSPQRERRRKKRGLFGAIAGFIEGGWQGMVDGWYGYHHSN

EQGSGYAADKESTQKAIDGVTNKVNSIIDKMNTQFEAVGREFNNLERRIE

NLNKKMEDGFLDVWTYNAELLVLMENERTLDFHDSNVKNLYDKVRLQLRD

NAKELGNGCFEFYHKCDNECMESVRNGTYDYPQYSEEARLKREEISSGGG

GLNDIFEAQKIEWHERLVPRGSPGSGYIPEAPRDGQAYVRKDGEWVLLST

FLGHHHHHH

> A/Indonesia/05/2005 (H5N1)   (SEQ ID NO: 341)
MVLVNQSHQGFNKEHTSKMVSAIVLYVLLAAAAHSAFAADPGDQICIGYH

ANNSTEQVDTIMEKNVTVTHAQDILEKTHNGKLCDLDGVKPLILRDCSVA

GWLLGNPMCDEFINVPEWSYIVEKANPTNDLCYPGSFNDYEELKHLLSRI

NHFEKIQIIPKSSWSDHEASSGVSSACPYLGSPSFFRNVVWLIKKNSTYP

TIKKSYNNTNQEDLLVLWGIHHPNDAAEQTRLYQNPTTYISIGTSTLNQR

LVPKIATRSKVNGQSGRMEFFWTILKPNDAINFESNGNFIAPEYAYKIVK

KGDSAIMKSELEYGNCNTKCQTPMGAINSSMPFHNIHPLTIGECPKYVKS

NRLVLATGLRNSPQRESRRKKRGLFGAIAGFIEGGWQGMVDGWYGYHHSN

EQGSGYAADKESTQKAIDGVTNKVNSIIDKMNTQFEAVGREFNNLERRIE

NLNKKMEDGFLDVWTYNAELLVLMENERTLDFHDSNVKNLYDKVRLQLRD

NAKELGNGCFEFYHKCDNECMESIRNGTYNYPQYSEEARLKREEISSGGG

GLNDIFEAQKIEWHERLVPRGSPGSGYIPEAPRDGQAYVRKDGEWVLLST

FLGHHHHHH

>A/turkey/Massachusetts/3740/1965   (SEQ ID NO: 342)
(H6N2)
24
MVLVNQSHQGFNKEHTSKMVSAIVLYVLLAAAAHSAFAADPGDKICIGYH

ANNSTTQVDTILEKNVTVTHSVELLESQKEERFCRVLNKTPLDLKGCTIE

GWILGNPQCDILLGDQSWSYIVERPGAQNGICYPGVLNEVEELKAFIGSG

EKVQRFEMFPKSTWTGVDTNSGVTRACPYTTSGSSFYRNLLWIIKTRSAA

YPVIKGTYNNTGSQPILYFWGVHHPPNTDEQNTLYGSGDRYVRMGTESMN

FAKSPEIAARPAVNGQRGRIDYYWSVLKPGETLNVESNGNLIAPWYAYKF

TSSNNKGAIFKSNLPIENCDAVCQTVAGALKTNKTFQNVSPLWIGECPKY

VKSESLRLATGLRNVPQAETRGLFGAIAGFIEGGWTGMIDGWYGYHHENS

QGSGYAADKESTQKAIDGITNKVNSIIDKMNTQFEAVEHEFSNLERRIDN

LNKRMEDGFLDVWTYNAELLVLLENERTLDLHDANVKNLYEKVKSQLRDN

AKDLGNGCFEFWHKCDDECINSVKNGTYDYPKYQDESKLNRQEIDSVSGG

GGLNDIFEAQKIEWHERLVPRGSPGSGYIPEAPRDGQAYVRKDGEWVLLS

TFLGHHHHHH

>A/turkey/Wisconsin/1/1966 (H9N2)   (SEQ ID NO: 343)
MVLVNQSHQGFNKEHTSKMVSAIVLYVLLAAAAHSAFAADPGDKICIGYQ

STNSTETVDTLTESNVPVTHTKELLHTEHNGMLCATDLGHPLILDTCTIE

GLIYGNPSCDILLGGKEWSYIVERSSAVNGMCYPGNVENLEELRSLFSSA

KSYKRIQIFPDKTWNVTYSGTSRACSNSFYRSMRWLTHKSNSYPFQNAHY

TNNERENILFMWGIHHPPTDTEQTDLYKNADTTTSVTTEDINRTFKPVIG

PRPLVNGQQGRIDYYWSVLKPGQTLRIRSNGNLIAPWYGHVLTGESHGRI

LKTDLNNGNCVVQCQTEKGGLNTTLPFHNISKYAFGNCPKYVGVKSLKLA

VGLRNVPAVSSRGLFGAIAGFIEGGWPGLVAGWYGFQHSNDQGVGMAADK

GSTQKAIDKITSKVNNIIDKMNKQYEVIDHEFNELEARLNMINNKIDDQI

QDIWAYNAELLVLLENQKTLDEHDANVNNLYNKVKRALGSNAVEDGNGCF

ELYHKCDDQCMETIRNGTYDRQKYQEESRLERQKIEGVSGGGGLNDIFEA

QKIEWHERLVPRGSPGSGYIPEAPRDGQAYVRKDGEWVLLSTFLGHHHHH

H

>A/duck/Alberta/60/1976 (H12N5)   (SEQ ID NO: 344)
MVLVNQSHQGFNKEHTSKMVSAIVLYVLLAAAAHSAFAADPGDTICVGYH

ANNSTDTVDTVLEKNVTVTHSVNLLEDSHNGKLCSLNGIAPLQLGKCNVA

GWLLGNPECDLLLTANSWSYIIETSNSENGTCYPGEFIDYEELREQLSSI

SSFEKFEIFPKASSWPNHETTKGVTAACSYSGASSFYRNLLWITKKGTSY

PKLSKSYTNNKGKEVLVLWGVHHPPSVSEQQSLYQNADAYVSVGSSKYNR

RFAPEIAARPEVRGQAGRMNYYWTLLDQGDTITFEATGNLIAPWYAFALN

KGSDSGIITSDAPVHNCDTRCQTPHGALNSSLPFQNVHPITIGECPKYVK

STKLRMATGLRNVPSIQSRGLFGAIAGFIEGGWTGMIDGWYGYHHQNEQG

SGYAADQKSTQNAIDGITNKVNSVIEKMNTQFTAVGKEFNNLERRIENLN

KKVDDGFLDVWTYNAELLVLLENERTLDFHDSNVRNLYEKVKSQLRNNAK

EIGNGCFEFYHKCDDECMESVKNGTYDYPKYSEESKLNREEIDSGGGGLN

DIFEAQKIEWHERLVPRGSPGSGYIPEAPRDGQAYVRKDGEWVLLSTFLG

HHHHHH

TABLE 10-continued

Sequences of HAs used in binding studies.
The sequences listed below represent the full-length
ORF as cloned in the baculovirus transfer vector.
Most of the N-terminal signal peptide
MVLVNQSHQGFNKEHTSKMVSAIVLYVLLAAAAHSAFA
(SEQ ID NO: 212)) is presumably removed
during secretion, leaving four non-native
residues (ADPG) at the N-terminus of HA1.
The C-terminal biotinylation site, trimerization
domain, and His tag are retained on all.

>A/gull/Maryland/704/1977 (H13N6)    (SEQ ID NO: 345)
MVLVNQSHQGFNKEHTSKMVSAIVLYVLLAAAAHSAFAADPGDRICVGYL

STNSSERVDTLLENGVPVTSSIDLIETNHTGTYCSLNGVSPVHLGDCSFE

GWIVGNPACTSNFGIREWSYLIEDPAAPHGLCYPGELNNNGELRHLFSGI

RSFSRTELIPPTSWGEVLDGTTSACRDNTGTNSFYRNLVWFIKKNNRYPV

ISKTYNNTTGRDVLVLWGIHHPVSVDETKTLYVNSDPYTLVSTKSWSEKY

KLETGVRPGYNGQRSWMKIYWSLIHPGEMITFESNGGFLAPRYGYIIEEY

GKGRIFQSRIRMSRCNTKCQTSVGGINTNRFTQNIDKNALGDCPKYIKSG

QLKLATGLRNVPAISNRGLFGAIAGFIEGGWPGLINGWYGFQHQNEQGTG

IAADKESTQKAIDQITTKINNIIDKMNGNYDSIRGEFNQVEKRINMLADR

IDDAVTDIWSYNAKLLVLLENDKTLDMHDANVKNLHEQVRRELKDNAIDE

GNGCFELLHKCNDSCMETIRNGTYDHTEYAEESKLKRQEIDGISGGGGLN

DIFEAQKIEWHERLVPRGSPGSGYIPEAPRDGQAYVRKDGEWVLLSTFLG

HHHHHH

>A/black-headed gull/Sweden/4/99    (SEQ ID NO: 346)
(H16N3)
MVLVNQSHQGFNKEHTSKMVSAIVLYVLLAAAAHSAFAADPGDKICIGYL

SNNSTDTVDTLTENGVPVTSSIDLVETNHTGTYCSLNGVSPIHLGDCSFE

GWIVGNPSCASNINIREWSYLIEDPNAPHKLCFPGEVDNNGELRHLFSGV

NSFSRTELIPPSKWGDILEGTTASCQNRGANSFYRNLIWLVNKLNKYPVV

KGEYNNTTGRDVLVLWGIHHPDTEATANKLYVNKNPYTLVSTKEWSRRYE

LEIGTRIGDGQRSWMKIYWHLMHPGERITFESSGGLLAPRYGYIIEKYGT

GRIFQSGVRLAKCNTKCQTSMGGINTNKTFQNIERNALGDCPKYIKSGQL

KLATGLRNVPSIVERGLFGAIAGFIEGGWPGLINGWYGFQHQNEQGTGIA

ADKTSTQKAINEITTKINNIIEKMNGNYDSIRGEFNQVEKRINMIADRVD

DAVTDIWSYNAKLLVLIENDRTLDLHDANVRNLHEQIKRALKDNAIDEGD

GCFSILHKCNDSCMETIRNGTYNHEDYKEESQLKRQEIEGISGGGGLNDI

FEAQKIEWHERLVPRGSPGSGYIPEAPRDGQAYVRKDGEWVLLSTFLGHH

HHHH

>A/Netherlands/219/2003 (H7N7)    (SEQ ID NO: 347)
MVLVNQSHQGFNKEHTSKMVSAIVLYVLLAAAAHSAFAADPGDKICLGHH

AVSNGTKVNTLTERGVEVVNATETVERTNVPRICSKGKRTVDLGQCGLLG

TITGPPQCDQFLEFSADLIIERREGSDVCYPGKFVNEEALRQILRESGGI

DKETMGFTYSGIRTNGTTSACRRSGSSFYAEMKWLLSNTDNAAFPQMTKS

YKNTRKDPALIIWGIHHSGSTTEQTKLYGSGNKLITVGSSNYQQSFVPSP

GARPQVNGQSGRIDFHWLILNPNDTVTFSFNGAFIALDRASFLRGKSMGI

QSEVQVDANCEGDCYHSGGTIISNLPFQNINSRAVGKCPRYVKQESLLLA

TGMKNVPEIPKRRRRGLFGAIAGFIENGWEGLIDGWYGFRHQNAQGEGTA

ADYKSTQSAIDQITGKLNRLIEKTNQQFELIDNEFTEVERQIGNVINWTR

DSMTEVWSYNAELLVAMENQHTIDLADSEMNKLYERVKRQLRENAEEDGT

GCFEIFHKCDDDCMASIRNNTYDHSKYREEAIQNRIQIDPVSGGGGLNDI

FEAQKIEWHERLVPRGSPGSGYIPEAPRDGQAYVRKDGEWVLLSTFLGHH

HHHH

>A/chicken/Germany/n/1949 (H10N7)    (SEQ ID NO: 348)
MVLVNQSHQGFNKEHTSKMVSAIVLYVLLAAAAHSAFAADPGDRICLGHH

AVANGTIVKTLTNEQEEVTNATETVESTNLNKLCMKGRSYKDLGNCHPVG

MLIGTPVCDPHLTGTWDTLIERENAIAHCYPGATINEEALRQKIMESGGI

SKMSTGFTYGSSINSAGTTKACMRNGGDSFYAELKWLVSKTKGQNFPQTT

NTYRNTDTAEHLIIWGIHHPSSTQEKNDLYGTQSLSISVESSTYQNNFVP

VVGARPQVNGQSGRIDFHWTLVQPGDNITFSHNGGLIAPSRVSKLTGRGL

GIQSEALIDNSCESKCFWRGGSINTKLPFQNLSPRTVGQCPKYVNQRSLL

LATGMRNVPEVVQGRGLFGAIAGFIENGWEGMVDGWYGFRHQNAQGTGQA

ADYKSTQAAIDQITGKLNRLIEKTNTEFESIESEFSETEHQIGNVINWTK

DSITDIWTYQAELLVAMENQHTIDMADSEMLNLYERVRKQLRQNAEEDGK

GCFEIYHTCDDSCMESIRNNTYDHSQYREEALLNRLNINSVSGGGGLNDI

FEAQKIEWHERLVPRGSPGSGYIPEAPRDGQAYVRKDGEWVLLSTFLGHH

HHHH

>A/mallard/Astrakhan/263/1982    (SEQ ID NO: 349)
(H14N5)
MVLVNQSHQGFNKEHTSKMVSAIVLYVLLAAAAHSAFAADPGPIICLGHH

AVENGTSVKTLTDNHVEVVSAKELVETNHTDELCPSPLKLVDGQDCDLIN

GALGSPGCDRLQDTTWDVFIERPTAVDTCYPFDVPDYQSLRSILASSGSL

EFIAEQFTWNGVKVDGSSSACLRGGRNSFFSRLNWLTKATNGNYGPINVT

KENTGSYVRLYLWGVHHPSSDNEQTDLYKVATGRVTVSTRSDQISIVPNI

GSRPVRNQSGRISIYWTLVNPGDSIIFNSIGNLIAPRGHYKISKSTKST

VLKSDKRIGSCTSPCLTDKGSIQSDKPFQNVSRIAIGNCPKYVKQGSLML

ATGMRNIPGKQAKGLFGAIAGFIENGWQGLIDGWYGFRHQNAEGTGTAAD

LKSTQAAIDQINGKLNRLIEKTNEKYHQIEKEFEQVEGRIQDLEKYVEDT

TABLE 10-continued

Sequences of HAs used in binding studies.
The sequences listed below represent the full-length
ORF as cloned in the baculovirus transfer vector.
Most of the N-terminal signal peptide
MVLVNQSHQGFNKEHTSKMVSAIVLYVLLAAAAHSAFA
(SEQ ID NO: 212)) is presumably removed
during secretion, leaving four non-native
residues (ADPG) at the N-terminus of HA1.
The C-terminal biotinylation site, trimerization
domain, and His tag are retained on all.

KIDLWSYNAELLVALENQHTIDVTDSEMNKLFERVRRQLRENAEDQGNGC

FEIFHQCDNNCIESIRNGTYDHNIYRDEAINNRIKINPVSGGGGLNDIFE

AQKIEWHERLVPRGSPGSGYIPEAPRDGQAYVRKDGEWVLLSTFLGHHHH

HH

>A/shearwater/Western  (SEQ ID NO: 350)
Australia/2576/1979 (H15N9)
MVLVNQSHQGFNKEHTSKMVSAIVLYVLLAAAAHSAFAADPGDKICLGHH

AVANGTKVNTLTERGVEVVNATETVEITGIDKVCTKGKKAVDLGSCGILG

TIIGPPQCDLHLEFKADLIIERRNSSDICYPGRFTNEEALRQIIRESGGI

DKESMGFRYSGIRTDGATSACKRTVSSFYSEMKWLSSSMNNQVFPQLNQT

YRNTRKEPALIVWGVHHSSSLDEQNKLYGTGNKLITVGSSKYQQSFSPSP

GARPKVNGQAGRIDFHWMLLDPGDTVTFTFNGAFIAPDRATFLRSNAPSG

IEYNGKSLGIQSDAQIDESCEGECFYSGGTINSPLPFQNIDSRAVGKCPR

YVKQSSLPLALGMKNVPEKIRTRGLFGAIAGFIENGWEGLIDGWYGFRHQ

NAQGQGTAADYKSTQAAIDQITGKLNRLIEKTNKQFELIDNEFTEVEQQI

GNVINWTRDSLTEIWSYNAELLVAMENQHTIDLADSEMNKLYERVRRQLR

ENAEEDGTGCFEIFHRCDDQCMESIRNNTYNHTEYRQEALQNRIMINPVS

GGGGLNDIFEAQKIEWHERLVPRGSPGSGYIPEAPRDGQAYVRKDGEWVL

LSTFLGHHHHHH

REFERENCES FOR SUPPLEMENTAL MATERIAL

S1. J. Karanicolas et al., *Mol. Cell*, in press (2011).
S2. J. J. Gray et al., *J Mol Biol* 331, 281 (2003).
S3. D. C. Ekiert et al., *Science* 324, 246 (2009).
S4. R. L. Dunbrack, Jr., M. Karplus, *Nat Struct Biol* 1, 334 (1994).
S5. K. Henrick, J. M. Thornton, *Trends Biochem Sci* 23, 358 (1998).
S6. D. Schneidman-Duhovny, Y. Inbar, R. Nussinov, H. J. Wolfson, *Nucleic Acids Res* 33, W363 (2005).
S7. C. A. Smith, T. Kortemme, *J Mol Biol* 380, 742 (2008).
S8. B. Kuhlman et al., *Science* 302, 1364 (2003).
S9. J. J. Havranek, D. Baker, *Protein Sci* 18, 1293 (2009).
S10. T. Kortemme, D. Baker, *Proc. Natl. Acad. Sci. USA* 99, 14116 (2002).
S11. M. C. Lawrence, P. M. Colman, *J Mol Biol* 234, 946 (1993).
S12. S. Henikoff, J. G. Henikoff, *Proteins* 17, 49 (1993).
S13. *Acta Crystallogr D Biol Crystallogr* 50, 760 (1994).
S14. P. H. Brown, J. E. Cronan, M. Grotli, D. Beckett, *J Mol Biol* 337, 857 (2004).
S15. G. Chao et al., *Nat Protoc* 1, 755 (2006).
S16. C. P. Graff, K. Chester, R. Begent, K. D. Wittrup, *Protein Eng Des Sel* 17, 293 (2004).
S17. M. Throsby et al., *PLoS One* 3, e3942 (2008).
S18. L. M. Kunkel, A. P. Monaco, W. Middlesworth, H. D. Ochs, S. A. Latt, *Proc Natl Acad Sci USA* 82, 4778 (1985).
S19. T. A. Kunkel, *Proc Natl Acad Sci USA* 82, 488 (1985).
S20. F. W. Studier, *Protein Expr Purif* 41, 207 (2005).
S21. A. J. McCoy et al., *J Appl Crystallogr* 40, 658 (2007).
S22. P. D. Adams et al., *Acta Crystallogr D Biol Crystallogr* 66, 213 (2010).
S23. P. Emsley, B. Lohkamp, W. G. Scott, K. Cowtan, *Acta Crystallogr D Biol Crystallogr* 66, 486 (2010).
S24. Z. Dauter, *Acta Crystallogr D Biol Crystallogr* 55, 1703 (1999).
S25. I. K. McDonald, J. M. Thornton, *J. Mol. Biol.* 238, 777 (1994).
S26. S. Sheriff, W. A. Hendrickson, J. L. Smith, *J Mol Biol* 197, 273 (1987).
S27. R. Das, D. Baker, *Annu Rev Biochem* 77, 363 (2008).
S28. W. L. DeLano, *DeLano Scientific*, Palo Alto, Calif., USA, (2002).
S29. V. B. Chen et al., *Acta Crystallogr D Biol Crystallogr* 66, 12 (2010).
S30. E. T. Boder, K. S. Midelfort, K. D. Wittrup, *Proc Natl Acad Sci USA* 97, 10701 (2000).
S31. T. A. Steitz, *Structure* 15, 1523 (2007).
S32. S. K. Burley, A. Joachimiak, G. T. Montelione, I. A. Wilson, *Structure* 16, 5 (2008).
S33. J. M. Chandonia, S. E. Brenner, *Science* 311, 347 (2006).
S34. J. Chen, J. J. Skehel, D. C. Wiley, *Proc Natl Acad Sci USA* 96, 8967 (1999).
S35. C. E. Stebbins, J. E. Galan, *Nature* 412, 701 (2001).

Example 2

Yeast-Displayed Designs Protect HA from Undergoing pH-Induced Conformational Change SC1918/H1 HA was produced according to previous reports and was confirmed to be cleaved to HA1 & HA2 using denaturing gel electrophoresis. H1 HA was chemically biotinylated in PBS pH 7.4 at rt for 30 min using a 10-fold molar excess of sulfo-NHS-LC-biotin (Pierce), after which time the protein was desalted into 10 mM Tris, 150 mM NaCl, pH 8.0 using a desalting spin column (ThermoScientific) and stored at 4° C.

To determine whether H1 HA could undergo irreversible conformational changes in the absence of the protective effects of designs, 80 nM of H1 HA was incubated in a final volume of 100 uL at either buffer BBSF (20 mM BTP, 150 mM NaCl, 1 mg/mL Fraction V BSA, pH 7.4) or buffer pHBSF (100 mM sodium acetate, 150 mM NaCl, 1 mg/mL Fraction V BSA, pH 5.2) for 1 h at 37° C., after which the reactions were neutralized with 20 µL of 1 M Tris-HCl pH 8.0. Reaction mixtures were vortexed, spun at 20,000×g for 5 min, and the supernatant at 10-fold dilution was used to label yeast cells displayed with either CR6261 scFv or affinity-matured designs. Cells were labeled for 30 min at 22° C. in buffer, washed, and secondary labeled for 10 min on ice with anti-cmyc FITC (Miltenyi Biotec, Auburn, Calif.) and streptavidin-phycoerythrin (Invitrogen, Carlsbad, Calif.). After washing, cells were resuspended in BBSF buffer and fluorescence of 20,000 cells was quantified using an Accuri C6 flow cytometer. Both CR6261 scFv and the designed binders target an epitope on HA that is absent in the post-fusion conformational change. H1 HA treated at pH 5.2 for 1 h had significantly lower fluorescence relative to controls for all three surface-displayed HA binders, indicating that the H1

HA can undergo irreversible conformational change to the post-fusion state under these treatment conditions (data not shown).

To determine whether yeast-displayed designs can protect against H1 HA pH-induced conformational changes, 8 nM of H1 HA was used to label yeast cells displayed with either CR6261 scFv or affinity-matured designs. 2e6 cells were labeled for 30 min at 22° C. in 1 mL BBSF buffer, washed once, and resuspended in either BBSF or pHBSF buffer and incubated at 37° C. for 1-24 h. Periodically, samples were withdrawn in 100 μL volume and neutralized with 20 uL of 1 M Tris-HCl pH 8.0. Cells were pelleted, washed, and processed exactly as above. Sequential timepoints up to 24 h of this process were assessed. Notably, yeast cells displaying either the CR6261 scFv or the HB80.3 design show no significant difference in binding signal between the cells incubated in low pH or neutral pH buffer, showing that these designs most likely protect against the low-pH induced conformational change of H1 HA. Yeast cells displaying the HB36.4 design show no difference in binding signal between the low pH buffer and neutral pH buffer incubation until the 24 h timepoint, when a slight decrease in binding signal at the low pH incubation was seen.

Example 3

Profiling of the Sequence-Specific Determinants of Binding for Designs Using Selections Coupled to Next Generation DNA Sequencing Methods
Library Creation Single site saturation mutagenesis libraries for HB36.4 and HB80.3 were constructed from synthetic DNA by Genewhiz. Parental sequences are listed in Table 11 with mutagenic region highlighted in red. Yeast EBY100 cells were transformed with library DNA and linearized pETCON (Science, 2011) using established protocols, yielding 1.4e6 and 3.3e6 transformants for the HB36.4 & HB80.3 ssm libraries, respectively. After transformation, cells were grown overnight in SDCAA media in 30 mL cultures at 30° C., passaged once, and stored in 20 mM HEPES 150 mM NaCl pH 7.5, 20% (w/v) glycerol in 1e7 aliquots at −80° C.

TABLE 11

DNA sequences of the single site saturation mutagenesis libraries.

>HB36.4 (SEQ ID NO: 214)
GACGATTGAAGGTAGATACCCATACGACGTTCCAGACTACGCTCTGCAGG

CTAGTGGTGGAGGAGGCTCTGGTGGAGGCGGTAGCGGAGGCGGAGGGTCG

TABLE 11-continued

DNA sequences of the single site saturation mutagenesis libraries.

GCTAGC*CATATG*CACATGTCCAATGCTATGGATGGTCAACAA

TTGAACAGATTGTTATTGGAATGGATCGGTGCCTGGGACCCTTTTGGTTT

GGGTAAAGATGCTTATGACGTCGAAGCCGAAGCTGTTTTACAAGCAGTAT

ACGAAACTGAATCTGCATTTGATTTGGCCATGAGAATTATGTGGATCTAT

GTTTTTGCCTTCAAGAGACCAATTCCTTTCCCACACGCTCAAAAATTGGC

AAGAAGATTATTGGAATTGAAGCAAGCTGCATCTTCACCTTTACCATTGG

AA*CTCGAG*GGGGGCGGATCCGAACAAAAGCTTATTTCTGAAGAG

GACTTGTAATAGAGATCT

>HB80.3 (SEQ ID NO: 215)
GACGATTGAAGGTAGATACCCATACGACGTTCCAGACTACGCTCTGCAGG

CTAGTGGTGGAGGAGGCTCTGGTGGAGGCGGTAGCGGAGGCGGAGGGTCG

GCTAGC*CATATG*GCTTCTACTAGAGGTTCTGGTAGACCTTGG

GGTTTTTCCGAAAATTTGGCCTTCGAATTGGCTTTAAGTTTTACTAACAA

AGATACACCAGACAGATGGGCTAAGGTTGCACAATATGTATCTGGTAGAA

CACCTGAAGAAGTTAAAAAGCATTACGAA*CTCGAG*GGGGGCGGA

TCCGAACAAAAGCTTATTTCTGAAGAGGACTTGTAATAGAGATCT

Base in italics and enlarged font indicate start and end of design encoding sequence. Bases in bold font indicate region of single site saturation mutagenesis.

Yeast Display Selections

Cell aliquots were thawed on ice, centrifuged at 13,000 rpm for 30 s, resuspended in 1e7 cells per mL of SDCAA media, and grown at 30° C. for 6 h. Cells were then centrifuged for 13,000 rpm and resuspended at 1e7 cells per mL SGCAA media and induced at 22° C. between 16-24 h. Cells were labeled with either biotinylated Viet/2004/H5 HA or SC/1918/H1 HA, washed, secondary labeled with SAPE (Invitrogen) and anti-cmyc FITC (Miltenyi Biotech), and sorted by fluorescent gates as outlined in Table 12. Cells were recovered overnight at 2.5e5 collected cells per mL SDCAA media, whereupon at least 1e7 cells were spun down at 13,000 rpm for 1 min and stored as cell pellets at −80° C. before library prep for deep sequencing.

TABLE 12

Summary of selection conditions for yeast populations deep sequenced.

| Expt | Sample | Sort | Library | Labeling Condition | % Cells Collected | # Cells Collected |
|---|---|---|---|---|---|---|
| 1 | No Gate | 1 | HB36.4 | — | — | 2.5E+05 |
| 1 | Display | 1 | HB36.4 | — | 100% | 2.5E+05 |
| 1 | H1 bind (stringent) | 1 | HB36.4 | 18 nM H1 HA | 41% | 2.5E+05 |
| 1 | H1 bind | 1 | HB36.4 | 60 nM H1 HA | 45% | 2.5E+05 |
| 1 | H5 bind | 1 | HB36.4 | 36 nM H5 HA | 33% | 1.5E+05 |
| 1 | No Gate | 2 | HB36.4 | — | — | 2.5E+05 |
| 1 | Display | 2 | HB36.4 | — | 100% | 2.5E+05 |
| 1 | H1 bind (stringent) | 2 | HB36.4 | 3.5 nM H1 HA | 10% | 1.6E+05 |
| 1 | H1 bind | 2 | HB36.4 | 42 nM H1 HA | 64% | 2.5E+05 |

TABLE 12-continued

Summary of selection conditions for yeast populations deep sequenced.

| Expt | Sample | Sort | Library | Labeling Condition | % Cells Collected | # Cells Collected |
|---|---|---|---|---|---|---|
| 1 | H5 bind (stringent) | 2 | HB36.4 | 6 nM H5 HA | 6% | 6.0E+04 |
| 2 | No Gate | 1 | HB36.4 | — | — | 1.5E+05 |
| 2 | H1 bind | 1 | HB36.4 | 4 nM H1 HA | 19% | 1.5E+05 |
| 2 | No Gate | 2 | HB36.4 | — | — | 1.5E+05 |
| 2 | H1 off-rate | 2 | HB36.4 | 6 nM H1, 120' off with HB80.3 | 3% | 9.0E+04 |
| 2 | No Gate | 1 | HB80.3 | — | — | 1.5E+05 |
| 2 | H1 bind | 1 | HB80.3 | 4 nM H1 HA | 21% | 1.5E+05 |
| 2 | No Gate | 2 | HB80.3 | — | — | 1.5E+05 |
| 2 | H1 off-rate | 2 | HB80.3 | 6 nM H1 HA, 40' off with HB80.3 | 2% | 6.0E+04 |
| 3 | No Gate | 1 | HB36.4 | — | — | 5.0E+05 |
| 3 | Display | 1 | HB36.4 | — | 100% | 5.0E+05 |
| 3 | Good Display | 1 | HB36.4 | — | 10% | 5.0E+05 |
| 3 | Weak Display | 1 | HB36.4 | — | 27% | 5.0E+05 |
| 3 | H5 bind | 1 | HB36.4 | 10 nM H5 HA | 30% | 5.0E+05 |
| 3 | No Gate | 2 | HB36.4 | — | — | 5.0E+05 |
| 3 | H5 off-rate | 2 | HB36.4 | 3 nM H5 HA, 20' off with HB36.4 | 3% | 3.0E+05 |
| 3 | No Gate | 1 | HB80.3 | — | — | 5.0E+05 |
| 3 | Display | 1 | HB80.3 | — | 100% | 5.0E+05 |
| 3 | Good Display | 1 | HB80.3 | — | 9% | 5.0E+05 |
| 3 | Weak Display | 1 | HB80.3 | — | 20% | 5.0E+05 |
| 3 | H5 bind | 1 | HB80.3 | 10 nM H5 HA | 37% | 5.0E+05 |
| 3 | No Gate | 2 | HB80.3 | — | — | 5.0E+05 |
| 3 | H5 off-rate | 2 | HB80.4 | 3 nM H5 HA, 75' off with HB36.4 | 11% | 5.0E+05 |

Library Prep and Sequencing

Between 1-4e7 yeast cells were resuspended in Solution I (Zymo Research yeast plasmid miniprep II kit) with 25 U zymolase and incubated at 37° C. for 4 hrs. Cells were then freeze/thawed using a dry ice/ethanol bath and a 42° C. incubator. Afterwards, plasmid was recovered using a zymo research yeast plasmid miniprep II kit (Zymo Research, Irvine, Calif.) into a final volume of 30 µL 10 mM Tris-HCl pH 8.0. Contaminant genomic DNA was processed (per 20 µL rxn) using 2 µL ExoI exonuclease (NEB), 1 µL lambda exonuclease (NEB), and 2 µL lambda buffer at 30° C. for 90 min followed by heat inactivation of the enzymes at 80° C. for 20 min. Plasmid DNA was separated from the reaction mixture using a QIAGEN™ PCR cleanup kit (Qiagen). Next, 18 cycles of PCR (98° C. 10 s, 68° C. 30 s, 72° C. 10 s) using Phusion high fidelity polymerase (NEB, Waltham, Mass.) was used to amplify the template and add the Illumina adaptor sections. Primers used were sample-specific and are listed in Table 13. PCR reaction was purified using an Agencourt AMPURE™ XP kit (Agencourt, Danvers, Mass.) according to the manufacturer's specifications. Samples were quantified using Qubit dsDNA HS kit (Invitrogen) for a final yield of 1-4 ng/uL. Samples were combined in an equimolar ratio; from this pool, 0.4 fmol of total DNA was loaded on 2 separate lanes and sequenced using a Genome Analyzer IIx (Illumina) with appropriate sequencing primers (Table 13).

TABLE 13

List of sequencing primers used.

| Primer Name | Sequence | Use |
|---|---|---|
| PCR77_fwd | AATGATACGGCGACCACCGAGATCT ACACcggctagccatatggcttct (SEQ ID NO: 216) | NG lib construction |
| PCR77_rev_BC1 | CAAGCAGAAGACGGCATACGAGATC AAGGTCAgatccgccccctcgag (SEQ ID NO: 217) | NG lib construction |
| PCR77_rev_BC10 | CAAGCAGAAGACGGCATACGAGATA CGTACTCgatccgccccctcgag (SEQ ID NO: 218) | NG lib construction |
| PCR77_rev_BC11 | CAAGCAGAAGACGGCATACGAGATC TTCTAAGgatccgccccctcgag (SEQ ID NO: 219) | NG lib construction |
| PCR77_rev_BC12 | CAAGCAGAAGACGGCATACGAGATA CTATGACgatccgccccctcgag (SEQ ID NO: 220) | NG lib construction |

TABLE 13-continued

List of sequencing primers used.

| Primer Name | Sequence | Use |
|---|---|---|
| PCR77_rev_BC13 | CAAGCAGAAGACGGCATACGAGATGACGTTAAgatccgcccccctcgag (SEQ ID NO: 221) | NG lib construction |
| PCR77_rev_BC14 | CAAGCAGAAGACGGCATACGAGATACAAGATAgatccgcccccctcgag (SEQ ID NO: 222) | NG lib construction |
| PCR77_rev_BC15 | CAAGCAGAAGACGGCATACGAGATGACTAAGAgatccgcccccctcgag (SEQ ID NO: 223) | NG lib construction |
| PCR77_rev_BC16 | CAAGCAGAAGACGGCATACGAGATGTGTCTACgatccgcccccctcgag (SEQ ID NO: 224) | NG lib construction |
| PCR77_rev_BC17 | CAAGCAGAAGACGGCATACGAGATTTCACTAGgatccgcccccctcgag (SEQ ID NO: 225) | NG lib construction |
| PCR77_rev_BC18 | CAAGCAGAAGACGGCATACGAGATAATCGGATgatccgcccccctcgag (SEQ ID NO: 226) | NG lib construction |
| PCR77_rev_BC19 | CAAGCAGAAGACGGCATACGAGATAGTACCGAgatccgcccccctcgag (SEQ ID NO: 227) | NG lib construction |
| PCR77_rev_BC2 | CAAGCAGAAGACGGCATACGAGATGCATAACTgatccgcccccctcgag (SEQ ID NO: 228) | NG lib construction |
| PCR77_rev_BC3 | CAAGCAGAAGACGGCATACGAGATCTCTGATTgatccgcccccctcgag (SEQ ID NO: 229) | NG lib construction |
| PCR77_rev_BC30 | CAAGCAGAAGACGGCATACGAGATGTAGCAGTgatccgcccccctcgag (SEQ ID NO: 230) | NG lib construction |
| PCR77_rev_BC31 | CAAGCAGAAGACGGCATACGAGATGGATCATCgatccgcccccctcgag (SEQ ID NO: 231) | NG lib construction |
| PCR77_rev_BC32 | CAAGCAGAAGACGGCATACGAGATGTGAACGTgatccgcccccctcgag (SEQ ID NO: 232) | NG lib construction |
| HA77_f1_fwd | Cggctagccatatggcttct (SEQ ID NO: 233) | NG sequencing |
| HA77_f1_rev | Gtgcaaccttagcccatctgtctggtg (SEQ ID NO: 234) | NG sequencing |
| HA77_f2_fwd | Ggccttcgaattggctttaagttttactaacaaagat (SEQ ID NO: 235) | NG sequencing |
| HA77_f2_rev | Gatccgcccccctcgag (SEQ ID NO: 236) | NG sequencing |
| HA77_index | Ctcgagggggcggatc (SEQ ID NO: 237) | NG sequencing |
| PCR35_fwd | AATGATACGGCGACCACCGAGATCTACACgatcggtgcctgggac (SEQ ID NO: 238) | NG lib construction |
| PCR35_rev_BC20 | CAAGCAGAAGACGGCATACGAGATTTGCCTCAcagcttgcttcaattccaataatc (SEQ ID NO: 239) | NG lib construction |
| PCR35_rev_BC21 | CAAGCAGAAGACGGCATACGAGATTCGTTAGCcagcttgcttcaattccaataatc (SEQ ID NO: 240) | NG lib construction |

TABLE 13-continued

List of sequencing primers used.

| Primer Name | Sequence | Use |
|---|---|---|
| PCR35_rev_BC22 | CAAGCAGAAGACGGCATACGAGATT ATAGTTCcagcttgcttcaattccaataatc (SEQ ID NO: 241) | NG lib construction |
| PCR35_rev_BC23 | CAAGCAGAAGACGGCATACGAGATT GGCGTATcagcttgcttcaattccaataatc (SEQ ID NO: 242) | NG lib construction |
| PCR35_rev_BC24 | CAAGCAGAAGACGGCATACGAGATT GGACATGcagcttgcttcaattccaataatc (SEQ ID NO: 243) | NG lib construction |
| PCR35_rev_BC25 | CAAGCAGAAGACGGCATACGAGATA GGTTGCTcagcttgcttcaattccaataatc (SEQ ID NO: 244) | NG lib construction |
| PCR35_rev_BC26 | CAAGCAGAAGACGGCATACGAGATA TATGCTGcagcttgcttcaattccaataatc (SEQ ID NO: 245) | NG lib construction |
| PCR35_rev_BC27 | CAAGCAGAAGACGGCATACGAGATG TACAGTGcagcttgcttcaattccaataatc (SEQ ID NO: 246) | NG lib construction |
| PCR35_rev_BC40 | CAAGCAGAAGACGGCATACGAGATA ATCCTGCcagcttgcttcaattccaataatc (SEQ ID NO: 247) | NG lib construction |
| PCR35_rev_BC41 | CAAGCAGAAGACGGCATACGAGATG TTATATCcagcttgcttcaattccaataatc (SEQ ID NO: 248) | NG lib construction |
| PCR35_rev_BC42 | CAAGCAGAAGACGGCATACGAGATA CACACGTcagcttgcttcaattccaataatc (SEQ ID NO: 249) | NG lib construction |
| PCR35_rev_BC43 | CAAGCAGAAGACGGCATACGAGATA TACGACTcagcttgcttcaattccaataatc (SEQ ID NO: 250) | NG lib construction |
| PCR35_rev_BC44 | CAAGCAGAAGACGGCATACGAGATA TCTTCGTcagcttgcttcaattccaataatc (SEQ ID NO: 251) | NG lib construction |
| PCR35_rev_BC45 | CAAGCAGAAGACGGCATACGAGATA CATGTATcagcttgcttcaattccaataatc (SEQ ID NO: 252) | NG lib construction |
| PCR35_rev_BC46 | CAAGCAGAAGACGGCATACGAGATT CCACAGTcagcttgcttcaattccaataatc (SEQ ID NO: 253) | NG lib construction |
| PCR35_rev_BC47 | CAAGCAGAAGACGGCATACGAGATC AGTCTGTcagcttgcttcaattccaataatc (SEQ ID NO: 254) | NG lib construction |
| HA35_f1_fwd | Gatcggtgcctgggac (SEQ ID NO: 255) | NG sequencing |
| HA35_f1_rev | Tcttgaaggcaaaaacatagatccacataattctcatgg (SEQ ID NO: 256) | NG sequencing |
| HA35_f2_fwd | Acaagcagtatacgaaactgaatctgcatttgatttgg (SEQ ID NO: 257) | NG sequencing |
| HA35_f2_rev | Cagcttgcttcaattccaataatc (SEQ ID NO: 258) | NG sequencing |
| HA35_index | Gattattggaattgaagcaagct (SEQ ID NO: 259) | NG sequencing |
| Up-GS-pCons | Ggacaatagctcgacgattgaaggtagatacccata (SEQ ID NO: 260) | Universal fwd primer |

TABLE 13-continued

List of sequencing primers used.

| Primer Name | Sequence | Use |
|---|---|---|
| Down_Cmyc | Caagtcctcttcagaaataagcttttgttc (SEQ ID NO: 261) | Universal rev primer |
| HB80_front_rev | Tggtctaccggaacctctggtggatgc (SEQ ID NO: 262) | Elibrary construction |
| HB80_back_fwd | Actcctgaagaagtcaaaaagcattacgaa (SEQ ID NO: 263) | Elibrary construction |
| HB80_klenow | Ttcgtaatgcttttgacttcttc (SEQ ID NO: 264) | Elibrary construction |
| E80 ultramer | Gcatccaccagaggttccggtagaccatggrrgttcarsga aaacvttrmgtttgaamttgctttgtmttttacgaataaggac acaccagatagatggrvgaaggttgcayrstatgtaarsggt agaactcctgaagaagtcaaaaagcattacgaa (SEQ ID NO: 265) | Elibrary construction |
| HB36_front_rev | Gtcataggcatctttacccaaacc (SEQ ID NO: 266) | Elibrary construction |
| HB36_back_fwd | Catgcccaaaagttggctaga (SEQ ID NO: 267) | Elibrary construction |
| HB36_klenow | Tctagccaacttttgggcatgt (SEQ ID NO: 268) | Elibrary construction |
| E36 ultramer | Ccttttggtttgggtaaagatgcctatgackwtgaagccgm trvagttttamaggcagtatacgmgactramymtgcttttg acttggcaatgagaattmwktggatctatrwttttgcctwta agagammgattcctttcvyacatgcccaaaagttggctag a (SEQ ID NO: 269) | Elibrary construction |

Sequencing Analysis

Alignment and quality filtering of the sequencing data from raw Illumina reads were treated essentially as described previously. Each sequencing read was assigned to the correct pool on the basis of a unique 8 bp barcode identifier (Table 13). All pools were treated identically in sequence analysis and quality filtration. Custom scripts were used to align all paired-end reads with both reads above an average Phred quality score equal or above 20. Paired-end reads were aligned using a global Needleman-Wunsch algorithm, reads without gaps were merged into a single sequence and differences between sequences resolved using the higher quality score for the read. Sequencing technical replicates of the naïve library indicate that the enumeration error for the library prep and sequencing falls under a poisson distribution; therefore, bootstrapping was used to estimate confidence intervals for error analysis. All error listed is at the 95% confidence interval.

Affinity Maturation and Specificity

Beneficial mutations predicted to result in higher affinity for SC1918/H1 HA were combined into a single library. The DNA library for each design was constructed from SOE PCR using a single oligo encoding the variable region. Primers and sequences are listed in Table 13, while the DNA sequence for the libraries are listed in Table 14. Libraries were transformed into yeast EBY100 and subjected to 4 sorts of varying stringency against biotinylated SC1918 H1/HA.

TABLE 14

DNA sequences of the affinity maturation libraries constructed from the information contained in the deep sequencing experiment.

>HB36.4_elibrary (SEQ ID NO: 201)

GACGATTGAAGGTAGATACCCATACGACGTTCCAGACTACGCTCTGCAGGCTAGT
GGTGGAGGAGGCTCTGGTGGAGGCGGTAGCGGAGGCGGAGGGTCGGCTAGCCAT
ATGCACATGTCCAATGCTATGGATGGTCAACAATTGAACAGATTGTTATTGGAAT
GGATCGGTGCCTGGGAC
CCT TTT GGT TTG GGT AAA GAT GCT TAT GMT KWT GAA GCC GAA RVA GTT
TTA MAG GCA GTA TAC GMG ACT RAM YMT GCA TTT GAT TTG GCC ATG AGA
ATT MWK TGG ATC TAT RWT TTT GCC TWT AAG AGA MMG ATT CCT TTC VYA
CAC GCT CAA AAA TTG GCA AGA
AGATTATTGGAATTGAAGCAAGCTGCATCTTCACCTTTACCATTGGAACTCGAGG
GGGGCGGATCCGAACAAAAGCTTATTTCTGAAGAGGACTTGTAATAGAGATCT

TABLE 14-continued

DNA sequences of the affinity maturation libraries constructed from the information contained in the deep sequencing experiment.

```
>HB80.3_elibrary                                     (SEQ ID NO: 203)
GACGATTGAAGGTAGATACCCATACGACGTTCCAGACTACGCTCTGCAGGCTAGT
GGTGGAGGAGGCTCTGGTGGAGGCGGTAGCGGAGGCGGAGGGTCGGCTAGCCAT
ATG
GCT TCT ACT AGA GGT TCT GGT AGA CCT TGG RRG TTT ARS GAA AAT GTT
RMG TTC GAA MTT GCT TTA TMT TTT ACT AAC AAA GAT ACA CCA GAC AGA
TGG RVG AAG GTT GCA YDS TAT GTA ARS GGT AGA ACA CCT GAA GAA GTT
AAA AAG CAT TAC GAA
CTCGAGGGGGGCGGATCCGAACAAAAGCTTATTTCTGAAGAGGACTTGTAATAG
AGATCT
```

For the HB36.4 epistatic library, no dominant lineage was converged after four sorts (Table 15). Promising constructs were subcloned (NdeI/XhoI) into the pET29b (Novagen) *E. coli* expression plasmid. For the HB80.4 epistatic library, clones after four sorts converged to two dominant lineages, each with at least 5 amino acid mutations from the starting HB80.3 sequence (Tables 16). Promising constructs were subcloned into a custom pET plasmid (NdeI/XhoI) with an N-terminal FLAG tag and a C-terminal His$_6$ tag and subjected to a solubility screen.

TABLE 15

FASTA sequences of selected constructs from the HB36.4 epistatic library after four sorts. All clones significantly outperform HB36.4 on yeast-surface display titrations.

>HB36.4_s4_E03                                       (SEQ ID NO: 69)
MSNAMDGQQLNRLLLEWIGAWDPFGLGKDAYDDEAAAVLQAVYETNHAFD

LAMRIHWIYVFAFKRKIPFLHAQKLARRLLELKQAASSPLP

>HB36.4_s4_E05                                       (SEQ ID NO: 70)
MSNAMDGQQLNRLLLEWIGAWDPFGLGKDAYDVEAAAVLKAVYATNSAFD

LAMRIIWIYVFAYKRKIPFAHAQKLARRLLELKQAASSPLP

>HB36.4_s4_E06                                       (SEQ ID NO: 71)
MSNAMDGQQLNRLLLEWIGAWDPFGLGKDAYDFEADKVLQAVYETNSAFD

LAMRINWIYVFAFKRPIPFVHAQKLARRLLELKQAASSPLP

>HB36.4_s4_E07                                       (SEQ ID NO: 72)
MSNAMDGQQLNRLLLEWIGAWDPFGLGKDAYDVEAAAVLKAVYETNSAFD

LAMRINWIYVFAFKRKIPFAHAQKLARRLLELKQAASSPLP

>HB36.4_s4_E08                                       (SEQ ID NO: 73)
MSNAMDGQQLNRLLLEWIGAWDPFGLGKDAYDVEADKVLQAVYDTNSAFD

LAMTIHWIYNFAFKRKIPFLHAPKLARRLLELKLAASSPLP

>HB36.4_s4_E09                                       (SEQ ID NO: 74)
MSNAMDGQQLNRLLLEWIGAWDPFGLGKDAYDDEADRVLQAVYETNSAFD

LAMRINWIYVFAFKRTIPFAHAQKLARRLLELKQAASSPLP

>HB36.4_s4_E10                                       (SEQ ID NO: 75)
MSNAMDGQQLNRLLLEWIGAWDPFGLGKDAYDYEADKVLQAVYETNSAFD

LAMRIHWIYIFAFKRPIPFVHAQKLARRLLELKQAASSPLP

>HB36.4_s4_E11                                       (SEQ ID NO: 76)
MSNAMDGQQLNRLLLEWIGAWDPFGLGKDAYDVEADAVLKAVYATNSAFD

LAMRIHWIYNFAFKRKIPFVHAQKLARRLLELKQAASSPLP

TABLE 15-continued

FASTA sequences of selected constructs from the HB36.4 epistatic library after four sorts. All clones significantly outperform HB36.4 on yeast-surface display titrations.

>HB36.4_s4_E12                                       (SEQ ID NO: 77)
MSNAMDGQQLNRLLLEWIGAWDPFGLGKDAYDDEADKVLQAVYATNSAFD

LAMRIHWIYNFAYKRTIPFVHAQKLARRLLELKQAASSPLP

>HB36.4_s4_E13                                       (SEQ ID NO: 78)
MSNAMDGQQLNRLLLEWIGAWDPFGLGKDAYDDEAARVLKAVYATDSAFD

LAMRIHWIYNFAFKRKIPFLHAQKLARRLLELKQAASSPLP

>HB36.4_s4_E14                                       (SEQ ID NO: 79)
MSNAMDGQQLNRLLLEWIGAWDPFGLGKDAYDVEADKVLQAVYATNSAFD

LAMRIHWIYIFAFKRTIPFIHAQKLARRLLELKQAASSPLP

>HB36.4_s4_E17                                       (SEQ ID NO: 80)
MSNAMDGQQLNRLLLEWIGAWDPFGLGKDAYDYEADEVLKAVYATNSAFD

LAMRIHWIYNFAFKRKIPFTHAQKLARRLLELKQAASSPLP

>HB36.4_s4_E1 8                                      (SEQ ID NO: 81)
MSNAMDGQQLNRLLLEWIGAWDPFGLGKDAYDVEAAKVLQAVYETNSAFD

LAMKIHWIYNFAFKRTIPFVHAQKLARRLLELKQAASSPLPLE

>HB36.4_s4_E19                                       (SEQ ID NO: 82)
MSNAMDGQQLNRLLLEWIGAWDPFGLGKDAYDVEADKVLQAVYATNSAFD

LAMKIHWIYIFAFKRTIPFIHAQKLARRLLELKQAASSPLP

TABLE 16

FASTA sequences of selected constructs from the HB80.3 epistatic library after four or five sorts. All clones significantly outperform HB80.3 on yeast-surface display titrations.

>HB80.3_s4_E81                                       (SEQ ID NO: 187)
MASTRGSGRPWRFSENVAFEIALSFTNKDTPDRWKKVARYVRGRTPEEVK

KHYE

>HB80.3_s4_E82                                       (SEQ ID NO: 188)
MASTRGSGRPWKFSENVAFEIALSFTNKDTPDRWAKVARYVRGRTPEEVK

KHYE

>HB80.3_s4_E83                                       (SEQ ID NO: 189)
MASTRGSGRPWGFRENIAFEIALYFTNKDTPDRWRKVARYVKGRTPEEVK

) KHYE

TABLE 16-continued

FASTA sequences of selected constructs from the HB80.3 epistatic library after four or five sorts. All clones significantly outperform HB80.3 on yeast-surface display titrations.

```
>HB80.3_s4_E84                           (SEQ ID NO: 190)
MASTRGSGRPWRFSENVAFEIALSFTNKDTPDRWRKVARYVRGRTPEEVK
KHYE

>HB80.3_s4_E85                           (SEQ ID NO: 191)
MASTRGSGRPWGFSENIAFELALYFTNKDTPDRWGKVARYVRGRTPEEVK
KHYE

>HB80.3_s4_E86                           (SEQ ID NO: 192)
MASTRGSGRPWKFSENVAFELALYFTNKDTPDRWKKVARYVKGRTPEEVK
KHYE

>HB80.3_s4_E87                           (SEQ ID NO: 193)
MASTRGSGRPWKFSENIAFELALYFTNKDTPDRWKKVARYVKGRTPEEVK
KHYE

>HB80.3_s4_E88                           (SEQ ID NO: 194)
MASTRGSGRPWKFKENLEFEIALSFTNKDTPDRWKKVAYYVRGRTPEEVK
KHYE

>HB80.3_s4_E89                           (SEQ ID NO: 190)
MASTRGSGRPWRFSENVAFEIALSFTNKDTPDRWRKVARYVRGRTPEEVK
KHYE

>HB80.3_s4_E90                           (SEQ ID NO: 196)
MASTRGSGRPWKFSENVAFELALYFTNKDTPDRWTKVARYVRGRTPEEVK
KHYE

>HB80.3_s4_E91                           (SEQ ID NO: 196)
MASTRGSGRPWKFSENVAFELALYFTNKDTPDRWTKVARYVRGRTPEEVK
KHYE

>HB80.3_s4_E92                           (SEQ ID NO: 198)
MASTRGSGRPWKFSENVAFEIALSFTNKDTPDRWRKVARYVRGRTPEEVK
KHYE

>HB80.3_s4_E93                           (SEQ ID NO: 199)
MASTRGSGRPWKFSENVAFELALYFTNKDTPDRWGKVAQYVRGRTPEEVK
KHYE

>HB80.3_s4_E94                           (SEQ ID NO: 200)
ASTRGSGRPWKFSENVAFELALYFTNKDTPDRWAKVARYVRGRTPEEVK
KHYE

>HB80.3_s4_E95                           (SEQ ID NO: 196)
MASTRGSGRPWKFSENVAFELALYFTNKDTPDRWTKVARYVRGRTPEEVK
KHYE

>HB80.3_s4_E96                           (SEQ ID NO: 202)
MASTRGSGRPWKFSENVAFELALYFTNKDTPDRWRKVAYYVRGRTPEEVK
KHYE

>HB80.3_s4_E97                           (SEQ ID NO: 190)
MASTRGSGRPWRFSENVAFEIALSFTNKDTPDRWRKVARYVRGRTPEEVK
KHYE

>HB80.3_s4_E98                           (SEQ ID NO: 204)
MASTRGSGRPWRFSENVAFEIALSFTNKDTPDRWAKVARYVRGRTPEEVK
KHYE

>HB80.3_s4_E99                           (SEQ ID NO: 205)
MASTRGSGRPWKFSENLAFELALYFTNKDTPDRWAKVAYYVKGRTPEEVK
KHYE

>HB80.3_s4_E100                          (SEQ ID NO: 206)
MASTRGSGRPWRFSENVAFEIALSFTNKDTPDRWKKVARYVKGRTPEEVK
KHYE

>HB80.3_s5_E01                           (SEQ ID NO: 207)
MASTKGSGKPWKFSENVAFEIALSFTNKDTPDRWRKVARYVRGKTPEEVK
KHYE

>HB80.3_s5_E04                           (SEQ ID NO: 198)
MASTRGSGRPWKFSENVAFEIALSFTNKDTPDRWRKVARYVRGRTPEEVK
KHYE

>HB80.3_02                               (SEQ ID NO: 209)
MASTRGSGRPWKFSENIAFEIALSFTNKDTPDRWKKVAQYVKGRTPEEVK
KHYE
```

Solubility Screening

HB80.3 clones selected from the affinity maturation library were screened by solubility in an *E. coli* expression system using a dot-blot assay. Cells were grown from colonies in deep well plates overnight, and diluted 25-fold into deep well plates at 37° C. for 3 h, followed by IPTG induction (1 mM) for 4 h at 37° C. Following induction, cells were separated from spent media by centrifugation at 3,000×g for 15 min at 4° C. and stored as pellets overnight at −20° C. The next morning, plates were thawed on ice for at least 15 min and 200 uL binding buffer (200 mM HEPES, 150 mM NaCl, pH 7.5) was added to each well. The plate was sonicated using the Ultrasonic Processor 96-well sonicator for 3 min at 70% pulsing power and lysate centrifuged for 4000 rpm for 30 min at 4° C. Supernatant at 100-fold dilution was transferred to a dot blot manifold MINIFOLD™ I (Whatman) and dried onto nitrocellulose membrane for 5 min. The membrane was then labeled with an anti-FLAG HRP conjugated mouse antibody (Sigma, St. Louis, Mo.) and visualized with DAB substrate (Pierce).

Table 17 provides per position allowable substitutions on an HB36.4 scaffold.

HB36.4: Central helix recognition motif from Serine 47-Phenylalanine 63 (SAFDLAMRIMWIYVFAF (SEQ ID NO: 7)); Also Phe 69 outside of that recognition motif (MSNAMDGQQLNRLLLEWIGAWDPFGLGK-DAYDVEAEAVLQAVYETESAFDLAMR IMWIYV-FAFKRPIPFPHAQKLARRLLELKQAASSPLPLE (SEQ ID NO: 65))

(2) Allowable positions were determined from yeast display selections of HB36.4 variants to SC1918/H1 HA coupled to deep sequencing (see attached for further details). The threshold was no more than 80% depletion in the frequency of a given mutant in the selection library after two selection sorts by FACS. Positions listed in bold font indicate positions that make contact with the HA surface.

TABLE 17

Allowable substitutions on an HB36.4 scaffold

| Position | HB36.4 Residue | Allowable |
|---|---|---|
| 47 R1 | Ser | ala, phe, his, lys, met, asn, gln, thr, val, tyr, |
| 48 R2 | Ala | All Amino Acids |
| 49 | Phe | Phe |
| 50 R3 | Asp | Ala, Glu, Gly, Asn, Pro, Ser, Tyr |
| 51 R4 | Leu | Phe |
| 52 R5 | Ala | All Amino Acids |
| 53 R6 | Met | Phe, His, Ile, Leu, Gln, Thr |
| 54 R7 | Arg | gly, lys, gln, thr |
| 55 R8 | Ile | asn, gln, val, trp |
| 56 R9 | Met | Gly, Ile, Lys, Leu, Asn, Arg, Ser, Thr, Val, Tyr, His |
| 57 R10 | Trp | Phe |
| 58 R11 | Ile | phe, ser, thr, val |
| 59 R12 | Tyr | cys, asp, phe, his, asn, ser |
| 60 R13 | Val | Ala, Phe, Ile, Leu, Asn, Gln, Thr, Tyr |
| 61 R14 | Phe | Glu, Leu |
| 62 R15 | Ala | gly, lys, arg, ser |
| 63 R16 | Phe | cys, his, lys, leu, met, asn, gln, arg, thr, val, trp, tyr |
| 69 R17 | Phe | Tyr |

The table below shows where single point mutants from HB36.4 (SAFDLAMRIMWIYVFAF (SEQ ID NO: 7)) are shown to result in increased binding affinity.

TABLE 18

HB36.4 point mutations resulting in increased binding affinity

| Position | HB36.4 Residue | Increased Affinity |
|---|---|---|
| 47 R1 | Ser | His |
| 54 R7 | Arg | Lys |
| 56 R9 | Met | His, Asn, Tyr |
| 60 R13 | Val | Phe, Leu, Thr, Asn |
| 63 R16 | Phe | Tyr |

The table below provides per position allowable substitutions on an HB80.3 scaffold.

(1 Central helix recognition motif from Phenylalanine 13-Phenylalanine 25; Also Tyrosine 40 that is outside of that recognition motif).

(SEQ ID NO: 184)
(MASTRGSGRPWGFSENLAFELALSFTNKDTPDRWAKVAQYVSGRTPEEV KKHYE)

Allowable positions were determined from yeast display selections of HB80.3 variants to SC1918/H1 HA coupled to deep sequencing (see attached for further details). The threshold was no more than 80% depletion in the frequency of a given mutant in the selection library after two selection sorts by FACS. Positions listed in bold font indicate positions that make contact with the HA surface.

TABLE 19

Allowable substitutions on an HB80.3 scaffold

| Position | HB80.3 Residue | Allowable |
|---|---|---|
| 13 R1 | Phe | Val |
| 14 R2 | Ser | Ala, Phe, Gly, Ile, Lys, Leu, Met, Asn, Pro, Gln, Arg, Thr, Val |
| 15 R3 | Glu | Asp |
| 16 R4 | Asn | His, Ile, Lys, Leu, Met, Arg, Ser, Thr |
| 17 R5 | Leu | Phe, Ile, Met, Asn, Gln, Val |
| 18 R6 | Ala | Asp, Lys, Met, Asn, Gln, Arg, Val |
| 19 R7 | Phe | Asp, Asn, Tyr |
| 20 R8 | Glu | Ala, Asp, Gly, His, Lys, Leu, Met, Asn, Gln, Arg, Ser, Thr, Val, Trp |
| 21 R9 | Leu | Phe, Ile, Met, Val |
| 22 | Ala | Ala |
| 23 R10 | Leu | Ile, Met, Tyr |
| 24 R11 | Ser | Ala, Gly, Tyr |
| 25 | Phe | Phe |
| 39 R12 | Gln | Tyr, Phe, Met, Arg, Lys, Gly |
| 40 R13 | Tyr | Asp, Met, Asn, Ser |
| 42 R14 | Ser | Arg, Lys |

The table below shows where single point mutants from HB80.3 are shown to result in increased binding affinity.

TABLE 20

HB80.3 point mutations resulting in increased binding affinity

| Position | HB80.3 Residue | Increased Affinity |
|---|---|---|
| 14 R2 | Ser | Ala, Gly, Ile, Lys, Arg, Thr, Val |
| 17 R5 | Leu | Ile, Val |
| 18 R6 | Ala | Lys, Arg |
| 20 R8 | Glu | Ser |
| 21 R9 | Leu | Ile |
| 24 R11 | Ser | Tyr |

We claim:

1. A polypeptide comprising the amino acid sequence according to general formula I
R1-R2-Phe-R3-R4-R5-R6-R7-R8-R9-R10-R11-R12-R13-R14-R15-R16-X1-R17 (SEQ ID NO: 2), wherein
R1 is selected from the group consisting of Ser, Ala, Phe, His, Lys, Met, Asn, Gln, Thr, Val, Tyr, and Asp;
R2 can be any amino acid;
R3 is selected from the group consisting of Asp, Ala, Glu, Gly, Asn, Pro, Ser, and Tyr;
R4 is selected from the group consisting of Leu and Phe;
R5 can be any amino acid;
R6 is selected from the group consisting of Met, Phe, His, Ile, Leu, Gln, and Thr;
R7 is selected from the group consisting of Arg, Gly, Lys, Gln, and Thr;
R8 is selected from the group consisting of Ile, Asn, Gln, Val, and Trp;
R9 is selected from the group consisting of Met, Gly, Ile, Lys, Leu, Asn, Arg, Ser, Thr, Val, His, and Tyr;
R10 is selected from the group consisting of Trp and Phe;
R11 is selected from the group consisting of Ile, Phe, Ser, Thr, and Val;
R12 is selected from the group consisting of Tyr, Cys, Asp, Phe, His, Asn, and Ser;
R13 is selected from the group consisting of Val, Ala, Phe, Ile, Leu, Asn, Gln, Thr, and Tyr;
R14 is selected from the group consisting of Phe, Glu, and Leu;
R15 is selected from the group consisting of Ala, Gly, Lys, Arg, and Ser;
R16 is selected from the group consisting of Phe, Cys, His, Lys, Leu, Met, Asn, Gln, Arg, Thr, Val, Trp, and Tyr;
X1 is the amino acid sequence Z1-Arg-Z2-Ile-Pro (SEQ ID NO: 3), wherein Z1 is Lys or Asn, and Z2 is selected from the group consisting of Lys, Pro, Gln, and Thr; and
R17 is Phe or Tyr.

2. The polypeptide of claim 1, wherein Z2 is Gln.

3. The polypeptide of claim 1, wherein general formula I is A1-R1-R2-Phe-R3-R4-R5-R6-R7-R8-R9-R10-R11-R12-R13-R14-R15-R16-X1-R17-B1 (SEQ ID NO: 4), wherein one or both of A1 and B1 are present, and wherein A1 comprises the amino acid sequence:
MSNAMDGQQLNRLLLEWIGAWDPFGLGKDAYD(D/V/Y/F)EA(A/D)(A/K/R/E)VL(Q/K)A VY(E/A)T (N/D/E) (SEQ ID NO: 5); and
B1 comprises the amino acid sequence (L/A/V/D/I/P)HA(Q/P)KLARRLLELK(Q/L)AASSPLP (SEQ ID NO: 6).

4. The polypeptide of claim 3, wherein A1 is present and comprises the amino acid sequence MSNAMDGQQLNR-LLLEWIGAWDPFGLGKDAYD(F)EA(A/D)(E)VL(Q/K)AVY(E/A)T(E) (SEQ ID NO: 279).

5. The polypeptide of claim 3, wherein B1 is present and comprises the amino acid sequence (D/I/P)HA(Q/P)KLAR-RLLELK(Q/L)AASSPLP (SEQ ID NO: 278).

6. The polypeptide of claim 1, wherein the polypeptide comprises an amino acid sequence selected from the group consisting of

```
                                            (SEQ ID NO: 33)
SAFDLAMRIHWIYNFAF;

(SEQ ID NO: 281)
HAFDLAMRIHWIYNFAF;

(SEQ ID NO: 33)
SAFDLAMRIHWIYNFAF;

(SEQ ID NO. 282)
SAFDLAMRIMWIYVFAY (SEQ ID NO. 283)
HAFDLAMRIMWIYVFAY (SEQ ID NO: 30)
SAFDLAMRIHWIYNFAFKRKIPF;

(SEQ ID NO: 284)
HAFDLAMRIHWIYNFAFKRKIPF;

(SEQ ID NO: 30)
SAFDLAMRIHWIYNFAFKRKIPF;

(SEQ ID NO: 285)
(33Y)EA(36A)(37E)VL(40K)AVY(44E)T(46E)SAFDLAMRIHWI
YNFAFKRPIPFP;

(SEQ ID NO: 286)
(33D)EA(36A)(37R)VL(40K)AVY(44E)T(46D)SAFDLAMRIHWI
YNFAFKRPIPFP;

(SEQ ID NO: 287)
(33Y)EA(36D)(37E)VL(40K)AVY(44E)T(46N)SAFDLAMRIHWI
YNFAFKRPIPFP;

(SEQ ID NO: 288)
(33V)EA(36A)(37R)VL(40Q)AVY(44E)T(46N)SAFDLAMRI-
WIYNFAFKRPIPFP;

(SEQ ID NO: 289)
(33V)EA(36D)(37K)VL(40Q)AVY(44E)T(46N)SAFDLAMRIHWI
YNFAFKRPIPFP;
```

(SEQ ID NO: 290)
(33V)EA(36D)(37A)VL(40K)AVY(44A)T(46N)SAFDLAMRIHWI
YNFAFKRPIPFP;

(SEQ ID NO: 291)
(33Y)EA(36A)(37E)VL(40K)AVY(44E)T(46E)HAFDLAMRIHWI
YNFAFKRPIPFP;

(SEQ ID NO: 292)
(33Y)EA(36A)(37E)VL(40E)AVY(44E)T(46E)SAFDLAMRIHWI
YNFAFKRPIPFP;

(SEQ ID NO: 293)
(33Y)EA(36A)(37E)VL(40K)AVY(44E)T(46E)SAFDLAMRIHWI
YNFAFKRPIPFP;

(SEQ ID NO: 351)
SAFDLAMRIMWIYVFAYNRPIPF(HB36.3);

(SEQ ID NO: 282)
SAFDLAMRIMWIYVFAY(HB36.3 and HB36.4);

(SEQ ID NO: 352)
SAFDLAMRIMWIYVFAYKRPIPF(HB36.4);

(SEQ ID NO: 352)
SAFDLAMRIMWIYVFAYKRPIPF;

(SEQ ID NO: 353)
MSNAMDGQQLNRLLLEWIGAWDPFGLGKDAYDVEAEAVLQAVYETESAFD
LAMRIMWIYVFAYKRPIPFPHAQKLARRLLELKQAASSPLPLE;

(SEQ ID NO: 354)
MSNAMDGQQLNRLLLEWIGAWDPFGLGKDAYDVEAEAVLQAVYETESAFD
LAMRIMWIYVFAYNRPIPFSHAQKLARRLLELKQAASSPLPLE;

(SEQ ID NO: 294)
MSNAMDGQQLNRLLLEWIGAWDPFGLGKDAYD(33Y)EA(36A)(37E)
VL(40K)AVY(44E)T(46E)SAFDLAMRIHWIYNFAFKRPIPFPPHAQ
KLARRLLELKQAASSPLPLE;

(SEQ ID N

B1 comprises the amino acid sequence (L/A/V/D/I/P)HA(Q/P)KLARRLLELK(Q/L)AASSPLP (SEQ ID NO: 6).

16. The method of claim 15, wherein A1 and B1 are both present, and wherein A1 comprises the amino acid sequence MSNAMDGQQLNRLLLEWIGAWDPFGLGKDAYD(F)EA(A/D)(E)VL(Q/K)AVY(E/A)T(E) (SEQ ID NO: 279), and B1 comprises the amino acid sequence (D/I/P)HA(Q/P)KLARRLLELK(Q/L)AASSPLP (SEQ ID NO: 278).

17. The method of claim 15, wherein the polypeptide comprises the amino acid sequence of a peptide selected from the group consisting of SEQ ID NOS: 30, 33, 65, 281-302, and 351-354.

18. The method of claim 16, wherein the one or more polypeptides are of general formula I wherein is A1-R1-R2-Phe-R3-R4-R5-R6-R7-R8-R9-R10-R11-R12-R13-R14-R15-R16-X1-R17-B1 (SEQ ID NO: 4), wherein one or both of A1 and B1 are present, and wherein A1 comprises the amino acid sequence:

MSNAMDGQQLNRLLLEWIGAWDPFGLGKDAYD(D/V/Y/F)EA(A/D)(A/K/R/E)VL (Q/K)AVY(E/A)T(N/D/E) (SEQ ID NO: 5); and B1 comprises the amino acid sequence (L/A/V/D/I/P)HA(Q/P)KLARRLLELK(Q/L)AASSPLP (SEQ ID NO: 6).

19. The method of claim 18, wherein A1 and B1 are both present, and wherein A1 comprises the amino acid sequence MSNAMDGQQLNRLLLEWIGAWDPFGLGKDAYD(F)EA(A/D)(E)VL(Q/K)AVY(E/A)T(E) (SEQ ID NO: 279), and B1 comprises the amino acid sequence (D/I/P)HA(Q/P)KLARRLLELK(Q/L)AASSPLP (SEQ ID NO: 278).

20. The method of claim 14, wherein the polypeptide comprises the amino acid sequence of a peptide selected from the group consisting of SEQ ID NOS: 30, 33, 65, 28 1-302, and 351-354.

* * * * *